US008461301B2

(12) United States Patent
Gat et al.

(10) Patent No.: US 8,461,301 B2
(45) Date of Patent: Jun. 11, 2013

(54) SYNTHETIC DRAGLINE SPIDER SILK-LIKE PROTEINS

(75) Inventors: Uri Gat, Jerusalem (IL); Shmulik Ittah, Jerusalem (IL); Noaa Barak, Neot Hakikar (IL)

(73) Assignee: Yissum Research Development Company of The Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/113,453

(22) Filed: May 23, 2011

(65) Prior Publication Data
US 2012/0022005 A1 Jan. 26, 2012

Related U.S. Application Data

(60) Provisional application No. 61/347,634, filed on May 24, 2010, provisional application No. 61/347,973, filed on May 25, 2010.

(51) Int. Cl.
| | | |
|---|---|---|
| *C07K 14/00* | (2006.01) | |
| *C07H 21/04* | (2006.01) | |
| *C12N 15/00* | (2006.01) | |
| *C12N 5/07* | (2010.01) | |
| *C12N 5/04* | (2006.01) | |
| *C12N 1/20* | (2006.01) | |
| *C12N 1/00* | (2006.01) | |

(52) U.S. Cl.
USPC ...... 530/350; 536/23.1; 536/23.4; 435/320.1; 435/325; 435/419; 435/252.3; 435/254.11

(58) Field of Classification Search
None
See application file for complete search history.

(56) References Cited

U.S. PATENT DOCUMENTS

2007/0214520 A1* 9/2007 Scheibel et al. .............. 800/288

FOREIGN PATENT DOCUMENTS

| WO | WO 03/060099 A2 | 7/2003 |
| WO | WO 03/060099 A3 | 8/2003 |

OTHER PUBLICATIONS

Dang et al., Clin Cancer Res 5:471-474, 1999.*
Fox, Nat Biotechnol 21:217, 2003.*
Juengst, BMJ 326:1410-1411, 2003.*
Ittah et al., Biopolymers 93:458-468, Dec. 14, 2009.*
Invitrogen "Bac-to-Bac® Baculovirus Expression System", Apr. 2004, 78 pages.*
Anonymous; GenBank: U47856.1 printed on Mar. 31, 2011 (1 page).
Ayoub, N.A. et al. ( ) "*Blueprint for a High-Performance Biomaterial: Full-Length Spider Dragline Silk Genes*," PLoS One 6:e514 (pp. 1-13), 2007.
Brooks, A.E. et al. (2008) "*Properties of Synthetic Spider Silk Fibers Based on Argiope aurantia MaSp2,*" Biomacromolecules 9:1506-1510.
Cunniff, P.M. et al. (1994) "*Mechanical and Thermal Properties of Dragline Silk from the Spider Nephila clavipes,*" Polymers for Advanced Technologies 5:401-410.
Fahnestock, S.R. et al. (1997) "*Synthetic Spider Dragline Silk Proteins and Their Production in Escherichia coli,*" Appl. Microbiol. Biotechnol. 47:23-32.
Gatesy, J. et al. (2001) "*Extreme Diversity, Conservation, and Convergence of Spider Silk Fibroin Sequences,*" Science 291:2603-2605.
Gosline, J.M. et al. (1999) "*The Mechanical Design of Spider Silks: From Fibroin Sequence to Mechanical Function,*" J. Exper. Biol. 202:3295-3303.
Guerette, P.A. et al. (1996) "*Silk Properties Determined by Gland-Specific Expression of a Spider Fibroin Gene Family,*" Science 172:112-115.
Hayashi, C.Y. et al. (1999) "*Hypotheses That Correlate the Sequence, Structure, and Mechanical Properties of Spider Silk Proteins,*" Intl. J. Biol. Macromol. 24:271-275.
Hayashi, C.Y. et al. (2000) "*Molecular Architecture and Evolution of a Modular Spider Silk Protein Gene,*" Science 287:1477-1479.
Hinman, M. et al. (1992)"*Spider Silk: a Mystery Starting to Unravel,*" In: Results and Problems in Cell Differentiation 19: Biopolymers (Case, S.T. (ed.)) Springer-Verlag, Berlin Germany; Chapter 8, pp. 227-254.
Huemmerich, D. et al. (2004) "*Novel Assembly Properties of Recombinant Spider Dragline Silk Proteins,*" Current Biology 14:2070-2074.
Ittah, S. et al. (2006) "*An Essential Role for the C-Terminal Domain of a Dragline Spider Silk Protein in Directing Fiber Formation,*" Biomacromolecules 7:1790-1795.
Ittah, S. et al. (2007) "*A Model for the Structure of the C-Terminal Domain of Dragline Spider Silk and the Role of Its Conserved Cysteine,*" Biomacromolecules 8:2768-2773.
Lewis, R.V. (2006) "*Spider Silk: Ancient Ideas for New Biomaterials,*" Chem. Rev. 106: 3762-3774.
Prince, J.T. et al. (1995) "*Construction, Cloning, and Expression of Synthetic Genes Encoding Spider Dragline Silk,*" Biochemistry 34:10879-10885.

(Continued)

*Primary Examiner* — David J Steadman
(74) *Attorney, Agent, or Firm* — William C. Schrot; Jeffrey I. Auerbach; The Auerbach Law Firm, LLC

(57) ABSTRACT

The present application relates to isolated amino acid sequence comprising multiple repeats of a semi-synthetic spider silk protein domain, or any functional homolog, variant, derivative, fragment or mutant thereof. The amino acid sequence of the invention further comprises an N-terminal region and a C-terminal region. The invention further provides a nucleic acid encoding the amino acid sequence of the invention, an expression vector comprising said nucleic acid, a host cell transformed with said expression vector, a recombinant spider silk protein thus produced and a fiber composed of the recombinant spider silk protein. The invention further encompasses a composition comprising as an active ingredient said amino acid sequence or any said recombinant protein or fiber comprising the same. Lastly, the invention relates to an article comprising at least one fiber composed of said recombinant spider silk protein.

18 Claims, 7 Drawing Sheets

OTHER PUBLICATIONS

Rising, A. et al. (2007) "*Major Ampullate Spidroins From Euprosthenops australis: Multiplicity At Protein, mRNA and Gene Levels,*" Insect Molecular Biology 16(5):551-561.

Stark, M. et al. (2007) "*Macroscopic Fibers Self-Assembled from Recombinant Miniature Spider Silk Proteins,*" Biomacromolecules 8:1695-1701.

Vollrath, F. et al. (2001) "*Liquid Crystalline Spinning of Spider Silk,*" Nature 410:541-548.

Winkler, S. et al. (2000) "*Molecular Biology of Spider Silk,*" Reviews in Molecular Biotechnology 74: 85-93.

Hedhammar, M. "*Structural Properties of Recombinant Nonrepetitive and Repetitive Parts of Major Ampullate Spidron 1 from Euprosthenops australis: Implications for Fiber Formation,*" Biochemistry 47:3407-3417 (2008).

\* cited by examiner

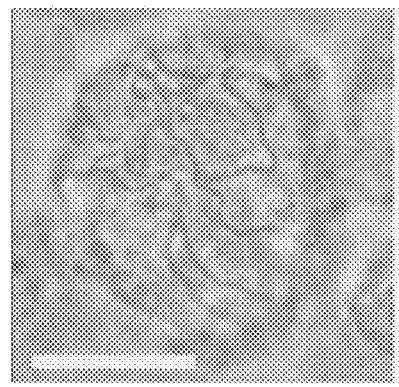 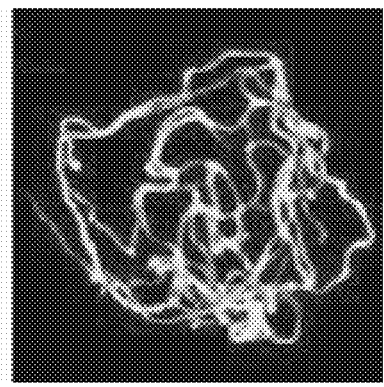
Fig. 2A     Fig. 2B
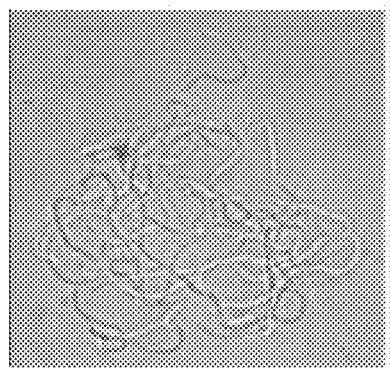 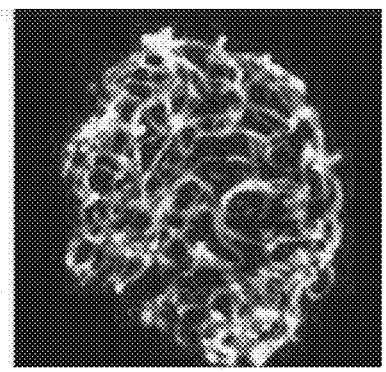
Fig. 2C     Fig. 2D
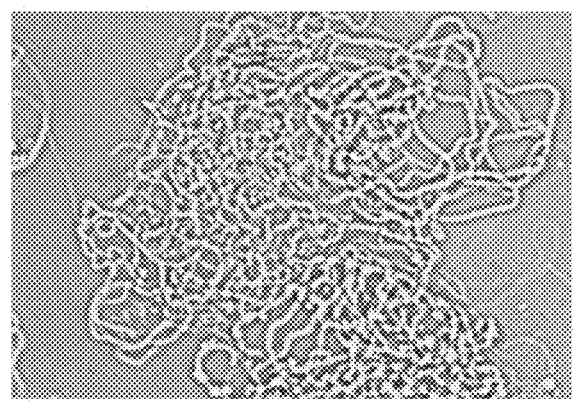
Fig. 2E

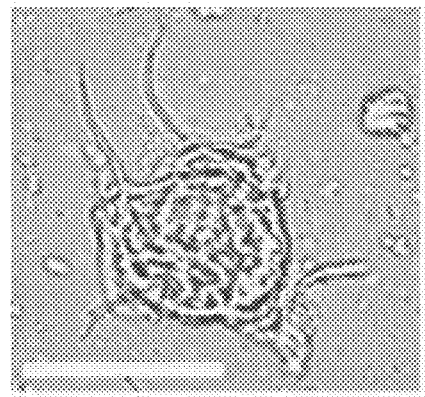 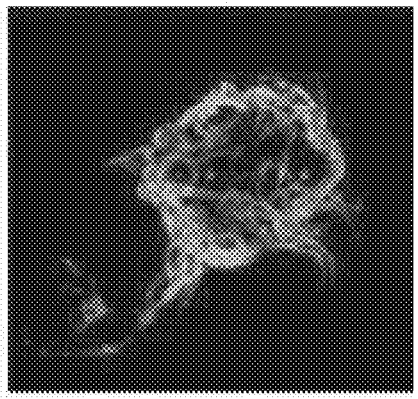
Fig. 3A    Fig. 3B
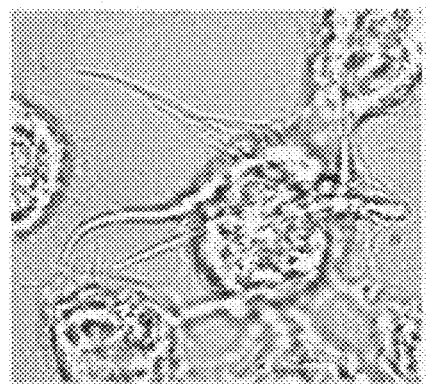 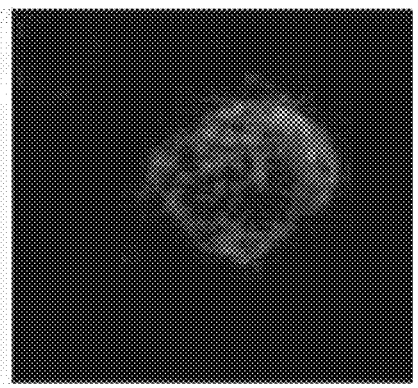
Fig. 3C    Fig. 3D
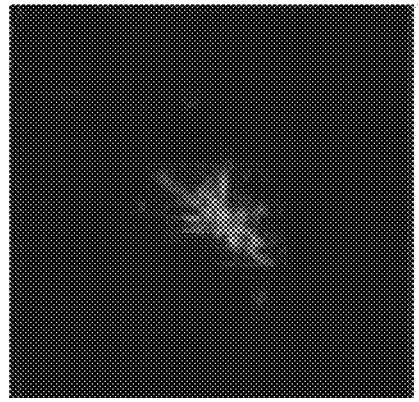 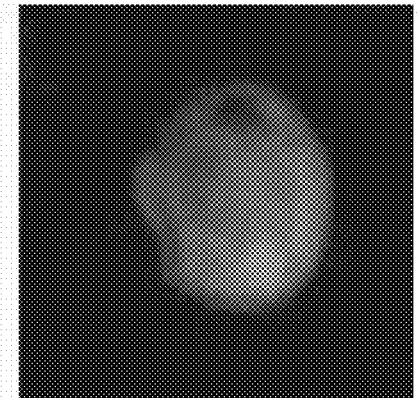
Fig. 3E    Fig. 3F

Fig. 6

Araneus diadematus fibroin-4 mRNA, partial cds

Fig. 6 (cont.)

ORIGIN
```
   1 gcaggatctt cagcagcagc ggccgcagca gcaagtggat ctggaggata cggacctgaa
  61 aaccaaggac catctggacc tgtagcatat ggactggtg gaccgtatc ttcagctgca
 121 gcagcagccg ctgcaggaag ctgcagggac ctgaaaacca cagcagcagc aggaccatct
 181 ggacccggag gatatggacc tgtggttcc ggatcttcag cagcttcag agccggctgca
 241 gcaagtggac ctggaggata tggacctgga agccaagtac tctgacctg tgtggatcc
 301 ggaggatatg gcccggaga ccaaggggca ggaactggaa gtggcctgc ttcatctgcg
 361 gcagcagcag gacctggagc tgcagcagc tgcaggaag gatatggacc tgaagcaa
 421 ggaccatctg gacctggagc atatggaccg tggacctgga gatcttcagc tgcagcagca
 481 gcgctgtcag caagtggtgg accggatact ggaacttgaa gcagcagccg atctggaccg
 541 ggagtatatg gacctggtgg gaccgggacc tgagcagcg caagcagcgc tgcaggaact
 601 ggacctgtgt gatacggac ctgaaaacaa ggaccatctg gacctggagg atatggacct
 661 gctgttccgg gatcttcag agcagcagcc gtcgtgcag caagtggacc tggaggatat
 721 ggacctggag gcaagcagc atctggacct gtcgatccg gatgatccg ttcccggaagg
 781 caaggggtga ctggacctgg gaccccatc tccttctgct gcatcagcag cgttgcagc
 841 ggaggatatg gacctggaag atgcccatc tggtcctcc cgaagcagcc cgttattctct
 901 cctggagcat ctcgtgcagc cctcgtgctc ggtgtctcag gctgatatgt gcgtatgcgt
 961 gcgctgcagc ctgctgttc tggagcttg aatagtctag tatctccagat tagctactag
``` http://www.ncbi.nlm.nih.gov/nuccore

SYNTHETIC DRAGLINE SPIDER SILK-LIKE PROTEINS

CROSS-REFERENCE TO RELATED APPLICATIONS

This application is based on U.S. Provisional Application Ser. No. 61/347,634, filed on May 24, 2010, and on U.S. Provisional Application Ser. No. 61/347,973 filed on May 25, 2010, both of which applications are incorporated herein by reference and to which priority is claimed.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entireties.

FIELD OF THE INVENTION

The invention relates to novel recombinant spider silk protein analogs of the natural spider dragline of *Araneus diadematus*. More specifically, recombinant spider dragline protein comprising synthetic repeating units has been produced in *Spodoptera frugiperda* insect cells using a baculovirus recombinant expression system. The expressed spider silk protein analogs self-assemble to dragline spider silk-like insoluble fibers.

BACKGROUND OF THE INVENTION

Spider silk and spider webs have attracted the interest of man since ancient times [Lewis R. V. Chem. Rev. 2006, 106: 3762-3774]. For several centuries, scientists have realized the potential of using spider silk as a material in the use of mankind, taking advantage of its remarkable strength. However, unlike silk, which is commercially produced from silkworms in quantities, spiders cannot be cultured in captivity due to their territorial and aggressive behavior. Thus, an artificial system must be used to synthesize spider silk.

Spiders have impressive fiber spinning abilities and produce up to seven different types of silk, each of which is stored and secreted by a specialized gland and utilized for a specific function during the life time of the spider [Gosline, J. M. et al., J. Exp. Biol. 1999, 202 Part 23, 3295-3303; 115; Lewis, R. V. Chem, Rev, 2006, 106, 3762-3774]. Among the different types of spider silk, the "dragline silk" is studied most intensely. The dragline silk is used by the orb-web weaving spiders to construct the frame and radii of their webs as well a life line when they fall or escape danger [Vollrath, F. and Knight, D. P. Nature 2001]. To be able to perform these tasks, the dragline fiber displays a remarkably high toughness due to combination of high elasticity and strength, which places it as the toughest fiber, whether natural or man-made [Gosline, J. M. et al., J. Exp. Biol. 1999, 202 Part 23, 3295-3303; Lewis, R. V. Chem, Rev, 2006, 106, 3762-3774]. For instance, dragline is six times as strong as high-tensile steel in its diameter and three times tougher than Kevlar that is one of the strongest synthetic fibers ever made [Gosline J. M. et al., J. Exp. Biol. 1999, 202 Pt 23:3295-3303]. Thus, it is no wonder that this material is regarded as having a huge potential as a biomaterial in the service of man [Lewis R. V. Chem. Rev. 2006, 106:3762-3774].

The building blocks of this extraordinary biological polymer are two paralogous structural proteins belonging to the fibroins family, secreted from the major ampullate gland, named MaSp1 and MaSp2 [Winkler, S. and Kaplan, D. L., J. Biotechnol. 2000, 74, 85-93].

These proteins were found to be composed of three different domains; a predominant central repetitive core consisting of hundreds of repeats, flanked with much shorter, nonrepetitive N and C-terminal domains [Ayoub, N. et al., PLoS One 2007, 2, e514], both non-repetitive domains are most highly conserved between different spider species. The C-terminal domain is important for the formation of the proper structure and assembly of the dragline fiber [Ittah, S. et al., Biomacromolecules 2006, 7, 1790-1795; Ittah, S. et al., Biomacromolecules 2007, 8, 2768-2773]. The N-terminal sequence, which contains a signal peptide, may also have a structural role but probably mainly serves to secrete the proteins into the lumen of the major ampullate gland [Ayoub, N. A. et al., PLoS One 2007, 2, e514; Hayashi, C. Y. and Lewis, R. V. Science 2000, 287, 1477-1479]. Only lately the full sequences of entire dragline spider silk proteins of the black widow were derived, which has unraveled the huge size of their genes (~9.4-11.3 kb) and their precise genomic structure [Ayoub, N. A. et al., PLoS One 2007, 2, e514; Hayashi, C. Y. and Lewis, R. V. Science 2000, 287, 1477-1479].

The reiterated repeats sequences of these proteins vary slightly, but always contain poly-A stretches, separated by glycine-rich motifs such as GPGXX or GGX [Gosline, J. et al., J. Exp. Biol. 1999, 202 Part 23, 3295-3303; Lewis, R. V. Chem. Rev. 2006, 106, 3762-3774;]. Poly-A stretches are known to adopt a β-strand structure and a number of β-strands gather to create a β-sheet. The latter have the ability to create an ordered structure known as β-pleated sheet—a layered structure that is energetically preferred due to the burying of the hydrophobic methyl side chain of the alanines.

This structure gives rise to the mini-crystals found in native dragline silk, and due to its highly ordered structure, this domain is considered to be responsible for the typical melting point of the fiber [Cunniff, P. M. Polym. Adv. Technol. 1994, 5, 401-410]. The glycine-rich regions are sometimes referred to as "amorphous" and thought to adopt a $3_{10}$ helix structure as well as β-turns and coils, loose structures that are considered to confer the final fiber its elasticity property [Hayashi, C. Y. et al., Int. J. Biol. Macromol. 1999, 24, 271-275].

Most araneoid spider species produce an MaSp1 fibroin, which does not contain prolines in its repetitive sequences and a proline-rich MaSp2 fibroin. However, *A. diadematus* secretes two proline-rich dragline fibroins, ADF3 and ADF4, which may thus be considered as MaSp2 proteins [Gatesy, J. et al., Science 2001, 291, 2603-2605]. Previously, the inventors have suggested that comparison of the sequences of these two fibroins to other MaSp fibroins reveals that ADF4, presented in FIG. 6, like all the MaSp1 fibroins that were analyzed, was more hydrophobic than ADF3 and the MaSp2 fibroins [Huemmerich, D. et al., Curr. Biol. 2004, 14, 2070-2074]. ADF4, like MaSp1 fibroins, also has a low content of glutamine, which is a polar amino-acid, in contrast to ADF3 and MaSp2 fibroins that have a higher glutamine content and display a QQ motif in their repeats. Thus, except for the proline content ADF4 resembles MaSp1 fibroins, and as described in the following, it tends to aggregate into fibers under several different experimental conditions, most likely due to its hydrophobic nature.

The scope of applications for which dragline spider silk may be employed is very wide and is only limited by the imagination of the beholder. It has been suggested for instance that if this material can be manufactured at a relatively large scale then it may be used for making low weight bullet-proof vests, new type of enforced fishing lined as well as a new type of textile. It has been suggested for use in biomedicine as biodegradable surgical sutures for microsurgery and in electronics as microconductors if the microfibers can be coated by heavy metals binding to amino acid analogues [Vollrath F. and Knight D. P. Nature 2001, 410:541-548]. However, since spiders cannot be cultured in captivity due to their solitary and predatory nature, in order to efficiently synthesize spider silk a heterologous artificial system must be used.

During the last two decades, many attempts were made to artificially synthesize spider silk proteins in heterologous hosts using genetic engineering techniques. Cloning of partial cDNAs coding for dragline proteins was achieved by several groups [Guerette, P. A. et al., Science 1996, 272, 112-115; Hinman, M. Results Probl. Cell. Differ. 1992, 19, 227-254; Rising, A. et al., Insect Mol. Biol. 2007, 16, 551-561]. Expression of natural and synthetic recombinant dragline silk proteins took place using bacteria, yeast, plants, mammalian cells, and transgenic goats [Lewis, R. V. Chem. Rev. 2006, 106, 3762-3774]. However, due to the highly repetitive nature of the sequence, as well as the restricted pool of amino acids composing the major part of the proteins, transcription and translation of the sequences were usually problematic, resulting in premature termination and low yields. Previous attempts to purify soluble dragline proteins, whether native or synthetic and artificially spin them, resulted in fibers with inferior properties as compared with the native dragline fiber [Brooks, A. E. et al., Biomacromolecules 2008, 9, 1506-1510].

Lately, a new approach to overcome the problematic solubility of spidroins led to successful self-assembly of dragline-based synthetic proteins [Stark, M. et al., Biomacromolecules 2007, 8, 1695-1701]. In this study, synthetic constructs containing four repeats of poly-A and glycine-rich regions, ending with the native C-terminal domain of MaSp1 originated from *E. australis*, were fused to a solubility enhancing fusion protein, thioredoxin. The protein was expressed in *E. coli* and remained soluble after its purification. Cleavage of the fusion protein initiated spontaneous self-assembly of the synthetic dragline proteins into fibers that were tested and found to be of high tensile strength and toughness but inferior to that of the native dragline fiber of this species [Stark, M. et al., Biomacromolecules 2007, 8, 1695-1701; Hedhammar, M. et al., Biochemistry 2008, 47, 3407-3417].

SUMMARY OF THE INVENTION

In the present invention, use is made of the inventors' model baculoviral expression system in insect cells supporting self-assembly of native dragline proteins into fibers that resemble the native ones by several aspects including shape and chemical resistance [Ittah, S. et al., Biomacromolecules 2006, 7, 1790-1795; Ittah, S. et al., Biomacromolecules 2007, 8, 2768-2773; Huemmerich, D. et al., Curr. Biol. 2004, 14, 2070-2074]. To study the repetitive domain and be able to genetically engineer the sequence of the repeats and their number, it was no longer possible to use the native versions of MaSp proteins. Thus, the inventors used their own version of a general reiterative cloning strategy [Prince, J. T. et al., Biochemistry 1995, 34, 10879-10885; Fahnestock, S. R. and Irwin, S. L., Appl. Microbiol. Biotechnol. 1997, 47, 23-32] to design a representative building block of the repetitive domain and used it to express an array of synthetic ADF4-like genes, varying in the number of their identical repeats and ending with the native C-terminal sequence. This approach permitted the inventors to define the minimal number of repeats facilitating fiber formation on one hand and on the other to express the largest dragline protein to date, repeats with a molecular weight of ~106 kDa.

An overall of 10 viruses coding for semi-synthetic proteins containing 0-32 identical repeats followed by the native C-terminus sequence were constructed. The expressed proteins were characterized and found to give rise to a range of phenotypes: from a fully soluble protein, through several different aggregation forms, to bona fide fibers that are longer and more homogenous than previously-expressed native like r-ADF4 fibers demonstrated previously by the inventors [Huemmerich, D. et al., Curr. Biol. 2004, 14, 2070-2074]. Exploring the correlations between the repeat number and the different fiber phenotypes, resilience properties, ultrastructure, and thermal profiles enhances the understanding of the structure and intermolecular interactions of the repetitive and nonrepetitive domains constituting the fiber building blocks. Synthesis of all data collected in this study and the past yields a comprehensive hypothetical model for the dragline silk self-assembly mechanism.

In their previous publications, the inventors disclosed the use of the baculovirus-mediated expression system for the production of a recombinant *Araneus diadematus* spider silk dragline ADF4 protein and its self-assembly into intricate fibers in host insect cells. Here, the aim of the inventors was to explore the function of the major repetitive domain of the dragline spider silk. Thus, an array of synthetic proteins was generated, each containing a different number of identical repeats up to the largest recombinantly-expressed spider silk to date. Study of the self-assembly properties of these proteins showed that depending on the increasing number of repeats they give rise to different assembly phenotypes, from a fully soluble protein to bona fide fibers with superior qualities. The different assembly forms, the corresponding chemical resistance properties obtained as well as ultrastructural studies, revealed novel insights concerning the structure and intermolecular interactions of the repetitive and nonrepetitive domains.

Thus, one object of the invention is the provision of a self-assembling semi-synthetic dragline silk recombinant proteins and fibers, having properties equivalent to the native dragline silk protein. These and other objects of the invention will become apparent as the description proceeds.

In the first aspect, the invention provides an isolated amino acid sequence comprising n repeats of a semi synthetic spider-silk protein repetitive unit. Specifically, the repetitive unit of the invention may have the sequence of SEQ ID NO.:4, or of a functional homolog, variant, derivative, fragment or mutant thereof, wherein n is an integer above 2. The amino acid sequence of the invention may further comprise at least one of a C-terminal region, specifically, a region denoted as SEQ ID NO.: 10; and N-terminal region, specifically a region selected from the amino acid sequences having a sequence denoted as SEQ ID NO.: 5 and 83.

In the second aspect, the invention relates to an isolated nucleic acid sequence encoding an amino acid sequence comprising n repeats of SEQ ID NO.:4, or of a functional homolog, variant, derivative, fragment or mutant thereof, wherein n is an integer above 2. In specific embodiments, the nucleic acid sequence of the invention encodes an amino acid sequence that may further comprise at least one of a C-terminal region, specifically, a region denoted as SEQ ID NO.: 10, encoded by SEQ ID NO. 9; and an N-terminal region, specifically a region selected from the amino acid sequences having a sequence denoted as SEQ ID NO.: 5 and 83 and encoded by SEQ ID NO. 6 and SEQ ID NO. 84, respectively.

In the third aspect, the invention is directed to an expression vector comprising the nucleic acid sequence of the invention. It should be noted that the nucleic acid sequence is under expression control of an operably linked promoter and, optionally, regulatory sequences.

In a further aspect, the invention provides a host cell transformed with an expression vector comprising the nucleic acid sequence of the invention, encoding the spider silk recombinant protein of the invention.

In another aspect, the invention relates to a recombinant spider silk protein comprising n repeats of SEQ ID NO.:4, or of a functional homolog, variant, derivative, fragment or mutant thereof, wherein n is an integer above 2. It should be noted that in certain embodiments, the recombinant spider silk protein of the invention may further comprise at least one of a C-terminal region, specifically, a region denoted as SEQ ID NO.: 10; and an N-terminal region, specifically a region selected from the amino acid sequences having a sequence denoted as SEQ ID NO.: 5 and 83.

In yet a further aspect, the invention provides a fiber composed of the recombinant spider silk protein comprising n repeats of SEQ ID NO.:4, or of a functional homolog, variant, derivative, fragment or mutant thereof, wherein n is an integer above 2. The protein optionally further comprises at least one of a single C-terminal region denoted as SEQ ID NO.: 10 and a single N-terminal region selected from the amino acid sequences having a sequence denoted as SEQ ID NO.: 5 and 83.

In yet a further aspect, the invention is directed to a composition comprising as an active ingredient the amino acid sequence of the invention or any recombinant protein or fiber comprising the same.

In another aspect, the invention provides an article comprising at least one fiber composed of the recombinant spider silk protein of the invention.

Multimerization of Synthetic Repeat Sequences

Figure 1A:
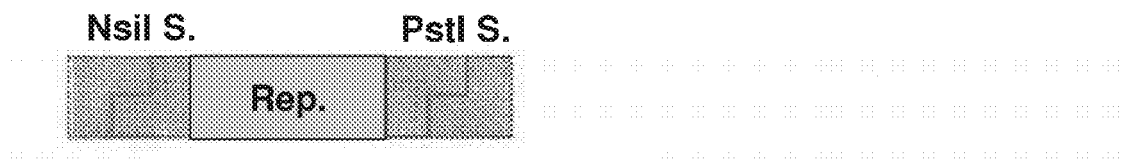
FIG. 1A-1D

FIG. 1A. A single synthetic repeat of 105 bp is depicted flanked by the compatible restriction sites NsiI and PstI.

Figure 1B:
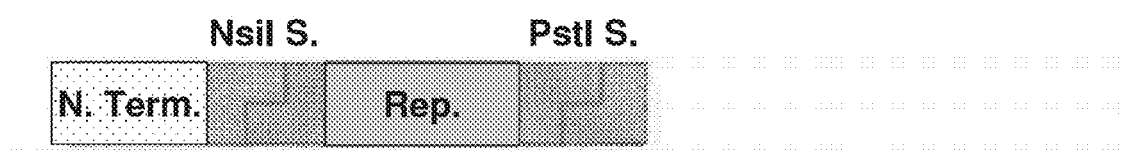

FIG. 1B. The single repeat is inserted into the baculovirus donor plasmid in frame to the artificial N-terminal sequence.

Figure 1C:
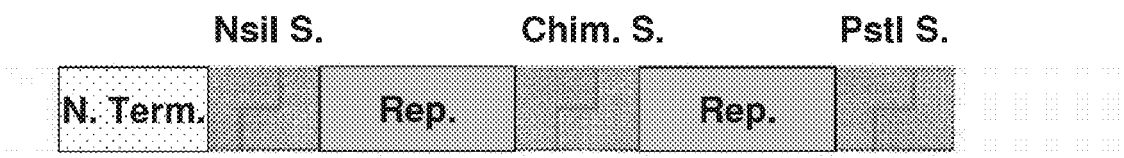

FIG. 1C. Insertion of the repeat unit as depicted in (1A) into the PstI site of (B) will lead to a vector containing two repeats. A double digestion with NsiI and PstI yielding a 210-bp element will verify the in frame orientation of the inserted repeat. This process is reiterated to obtain a donor plasmid containing multiple repeats using donor plasmids and inserts containing varying number of repeats as building blocks.

Figure 1D:
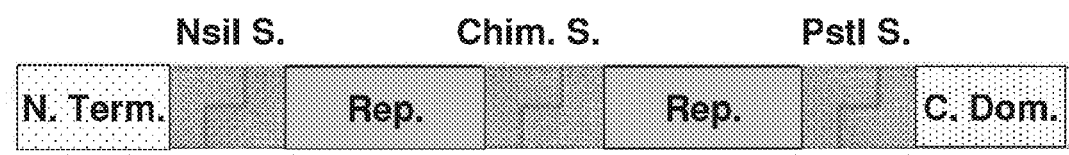

FIG. 1D. The native C-terminal domain coding sequence was inserted in frame to the 3' repeat at the PstI site in order to obtain the final construct ready for baculovirus expression.

Abbreviations: NsiI S. (NsiI restriction site); PstI S. (PstI restriction site); Rep. (repeat); N-term. (N-terminus); C. Dom. (C-terminal domain).

FIG. 2A-2E

Characterization of Filaments Made of the Synthetic 16-Repeat Protein

FIG. 2A. Filaments in a cell infected with a 16-repeat coding baculovirus at 2d postinfection as viewed by light microscopy.

FIG. 2B. Fluorescence microscopy using anti-His$_6$-tag antibodies of an infected cell verifies the filaments identity.

FIG. 2C. A single 16-repeat protein coiled filament purified from an infected cell as viewed by light microscopy.

FIG. 2D. A representative confocal microscopy of anti-His$_6$-tag antibodies labeling of a cell infected with a baculovirus coding for 24 repeats. Similar fibers were observed also for the 8, 12, 20, 32 repeats proteins. The scale bar represents 10 m.

FIG. 2E. A single 24-repeat protein coiled filament purified from an infected cell as viewed by light microscopy.

FIG. 3A-3F

Self-Assembly Phenotypes of Synthetic Proteins Containing Four Repeats and Less

FIG. 3A. Filaments in a cell infected with a four repeat coding baculovirus at three days post-infection. The rod-shaped ending of the fibers protrude through the cell boundary, as viewed by light microscope.

FIG. 3B. The filaments of (FIG. 3A) as viewed by confocal microscope using anti-His$_6$-tag antibodies.

FIG. 3C. Filaments in a cell infected with a two repeat coding baculovirus at three days post-infection. A phenotype similar to that of the four-repeat protein can be seen by light microscopy.

FIG. 3D. The filaments of (FIG. 3C) as viewed by confocal microscopy using anti-His$_6$-tag antibodies.

FIG. 3E. Cells infected with a single repeat coding baculovirus at three days post-infection display a soluble and low ordered assembly of the protein as viewed by confocal microscopy using anti-His$_6$-tag antibodies.

FIG. 3F. Cells infected with a C-terminal domain only coding baculovirus at three days post-infection display a fully soluble pattern as viewed by confocal microscopy using anti-His$_6$-tag antibodies. The scale bar represents 10 m.

FIG. 4A-4E

Transmission Electron Microscope Analysis of ADF4, 32, 12, and 4 Repeats Fibers

Figures 4A, 4B, 4C:
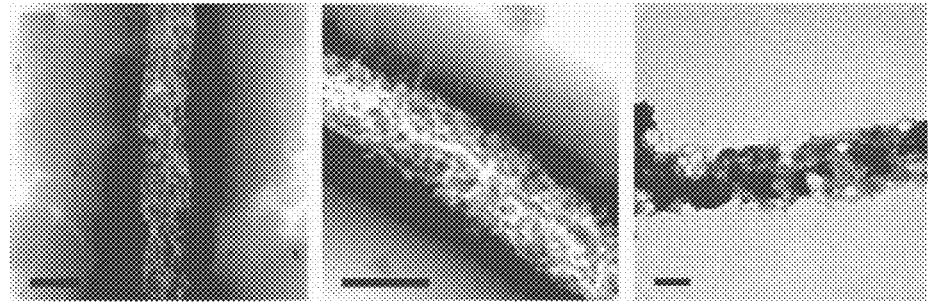

FIG. 4A. A mesh of smaller filaments composes the final ADF4 fiber.

FIG. 4B. Nano fibers extending beyond the contour of a 32 repeats fiber.

FIG. 4C. A four repeats fiber displaying less dense and homogenous organization of its substructures. Some round empty spaces are spread throughout the fiber.

Figures 4D, 4E:
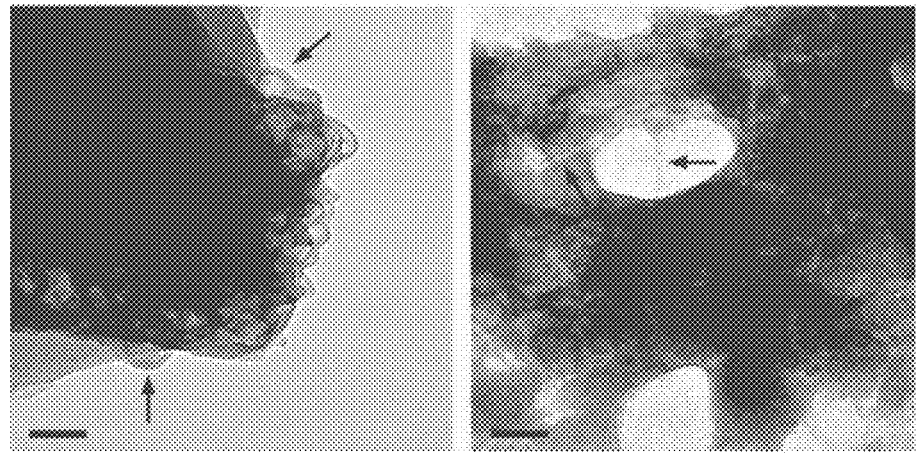

FIG. 4D. An exposed edge of a 12 repeats fiber composed of a nanofibril network can be clearly seen. Distinctive nanofibrils (arrows) were measured to be ~7 nm in diameter.

FIG. 4E. Higher magnification of a four repeats fiber verifies its loosely packed nanofibrilar nature accompanied by empty spaces. Distinctive nanofibers (arrows) can be clearly observed. Scale bars in panels A-C are 200 nm and in D-E, 50 nm.

FIG. 5A-5D

Proposed Model for the Mechanism of Dragline Proteins Self-Assembly

Figures 5A, 5B, 5C, 5D:
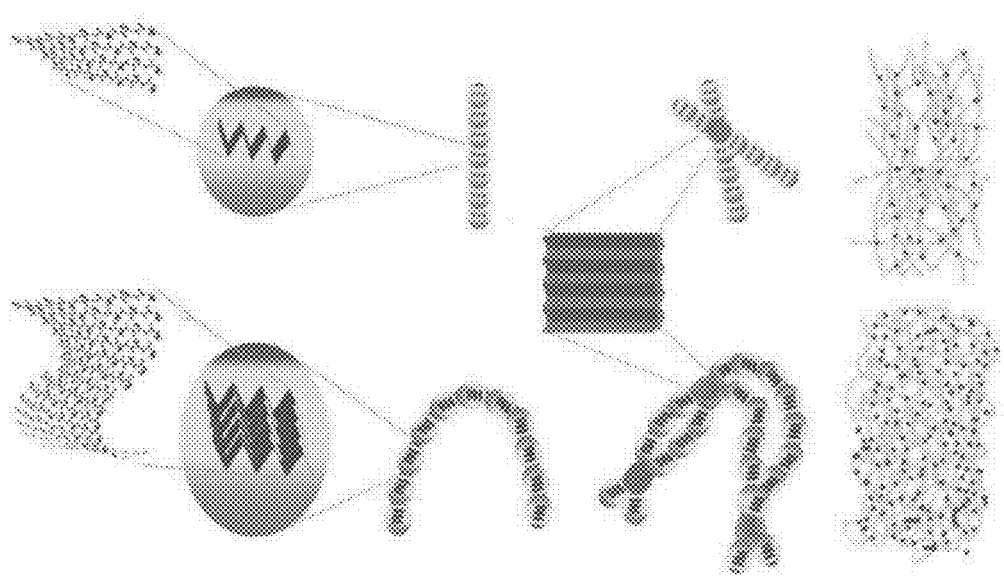

FIG. 5A. An illustration of 4 and 16 repeats monomers (top and bottom, respectively). Each monomer contains a poly-A based-sheet as part of the repetitive core domain flanked by N (top of oval) and C (bottom of oval) terminal domains.

FIG. 5B. A nanofibril that is the end result of an oriented head-to-tail elongation in which the C-terminal domain of each monomer interacts with the N-terminal zone of the repetitive domain of its counterpart.

FIG. 5C. A basic interaction between two nanofibrils. High proximity between two monomers from different nanofibrils (emphasized and enlarged), in which the-sheets are similarly oriented, leads to their pleating and formation of a joint minicrystal (inset).

FIG. 5D. A depiction of a segment from the final "super" fiber. The differences between the four repeat filaments and the fibers composed of higher number of repeats (represented here by the 16 repeat form) are mainly the loose packaging of the nanofibrils composing the four repeat, leading to less events of joint mini-crystals formation (dots), accompanied by empty spaces as part of the main fiber.

FIG. 6

*Araneus diadematus* Fibroin-4 mRNA

An mRNA partial CDS of *Araneus diadematus* fibroin-4 as appearing in GenBank entry U47856.1 (the disclosed nucleotide sequence is SEQ ID NO:1; the disclosed protein protein is SEQ ID NO:2).

DETAILED DESCRIPTION OF THE INVENTION

Due to its physical and chemical properties, spider silk is a sought-after material, and many attempts were made to produce it in commercial quantities. Spider silk is a remarkably strong material. Its tensile strength is comparable to that of high-grade steel (1500 MPa), and about half as strong as aramid filaments, such as Twaron or Kevlar (3000 MPa). Spider silk is about a fifth of the density of steel; a strand long enough to circle the Earth would weigh less than 500 grams (18 oz). Spider silk is also especially ductile, able to stretch up to 1.4 times its relaxed length without breaking. It can hold its strength below −40° C.

Many species of spider have different glands to produce silk with different properties for different purposes, including housing, web construction, defense, capturing and detaining prey, egg protection, and mobility. Different specialized silks have evolved with properties suitable for different uses. For example, *Argiope argentata* has five different types of silk, each used for a different purpose: dragline silk is used for the web outer rim and spokes and the lifeline. It is as strong per unit weight as steel, but much tougher. Capture-spiral silk is used for the capturing lines of the web. It is sticky, extremely stretchy and tough. Tubiliform silk is used for protective egg sacs. It is the stiffest silk. Aciniform silk is used to wrap and secure freshly captured prey. It is two to three times as tough as the other silks, including dragline. Finally, minor-ampullate silk is used for temporary scaffolding during web construction.

Although different species of spiders and different types of silk have different protein sequences, a general trend in spider silk structure is a sequence of amino acids (usually alternating glycine and alanine, or alanine alone) that self-assemble into a beta sheet conformation. These "Ala rich" blocks are separated by segments of amino acids with bulky side-groups. The beta sheets stack to form crystals, whereas the other segments form amorphous domains. Typically, the biofilament's amorphous domain forms a beta-type sheet where the spaces between the sheets are between 3 ångströms and 8 ångströms, or more specifically, between 3.5 ångströms and 7.5 ångströms.

It is the interplay between the hard crystalline segments, and the strained elastic semi amorphous regions that gives spider silk its extraordinary properties. The high toughness is due to the breaking of hydrogen bonds in these regions.

Spider silk is as strong as many industrial fibers, stronger than many and tougher than all, and so there is commercial interest in duplicating spider silk artificially, since spiders use renewable materials as input and operate at room temperature, low pressures and using water as a solvent. However, it has been difficult to find a commercially viable process to mass-produce spider silk.

Therefore it is an object of the present invention to provide recombinant silk spider proteins having enhanced characteristics as, in particular, improved capability of being expressed in high yield and improved strength and flexibility, i.e. better quality. Furthermore, it is an object of the present invention to provide recombinant spider silk proteins, which can be conveniently expressed in efficient and well established expression systems.

Figure 6:
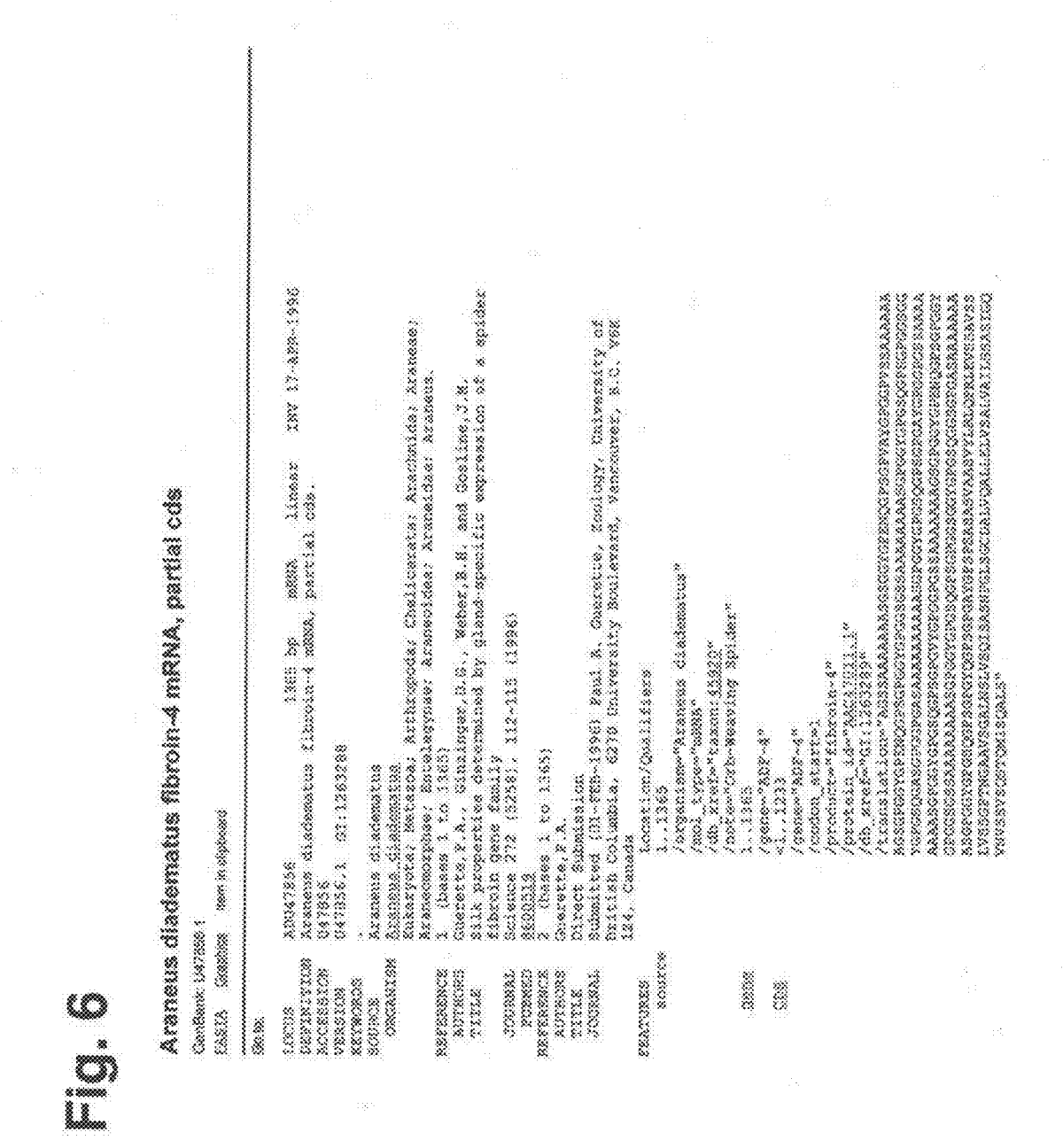

After having demonstrated the role of the conserved C-terminal domain in their previous work [Ittah, S. et al., Biomacromolecules 2006, 7, 1790-1795; Ittah, S. et al., Biomacromolecules 2007, 8, 2768-2773], here the inventors explore the significance of the major domain of dragline silks and thus set out to study the repetitive domain of their model dragline spider silk protein, ADF4, the GenBank entry of the mRNA coding for which is presented in FIG. 6. The inventors have designed a unique protocol allowing the construction and expression of several versions of semi-synthetic proteins, containing different numbers of identical repeats, which were based on a consensus sequence derived from the native sequence. To this synthetic domain, the native C-terminal domain of ADF4 was appended, and these semi-synthetic genes were expressed in order to determine the effect of repeat number on fiber formation and attributes.

The finding presented here, teaching that genes consisting of synthetic repeats can give rise to spider silk-like fibers similar to the previous r-ADF4 fibers, demonstrate that the heterogeneity of native repeats is not important for the formation of resistant fibers. That said, without being bound by theory, the inventors speculate that the natural diversity between the repeats might be important in the prevention of premature assembly of fibrils in the secreting cells of the spider's glands, which would be lethal to the animal. In addition, prevention of the polymerization process along the path of the large ampullate gland is most likely important for the spinning process and may also require non-identical repeats. Further, the regulation of timely polymerization during spinning and proper fiber formation may possibly rely on the presence of the more soluble and less hydrophobic MaSp2/ADF3 type of fibroins.

The size of a typical native dragline protein is ~250 kDa [Ayoub, N. A. et al., PLoS One 2007, 2, e514]. Using the system provided herein, the inventors were able to express a protein containing 32 repeats, 105.6 kDa in size, which is the closest to the native protein as reported so far. No significant differences in shape or chemical attributes were found between the fibers formed from proteins harboring 8-32 repeats, which may suggest that the assembly conditions in said system are not affected by the repeat number over a certain threshold. This may be the case also in the natural spinning process in spiders, wherein the large size of the native proteins may have evolved due to evolutionary events, in which a large number of repeats was an advantage in generating a repertoire of silk genes. One can speculate that having a large number of similar repeats may have increased the likelihood of homologous recombination-driven events that allowed the advent of different fibroins. It is also possible, though, that in the natural spinning process the size of the proteins does play a role in fiber formation due to faster kinetics that may be required or due to the drawing mechanism thereby involved.

The present invention is thus directed to recombinant spider silk amino acid sequences, proteins, nucleic acids coding for said amino acid sequences, as well as hosts suitable for expressing them. Specifically, the invention provides a recombinant spider-silk protein comprising a repeat array of n repeats of synthetic repetitive units having the amino acid sequence of SEQ ID NO. 4. Furthermore, the present invention is directed to a method of production and isolation of spider silk proteins and the use of the proteins in the field of biotechnology and/or medicine and other industrial fields, in particular in the manufacture of bullet-proof vests, surgical and suture fibers, automotive parts, in the aircraft construction, new textiles and clothes, in the processing of textiles and leather, as well as in the manufacture and processing of paper and the like.

Thus, in the first aspect, the present invention provides an isolated amino acid sequence comprising n repeats of SEQ ID NO.:4, or of a functional homolog, variant, derivative, fragment or mutant thereof, wherein n is an integer above 2.

"Amino acid" as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

"Amino acid sequence" or "peptide sequence" is the order in which amino acid residues, connected by peptide bonds, lie in the chain in peptides and proteins. The sequence is generally reported from the N-terminal end containing free amino group to the C-terminal end containing free carboxyl group Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, sulfhydryl bond formation, cleavage and the likes.

As indicated above, the invention provides isolated and purified amino acid sequence. As used herein, "isolated" or "substantially purified", in the context of synthetic spider silk amino-acid sequences or nucleic acid molecules encoding the same, as exemplified by the invention, means the amino-acid sequences or polynucleotides have been removed from their natural milieu or have been altered from their natural state. As such "isolated" does not necessarily reflect the extent to which the amino-acid sequences or nucleic acid molecules have been purified. However, it will be understood that such molecules that have been purified to some degree are "isolated". If said molecules do not exist in a natural milieu, i.e. it does not exist in nature, the molecule is "isolated" regardless of where it is present. By way of example, amino-acid sequences or polynucleotides that do not naturally exist in humans are "isolated" even when they are present in humans.

Furthermore, the term "isolated" or "substantially purified", when applied to an amino acid sequence or nucleic acid, denotes that the amino acid sequence or nucleic acid is essentially free of other cellular components with which they are associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. An amino acid sequence or nucleic acid which is the predominant species present in a preparation is substantially purified.

In specific embodiments, the amino acid sequence of the invention comprises a repeat array composed of n repeats of SEQ ID NO. 4. The term "repeat" or, "synthetic repetitive sequence" as used herein is to be understood as a recombinant protein sequence, which cannot be found in nature, and is derived from repeat units, which naturally occur multiple times in spider silk amino acid sequences. These repeats occur at least once in the synthetic spider silk amino acid sequences according to the invention, and more specifically, at least twice. As indicated herein, each repetitive sequence comprises up to 60 amino acids. In specific embodiments, each repetitive sequence comprises about 5 to about 60 amino acids, about 8 to about 57 amino acids, about 11 to about 54 amino acids, about 14 to about 51 amino acids, about 17 to about 48 amino acids, about 20 to about 45 amino acids, about 23 to about 42 amino acids, about 25 to about 39 amino acids or about 28 to about 36 amino acids. More specifically, each repetitive sequence comprises about 30 to about 40 amino acids, and most specifically, each repetitive sequence comprises about 35 amino acids, specifically, the repeat unit has the amino acid sequence of SEQ ID NO. 4. The naturally occurring repeat units comprehend a limited set of distinct amino acid motifs. Those repeat units confer inter alia tensile strength and elasticity to the thread, which may be later on formed from the spider silk protein.

It should be noted that the repeat array forming the central region of the amino acid sequence of the invention, comprises according to certain and specific embodiments, n repeats of SEQ ID NO. 4. However, it should be appreciated that the invention further encompasses sequence comprising n repeats of any functional homolog, variant, fragment, mutant or derivative of SEQ ID NO. 4.

An amino acid sequence (peptide) or a nucleic acid is said to be a homolog of a corresponding amino acid sequence, peptide or a nucleic acid, when the homology is determined to be at least about 50%, at least about 55%, at least about 60%, at least about 65%, at least about 70%, at least about 75%, at least about 80%, at least about 85%, at least about 90%, at least about 92%, at least about 94%, at least about 96%, at least about 98% or at least about 99%.

Homology, as used herein, may be determined on the basis of percentage identity between two amino acid (peptide) or DNA sequences. In general the two sequences to be compared are aligned to give a maximum correlation between the sequences. The alignment of the two sequences is examined and the number of positions giving an exact amino acid (or nucleotide) correspondence between the two sequences determined, divided by the total length of the alignment multiplied by 100 to give a percentage identity figure. This percentage identity figure may be determined over the whole length of the sequences to be compared, which is particularly suitable for sequences of the same or very similar lengths and which are highly homologous, or over shorter defined lengths, which is more suitable for sequences of unequal length or which have a lower level of homology. Methods for comparing the identity of two or more sequences are well known in the art. Thus for instance, programs available in the Wisconsin Sequence Analysis Package, version 9.1, for example the programs GAP and BESTFIT, may be used to determine the percentage identity between two amino acid sequences and the percentage identity between two polynucleotides sequences. BESTFIT uses the "local homology"

algorithm of Smith and Waterman and finds the best single region of similarity between two sequences. BESTFIT is more suited to comparing two polypeptide or two polynucleotide sequences which are dissimilar in length, the program assuming that the shorter sequence represents a portion of the longer. In comparison, GAP aligns two sequences finding a "maximum similarity" according to the algorithm of Needleman and Wunsch. GAP is more suited to comparing sequences which are approximately the same length and an alignment is expected over the entire length. Preferably the parameters "Gap Weight" and "Length Weight" used in each program are 50 and 3 for polynucleotide sequences and 12 and 4 for polypeptide sequences, respectively. Preferably, percentage identities and similarities are determined when the two sequences being compared are optimally aligned.

As noted above, the amino acid sequence of the invention comprises a repeat array composed of n repeats of the synthetic repetitive unit of SEQ ID NO. 4, or of any homolog or substantially identical sequences thereof.

The terms "identical", "substantial identity", "substantial homology" or percent "identity", in the context of two or more amino acids or nucleic acids sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., amino acid sequence SEQ ID NO:4, 48 and 497), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical". This definition also refers to, or may be applied to, the compliment of a test sequence. The definition also includes sequences that have deletions and/or additions, as well as those that have substitutions. The preferred algorithms can account for gaps and the like. More specifically, said identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

It should be appreciated that the invention further encompasses amino acid sequence comprising n repeats of a variant of SEQ ID NO. 4. As used herein, the term "variant" or "substantially similar" comprises sequences of amino acids or nucleotides different from the specifically identified sequences, in which one or more, specifically, between 1 to 50, more specifically, 1, 2, 3, 4, 5, 6, 7, 8, 9, 10, 20, 30, 40 or 50, amino acid residues or nucleotides are deleted, substituted or added. The variants may be allelic variants occurring naturally or variants of non-natural origin. The variant or substantially similar sequences refer to fragments of amino acid sequences or nucleic acids that may be characterized by the percentage of the identity of their amino acid or nucleotide sequences with the amino acid or nucleotide sequences described herein, as determined by common algorithms used in the state-of-the-art. The preferred fragments of amino acids or nucleic acids are those having a sequence of amino acids or nucleotides with at least around 40 or 45% of sequence identity, preferentially around 50% or 55% of sequence identity, more preferentially around 60% or 65% of sequence identity, more preferentially around 70% or 75% of sequence identity, more preferentially around 80% or 85% of sequence identity, yet more preferentially around 90%, 91%, 92%, 93%, 94%, 95%, 96%, 97%, 98% or 99% of sequence identity when compared to the sequence of reference.

The terms derivatives and functional derivatives as used herein mean the amino acid sequence of the invention with any insertions, deletions, substitutions and modifications. It should be appreciated that by the term "insertions", as used herein it is meant any addition of amino acid residues to the sequence of the invention, of between 1 to 50 amino acid residues, specifically, between 20 to 1 amino acid residues, and more specifically, between 1 to 10 amino acid residues. Most specifically, 1, 2, 3, 4, 5, 6, 7, 8, 9 and 10 amino acid residues. Further, the amino acid sequence of the invention may be extended at the N-terminus and/or C-terminus thereof with various identical or different amino acid residues.

Amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

In another embodiment, the amino acid sequence of the invention comprises n repeats of a sequence that has 17 or fewer, 16 or fewer, 15 or fewer, 14 or fewer, 13 or fewer, 12 or fewer, 11 or fewer, 10 or fewer, 9 or fewer, 8 or fewer, or 7 or fewer amino acid substitutions to the sequence of SEQ ID NO. 4. In one embodiment, the amino acid sequence of the invention comprises n repeats of a sequence that has at least 2, at least 3, at least 4, at least 5, at least 6, at least 7, at least 8, at least 9, at least 10, at least 11, at least 12, or at least 13 amino acid substitutions to the sequence of SEQ ID NO. 4. It is appreciated that the number of substitutions reflects the amino acid replacement occurrences in a given amino acid sequences as compared to the appropriate reference amino acid sequence, specified herein as SEQ ID NO. 4.

With respect to amino acid sequences, one of skill will recognize that individual substitutions, deletions or additions to an amino acid, nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

Variants of the amino acid sequences of the invention may have at least 80% sequence similarity, often at least 85% sequence similarity, 90% sequence similarity, or at least 95%, 96%, 97%, 98%, or 99% sequence similarity at the amino acid level, with the synthetic repetitive units of the spider silk protein of the invention, specifically, the repeating unit denoted by SEQ ID NO. 4.

The amino acid sequence of the invention may comprise n repeats of SEQ ID NO. 4 or of any fragment thereof. A "fragment" constitutes a fraction of the amino acid or DNA sequence of a particular region. A fragment of the peptide sequence is at least one amino acid shorter than the particular region, and a fragment of a DNA sequence is at least one base-pair shorter than the particular region. The fragment may be truncated at the C-terminal or N-terminal sides, or both. An amino acid fragment may comprise at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 24, at least 26, at least 27, at least 28, at least 29, at least 30, at least 31, at least 32, at least 33 or at least 34 amino acids of SEQ ID NO. 4. A nucleic acid fragment of a sequence encoding the amino acid sequence of SEQ ID NO. 4, specifically SEQ ID NO. 3, may comprise at least 3, at least 4, at least 5, at least 6, at least 7, at least 8, at least 9, at least 10, at least 20, at least 30, at least 40, at least 50, at least 60, at least 70, at least 80, at least 90, at least 100, at least 101, at least 102, at least 103, at least 104 or at least 105 nucleic acids.

Mutants of the amino acid sequences of the invention are characterized in the exchange of one (point mutant) or more, about up to 10, of its amino acids against one or more of another amino acid. They are the consequence of the corresponding mutations at the DNA level leading to different codons.

Still further, the invention concerns derivatives of the amino acid sequence of the invention. Derivatives of the amino acid sequences of the invention are, for example, where functional groups, such as amino, hydroxyl, mercapto or carboxyl groups, are derivatised, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are those of naturally occurring alcohols, e.g. methanol or ethanol. Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

As used herein, the term "functional fragment", "functional mutant", "functional derivative" or "functional variant" refers to an amino acid sequence which possesses biological function or activity that is identified through a defined functional assay. More specifically, the defined functional assay is the formation of self-assembling fibers in cells expressing said "functional fragment", "functional mutant", "functional derivative" or "functional variant".

The inventors further explored whether there is a minimal number of repeats that can still form fibers, and found that the eight repeats construct presented the minimal number required for the polymerization of the fibers so far encountered (r-ADF4 and semi-synthetic), which are flexible fibers that form coils freely in the cells and that are typified by a constant diameter and resistance to chemical assault such as 10% SDS. When the repeat number was reduced to four a surprising change was evident, which was manifested in fibers that seemed to have lost their flexibility and ended in multiple unique "bird beak" structures that were never observed in the eight repeat fibers. The loss of flexibility likely reflects an altered polymerization mechanism and internal composition change, since the repetitive domain is now close in size to the C-terminal domain (140 and 114 aa, respectively) and the β-sheet regions are smaller, isolated and less accessible for combining with other monomers. Explained in the model presented in FIG. 5, the resulting nanofibrils that form may have more topological constraints in their interactions and when they assemble into the final fiber, they may be more limited in their binding options.

Previous results in which synthetic E. australis miniature synthetic dragline-like proteins were produced in an E. coli expression system showed that a four repeat poly-A/glycine rich construct, which contains a C-terminal coding region, leads to macroscopic fiber formation, while less repeats lead to much shorter fibers [Stark, M. Biomacromolecules 2007, 8, 1695-1701]. Because of the very different nature of the expression system and to the production method, and in addition due to the different composition of the E. australis as compared to A. diadematus ADF4 genes, it is not surprising that there is a difference in the results obtained. However, one can speculate that due to the higher ratio of the poly-A motif in E. australis as compared to most other spider species studied, it may tend to form fibers more efficiently even when a relatively small repeat number is employed.

The two repeat products examined by the invention, could also form fibers that resembled the four repeat ones but have totally lost any resilience indicating that while the overall topology is similar, the bonds' strengths is reduced below a threshold that confers resistance. The single repeat construct formed fibers and those that formed were feeble. The inventors thus deduce that even a single repeat can lead to polymerization; however, the fibers that are formed are not of a consistent shape and tend to be very short as compared to the higher repeat fibers.

Using TEM, it was demonstrated that as previously shown for r-ADF4, the synthetic repeat fibers also consist of an underlying nanofiber network. Also demonstrated is that fibers' organization changes below a certain threshold, in that they become spongy and less dense while losing their flexibility in folding and coiling inside the cell, especially toward the multiple termini structures. Here, using an increased magnification power the nanofibrils were inspected at close range. Viewing an end of a fiber reveals a meshwork of closely knit homogenous nanofibrils with a diameter of 7 nm, which is speculated to be composed of the monomer building blocks.

No further species of fibers with less than four repeats could be explored by transmission electronic microscopy (TEM) as they lose their resilience and cannot be purified and concentrated by the provided isolation protocol.

Thus, in yet another alternative embodiment, the isolated amino acid sequence of the invention may comprise n repeats (synthetic repetitive sequence) of SEQ ID NO.:4, or of a functional homolog, variant, derivative, fragment or mutant thereof, wherein n is an integer equal to or above 1.

In some embodiments of said isolated amino acid sequence of the invention, n is an integer equal to or below 70. It is appreciated that in various embodiments of the isolated amino acid sequence of the invention, n may be equal to any one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 and 70.

In more specific embodiments of the isolated amino acid sequence of the invention, n is an integer equal to or between 4 and 32. In particular embodiments, n may be equal to any one of 2, 4, 8, 12, 16, 20, 24 and 32, as demonstrated in Examples 1 and 2 and exemplified in SEQ ID NOs.: 48, 49, 50, 51, 52, 53, 54 and 55, respectively.

In some embodiments, the amino acid sequence according to the invention may comprise a repeat array comprising n repeats of a homolog of SEQ ID NO. 4. In certain embodiments, such homolog shares at least 70% homology with SEQ ID NO.: 4.

More specifically, the homolog shares at least 70%, 75%, 80%, 85%, 90%, 95%, 96%, 97%, 98% or 99% homology with SEQ ID NO. 4. According to certain embodiments, a homolog comprised within the amino acid sequence of the invention shares at least 95% homology with SEQ ID NO.: 4.

According to other embodiments, the variants in each case comprise between 1 to 10, specifically, 1, 2, 3, 4, 5, 6, 7, 8, 9, or 10 amino acid substitutions, deletions, insertions, and/or additions, which do not negatively affect tensile strength and elasticity of a thread formed from a recombinant protein comprising said amino acid sequence.

"Insertions" or "deletions" are typically in the range of about 1 to 10 amino acids, specifically, 1, 2, 3, 4, 5, 6, 7, 8, 9, or 10. More specifically, insertions or deletions of about 1, 2 or 3 amino acids. Amino acid additions typically are not more than 100, more specifically not more than 80, more specifically not more than 50, most specifically not more than 20 amino acids, which are added on and/or inserted into the proteins of the present invention. It is noted that only those additions are contemplated in this invention, which do not negatively affect tensile strength and elasticity of a thread formed from a recombinant protein comprising said amino acid sequence.

It should be noted that "insertions" or "additions" of amino acid residues include incorporation of additional residues within the amino acid sequence of the invention. Additionally or alternatively, these terms encompass the amino acid sequence of the invention that is extended at the N-terminus and/or C-terminus thereof with various identical or different amino acid residues.

Particular embodiments envision the amino acid sequence according to the invention as further comprising a single C-terminal region denoted as SEQ ID NO.: 10, or any functional homolog, variant, derivative, fragment or mutant thereof.

It should be noted that the C-terminal region of SEQ ID NO.: 10 comprised within the amino acid sequence of the invention is a 114 amino acid sequence derived from the native C-terminal of the dragline spider silk protein ADF4. The C-terminus or C-terminal region (also known as the carboxyl-terminus, carboxy-terminus, C-terminal tail, C-terminal end, or COOH-terminus) of an amino acid sequence, a protein or polypeptide is the end of the amino acid chain terminated by a free carboxyl group (—COOH). When the protein is translated from messenger RNA, it is created from N-terminus to C-terminus. The convention for writing peptide sequences is to put the C-terminal end on the right and write the sequence from N- to C-terminus.

Thus, according to one specific embodiment, the amino acid sequence of the invention comprises a repeat region having n repeats of SEQ ID NO. 4, and a C-terminal domain having the sequence of SEQ ID NO. 10. More specifically, the amino acid sequence of the invention may be represented as follows:

```
[(SGPGGYGPGSQGPSGPGGYGPGGPGSSAAAAAAAA)n-
GPSGPGAYGPSPSASASVAASRLSSPAASSRVSSAVSSLVSSGPTNGAAV
SGALNSLVSQISASNPGLSGCDALVQALLELVSALVAILSSASIGQVNVS
SVSQSTQMISQALS]
or
[(SEQ ID NO.: 4)n-SEQ ID NO.: 10].
```

It should be noted that the invention further encompasses an amino acid sequence comprising a homolog or variant of the C-terminal region of SEQ ID NO. 10. In other particular embodiments, said homolog of said C-terminal region shares at least 70% homology with SEQ ID NO.: 10.

More specifically, the C-terminal region homolog may share at least 70%, 75%, 80%, 85%, 90%, 95%, 96%, 97%, 98% or 99% homology with SEQ ID NO. 10. According to certain embodiments, the homolog of the C-terminal region comprised within the amino acid sequence of the invention shares at least 95% homology with SEQ ID NO.: 10.

According to other embodiments, the variants in each case comprise between 1 to 10, specifically, 1, 2, 3, 4, 5, 6, 7, 8, 9 or 10 amino acid substitutions, deletions, insertions, and/or additions, which do not negatively affect tensile strength and elasticity of a thread formed from a recombinant protein comprising said amino acid sequence.

According to specific embodiments, the amino acid sequence of the invention comprises two amino acid repeats (each repeat is denoted as SEQ ID NO.: 4, and two repeats is denoted by SEQ ID NO. 48) and a C-terminal region (denoted as SEQ ID NO.: 10) and has a sequence denoted as SEQ ID NO. 40. According to further embodiments, the amino acid sequence of the invention comprises four amino acid repeats (denoted as SEQ ID NO.: 49) and a C-terminal region (denoted as SEQ ID NO.: 10) and has a sequence denoted as SEQ ID NO. 41. According to further embodiments, the amino acid sequence of the invention comprises eight amino acid repeats (denoted as SEQ ID NO.: 50) and a C-terminal region (denoted as SEQ ID NO.: 10) and has a sequence denoted as SEQ ID NO. 42. According to further embodiments, the amino acid sequence of the invention comprises twelve amino acid repeats (denoted as SEQ ID NO.: 51) and a C-terminal region (denoted as SEQ ID NO.: 10) and has a sequence denoted as SEQ ID NO. 43. According to further embodiments, the amino acid sequence of the invention comprises sixteen amino acid repeats (denoted as SEQ ID NO.: 52) and a C-terminal region (denoted as SEQ ID NO.: 10) and has a sequence denoted as SEQ ID NO. 44. According to further embodiments, the amino acid sequence of the invention comprises twenty amino acid repeats (denoted as SEQ ID NO.: 53) and a C-terminal region (denoted as SEQ ID NO.: 10) and has a sequence denoted as SEQ ID NO. 45. According to further embodiments, the amino acid sequence of the invention comprises twenty-four amino acid repeats (denoted as SEQ ID NO.: 54) and a C-terminal region (denoted as SEQ ID NO.: 10) and has a sequence denoted as SEQ ID NO. 46. According to further embodiments, the amino acid sequence of the invention comprises thirty-two amino acid repeats (denoted as SEQ ID NO.: 55) and a C-terminal region (denoted as SEQ ID NO.: 10) and has a sequence denoted as SEQ ID NO. 47.

The amino acid sequence of the invention may comprise *Araneus diadematus* C-terminal domain, however, it should be appreciated that in certain embodiments, the C-terminal domain of any other spider species may be used for the amino acid sequence of the invention.

In other embodiments, the amino acid sequence according to the invention comprising a repeat array of n repeats of SEQ ID NO. 4, and single C-terminal region denoted as SEQ ID NO.: 10, further comprises a single N-terminal region selected from the amino acid sequences having a sequence denoted as SEQ ID NO.: 5 and 83, or any functional homolog, variant, derivative, fragment or mutant thereof.

Importantly, it should be appreciated that the N-terminal region may be natural or native, i.e., identical to the N-terminal region of the ADF4 N-terminal region in *Araneus diadamatus, Latrodectus Hesperus, E. australis* or other spiders, or it may be synthetic. Examples for natural and synthetic N-terminal sequences are denoted as SEQ ID NO.: 83 and 5, respectively.

Notably, it was recently found that the N-terminus is a pH mediated switch which inhibits fiber formation under neutral pH and facilitates polymerization under a low pH such as 6. Thus, the natural N-terminus allows a pH-mediated control of fiber assembly and its addition to the silk protein sequence may facilitate the regulation of the silk protein polymerization. It may further serve to prevent premature aggregation. While in the insect cells demonstrated herein there was no need for the natural N-terminus as the protein self assembled into fibers spontaneously, in many other expression systems it may be required to control against premature aggregation.

According to one specific embodiment, the N-terminal region may be an ADF4 natural N-terminal region and have a sequence denoted as SEQ ID NO.: 83, or any functional homolog, variant, derivative, fragment or mutant thereof.

In yet another specific embodiment, the N-terminal region may be a synthetic N-terminal region, specifically, a region having a sequence denoted as SEQ ID NO.: 5, or any functional homolog, variant, derivative, fragment or mutant thereof.

Thus, according to a specific embodiment, the amino acid sequence of the invention comprises:
a) a single N-terminal region, specifically a region selected from the amino acid sequences having a sequence denoted as SEQ ID NO.: 5 and 83, or any functional homolog, variant, derivative, fragment or mutant thereof.
b) a repeat array comprising n repeats of a synthetic repetitive unit, specifically, of SEQ ID NO. 4, or any functional homolog, variant, derivative, fragment or mutant thereof; and
c) a single C-terminal region, specifically a region denoted as denoted as SEQ ID NO.: 10, or any functional homolog, variant, derivative, fragment or mutant thereof.

In certain embodiments, the formula of said amino acid sequence may be represented as follows:

[DYDIPTTENLYFQGAMDPEFKGLRRRAQLVRPLSNLDNA- (SGPGGYGPGSQGPSGPGGYGPGGPGSSAAAAAAAA)n-

GPSGPGAYGPSPSASASVAASRLSSPAASSRVSSAVSSLVSSGPTNGAAV

SGALNSLVSQISASNPGLSGCDALVQALLELVSALVAILSSASIGQVNVS

SVSQSTQMISQALS]
or

[SEQ ID NO.: 5-(SEQ ID NO.: 4)n-SEQ ID NO.: 10].

In other embodiments, the formula of said amino acid sequence may be represented as follows:

[MTWSTRLALSFLFVLCTQSLYALAQANTPWSSKANADAFINSFISAASN

TGSFSQDQMEDMSLIGNTLMAAMDNMGGRITPSKLQALDMAFASSVAEIA

ASEGGDLGVTTNAIADALTSAFYQTTGVVNSRFISEIRSLIGMFAQASAN

DVYASAGSSGGGGYGASSASAASASAAAPSGVAYQAPAQAQISFTLRGQQ

PVSYA-(SGPGGYGPGSQGPSGPGGYGPGGPGSSAAAAAAAA)n-

GPSGPGAYGPSPSASASVAASRLSSPAASSRVSSAVSSLVSSGPTNGAAV

SGALNSLVSQISASNPGLSGCDALVQALLELVSALVAILSSASIGQVNVS

SVSQSTQMISQALS]
or

[SEQ ID NO.: 83-(SEQ ID NO.: 4)n-SEQ ID NO.: 10].

The N-terminus, or the N-terminal region as used herein (also known as the amino-terminus, $NH_2$-terminus, N-terminal end or amine-terminus) refers to the start of a protein or polypeptide terminated by an amino acid with a free amine group ($—NH_2$). The convention for writing peptide sequences is to put the N-terminus on the left and write the sequence from N- to C-terminus. When the protein is translated from messenger RNA, it is created from N-terminus to C-terminus.

According to one embodiment, in this amino acid sequence, a homolog of the N-terminal region shares at least 70% homology with SEQ ID NO.: 5.

More specifically, the homolog shares at least 70%, 75%, 80%, 85%, 90%, 95%, 96%, 97%, 98% or 99% homology with SEQ ID NO. 5. According to certain embodiments, a homolog of the N-terminal region comprised within the amino acid sequence of the invention shares at least 95% homology with SEQ ID NO.: 5.

According to other embodiments, variants of the N-terminal region of SEQ ID NO. 5, in each case comprise between 1 to 10, specifically, 1, 2, 3, 4, 5, 6, 7, 8, 9 or 10 amino acid substitutions, deletions, insertions, and/or additions, which do not negatively affect tensile strength and elasticity of a thread formed from a recombinant protein comprising said amino acid sequence.

According to a particular embodiment, in this amino acid sequence, a homolog of the N-terminal region shares at least 70% homology with SEQ ID NO.: 83.

More specifically, the homolog shares at least 70%, 75%, 80%, 85%, 90%, 95%, 96%, 97%, 98% or 99% homology with SEQ ID NO. 83. According to certain embodiments, a homolog of the N-terminal region comprised within the amino acid sequence of the invention shares at least 95% homology with SEQ ID NO.: 83.

According to other embodiments variants of the N-terminal region of SEQ ID NO. 83, in each case comprise between 1 to 10, specifically, 1, 2, 3, 4, 5, 6, 7, 8, 9 or 10 amino acid substitutions, deletions, insertions, and/or additions, which do not negatively affect tensile strength and elasticity of a thread formed from a recombinant protein comprising said amino acid sequence.

According to specific embodiments, the amino acid sequence of the invention comprises two amino acid repeats (each denoted as SEQ ID NO.: 4, and two repeats are denoted by SEQ ID NO. 48), an N-terminal region (denoted as SEQ ID NO. 5 or SEQ ID NO. 83) and a C-terminal region (denoted as SEQ ID NO.: 10) and has a sequence denoted as SEQ ID NO. 24. According to further embodiments, the amino acid sequence of the invention comprises four amino acid repeats (denoted as SEQ ID NO.: 49), an N-terminal region (denoted as SEQ ID NO. 5 or SEQ ID NO. 83) and a C-terminal region (denoted as SEQ ID NO.: 10) and has a sequence denoted as SEQ ID NO. 25. According to further embodiments, the amino acid sequence of the invention comprises eight amino acid repeats (denoted as SEQ ID NO.: 50), an N-terminal region (denoted as SEQ ID NO. 5 or SEQ ID NO. 83) and a C-terminal region (denoted as SEQ ID NO.: 10) and has a sequence denoted as SEQ ID NO. 26. According to further embodiments, the amino acid sequence of the invention comprises twelve amino acid repeats (denoted as SEQ ID NO.: 51), an N-terminal region (denoted as SEQ ID NO. 5 or SEQ ID NO. 83) and a C-terminal region (denoted as SEQ ID NO.: 10) and has a sequence denoted as SEQ ID NO. 27. According to further embodiments, the amino acid sequence of the invention comprises sixteen amino acid repeats (denoted as SEQ ID NO.: 52), an N-terminal region (denoted as SEQ ID NO. 5 or SEQ ID NO. 83) and a C-terminal region (denoted as SEQ ID NO.: 10) and has a sequence denoted as SEQ ID NO. 28. According to further embodiments, the amino acid sequence of the invention comprises twenty amino acid repeats (denoted as SEQ ID NO.: 53), an N-terminal region (denoted as SEQ ID NO. 5 or SEQ ID NO. 83) and a C-terminal region (denoted as SEQ ID NO.: 10) and has a sequence denoted as SEQ ID NO. 29. According to further embodiments, the amino acid sequence of the invention comprises twenty-four amino acid repeats (denoted as SEQ ID NO.: 54), an N-terminal region (denoted as SEQ ID NO. 5 or SEQ ID NO. 83) and a C-terminal region (denoted as SEQ ID NO.: 10) and has a sequence denoted as SEQ ID NO. 30. According to further embodiments, the amino acid sequence of the invention comprises thirty-two amino acid repeats (denoted as SEQ ID NO.: 55), an N-terminal region (denoted as SEQ ID NO. 5 or SEQ ID NO. 83) and a C-terminal region (denoted as SEQ ID NO.: 10) and has a sequence denoted as SEQ ID NO. 31.

In certain embodiments, the amino acid sequence according to the invention comprising a single N-terminal region selected from the amino acid sequences having a sequence denoted as SEQ ID NO.: 5 and 83, a repeat array comprising n repeats of SEQ ID NO. 4, and a single C-terminal region denoted as SEQ ID NO.: 10, further comprises at least one N-terminal tag sequence.

The term "tag", as used herein, refers to a molecule that can be attached to a larger macromolecule, and which can be used to separate that macromolecule from macromolecules that do not have the tag, or facilitate the specific visualization of said macromolecule. More specifically, the tag referred to herein are protein tags, which consist of specific amino acid sequences that are recognized and bound by known ligands.

It is understood that, where appropriate, when adding an N-terminal tag to a polypeptide, the polypeptide initial methionine encoded by the initiation codon (ATG) may be re-located to the N-terminus of said tag, to facilitate translation initiation.

In some embodiments, the amino acid sequence according to the invention comprises an N-terminal tag sequence, the N-terminal tag sequence being the $His_6$-containing sequence HHHHHH, also denoted as SEQ ID NO.: 11. It should be noted that in some embodiments, a DNA sequence encoding HHHHHH may be CATCACCATCACCATCAC, as denoted by SEQ ID NO. 80.

According to other embodiments, the N-terminal tag sequence is MSYYHHHHHH, being another version of $His_6$-containing sequence, also denoted as SEQ ID NO.: 12. In particular embodiments the DNA sequence encoding MSYYHHHHHH may be ATGTCGTACTACCATCACCATCACCATCAC, as denoted by SEQ ID NO. 81.

According to yet further embodiments, the N-terminal tag sequence may be a HA containing sequence being YPYDVPDYA, also denoted as SEQ ID NO.: 13. In some embodiments, the DNA sequence encoding the HA Tag, YPYDVPDYA, may be TACCCATACGATGTTCCAGATTACGCT, as denoted by SEQ ID NO. 82.

According to specific embodiments, the amino acid sequence of the invention comprises two amino acid repeats (each repeating unit is denoted as SEQ ID NO.: 4, and two repeats are denoted by SEQ ID NO. 48), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 72. According to further embodiments, the amino acid sequence of the invention comprises four amino acid repeats (denoted as SEQ ID NO.: 49), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 73. According to further embodiments, the amino acid sequence of the invention comprises eight amino acid repeats (denoted as SEQ ID NO.: 50), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 74. According to further embodiments, the amino acid sequence of the invention comprises twelve amino acid repeats (denoted as SEQ ID NO.: 51), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 75. According to further embodiments, the amino acid sequence of the invention comprises sixteen amino acid repeats (denoted as SEQ ID NO.: 52), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 76. According to further embodiments, the amino acid sequence of the invention comprises twenty amino acid repeats (denoted as SEQ ID NO.: 53), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 77. According to further embodiments, the amino acid sequence of the invention comprises twenty-four amino acid repeats (denoted as SEQ ID NO.: 54), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 78. According to further embodiments, the amino acid sequence of the invention comprises thirty-two amino acid repeats (denoted as SEQ ID NO.:

55), an N-terminal region (denoted as SEQ ID NO. 5 or 83), a C-terminal region (denoted as SEQ ID NO.: 10) and an N-terminal tag (denoted as SEQ ID NO. 12) and has a sequence denoted as SEQ ID NO. 79.

In the second aspect, the present invention is directed to an isolated nucleic acid sequence encoding an amino acid sequence comprising n repeats of SEQ ID NO.:4, or of a functional homolog, variant, derivative, fragment or mutant thereof, wherein n is an integer above 2.

"Nucleic acid" refers to a molecule which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

According to certain embodiments, the nucleic acid sequence according to the invention comprises n repeats of SEQ ID NO.:3 (encoding the repetitive unit of SEQ ID NO. 4), or of a functional homolog, variant, derivative, fragment or mutant thereof, wherein n is an integer above 2.

The formula of said nucleic acid sequence is represented as follows:

[(TCTGGTCCTGGAGGTTATGGCCCAGGAAGCCAAGGACCATCTGGTCCA

GGAGGATATGGTCCAGGCGGACCTGGCTCTAGTGCAGCAGCTGCCGCAGC

AGCTGCA)n]
or

[(SEQ ID NO.: 3)n].

In one embodiment, the nucleic acid sequence according to the invention is contemplated, wherein n is an integer equal to or below 70. More specifically, n may be an integer equal to or between 4 to 32.

According to a particular embodiment, the nucleic acid encodes an amino acid sequence denoted as SEQ ID NO. 4 and has the sequence denoted as SEQ ID NO. 3. According to another embodiment, the nucleic acid encodes two amino acid repeats having the sequence denoted as SEQ ID NO. 48 and has the sequence denoted as SEQ ID NO. 56. According to another embodiment, the nucleic acid encodes four amino acid repeats having the sequence denoted as SEQ ID NO. 49 and has the sequence denoted as SEQ ID NO. 57. According to another embodiment, the nucleic acid encodes eight amino acid repeats having the sequence denoted as SEQ ID NO. 50 and has the sequence denoted as SEQ ID NO. 58. According to another embodiment, the nucleic acid encodes twelve amino acid repeats having the sequence denoted as SEQ ID NO. 51 and has the sequence denoted as SEQ ID NO. 59. According to another embodiment, the nucleic acid encodes sixteen amino acid repeats having the sequence denoted as SEQ ID NO. 52 and has the sequence denoted as SEQ ID NO. 60. According to another embodiment, the nucleic acid encodes twenty amino acid repeats having the sequence denoted as SEQ ID NO. 53 and has the sequence denoted as SEQ ID NO. 61. According to another embodiment, the nucleic acid encodes twenty-four amino acid repeats having the sequence denoted as SEQ ID NO. 54 and has the sequence denoted as SEQ ID NO. 62. According to another embodiment, the nucleic acid encodes thirty-two amino acid repeats having the sequence denoted as SEQ ID NO. 55 and has the sequence denoted as SEQ ID NO. 63.

Some embodiments consider the nucleic acid sequence according to the invention, wherein each said homolog of every repeating unit encoding sequence shares at least 70% homology with SEQ ID NO.: 3.

More specifically, the homolog shares at least 70%, 75%, 80%, 85%, 90%, 95%, 96%, 97%, 98% or 99% homology with SEQ ID NO. 3. According to certain embodiments, a homolog comprised within the nucleic acid sequence of the invention shares at least 95% homology with SEQ ID NO.: 3.

According to other embodiments, the variants in each case comprise between 1 to 30, specifically, 1, 2, 3, 4, 5, 6, 7, 8, 9, 10, 11, 12, 13, 14, 15, 20, 25 or 30 nucleic acid substitutions, deletions, insertions, and/or additions, which do not negatively affect tensile strength and elasticity of a thread formed from a recombinant protein encoded by said nucleic acid sequence.

The invention further encompasses variants of the nucleic acid sequence of the invention. As noted above, the term "variants" can be applied to both amino acid and nucleic acid sequences. With respect to particular nucleic acid sequences, conservatively modified variants are preferred. These variants refer to those nucleic acid sequences which encode identical or substantially identical amino acid sequences, or if the nucleic acid does not encode an amino acid sequence, to substantially or essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

The variation allowed may be experimentally determined by systematically making insertions, deletions, or substitutions of amino acids in a protein using recombinant DNA techniques and assaying the resulting recombinant variants for activity. This does not require more than routine experiments for the skilled artisan.

According to specific embodiments, the nucleic acid sequence according to the invention encodes an amino acid sequence that further comprises a C-terminal region denoted as SEQ ID NO.: 10, or any functional homolog, variant, derivative, fragment or mutant thereof.

In one embodiment, the C-terminal region of SEQ ID NO.: 10 may be encoded by SEQ ID NO. 9 or any functional homolog, variant, derivative, fragment or mutant thereof. Thus, in certain embodiments, the nucleic acid sequence of the invention comprises n repeats of SEQ ID NO. 3 and a single C-terminal region encoded by SEQ ID NO. 9.

Thus, in certain embodiments, the nucleic acid sequence of the invention encodes an amino acid sequence comprising:
a) a repeat array comprising n repeats of the synthetic repetitive unit of SEQ ID NO. 4, specifically, encoded by the nucleic acid sequence of SEQ ID NO. 3; and
c) a single C-terminal region of SEQ ID NO. 10, specifically, encoded by the nucleic acid sequence of SEQ ID NO. 9.

In certain embodiments, the formula of said nucleic acid sequence is represented as follows:

[(TCTGGTCCTGGAGGTTATGGCCCAGGAAGCCAAGGACCATCTGGTCCA

GGAGGATATGGTCCAGGCGGACCTGGCTCTAGTGCAGCAGCTGCCGCAGC

AGCTGCA)n-GGCCCTAGTGGTCCTGGAGCATATGGCCCATCTCCTTCTG

CTTCCGCATCCGTTGCAGCCTCTCGTTTATCTTCGCCTGCAGCCTCGTCT

AGAGTGTCTTCCGCTGTATCGTCTTTAGTGTCTAGCGGACCTACGAATGG

TGCTGCTGTTTCTGGAGCTTTGAATAGTTTAGTATCTCAGATTAGTGCAA

GTAATCCAGGTTTATCGGGATGTGATGCTCTTGTGCAGGCATTATTGGAA

TTAGTGTCTGCTCTTGTGGCAATTCTTTCATCTGCAAGTATTGGCCAAGT

CAACGTCAGCTCTGTTAGTCAGTCAACTCAAATGATTAGCCAAGCTCTTT

CA]
or

[(SEQ ID NO.: 3)n-SEQ ID NO.: 9].

According to other embodiments, the nucleic acid of the invention encodes an amino acid sequence comprising two amino acid repeats and a C-terminal region and having a sequence denoted as SEQ ID NO. 40, said nucleic acid sequence is denoted as SEQ ID NO. 32. According to other embodiments, the nucleic acid encodes an amino acid sequence comprising four amino acid repeats and a C-terminal region and having a sequence denoted as SEQ ID NO. 41, said nucleic acid sequence is denoted as SEQ ID NO. 33. According to other embodiments, the nucleic acid encodes an amino acid sequence comprising eight amino acid repeats and a C-terminal region and having a sequence denoted as SEQ ID NO. 42, said nucleic acid sequence is denoted as SEQ ID NO. 34. According to other embodiments, the nucleic acid encodes an amino acid sequence comprising twelve amino acid repeats and a C-terminal region and having a sequence denoted as SEQ ID NO. 43, said nucleic acid sequence is denoted as SEQ ID NO. 35. According to other embodiments, the nucleic acid encodes an amino acid sequence comprising sixteen amino acid repeats and a C-terminal region and having a sequence denoted as SEQ ID NO. 44, said nucleic acid sequence is denoted as SEQ ID NO. 36. According to other embodiments, the nucleic acid encodes an amino acid sequence comprising twenty amino acid repeats and a C-terminal region and having a sequence denoted as SEQ ID NO. 45, said nucleic acid sequence is denoted as SEQ ID NO. 37. According to other embodiments, the nucleic acid encodes an amino acid sequence comprising twenty-four amino acid repeats and a C-terminal region and having a sequence denoted as SEQ ID NO. 46, said nucleic acid sequence is denoted as SEQ ID NO. 38. According to other embodiments, the nucleic acid encodes an amino acid sequence comprising thirty-two amino acid repeats and a C-terminal region and having a sequence denoted as SEQ ID NO. 47, said nucleic acid sequence is denoted as SEQ ID NO. 39.

In a further embodiment, the nucleic acid sequence according to the invention is considered, wherein said sequence comprises a region encoding the C-terminal region of SEQ ID NO. 10, specifically, a nucleic acid sequence denoted by SEQ ID NO. 9 or any homolog or variant thereof. It should be noted that such homolog shares at least 70% homology with SEQ ID NO.: 9.

More specifically, said C-terminal region encoding homolog shares at least 70%, 75%, 80%, 85%, 90%, 95%, 96%, 97%, 98% or 99% homology with SEQ ID NO. 9. According to certain embodiments, the C-terminal region encoding homolog comprised within the nucleic acid sequence of the invention shares at least 95% homology with SEQ ID NO.: 9.

According to other embodiments, the variants in each case comprise between 1 to 30, specifically, 1, 2, 3, 4, 5, 6, 7, 8, 9, 10, 11, 12, 13, 14, 15, 20, 25 or 30, nucleic acid substitutions, deletions, insertions, and/or additions, which do not negatively affect tensile strength and elasticity of a thread formed from a recombinant protein encoded by said nucleic acid sequence.

The invention also provides embodiments where the nucleic acid sequence according to the invention encodes an amino acid sequence that further comprises an N-terminal region. It should be appreciated that the N-terminal region may be natural or native, i.e., identical to the N-terminal region of the ADF4 N-terminal region in *Araneus diadamatus, Latrodectus Hesperus, E. australis* or other spiders, or it may be synthetic. Examples for natural and synthetic N-terminal sequences are denoted as SEQ ID NO.: 83 and 5, respectively. Thus, in certain embodiments, the N-terminal region may be selected from the amino acid sequences having a sequence denoted as SEQ ID NO.: 5 and 83, or any functional homolog, variant, derivative, fragment or mutant thereof.

In a specific embodiment, the N-terminal region of SEQ ID NO.: 5 is encoded by SEQ ID NO. 6, or any functional homolog, variant, derivative, fragment or mutant thereof. Thus, in certain embodiments, the nucleic acid sequence of the invention encodes an amino acid sequence comprising:
a) a single N-terminal region of SEQ ID NO.: 5, specifically, encoded by the nucleic acid sequence of SEQ ID NO. 6;
b) a repeat array comprising n repeats of the synthetic repetitive unit of SEQ ID NO. 4, specifically, encoded by the nucleic acid sequence of SEQ ID NO. 3; and
c) a single C-terminal region of SEQ ID NO. 10, specifically, encoded by the nucleic acid sequence of SEQ ID NO. 9.

In certain embodiments, the formula of said nucleic acid sequence is represented as follows:

[ATGTCGTACTACCATCACCATCACCATCACGATTACGATATCCCAACGA

CCGAAAACCTGTATTTTCAGGGCGCCATGGATCCGGAATTCAAAGGCCTA

CGTCGACGAGCTCAACTAGTGCGGCCGCTTTCGAATCTAGATAATGCA- (TCTGGTCCTGGAGGTTATGGCCCAGGAAGCCAAGGACCATCTGGTCCAG

GAGGATATGGTCCAGGCGGACCTGGCTCTAGTGCAGCAGCTGCCGCAGCA

GCTGCA)n-GGCCCTAGTGGTCCTGGAGCATATGGCCCATCTCCTTCTGC

TTCCGCATCCGTTGCAGCCTCTCGTTTATCTTCGCCTGCAGCCTCGTCTA

GAGTGTCTTCCGCTGTATCGTCTTTAGTGTCTAGCGGACCTACGAATGGT

GCTGCTGTTTCTGGAGCTTTGAATAGTTTAGTATCTCAGATTAGTGCAAG

TAATCCAGGTTTATCGGGATGTGATGCTCTTGTGCAGGCATTATTGGAAT

TAGTGTCTGCTCTTGTGGCAATTCTTTCATCTGCAAGTATTGGCCAAGTC

AACGTCAGCTCTGTTAGTCAGTCAACTCAAATGATTAGCCAAGCTCTTTC

A]
or

[SEQ ID NO.: 6-(SEQ ID NO.: 3)n-SEQ ID NO.: 9].

According to certain embodiments, the nucleic acid of the invention encodes an amino acid sequence comprising two amino acid repeats (each repeating unit is denoted as SEQ ID NO.:4, and the sequence of two repeats is denoted by SEQ ID NO. 48), a C-terminal region (denoted as SEQ ID NO.:10) and an N-terminal region (denoted as SEQ ID NO.:5). In a specific embodiment, such nucleic acid sequence is denoted as SEQ ID NO. 16, or any functional homolog, variant, derivative, fragment or mutant thereof.

According to further embodiments, the nucleic acid of the invention encodes an amino acid sequence comprising four amino acid repeats (denoted as SEQ ID NO.:49), a C-terminal region (denoted as SEQ ID NO.:10), and an N-terminal region (denoted as SEQ ID NO.:5). In a specific embodiment, such nucleic acid sequence is denoted as denoted as SEQ ID NO:17, or any functional homolog, variant, derivative, fragment or mutant thereof.

According to further embodiments, the nucleic acid of the invention encodes an amino acid sequence comprising eight amino acid repeats (denoted as SEQ ID NO.:50), a C-terminal region (denoted as SEQ ID NO.:10) and an N-terminal region (denoted as SEQ ID NO.:5). In a specific embodiment, such nucleic acid sequence is denoted as SEQ ID NO. 18, or any functional homolog, variant, derivative, fragment or mutant thereof.

According to further embodiments, the nucleic acid of the invention encodes an amino acid sequence comprising twelve amino acid repeats (denoted as SEQ ID NO.:51), a C-terminal region (denoted as SEQ ID NO.:10), and an N-terminal region (denoted as SEQ ID NO.:5). In a specific embodiment, such nucleic acid sequence is denoted as SEQ ID NO:19, or any functional homolog, variant, derivative, fragment or mutant thereof.

According to further embodiments, the nucleic acid of the invention encodes an amino acid sequence comprising sixteen amino acid repeats (denoted as SEQ ID NO.:52), a C-terminal region (denoted as SEQ ID NO.:10), an N-terminal region (denoted as SEQ ID NO.:5). In a specific embodiment, such nucleic acid sequence is denoted as SEQ ID NO. 20, or any functional homolog, variant, derivative, fragment or mutant thereof.

According to further embodiments, the nucleic acid of the invention encodes an amino acid sequence comprising twenty amino acid repeats (denoted as SEQ ID NO.:53), a C-terminal region (denoted as SEQ ID NO.:10), and an N-terminal region (denoted as SEQ ID NO.:5). In a specific embodiment, such nucleic acid sequence is denoted as SEQ ID NO:21, or any functional homolog, variant, derivative, fragment or mutant thereof.

According to further embodiments, the nucleic acid of the invention encodes an amino acid sequence comprising twenty-four amino acid repeats (denoted as SEQ ID NO.:54), a C-terminal region (denoted as SEQ ID NO.:10), and an N-terminal region (denoted as SEQ ID NO.:5). In a specific embodiment, such nucleic acid sequence is denoted as SEQ ID NO. 22, or any functional homolog, variant, derivative, fragment or mutant thereof.

According to further embodiments, the nucleic acid of the invention encodes an amino acid sequence comprising thirty-two amino acid repeats (denoted as SEQ ID NO.:55), a C-terminal region (denoted as SEQ ID NO.:10), and an N-terminal region (denoted as SEQ ID NO.:5). In a specific embodiment, such nucleic acid sequence is denoted as SEQ ID NO:23, or any functional homolog, variant, derivative, fragment or mutant thereof.

In certain embodiments, the nucleic acid sequence of the invention comprises a region encoding the amino acid sequence of the N-terminal region (denoted as SEQ ID NO.: 5), being the nucleic acid sequence of SEQ ID NO.: 6, or any homolog, variant or derivatives thereof. In one embodiment, said homolog shares at least 70% homology with SEQ ID NO.: 6.

More specifically, said homolog shares at least 70%, 75%, 80%, 85%, 90%, 95%, 96%, 97%, 98% or 99% homology with SEQ ID NO. 6 encoding the amino acid sequence of the N-terminal region of SEQ ID NO. 5. According to certain embodiments, the homolog comprised within the nucleic acid sequence of the invention shares at least 95% homology with SEQ ID NO.: 6.

According to other embodiments, the variants in each case comprise between 1 to 15, specifically, 1, 2, 3, 4, 5, 6, 7, 8, 9, 10, 11, 12, 13, 14 or 15 nucleic acid substitutions, deletions, insertions, and/or additions, which do not negatively affect tensile strength and elasticity of a thread formed from a recombinant protein encoded by said nucleic acid sequence.

In a specific embodiment, the N-terminal region of SEQ ID NO.: 83 is encoded by SEQ ID NO. 84, or any functional homolog, variant, derivative, fragment or mutant thereof. Thus, in certain embodiments, the nucleic acid sequence of the invention encodes an amino acid sequence comprising:
a) a single N-terminal region of SEQ ID NO.: 83, specifically, encoded by the nucleic acid sequence of SEQ ID NO. 84;
b) a repeat array comprising n repeats of the synthetic repetitive unit of SEQ ID NO. 4, specifically, encoded by the nucleic acid sequence of SEQ ID NO. 3; and
c) a single C-terminal region of SEQ ID NO. 10, specifically, encoded by the nucleic acid sequence of SEQ ID NO. 9.

In certain embodiments, the formula of said nucleic acid sequence is represented as follows:

[ATGACATGGTCCACCCGTTTGGCTCTCTCCTTCCTCTTCGTTCTCTGCA

CCCAGTCGCTCTACGCTCTCGCTCAAGCTAACACTCCCTGGTCCTCTAAG

GCCAACGCTGACGCCTTCATCAACAGCTTCATCTCAGCTGCCTCGAACAC

CGGCTCATTCTCGCAGGACCAAATGGAGGATATGTCCTTGATCGGAAACA

CTCTGATGGCTGCCATGGACAACATGGGTGGCAGGATCACACCCTCCAAG

CTCCAGGCTCTGGACATGGCTTTCGCCAGCTCAGTTGCTGAGATCGCTGC

CAGCGAAGGAGGTGACCTCGGAGTGACCACTAACGCTATCGCCGATGCTT

TGACTTCAGCTTTCTACCAGACAACCGGCGTGGTCAACTCCCGTTTCATC

TCTGAAATCCGCAGCCTGATCGGCATGTTCGCCCAGGCTTCCGCCAACGA

CGTCTACGCTTCGGCCGGATCGTCCGGCGGAGGTGGCTACGGTGCCTCTA

GCGCTTCCGCTGCCTCCGCTTCTGCTGCCGCTCCATCTGGAGTTGCTTAC

CAAGCTCCTGCCCAGGCTCAAATCTCCTTCACCCTCCGTGGTCAACAGCC

CGTCTCCTATGCATCC- (TCTGGTCCTGGAGGTTATGGCCCAGGAAGCCA

AGGACCATCTGGTCCAGGAGGATATGGTCCAGGCGGACCTGGCTCTAGTG

CAGCAGCTGCCGCAGCAGCTGCA)n-GGCCCTAGTGGTCCTGGAGCATAT

GGCCCATCTCCTTCTGCTTCCGCATCCGTTGCAGCCTCTCGTTTATCTTC

GCCTGCAGCCTCGTCTAGAGTGTCTTCCGCTGTATCGTCTTTAGTGTCTA

GCGGACCTACGAATGGTGCTGCTGTTTCTGGAGCTTTGAATAGTTTAGTA

TCTCAGATTAGTGCAAGTAATCCAGGTTTATCGGGATGTGATGCTCTTGT

```
GCAGGCATTATTGGAATTAGTGTCTGCTCTTGTGGCAATTCTTTCATCTG

CAAGTATTGGCCAAGTCAACGTCAGCTCTGTTAGTCAGTCAACTCAAATG

ATTAGCCAAGCTCTTTCA]
or

[SEQ ID NO.: 84-(SEQ ID NO.: 3)n-SEQ ID NO.: 9].
```

According to certain embodiments, the nucleic acid of the invention encodes an amino acid sequence comprising two amino acid repeats (each repeating unit is denoted as SEQ ID NO.:4, and the sequence of two repeats is denoted by SEQ ID NO. 48), a C-terminal region (denoted as SEQ ID NO.:10) and an N-terminal region (denoted as SEQ ID NO.:83).

According to further embodiments, the nucleic acid of the invention encodes an amino acid sequence comprising four amino acid repeats (denoted as SEQ ID NO.:49), a C-terminal region (denoted as SEQ ID NO.:10), and an N-terminal region (denoted as SEQ ID NO.:83).

According to further embodiments, the nucleic acid of the invention encodes an amino acid sequence comprising eight amino acid repeats (denoted as SEQ ID NO.:50), a C-terminal region (denoted as SEQ ID NO.:10) and an N-terminal region (denoted as SEQ ID NO.:83).

According to further embodiments, the nucleic acid of the invention encodes an amino acid sequence comprising twelve amino acid repeats (denoted as SEQ ID NO.:51), a C-terminal region (denoted as SEQ ID NO.:10), and an N-terminal region (denoted as SEQ ID NO.:83).

According to further embodiments, the nucleic acid of the invention encodes an amino acid sequence comprising sixteen amino acid repeats (denoted as SEQ ID NO.:52), a C-terminal region (denoted as SEQ ID NO.:10), an N-terminal region (denoted as SEQ ID NO.:83).

According to further embodiments, the nucleic acid of the invention encodes an amino acid sequence comprising twenty amino acid repeats (denoted as SEQ ID NO.:53), a C-terminal region (denoted as SEQ ID NO.:10), and an N-terminal region (denoted as SEQ ID NO.:83).

According to further embodiments, the nucleic acid of the invention encodes an amino acid sequence comprising twenty-four amino acid repeats (denoted as SEQ ID NO.:54), a C-terminal region (denoted as SEQ ID NO.:10), and an N-terminal region (denoted as SEQ ID NO.:83).

According to further embodiments, the nucleic acid of the invention encodes an amino acid sequence comprising thirty-two amino acid repeats (denoted as SEQ ID NO.:55), a C-terminal region (denoted as SEQ ID NO.:10), and an N-terminal region (denoted as SEQ ID NO.:83).

In certain embodiments, the nucleic acid sequence of the invention comprises a region encoding the amino acid sequence of the N-terminal region (denoted as SEQ ID NO.: 83), being the nucleic acid sequence of SEQ ID NO.: 84, or any homolog, variant or derivatives thereof. In one embodiment, said homolog shares at least 70% homology with SEQ ID NO.: 84.

More specifically, said homolog shares at least 70%, 75%, 80%, 85%, 90%, 95%, 96%, 97%, 98% or 99% homology with SEQ ID NO. 84 encoding the amino acid sequence of the N-terminal region of SEQ ID NO. 83. According to certain embodiments, the homolog comprised within the nucleic acid sequence of the invention shares at least 95% homology with SEQ ID NO.: 84.

According to other embodiments, the variants in each case comprise between 1 to 15, specifically, 1, 2, 3, 4, 5, 6, 7, 8, 9, 10, 11, 12, 13, 14 or 15 nucleic acid substitutions, deletions, insertions, and/or additions, which do not negatively affect tensile strength and elasticity of a thread formed from a recombinant protein encoded by said nucleic acid sequence.

In certain embodiments, the nucleic acid sequence encodes an amino acid sequence that further comprises an N-terminal tag sequence.

According to one embodiment, the N-terminal tag sequence is a $His_6$-containing sequence being HHHHHH, also denoted as SEQ ID NO.: 11, encoded by the nucleic acid sequence denoted as SEQ ID NO. 80.

In yet another embodiment, the N-terminal tag sequence may be MSYYHHHHHH, also denoted as SEQ ID NO.: 12, encoded by the nucleic acid sequence denoted as SEQ ID NO. 81.

Still further, the N-terminal tag sequence may be an HA-containing sequence being YPYDVPDYA, also denoted as SEQ ID NO.: 13, encoded by the nucleic acid sequence of SEQ ID NO. 82.

According to certain embodiments, the nucleic acid sequence of the invention encodes an amino acid sequence comprising 2, 4, 8, 12, 16, 20, 24 and 32 repeats of SEQ ID NO. 4, a C-terminal domain of SEQ ID NO. 10, an N-terminal domain of SEQ ID NO. 5, and the N-Tag of SEQ ID NO. 12, as denoted by SEQ ID NO. 72, 73, 74, 75, 76, 77, 78 and 79, respectively. In specific embodiments, such nucleic acid sequences are selected from the group: SEQ ID NO.: 64, SEQ ID NO.: 65, SEQ ID NO.: 66, SEQ ID NO.: 67, SEQ ID NO.: 68, SEQ ID NO.: 69, SEQ ID NO.: 70, and SEQ ID NO.: 71, respectively.

It is understood that the nucleic acid sequence of the invention may encode an amino acid sequence comprising 2, 4, 8, 12, 16, 20, 24 and 32 repeats of SEQ ID NO. 4, a C-terminal domain of SEQ ID NO. 10, an N-terminal domain of SEQ ID NO. 83, and the N-Tag of SEQ ID NO. 12.

Due to the degenerative nature of the genetic code it is clear that a plurality of different nucleic acid sequences can be used to code for the amino acid sequences of the invention. It should be appreciated that the codons comprised in the nucleic acid sequence of the invention may be optimized for expression in Sf9 host cells.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Within the context of the present invention, genes and DNA coding regions are codon-optimized for optimal expression in host cells, and in a specific example, Sf9 *Spodoptera frugiperda* insect cells.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

In the third aspect, the invention relates to an expression vector comprising a nucleic acid sequence encoding an amino acid sequence comprising n repeats of SEQ ID NO.:4, or of a functional homolog, variant, derivative, fragment or mutant thereof, wherein n is an integer above 2. The amino acid sequence encoded by the nucleic acid sequence comprised within the expression vector of the invention may optionally further comprise at least one of a C-terminal region denoted as SEQ ID NO.: 10; and an N-terminal region selected from the amino acid sequences having a sequence denoted as SEQ ID NO.: 5 and 83. It should be noted that the nucleic acid sequence is under expression control of operably linked promoter and, optionally, regulatory sequences.

As used herein, a "vector", "expression vector" or "plasmid" as referred to herein is an extra-chromosomal element often carrying genes which are not part of the central metabolism of the cell, and usually in the form of circular double-stranded DNA molecules. It may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. As used herein, "transformation" or "transfection" is the acquisition of new genes in a cell by the incorporation of nucleic acid. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined, namely, the expression of the synthetic spider silk proteins.

In specific embodiments, the vector is a viral vector, most specifically a baculovirus vector system or a vaccinia virus vector system. Examples of such commercially available baculovirus systems Baculo-Gold®, Flash-Bac® and the bac to bac system. Further viral vector systems may also be used in this invention. From case to case, a modification of the vector may be needed. Examples for further viral vectors are adenoviruses and all negative-strand RNA-viruses, e.g. rabies, measles, RSV, etc.

In particular embodiments, the inventors used a baculovirus system for expressing the synthetic silk protein of the invention. Baculoviruses are a family of large rod-shaped viruses that can be divided to two genera: nucleopolyhedroviruses and granulo-viruses. They have a restricted range of hosts that they can infect that is typically restricted to a limited number of closely related insect species. Because baculoviruses are not harmful to humans they are a safe option for use in research and commercial or industrial applications. Baculovirus expression in insect cells represents a robust method for producing recombinant glycoproteins, a significant advantage over prokaryotic expression which is lacking in terms of glycosylation, and consequently, proper protein folding.

As indicated above, the expression vector of the invention is operably linked to a promoter. The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene. The term "suitable promoter" will refer to any eukaryotic or prokaryotic promoter capable of driving the expression of a synthetic spider silk variant gene.

Promoters which are useful to drive expression of heterologous DNA fragments in Sf9 are numerous and familiar to those skilled in the art. Virtually any promoter capable of driving the gene encoding a silk variant protein is suitable for the present invention. For example, polyhedrin, basic protein, p10, OpIE2 and gp4 promoters may be suitable promoters for said expression.

A coding sequence and regulatory sequences are said to be "operably linked" or "operably joined" when they are covalently linked in such a way as to place the expression or transcription of the coding sequence under the influence or control of the regulatory sequences. If the regulatory sequence is positioned relative to the gene such that the regulatory sequence is able to exert a measurable effect on the amount of gene product produced, then the regulatory sequence is operably linked to the gene. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence. Especially, such 5' non-transcribing regulatory sequences will include a promoter region which includes a promoter sequence for transcriptional control of the operably joined gene. Regulatory sequences may also include enhancer sequences or upstream activator sequences, as desired.

"Regulation" and "regulate" refer to the modulation of gene expression controlled by DNA sequence elements located primarily, but not exclusively upstream of (5' to) the transcription start of a gene. Regulation may result in an all or none response to stimulation, or it may result in variations in the level of gene expression.

Other specific embodiments of the invention provide an expression vector comprising the nucleic acid sequence selected from the group: SEQ ID NO.: 3 SEQ ID NO.: 56, SEQ ID NO.: 57, SEQ ID NO.: 58, SEQ ID NO.: 59, SEQ ID NO.: 60, SEQ ID NO.: 61, SEQ ID NO.: 62, SEQ ID NO.: 63, SEQ ID NO.: 32, SEQ ID NO.: 33, SEQ ID NO.: 34, SEQ ID NO.: 35, SEQ ID NO.: 36, SEQ ID NO.: 37, SEQ ID NO.: 38, SEQ ID NO.: 39, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 64, SEQ ID NO.: 65, SEQ ID NO.: 66, SEQ ID NO.: 67, SEQ ID NO.: 68, SEQ ID NO.: 69, SEQ ID NO.: 70, and SEQ ID NO.: 71.

In a further aspect, the invention provides a host cell transformed with the expression vector according to the invention.

"Cells", "host cells" or "recombinant host cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein.

"Host cell" as used herein refers to cells which can be recombinantly transformed with naked DNA or expression vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

The host cells of the invention are transformed or transfected with the expression vector descried herein to express the synthetic spider silk protein of the invention. "Transformation", as used herein, refers to a process in which a cell's genotype is changed as a result of the cellular uptake of exogenous DNA or RNA, and, for example, the transformed cell expresses a recombinant form of the desired synthetic spider silk protein. The term "transfection" means the introduction of a nucleic acid, e.g., naked DNA or an expression vector, into a recipient cells by nucleic acid-mediated gene transfer.

In one specific embodiment, the host cells transformed with the expression vector according to the invention are insect cells. As insect cells, *Lepidoptera* insect cells may be used, more specifically cells from *Spodoptera frugiperda* and from *Trichoplusia ni*. Most specifically, the insect cell is a Sf9, Sf21 or high 5 cells.

One advantage of insect cell expression system, for example regarding bacterial systems, resides in the fact that the proteins produced are glycosylated, thereby being a target for degradation by microorganisms. This characteristic may be of importance, for example, in the field of medicine, whenever the silk proteins are intended for an in vivo use, in which biological degradation is desired. This characteristic may in particular find application in suture materials and wound closure and coverage systems.

In yet a further aspect, the invention relates to a recombinant spider silk protein comprising n repeats of SEQ ID NO.:4, or of a functional homolog, variant, derivative, fragment or mutant thereof, wherein n is an integer above 2.

The invention thus encompasses a recombinant synthetic spider silk protein, specifically, a recombinant protein comprising the amino acid sequence of the invention. In more specific embodiments, the recombinant protein of the invention is produced by the expression vectors and the host cells of the invention.

The terms "protein" as used herein, or "peptide" and "polypeptide" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post translation expression modifications of the polypeptide, for example, glycosylation, acetylation, phosphorylation and the like. Furthermore, for purposes of the present invention, a "protein" refers to a polypeptide which includes modifications, such as deletions, additions and substitutions (generally conservative in nature), to the native sequence, so as long as the protein maintains the desired activity, i.e. assembly into fibers. These modifications may be deliberate, as through site-directed mutagenesis, or may be accidental, such as through mutations of hosts which produce the proteins or errors due to PCR amplification. A "recombinant protein" is a manipulated form of protein, which is generated in various ways to produce large quantities of proteins, modify gene sequences and manufacture useful commercial protein quantities. The formation of recombinant protein is carried out in vectors comprising recombinant nucleic acids which are expressed in host cells. Thus, a Recombinant protein is derived from recombinant DNA. A recombinant DNA is a spliced DNA formed from two or more different sources that have been joined, typically cleaved by restriction enzymes and joined by ligases, or alternatively, created synthetically.

The term "synthetic spider-silk protein" refers to a protein produced by an expression system having a sequence that may be based on an artificially produced nucleic acid sequence that encodes amino acid motives of spider web proteins, or a combination of such a nucleic acid sequence with a native web protein-encoding nucleic acid sequence derived from a spider.

The recombinant spider silk proteins having only synthetic repetitive sequences included can be used for some specific applications. These applications are—inter alia—bullet proof vests, automotive and aircraft parts, surface coatings, as well as wound closure systems and wound dressings. Or, in other words, applications, in which no thread structures of spider silk proteins are required.

In one embodiment, the invention provides the recombinant spider silk protein, wherein the protein optionally further comprises at least one of a single C-terminal region denoted as SEQ ID NO.: 10 and a single N-terminal region selected from the amino acid sequences having a sequence denoted as SEQ ID NO.: 5 and 83.

In some embodiments, the host cells of the invention express the synthetic spider silk protein of the invention in commercial quantities.

The term "commercial quantities" will refer to quantities of recombinantly-produced desired proteins where at least 1% of the total protein produced by an insect cell culture is the desired protein, i.e., the synthetic spider silk protein of the invention. It is understood that the expressed synthetic protein may be used to form spheres, nanofibrils, hydrogels, threads, foams, films for use in biotechnology, medicine, pharmaceutical and food applications, cosmetics, in electronic devices and for other commercial purposes.

Optionally it may be desired to produce the synthetic spider silk protein of the invention as a secretion product of a transformed host, such as Sf9 cells. Secretion of desired proteins into the growth media has the advantage of simplified and less costly purification procedures. It is well known in the art that secretion signal sequences are often useful in facilitating the active transport of expressible proteins across cell membranes. The creation of transformed Sf9 host cells capable of secretion may be accomplished by the incorporation of a DNA sequence that codes for a secretion signal functional in the Sf9 production host on the expression cassette, between the expression-controlling DNA and the DNA encoding the silk variant protein and in reading frame with the latter.

The recombinant spider-silk protein of the invention may comprise all the amino acid sequences as indicated herein above.

In another aspect, the invention provides a fiber composed of the recombinant protein according to the invention.

A "fiber" as used herein, is meant a fine cord of fibrous material composed of two or more filaments twisted together. By "filament" is meant a slender, elongated, threadlike object or structure of indefinite length, ranging from microscopic length to lengths of a mile or greater. Specifically, the synthetic spider silk filament is microscopic, and is proteinaceous. By "biofilament" is meant a filament created from a protein, including recombinantly produced spider silk protein.

In specific embodiments, the fibers of the invention may be composed of any of the recombinant spider-silk proteins of the invention, having any of the amino acid sequences selected from the group: SEQ ID NO.: 4 SEQ ID NO.: 48, SEQ ID NO.: 49, SEQ ID NO.: 50, SEQ ID NO.: 51, SEQ ID NO.: 52, SEQ ID NO.: 53, SEQ ID NO.: 54, SEQ ID NO.: 55, SEQ ID NO.: 40, SEQ ID NO.: 41, SEQ ID NO.: 42, SEQ ID NO.: 43, SEQ ID NO.: 44, SEQ ID NO.: 45, SEQ ID NO.: 46, SEQ ID NO.: 47, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 72, SEQ ID NO.: 73, SEQ ID NO.: 74, SEQ ID NO.: 75, SEQ ID NO.: 76, SEQ ID NO.: 77, SEQ ID NO.: 78, SEQ ID NO.: 79, SEQ ID NO.: 40, SEQ ID NO.: 41, SEQ ID NO.: 42, SEQ ID NO.: 43, SEQ ID NO.: 44, SEQ ID NO.: 45, SEQ ID NO.: 46 and SEQ ID NO.: 47. It is appreciated that the fibers of the invention may also be composed of the recombinant proteins according to the invention.

Furthermore it is understood that the N-terminal region in each of the above sequences of the recombinant spider-silk proteins of the invention making up the fibers of the composition may also be the amino acid sequence denoted as SEQ ID NO.: 83, or a functional homolog, variant, derivative, fragment or mutant thereof. In specific embodiments, it may be encoded by the nucleic acid sequence denoted as SEQ ID NO.: 84, or a functional homolog, variant, derivative, fragment or mutant thereof.

"Tenacity" or "tensile strength" refers to the amount of weight a filament can bear before breaking. The maximum specific stress that is developed is usually in the filament, yarn or fabric by a tensile test to break the materials. According to specific embodiments, the fiber of the invention has tensile strength of about 100-3000 MPa (MPa=N/mm$^2$), about 300-3000 MPa, about 500-2700 MPa, about 700-2500 MPa, about 900-2300 MPa, about 1100-2000 MPa, about 1200-1800 MPa, about 1300-1700 MPa or about 1400-1600 MPa. More specifically, about 1500 MPa.

"Toughness" refers to the energy needed to break the fiber. This is the area under the force elongation curve, sometimes referred to as "energy to break" or work to rupture. According to particular embodiments, the fiber of the invention a toughness of about 20-1000 MJ/m$^3$, about 50-950 MJ/m$^3$, about 100-900 MJ/m$^3$, about 120-850 MJ/m$^3$, about 150-800 MJ/m$^3$, about 180-700 MJ/m$^3$, about 180-750 MJ/m$^3$, about 250-700 MJ/m$^3$, about 280-600 MJ/m$^3$, about 300-580 MJ/m$^3$, about 310-560 MJ/m$^3$, about 320-540 MJ/m$^3$ or about 350-520 MJ/m$^3$, most specifically about 350-520 MJ/m$^3$.

"Elasticity" refers to the property of a body which tends to recover its original size and shape after deformation. Plasticity, deformation without recovery, is the opposite of elasticity. On a molecular configuration of the fiber, recoverable or elastic deformation is possible by stretching (reorientation) of inter-atomic and inter-molecular structural bonds. Conversely, breaking and re-forming of intermolecular bonds into new stabilized positions causes non-recoverable or plastic deformations.

"Extension" refers to an increase in length expressed as a percentage or fraction of the initial length.

By "fineness" is meant the mean diameter of a fiber or filament (e.g., a biofilament), which is usually expressed in microns (micrometers).

By "micro fiber" is meant a filament having a fineness of less than 1 denier (denier is defined as the mass in grams per 9,000 meters).

The fibers are preferably self-assembled but the proteins can also be produced in a soluble form and then mechanically spanned or electro-spanned using available techniques and spinning equipment. In fact, for several purposes natural silk threads can not be used directly, but have to be dissolved and reassembled into other morphologies such as films, foams, spheres, nanofibrils, hydrogels and the like. The microfibers may be solubilized and re-spun.

WO03060099 relates to methods and devices for spinning biofilament proteins into fibers. This invention is particularly useful for spinning recombinant silk proteins from aqueous solutions and enhancing the strength of the fibers and practicality of manufacture such as to render commercial production and use of such fibers practicable.

"Spinning" refers to the process of making filament or fiber by extrusion of a fiber forming substance, drawing, twisting, or winding fibrous substances.

By one embodiment, the fiber of the invention assembles by self assembly. By "self assembly" it is meant that monomers of said fibers, i.e., the synthetic spider silk protein of the invention, bind each other spontaneously, in an energetically favorable manner, under normal physiologic conditions, as demonstrated in Examples 1 and 2 and in FIGS. 2 and 3, or at room temperature, to create the macromolecular fiber structure having the properties described herein. Furthermore, the fibers of the invention are extremely resilient, and once assembled, may withstand extreme chemical assaults, such as solubilization in 10% SDS and boiling for 15 minutes.

One of the advantages of the presented expression system is that it permits the manipulation of the coding DNA sequence and its expression in an environment which supports self-assembly of the monomeric proteins into a defined and resilient fiber. Thus, this expression system allows exploring in a straightforward manner the different chemical and physical properties of the fibers, which are derived from their structure-to-function relationship. An overall consideration of the different fiber phenotypes combined with the differential resistance qualities and the TEM observations brought the inventors to propose a hypothetical model for the assembly mechanism of these extraordinary proteins in the system, shown in FIG. 5.

Without being bound by theory, the inventors propose a two-step assembly process: at first, the folded monomers (shown in FIG. 5A) are soluble, and gradually accumulate in the cell cytosol until they reach a critical concentration and undergo an oriented elongation process, in which the monomers interact in a head-to-tail manner, mainly through hydrogen and hydrophobic bonds between the C-terminal domain and the N-terminal margin of the repetitive domain. This is a kinetically favorable stage and therefore most of the free monomers at the infected cell cytosol will eventually end up as part of a nanofibril.

The second step takes place when the nanofibrils in their turn accumulate and reach a critical concentration, at which the repetitive domains from different nanofibrils get into high proximity, allowing β-sheets from different fibrils to interact and form bonds with each other, thus creating a joint mini-crystalline stack structure, which are illustrated in FIG. 5C. As a result of this lateral association of the nanofibers, the final superfiber, shown in FIG. 5D, is assembled and its width/radius results from the number of fibrils recruited from the surrounding cytosol, in which the nanofibrils accumulated and were initially spread evenly. The relatively constant fiber diameter results from this homogenous spread of nanofibrils and might differ from cell to cell due to differences in concentration of the nanofibrils at the time point in which the nanofibrils have assembled to create the final superfiber.

As evident from the DSC analysis, the expressed synthetic fibers share similar melting points with the native dragline silk. It is therefore assumed that the cause for this specific melting point for said synthetic fibers is the presence of mini-crystalline structures composed of poly-A based β-sheets.

These mini-crystals are known to be highly stable and thought to confer a crucial degree of chemical resilience to the fibers, whether native or synthetic. Thus, the inventors propose that a chemically stable fiber will be the end-product of a self-assembly process in which the mini-crystals congregate to join and bundle separate nanofibrils.

As can be deduced from the lack of chemical resistance of the two repeat-based filaments, no mini-crystals were formed. The inventors attribute this lack of mini-crystals to two different reasons; first, the insufficient number of β-strands in one monomer required to create a "functional" β-sheet, and second, the relatively small size of the repetitive domain, compared with the C-terminal domain (70 and 114 amino acids, respectively)—a fact that may cause steric interference for the interrepetitive domain interactions. Since the chemical resistance and melting point of the four repeat filaments resembles that of higher forms, the presence of joint mini-crystals from this repeat number and onwards is assumed.

The above-proposed mechanism provides a possible explanation for the higher stiffness and multiple endings of the four repeat filaments: The repetitive parts in this case are of the minimal size that enables fibril-fibril interaction that leads to productive joint mini-crystalline junctions. However, due to the relative short dimensions of these repetitive domains they are restricted in their mutual interactions when compared to higher forms wherein these domains are longer and presumably much more sterically flexible enabling more degrees of freedom of interaction (see model). This lack of flexibility is reflected in the rigid appearance of the four repeat fibers as seen in the infected cells (see FIG. 3A) and supported by the presented TEM analysis showing disoriented and loose fibrils that seem to fail to intertwine and assemble in a homogenous and tight fashion like the larger forms (see FIGS. 4C and 4E). As the assembly in the four repeat fibers is less efficient due to the less effective interfibril interaction the process is more susceptible to bifurcations, which give rise to the typical multiple endings of this form.

The presented results shed new light over the self-assembly process, reinforcing the current dogma regarding the secondary and tertiary structure of the dragline fiber and offer a possible mechanism for the enigmatic journey dragline proteins undergo from a soluble monomeric state to the final remarkable fiber. While doing so, the inventors provide synthetic spider-silk proteins which are readily expressed in host cells and self-assemble to high tensile-strength, elastic fibers.

The inventors also present data demonstrating the chemical resilience of the expressed self-assembled fibers.

In another aspect, the invention relates to a composition comprising as an active ingredient the amino acid sequence of the invention or any recombinant protein or fiber comprising the same. As indicated herein before, the amino acid sequence of the invention comprises n repeats of SEQ ID NO.:4, or of a functional homolog, variant, derivative, fragment or mutant thereof, wherein n is an integer above 2. Still further, the amino acid sequence of the invention optionally further comprises at least one of a C-terminal region denoted as SEQ ID NO.: 10; and an N-terminal region selected from the amino acid sequences having a sequence denoted as SEQ ID NO.: 5 and 83. It is understood that in certain embodiments, any of the compositions of the invention may optionally further comprise a pharmaceutically acceptable carrier, diluent or excipient.

According to particular embodiments, the composition may be provided in the form of a gel, foam, or a coating used to coat stents and implants, or in forms useful for tissue engineering purposes, in particular for engineering of tissues from mesenchymal origin. In other embodiments, the composition of the invention is a pharmaceutical composition.

It should be noted that the pharmaceutical composition of the invention may comprise at least one of the amino acid sequence, the recombinant protein and the fiber of the invention and be administered directly to the subject to be treated. Formulations typically comprise at least one active ingredient, as defined above, together with one or more acceptable carriers thereof.

Formulations are particularly suitable for topical administration, or for use as coating for invasive medical devices or as scaffolding for tissue engineering, however subcutaneous, intradermal, intramuscular, intraperitoneal, intravenous and even oral, rectal, nasal, or parenteral administration routes are not overlooked.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical compositions of the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

The pharmaceutical composition of the invention comprising at least one of the amino acid sequence, the recombinant protein and the fiber of the invention may be especially suited for the production of transdermal patches, i.e., a transdermal delivery systems, elastic wound dressing, sutures, coatings or medical fabrics requiring resilience, elasticity, tenacity which are non-toxic.

In yet further embodiments, the composition of the invention may be a cosmetic composition.

The term "cosmetic composition" relates to a composition having beneficial skin or other superficial tissue esthetic properties, such as improving or enhancing skin tone and color, hair color and shine, hiding superficial tissue imperfections such as blemishes and scars, or preventing future or cumulative damage such as sunlight damage and skin aging.

Dermatological or cosmetic compositions for the treatment according to the invention are applied topically on the epidermis as ointment pomades, lotions, creams and gels, and on mucous membranes as water emulsions such as creams, lotions or gels. The cosmetic products the may be produced using such a composition include products such as shaving cream, hand cream, shampoo, soap, conditioner, body cream, sun skin-protection, face cream, or body lotion. The ratio of components in the cosmetic composition according to this invention can be adjusted according to the intended application of the cosmetic composition.

In a further aspect, the invention provides an article comprising of at least one fiber composed of a recombinant protein according to the invention.

The term "article" or "an article of manufacture" is includes manufactured items which are tangible, movable and independent objects. More specifically, herein the term "article" refers to such manufactured items which comprise or incorporate at least one of the amino acid sequence, the recombinant protein and the fiber of the invention. Non-limiting example of such articles include: synthetic spider-silk coated stents and sutures, dermal patches, tissue scaffold material, fabrics, vests, bullet-proof vests, ropes, threads, cosmetics, etc.

Examples of such articles are threads used for surgical sutures, or threads used for weaving garments or the articles may be scaffolds used for various tissue engineering aspects.

Other examples of articles according to the invention include medical devices such as medical adhesive strips, skin grafts, replacement ligaments, and surgical mesh; and in a wide range of industrial and commercial products, such as clothing fabric, bullet-proof vest lining, container fabric, bag or purse straps, cable, rope, fishing line, adhesive binding material, non-adhesive binding material, strapping material, automotive covers and parts, aircraft construction material, weatherproofing material, flexible partition material, sports equipment; and, in fact, in nearly any use of fiber or fabric for which high tensile strength and elasticity are desired characteristics. Adaptability and use of the stable fiber product in other forms, such as a dry spray coating, bead-like particles, or use in a mixture with other compositions is also contemplated by the present invention.

The recombinant spider silk proteins of the present invention may be added to cellulose and keratin and collagen products and thus, the present invention is also directed to a paper or a skin care and hair care product, comprising cellulose and/or keratin and/or collagen and the spider silk proteins of the present invention. Papers and skin care and hair care products, in which the proteins of the present invention are incorporated are showing improved characteristics, in particular improved tensile strength or tear strength.

The invention further provides a method for producing an amino acid sequence comprising n repeats of SEQ ID NO.:4, or of a functional homolog, variant, derivative, fragment or mutant thereof, wherein n is an integer above 2. The amino acid sequence of the invention optionally further comprises at least one of a single C-terminal region denoted as SEQ ID NO.: 10; and a single N-terminal region selected from the amino acid sequences having a sequence denoted as SEQ ID NO.: 5 and 83. In specific embodiments, the method of the invention comprises the steps of:
a. providing an expression vector comprising a nucleic acid sequence encoding said amino acid sequence, wherein said nucleic acid is under expression control of operably linked promoter and, optionally, regulatory sequences;
b. transforming a host cell with the expression vector of (a);
c. providing conditions for expression of heterologous proteins by the host cell of (b); and
d. isolating the expressed proteins, thereby obtaining the synthetic amino acid sequences of the invention.

Still further, the invention provides a method of producing fibers composed of the amino acid sequence of the invention or a recombinant protein comprising the same. The amino acid sequence comprising n repeats of SEQ ID NO.:4, or of a functional homolog, variant, derivative, fragment or mutant thereof, wherein n is an integer above 2. The amino acid sequence of the invention optionally further comprises at least one of a single C-terminal region denoted as SEQ ID NO.: 10; and a single N-terminal region selected from the amino acid sequences having a sequence denoted as SEQ ID NO.: 5 and 83. The method comprising the steps of:
a. providing an expression vector comprising a nucleic acid sequence encoding said amino acid sequence, wherein said nucleic acid is under expression control of operably linked promoter and, optionally, regulatory sequences;
b. transforming a host cell with the expression vector of (a);
c. providing conditions for expression of heterologous proteins by the host cell of (b); and
d. isolating the expressed heterologous proteins by lysis of the host cells followed by sedimentation.

It is appreciated that while the invention generally relates to synthetic spider silk proteins or any fragments or parts thereof derived from *Araneus diadematus* dragline silk, many other spider species may be used to derive synthetic spider silk in a similar manner. More preferably, the dragline proteins are derived from one or more of the following spiders: *Arachnura higginsi, Araneus circulissparsus, Araneus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis* (elipsoides)), Curved Spiny Spider (*Gasteracantha arcuata*), *Cyrtophora moluccensis, Cyrtophora parnasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa*, Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island Cyclosa Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied Cyclosa Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet Acusilas (*Acusilas coccineus*), Silver Argiope (*Argiope argentata*), Spinybacked Orbweaver (*Gasteracantha cancriformis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), Nephila species, e.g. *Nephila clavipes, Nephila senegalensis, Nephila madagascariensis* and many more.

Furthermore, the synthetic spider silk may be enhanced not only by selection of a different spider species to be derived from, but also by the use of various compounds other than protein. Pyrrolidine has hygroscopic properties and helps to keep the thread moist. It occurs in especially high concentration in glue threads. Potassium hydrogen phosphate releases protons in aqueous solution, resulting in a pH of about 4, making the silk acidic and thus protecting it from fungi and bacteria that would otherwise digest the protein. Potassium nitrate is believed to prevent the protein from denaturing in the acidic milieu.

It should be noted that the sequences referred to by the invention are listed as described by the following table.

TABLE 1

| SEQ ID NO. | Sequence name |
|---|---|
| 1 | *Araneus diadematus* fibroin-4 mRNA, partial cds |
| 2 | Translated *Araneus diadematus* fibroin-4 mRNA, partial cds |
| 3 | DNA encoding repeat region synthetic sequence |
| 4 | 35 aa repeat region synthetic sequence |
| 5 | N-terminal peptide (without tag) |
| 6 | N-terminal encoding sequence |
| 7 | His6-N-terminal amino acid sequence |
| 8 | HA-N-terminal amino acid sequence |
| 9 | C-terminal encoding sequence |
| 10 | C-terminal amino acid sequence |
| 11 | His6 tag |
| 12 | his6 tag version 2 |
| 13 | HA tag |
| 14 | 5'-primer |
| 15 | 3'-primer |
| 16 | DNA full sequence (N-term + 2 repeats + C-term) |
| 17 | DNA full sequence (N-term + 4 repeats + C-term) |
| 18 | DNA full sequence (N-term + 8 repeats + C-term) |
| 19 | DNA full sequence (N-term + 12 repeats + C-term) |
| 20 | DNA full sequence (N-term + 16 repeats + C-term) |
| 21 | DNA full sequence (N-term + 20 repeats + C-term) |
| 22 | DNA full sequence (N-term + 24 repeats + C-term) |
| 23 | DNA full sequence (N-term + 32 repeats + C-term) |
| 24 | Full sequence (N-domain + 2 repeats + C-domain) of polymerizing synthetic protein |
| 25 | Full sequence (N-domain + 4 repeats + C-domain) of polymerizing synthetic protein |
| 26 | Full sequence (N-domain + 8 repeats + C-domain) of polymerizing synthetic protein |
| 27 | Full sequence (N-domain + 12 repeats + C-domain) of polymerizing synthetic protein |
| 28 | Full sequence (N-domain + 16 repeats + C-domain) of polymerizing synthetic protein |
| 29 | Full sequence (N-domain + 20 repeats + C-domain) of polymerizing synthetic protein |
| 30 | Full sequence (N-domain + 24 repeats + C-domain) of polymerizing synthetic protein |
| 31 | Full sequence (N-domain + 32 repeats + C-domain) of polymerizing synthetic protein |
| 32 | DNA sequence 2 repeats + C domain of polymerizing synthetic protein |
| 33 | DNA sequence 4 repeats + C domain of polymerizing synthetic protein |
| 34 | DNA sequence 8 repeats + C domain of polymerizing synthetic protein |
| 35 | DNA sequence 12 repeats + C domain of polymerizing synthetic protein |
| 36 | DNA sequence 16 repeats + C domain of polymerizing synthetic protein |
| 37 | DNA sequence 20 repeats + C domain of polymerizing synthetic protein |
| 38 | DNA sequence 24 repeats + C domain of polymerizing synthetic protein |
| 39 | DNA sequence 32 repeats + C domain of polymerizing synthetic protein |
| 40 | 2 repeats + C domain of polymerizing synthetic protein |
| 41 | 4 repeats + C domain of polymerizing synthetic protein |
| 42 | 8 repeats + C domain of polymerizing synthetic protein |
| 43 | 12 repeats + C domain of polymerizing synthetic protein |
| 44 | 16 repeats + C domain of polymerizing synthetic protein |
| 45 | 20 repeats + C domain of polymerizing synthetic protein |
| 46 | 24 repeats + C domain of polymerizing synthetic protein |
| 47 | 32 repeats + C domain of polymerizing synthetic protein |
| 48 | 2X amino acid repeat sequence |
| 49 | 4X amino acid repeat sequence |
| 50 | 8X amino acid repeat sequence |
| 51 | 12X amino acid repeat sequence |
| 52 | 16X amino acid repeat sequence |
| 53 | 20X amino acid repeat sequence |
| 54 | 24X amino acid repeat sequence |
| 55 | 32X amino acid repeat sequence |
| 56 | DNA encoding 2x repeating sequence |
| 57 | DNA encoding 4x repeating sequence |
| 58 | DNA encoding 8x repeating sequence |
| 59 | DNA encoding 12x repeating sequence |
| 60 | DNA encoding 16x repeating sequence |
| 61 | DNA encoding 20x repeating sequence |
| 62 | DNA encoding 24x repeating sequence |
| 63 | DNA encoding 32x repeating sequence |
| 64 | Full DNA sequence (N-domain + 2 repeats + C-domain) + N-terminal tag |
| 65 | Full DNA sequence (N-domain + 4 repeats + C-domain) + N-terminal tag |
| 66 | Full DNA sequence (N-domain + 8 repeats + C-domain) + N-terminal tag |
| 67 | Full DNA sequence (N-domain + 12 repeats + C-domain) + N-terminal tag |
| 68 | Full DNA sequence (N-domain + 16 repeats + C-domain) + N-terminal tag |
| 69 | Full DNA sequence (N-domain + 20 repeats + C-domain) + N-terminal tag |
| 70 | Full DNA sequence (N-domain + 24 repeats + C-domain) + N-terminal tag |
| 71 | Full DNA sequence (N-domain + 32 repeats + C-domain) + N-terminal tag |
| 72 | Full peptide sequence (N-domain + 2 repeats + C-domain) + N-terminal tag |
| 73 | Full peptide sequence (N-domain + 4 repeats + C-domain) + N-terminal tag |
| 74 | Full peptide sequence (N-domain + 8 repeats + C-domain) + N-terminal tag |

TABLE 1-continued

Sequence listing

| SEQ ID NO. | Sequence name |
|---|---|
| 75 | Full peptide sequence (N-domain + 12 repeats + C-domain) + N-terminal tag |
| 76 | Full peptide sequence (N-domain + 16 repeats + C-domain) + N-terminal tag |
| 77 | Full peptide sequence (N-domain + 20 repeats + C-domain) + N-terminal tag |
| 78 | Full peptide sequence (N-domain + 24 repeats + C-domain) + N-terminal tag |
| 79 | Full peptide sequence (N-domain + 32 repeats + C-domain) + N-terminal tag |
| 80 | His6 tag encoding nucleic acid sequence |
| 81 | His6 tag version 2 nucleic acid sequence |
| 82 | HA tag nucleic acid sequence |
| 83 | Native N-terminal sequence from *Latrodectus Hesperus* - amino acid sequence |
| 84 | Native N-terminal sequence from *Latrodectus Hesperus* - DNA |

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

As used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXAMPLES

Materials and Equipment

Plasmids:
DNA sequence as denoted by SEQ ID NO. 3 in a PCR-ScriptAmpSK(+) plasmid obtained from Geneart (Regensburg, Germany).
pFastBacHTa obtained from Invitrogen.
Restriction Enzymes:
PstI, HindIII, NsiI, obtained from (New England Biolabs, MA, USA).
Transfection and Transformation:
Competent *E. coli* DH10BAC cells, containing bacmid and a helper plasmid were from Invitrogen.
ESCORT transfection reagent obtained from Sigma-Aldrich.
Media:
BIOINSECT-1 serum-free insect cell culture medium obtained from Biological Industries.
Cells:
SF9—*Spodoptera frugiperda* insect cells grow in suspension (ATCC#: CRL-1711).
Antibodies:
Mouse anti-His$_6$ monoclonal antibody obtained from Roche.
Texas Red conjugated anti-mouse secondary IgG obtained from Jackson laboratories.

Dyes:
NanoVan (Nanoprobes, NY, USA).
Imaging:
Olympus BX51 fluorescence microscope.
Magnafire SP camera was from Optronics.
Experimental Procedures
Synthesis of a Sequence Encoding for a Single Repeat Unit of a Dragline Spider Silk Protein A 35 amino acid long sequence representing an average consensus sequence of the 15 repeats constituting the repetitive region of ADF-4 (Genbank entry U47856; also denoted as SEQ ID NO. 2 and encoded by the sequence denoted as SEQ ID NO.: 1) was designed. The average consensus sequence peptide sequence is: SGPGGYGPGSQGPSGPG-GYGPGGPGSSAAAAAAAA (denoted as SEQ ID NO. 4), which is encoded by the 105 DNA base pair sequence: 5'-TCTGGTCCTGGAGGTTATGGCCCAG-GAAGCCAAGGACCATCTGGTCCAGGAGGA TATG-GTCCAGGCGGACCTGGCTCTAGTGCAG-CAGCTGCCGCAGCAGCTGCA-3' (denoted as SEQ ID NO. 3).

The above synthetic DNA (denoted as SEQ ID NO. 3) was obtained in a PCR-ScriptAmpSK(+) plasmid. The sequence was optimized for expression according to the codon usage of *Spodoptera frugiperda*, cells of which are used for the synthesis of the spider silk proteins and fibers.
Donor Plasmid Construction The ScriptAmpSK(+) plasmid was excised with Xba I and Xho I, and a 136-bp sequence containing the basic repeat sequence flanked with Nsi I and Pst I restriction sites (see FIG. 1A) was isolated and cloned into the multiple cloning site (MCS) of the baculoviral donor plasmid pFastBacHTa. Thus, the basic donor plasmid coding for an artificial 49 amino acid N-terminal domain (SEQ ID NO. 7) and a 35 amino acid core domain (SEQ ID NO. 4) was generated (see FIG. 1B).

Multimerization of the Single Repeat

The basic module coding for one repeat (monomer) of spider silk protein is flanked by the restriction enzymes sites NsiI and PstI, which are compatible (FIG. 1A). In the first step the monomer is released by double restriction and is inserted in frame into the same donor plasmid cut with PstI. Only if the insert is ligated in the correct sense orientation will a double cut release a dimer [the restriction site between the two repeats was eliminated upon ligation (FIG. 1A)]. In a second step the dimer was released and then reinserted in the same fashion to obtain a vector with four repeats. In following steps, this procedure was reiterated to obtain a donor plasmid containing multiple synthetic repeats. Constraints resulting from the molecular biology tools employed and the repetitive nature of the sequence limit the maximum achievable number of identical repeats.

Ligation of the Native C-Terminal Domain Downstream to the Synthetic Repeats

Insertion of the C-terminal domain of ADF4 114 amino acids took place using PCR with the following primers: A sense primer having the sequence 5'-ATATG CTGCAGGCCCTAGTGGTCCTGGA-3' (also denoted as SEQ ID NO. 14) containing a PstI restriction site (underlined) and an anti-sense primer having the sequence 5'-TCGAC AAGCTTGGTACCGCA-3' (also denoted as SEQ ID NO. 15) coding for a 3' HindIII restriction site (underlined).

The donor plasmid vectors with different number of repeats and the PCR product were excised with PstI and HindIII, purified and ligated, resulting in a pFastBacHTa donor plasmid coding for a His$_6$ tag which is part of an artificial N terminal domain (said His$_6$ tag and N terminal domain form an amino acid sequence denoted a SEQ ID NO.: 7), followed by a varied number of identical repeats (the inventors obtained constructs containing 1, 2, 4, 8, 12, 16, 20, 24, 32 repeats of the nucleic acid sequence denoted as SEQ ID NO.: 3) and the native C terminal domain (denoted as SEQ ID NO: 10 and encoded by a nucleic acid sequence denoted as SEQ ID NO.: 9).

Cell Culture

Sf9 cells were propagated at 27° C. in BIOINSECT-1 serum-free insect cell culture medium. Sf9 cells were grown either as monolayers on cover slips in 6 well plates or in shaker flasks agitated at 120 rpm.

Production of Recombinant Baculovirus

Competent E. coli DH10BAC cells, containing bacmid (baculovirus shuttle vector plasmid) and a helper plasmid, were used to generate recombinant bacmids according to the manufacturer's protocol (Invitrogen). Insertion of the gene into the bacmid was verified by PCR. Sf9 cells were transfected with recombinant bacmid DNA using ESCORT transfection reagent in 6-well plates. The cells were incubated for 5 h at 27° C., rinsed and incubated for another 72 h. Media were harvested, centrifuged, and the virus containing supernatant was used for 2-3 successive infections resulting in amplification of the virion titer.

Expression of Synthetic ADF-4 Based Proteins

Sf9 cells ($3*10^6$ cells/ml) were infected with the recombinant viruses at various MOIs (multiplicity of infection) ranging from 0.1 to 10. Three days post infection cells were harvested by centrifugation at 500 g for 5 min.

Purification of Synthetic Fibers

Infected cells were harvested 3-5 days post infection and centrifuged for 10 min at 16000 g. Cell pellet was resuspended in a 10% SDS solution, boiled for at least 15 min and protein assemblies were sedimented as above. Typical yields of purified fibers were about 50 mg/L of Sf9 insect cell culture. Purified fibers were resuspended at desired solution and volume. An example of 24 repeat purified fibers can be seen in FIG. 2E.

Differential Scanning Calorimeter (DSC) Measurement

Thermal analysis was performed on 0.5-3 mg fibroin samples using a Mettler DSC 822e thermo analyzer and an aluminum sample pan under an inert nitrogen atmosphere. The thermo grams ranged from 258 C to 3508 C at 58 C/min heating rate.

Immunocytochemistry

Cells grown on cover slips at 50% confluency were infected with recombinant viruses at MOI=10. Three days post infection cells were fixed with methanol at −20° C. Cover slips were incubated with mouse anti-$His_6$ monoclonal antibody at a 1:300 dilution followed by Texas Red conjugated anti-mouse secondary IgG at 1:500 dilutions. Cells were observed with an Olympus BX51 fluorescence microscope and images were taken with a Magnafire SP camera or analyzed by confocal microscopy.

Transmission Electron Microscopy (TEM)

For ultra-structural analysis, purified filaments were adsorbed onto 300 mesh copper holey carbon grids, as is, or negatively stained with vanadium (NanoVan1, Nanoprobes), viewed and photographed by a Tecnai T12 microscope, operated at 120 kV.

Example 1

Design, Expression and Characterization of a Multiple Repeat Dragline-Like Protein In previous studies, the inventors have established a model system for self-assembly of dragline proteins [Huemmerich, D. et al., Curr. Biol. 2004, 14, 2070-2074] and made use of it to determine the role of the nonrepetitive C-terminal domain and of its conserved cysteine residue, as well as to present a proposed 3D structure of this domain [Ittah, S. et al., Biomacromolecules 2006, 7, 1790-1795; Ittah, S. et al., Biomacromolecules 2007, 8, 2768-2773]. In the current disclosure, the inventors provide the structure and function of the repetitive part of the dragline silk, which is the major domain of the natural MaSp, constituting about 90% of its residues. When designing the synthetic unit, it was assumed that there is little significance for the small variability between the native repetitive units for expression in the experimental system. Thus, the 15 repeat sequences of the native ADF4 (Genebank entry U47856, also denoted as SEQ ID NO.: 2, encoded by the sequence denoted as SEQ ID NO.:1) were aligned starting with the poly-A stretches (with more than two sequential alanines) resulting in a representative consensus repeat unit containing 35 amino acids (also denoted as SEQ ID NO.: 4, encoded by the sequence denoted as SEQ ID NO.:3). This consensus sequence does not however fully match any part of the native sequence.

To explore whether this approach is valid, the initial goal was to express a semi-synthetic protein, the properties of which could be compared to the previously reported expressed r-ADF4 protein, in terms of total size and repeats number. To this purpose, the inventors used a reiterative cloning procedure employing restriction enzymes with compatible sites to serially multiply the basic monomeric repeat in order to receive a series of multiple repeat dragline-like coding sequences (see Experimental Procedures and FIG. 1). The procedure yielded a baculovirus coding for an artificial N-terminal domain containing a $His_6$ tag (49 amino acids, also denoted by SEQ ID NO. 7), followed by 16 identical synthetic repeats (560 amino acids, denoted by SEQ ID NO. 52) and ending with the native C-terminal domain (114 amino acids, denoted by SEQ ID NO. 10). Sf9 cells were infected with the above virus and, interestingly, when examined by light microscopy starting from two days post infection, distinct fibrous structures were seen in the cell cytosol, as seen in FIG. 2A. These structures were similar in their overall shape to the fibers previously observed in the "native" partial ADF4 product. Further investigation by Immunocytochemistry followed by confocal microscopy, using antibodies directed against the N-terminal $His_6$-tag, was performed to verify the identity of the protein constituting the fibers, shown in FIG. 2B. The synthetic fibers did, however, differ from the ADF4 fibers in several of the following unique characteristics: the fibers display an average smaller diameter (ca. 250 vs. 450 nm, respectively); they are significantly longer and tend to be more homogenous-creating fewer branches. In addition, the ends of the fibers are trimmed rather than forming bulges that are typical to the r-ADF4 fibers.

After having examined the phenotype of the semi-synthetic fibers, the inventors tested them for chemical resistance-one of the most remarkable properties of dragline spider silk. Lysis of infected cells using SDS, followed by centrifugation, resulted in purification of synthetic fibers shown in FIG. 2C, thus demonstrating the extraordinary chemical resilience reported beforehand for the natural ADF4 fibers.

Next, a physical analysis was undertaken to study the properties of the expressed semi-synthetic fibers of the invention, and compare to those of the ADF4 fibers. For this purpose, a calorimetric assay was used. Differential Scanning calorimetry (DSC) measures changes in the heat content of a sample as the temperature is consistently elevated, which allows detection of changes in heat absorption or emission, reflecting major structural changes and phase transitions. Purified semi-synthetic fibers subjected to DSC displayed one endothermic peak with a maximum at about 230° C. This large prominent peak most likely represents the disruption of the poly-alanine β-sheet "crystalline" regions, which are typical to dragline fibers. Interestingly, a similar thermal decomposition point was reported for r-ADF4 fibers, as well as for natural dragline fibers obtained from another spider species—*Nephila clavipes* [Ittah, S. et al., Biomacromolecules 2006, 7, 1790-1795; Cunniff, P. M. et al., Polym. Adv. Technol. 1994, 5, 401-410]. Results are not shown as the thermal profile is very similar to those the inventors have previously published in [Ittah, S. et al., Biomacromolecules 2006, 7, 1790-1795].

Example 2

Analysis of Impact of Consensus Sequence Repeat Number on Dragline-Like Protein Expression Phenotype To enhance the understanding of the repetitive sequence, the inventors explored the influence of the number of repeats on the protein pattern of assembly and fiber-forming properties. For this purpose, first analyzed was the effect of increasing the number of the repeats, which would render the proteins closer in repeat number to the natural spider silk proteins that usually contain hundreds of repeats. Thus, three additional baculoviruses were engineered that contained 20, 24, and 32 repeats. Because of cloning constraints, resulting from the repetitive nature and size of the coding sequence, 32 repeats (equal to 1283 aa) was the upper limit achievable. Sf9 cells were infected by the recombinant baculoviruses and all produced fibers, which resembled the 16 repeats fibers when viewed by immunostaining in a confocal microscope, shown in FIG. 2D. Testing for chemical resistance and thermal profile produced the same results as for the 16 repeat fibers.

Next, the influence of decreasing the number of repeats on fiber-forming ability was examined. For this purpose, the aforementioned system was employed to produce two further baculoviruses coding for semi-synthetic proteins containing 12, and 8 repeats. All infected cells produced fibers that upon examination showed no deviation from the properties observed beforehand for fibers of 16 repeats and above.

To discover if there is a bottom limit for self-assembly into fibers, in terms of repeat number, the inventors further decreased the number of repeats and produced a baculovirus coding for a four repeat protein. Unlike the cases described above, a peculiar assembly pattern was observed in the cells infected with the four repeat coding baculovirus. When viewed using light microscopy starting from 2 days post infection, a distinct phenotype was identified, in which the typical fibrous structure, observed for proteins of eight repeats and above, was accompanied by multiple rigid spine-like structures protruding in all directions toward the cell periphery. Thus, in contrast to all the previous structures, which had few visible termini and adopted the shape of the cells, these fibers seemed to force an adjustment of cell boundaries as they expanded outward in a ray-like fashion as illustrated by FIG. 3A. To verify that these unique spikes are indeed composed of the expressed dragline protein and do not form as some unusual response of the infected cells to this particular protein immunocytochemistry was used, which resulted in specific staining in these structures, demonstrated by FIG. 3B. Surprisingly, these fiber networks were found to maintain similar chemical resistance and the thermal profiles, which the inventors have previously observed in the higher repeat containing dragline proteins.

When a two-repeat baculovirus was engineered and used to infect Sf9 cells, a phenotype resembling the one observed for the four repeat fiber was observed, as seen in FIG. 3C, and the identity of this structure was verified as for the four repeat fibers using Immunocytochemistry (see FIG. 3D). Interestingly, although this protein resembled the four repeat structure in shape, when examined for chemical resistance it exhibited no evident resistance to SDS, mild detergents such as Triton X-100, and denaturants like acetic acid. DSC analysis could thus not be done due to lack of resistance required for the purification process.

The inventors then infected cells with a baculovirus containing only a single basic repeat sequence together with the N- and C-termini. Although much of the protein that was expressed remained soluble, a fraction of it did undergo a nontypical self-assembly to very short fibrous structures with variable diameters up to about 100 nm, emerging from disordered aggregates, clearly seen in FIG. 3E. Similarly, to the two-repeat protein, no chemical resistance was observed and thus thermal investigation did not take place.

To test the possibility that the nonrepetitive N and C-terminal domains by themselves may be responsible to the assembly pattern seen in the one and two repeat proteins, cells were infected with a baculovirus coding for the N-terminal domain followed by the C-terminal domain and lacking the repetitive core. As could be expected from previous work of the inventors, the protein was fully soluble in the cytosol and no form of self-assembly could be detected, as shown in FIG. 3F.

Example 3

Ultrastructural Analysis of the Multiple Consensus Sequence Repeat Dragline-Like Protein Intrigued by the different assembly phenotypes, the inventors turned to ultrastructural analysis using TEM to gain more insights regarding the assembly process of the natural and synthetic proteins. Before this study, TEM was used to study the dragline like r-ADF4 fibers produced in insect cells and it has been reported that they are composed of a nanofibrils network [Huemmerich, D. et al., Curr. Biol. 2004, 14, 2070-2074]. The inventors now explored whether TEM would show any difference between the synthetic fibers introduced here to the prior, more "natural", r-ADF4 fibers and whether any ultrastructural changes could be discerned between fibers of varying repeat numbers.

Several types of fibers, including the previously reported r-ADF4 fibers of the inventors, were purified from infected cells, mounted on EM grids without further treatment, or negatively stained with NanoVan, a vanadium-based reagent.

Starting from the lowest magnification enabling to distinguish subfiber structures (×80,000), the fibers appeared as composed of a mesh of smaller fibrils, which were not aligned in parallel, but were intertwined in a seemingly disordered fashion (see FIG. 4A). At a higher magnification (×160,000), it is possible to discern and identify single nanofibrils protruding out of the main fiber contour, as clearly seen in FIG. 4B. These observations are common to the r-ADF4 fibers, which the inventors have previously analyzed, and to all the synthetic fibers containing eight repeats and more. Since the form and shape of the four repeats fibers was different as compared to fibers composed of proteins containing higher number of repeats, it was interesting to determine in what way, if at all, their ultrastructure will differ. When the four repeats fibers were inspected by TEM, some major characteristics were clearly seen, including what looks like a somewhat loose packaging of the substructures composing the final fiber, with nonhomogenous spread as seen by the negative staining, accompanied by bright regions that indicate a very low content of material, demonstrated in FIG. 4C. FIG. 4D demonstrates that using a higher magnification, the nanofibrils composing the high-repeat fibers can still be seen as a tightly knit entangled mesh and their average diameter can be measured at ca. 7 nm. The four repeats fibers also displayed a nanofibril structure; however, these are less tightly packed and form irregular and variable regions in contrast to the uniform mesh of the higher fibers. As shown in FIG. 4E, this magnification also identifies the bright regions as empty spaces in the midst of the main fiber. Notably, even when using the largest magnification, TEM was unable to demonstrate significant variations in the diameter of the nanofibrils composing the different fibers.

The above examples and description have been provided only for the purpose of illustration, and are not intended to limit the invention in any way. As will be appreciated by the skilled person, the invention can be carried out in a great variety of ways, employing more than one technique from those described above, all without exceeding the scope of the invention.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. An isolated polypeptide comprising n repeats of the amino acid sequence of SEQ ID NO:4, wherein n is an integer above 2.

2. The polypeptide according to claim 1, wherein n is an integer equal to or below 70.

3. The polypeptide according to claim 2, wherein n is an integer equal to or between 4 and 32.

4. The polypeptide according to claim 1, further comprising a C-terminal region having the amino acid sequence of SEQ ID NO:10.

5. The polypeptide according to claim 4, further comprising an N-terminal region having the amino acid sequence of SEQ ID NO:5.

6. The polypeptide according to claim 5, further comprising at least one N-terminal tag sequence.

7. An isolated nucleic acid molecule encoding a polypeptide comprising n repeats of the amino acid sequence of SEQ ID NO:4, wherein n is an integer above 2.

8. The nucleic acid molecule according to claim 7, wherein the amino acid sequence of SEQ ID NO:4 is encoded by the nucleotide sequence of SEQ ID NO:3.

9. The nucleic acid molecule according to claim 7, wherein the encoded polypeptide further comprises a C-terminal region having the amino acid sequence of SEQ ID NO:10.

10. The nucleic acid molecule according to claim 9, wherein the amino acid sequence of SEQ ID NO:10 is encoded by the nucleotide sequence of SEQ ID NO:9.

11. The nucleic acid molecule according to claim 9, wherein the encoded polypeptide further comprises an N-terminal region having the amino acid sequence of SEQ ID NO:5.

12. The nucleic acid molecule according to claim 11, wherein the amino acid sequence of SEQ ID NO:5 is encoded by the nucleotide sequence of SEQ ID NO:6.

13. An expression vector comprising a nucleic acid molecule encoding a polypeptide comprising n repeats of the amino acid sequence of SEQ ID NO:4, wherein n is an integer above 2, and wherein said polypeptide optionally further comprises at least one of a C-terminal region having the amino acid sequence of SEQ ID NO:10 and an N terminal region having the amino acid sequence of SEQ ID NO:5.

14. An isolated host cell transformed with the expression vector according to claim 13.

15. An isolated recombinant protein comprising n repeats of the amino acid sequence of SEQ ID NO:4, wherein n is an integer above 2, and wherein said protein optionally further comprises at least one of a C-terminal region having the amino acid sequence of SEQ ID NO:10 and an N-terminal region having the amino acid sequence of SEQ ID NO:5.

16. A fiber comprising the recombinant protein according to claim 15.

17. A composition comprising:
   an isolated polypeptide comprising n repeats of the amino acid sequence of SEQ ID NO:4, wherein n is an integer above 2, wherein said polypeptide optionally further comprises at least one of a C-terminal region having the amino acid sequence of SEQ ID NO:10 and an N-terminal region having the amino acid sequence of SEQ ID NO:5,
   a recombinant protein comprising the isolated polypeptide, or
   a fiber comprising the isolated polypeptide;
and optionally further comprising a carrier, diluent or excipient.

18. An article comprising at least one fiber, wherein the fiber comprises the recombinant protein according to claim 15.

* * * * *

```
                              SEQUENCE LISTING

<160> NUMBER OF SEQ ID NOS: 84

<210> SEQ ID NO 1
<211> LENGTH: 1365
<212> TYPE: DNA
<213> ORGANISM: Araneus diadematus

<400> SEQUENCE: 1
gcaggatctt cagcagcagc ggccgcggca gcaagtggat ctggaggata cggacctgaa      60
aaccaaggac catctggacc tgtagcatat ggacctggtg gacccgtatc ttcagctgca     120
gcagcagccg ctgcaggaag tggacctggt ggatacggac ctgaaaacca aggaccatct     180
ggacccggag gatatggacc tggtggttcc ggatcttcag cagcagcagc agccgctgca     240
gcaagtggac ctggaggata tggacctgga agccaaggac catctggacc tggtggatcc     300
ggaggatatg gtcccggaag ccaagggca tctggacctg gtgggcctgg tgcatctgcg     360
gcagcagcag cagcagccgc tgcagcaagt ggacctggag gatatggacc tggaagccaa     420
ggaccatctg gacctggagc atatggacct ggtggacccg gatcttcagc tgcagcagca     480
gccgctgcag caagtggacc tggaggatat ggacctggaa gccaaggacc atctggacct     540
ggagtatatg gacctggtgg acccggatct tcagctgcag cagcagccgc tgcaggaagt     600
ggacctggtg gatacggacc tgaaaaccaa ggaccatctg gacccggagg atatggacct     660
ggtggttccg gatcttcagc agcagcagca gccgctgcag caagtggacc tggaggatat     720
ggacctggaa gccaaggacc atctggacct ggtggatccg gaggatatgg tcccggaagc     780 caaggggggat ctggacctgg tgcatctgcg gcagcagcag ccgctgcagc aagtggacct     840
ggaggatatg gacctggaag ccaaggacca tctggacctg gatatcaagg ccctagtggt     900
cctggagcat atggcccatc tccttctgct tccgcatccg ttgcagcctc tgtttatctt     960
cgcctgcagc ctcgtctaga ggtgtcttcc gctgtatcgt ctttagtgtc tagcggacct    1020
acgaatggtg ctgctgtttc tggagctttg aatagtttag tatctcagat tagtgcaagt    1080
aatccaggtt tatcgggatg tgatgctctt gtgcaggcat tattggaatt agtgtctgct    1140
cttgtggcaa ttctttcatc tgcaagtatt ggccaagtca acgtcagctc tgttagtcag    1200
tcaactcaaa tgattagcca agctctttca taaacacttg gtaaaatata gtcgtctagt    1260
tcaaatgagt ttgtattgaa attcatttgt aattttttatt gaaatgtatt cccaagtatg    1320
aatttaataa attgttgatt gcaagtttaa aaaaaaaaaa aaaaa                     1365
```

<210> SEQ ID NO 2
<211> LENGTH: 410
<212> TYPE: PRT
<213> ORGANISM: Araneus diadematus

<400> SEQUENCE: 2

```
Ala Gly Ser Ser Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
            20                  25                  30

Gly Gly Pro Val Ser Ser Ala Ala Ala Ala Ala Ala Gly Ser Gly
            35                  40                  45

Pro Gly Gly Tyr Gly Pro Glu Asn Gln Gly Pro Ser Gly Pro Gly Gly
50                  55                  60

Tyr Gly Pro Gly Gly Ser Gly Ser Ser Ala Ala Ala Ala Ala
65                  70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
            100                 105                 110

Pro Gly Gly Pro Gly Ala Ser Ala Ala Ala Ala Ala Ala Ala
            115                 120                 125

Ala Ser Gly Pro Gly Gly Tyr Gly Pro Gly Ser Gln Gly Pro Ser Gly
            130                 135                 140

Pro Gly Ala Tyr Gly Pro Gly Gly Pro Gly Ser Ser Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
            180                 185                 190

Ala Ala Ala Ala Ala Ala Gly Ser Gly Pro Gly Gly Tyr Gly Pro Glu
            195                 200                 205

Asn Gln Gly Pro Ser Gly Pro Gly Gly Tyr Gly Pro Gly Ser Gly
210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Ser Gly Tyr
                245                 250                 255

Gly Pro Gly Ser Gln Gly Gly Ser Pro Gly Ala Ser Ala Ala Ala
            260                 265                 270

Ala Ala Ala Ala Ser Gly Pro Gly Gly Tyr Gly Pro Gly Ser Gln
            275                 280                 285

Gly Pro Ser Gly Pro Gly Tyr Gln Gly Pro Ser Gly Pro Gly Ala Tyr
            290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
            325                 330                 335

Ser Ser Gly Pro Thr Asn Gly Ala Ala Val Ser Gly Ala Leu Asn Ser
            340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
            370                 375                 380
```

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 3
<211> LENGTH: 105
<212> TYPE: DNA
<213> ORGANISM: Artificial
<220> FEATURE:
<223> OTHER INFORMATION: DNA encoding repeat region consensus sequence

<400> SEQUENCE: 3
tctggtcctg gaggttatgg cccaggaagc caaggaccat ctggtccagg aggatatggt     60
ccaggcggac ctggctctag tgcagcagct gccgcagcag ctgca                   105

<210> SEQ ID NO 4
<211> LENGTH: 35
<212> TYPE: PRT
<213> ORGANISM: Artificial
<220> FEATURE:
<223> OTHER INFORMATION: 35 aa repeat region consesus sequence

<400> SEQUENCE: 4

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
                20                  25                  30

Ala Ala Ala
        35

<210> SEQ ID NO 5
<211> LENGTH: 39
<212> TYPE: PRT
<213> ORGANISM: Araneus diadematus

<400> SEQUENCE: 5

Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
                20                  25                  30

Leu Ser Asn Leu Asp Asn Ala
        35

<210> SEQ ID NO 6
<211> LENGTH: 147
<212> TYPE: DNA
<213> ORGANISM: Artificial Sequence
<220> FEATURE:
<223> OTHER INFORMATION: N-terminal encoding sequence

<400> SEQUENCE: 6
atgtcgtact accatcacca tcaccatcac gattacgata tcccaacgac cgaaaacctg     60
tattttcagg gcgccatgga tccggaattc aaaggcctac gtcgacgagc tcaactagtg    120
cggccgcttt cgaatctaga taatgca                                       147

<210> SEQ ID NO 7
<211> LENGTH: 49
<212> TYPE: PRT
<213> ORGANISM: Artificial Sequence
<220> FEATURE:
<223> OTHER INFORMATION: His6 N terminal sequence

<400> SEQUENCE: 7

Met Ser Tyr Tyr His His His His His His Asp Tyr Asp Ile Pro Thr
1               5                   10                  15
Thr Glu Asn Leu Tyr Phe Gln Gly Ala Met Asp Pro Glu Phe Lys Gly
            20                  25                  30
Leu Arg Arg Arg Ala Gln Leu Val Arg Pro Leu Ser Asn Leu Asp Asn
        35                  40                  45
Ala

<210> SEQ ID NO 8
<211> LENGTH: 50
<212> TYPE: PRT
<213> ORGANISM: Artificial Sequence
<220> FEATURE:
<223> OTHER INFORMATION: HA-N-terminal sequence

<400> SEQUENCE: 8

Met Ser Tyr Pro Tyr Asp Val Pro Asp Tyr Ala Asp Tyr Asp Ile Pro
1               5                   10                  15
Thr Thr Glu Asn Leu Tyr Phe Gln Gly Ala Met Asp Pro Glu Phe Lys
            20                  25                  30
Gly Leu Arg Arg Arg Ala Gln Leu Val Arg Pro Leu Ser Asn Leu Asp
        35                  40                  45
Asn Ala
    50

<210> SEQ ID NO 9
<211> LENGTH: 342
<212> TYPE: DNA
<213> ORGANISM: Artificial Sequence
<220> FEATURE:
<223> OTHER INFORMATION: C-terminal encoding sequence

<400> SEQUENCE: 9
ggccctagtg gtcctggagc atatggccca tctccttctg cttccgcatc cgttgcagcc      60
tctcgtttat cttcgcctgc agcctcgtct agagtgtctt ccgctgtatc gtctttagtg     120
tctagcggac ctacgaatgg tgctgctgtt tctggagctt tgaatagttt agtatctcag     180
attagtgcaa gtaatccagg tttatcggga tgtgatgctc ttgtgcaggc attattggaa     240
ttagtgtctg ctcttgtggc aattctttca tctgcaagta ttggccaagt caacgtcagc     300
tctgttagtc agtcaactca aatgattagc caagctcttt ca                        342

<210> SEQ ID NO 10
<211> LENGTH: 114
<212> TYPE: PRT
<213> ORGANISM: Artificial Sequence
<220> FEATURE:
<223> OTHER INFORMATION: C-terminal sequence

<400> SEQUENCE: 10

Gly Pro Ser Gly Pro Gly Ala Tyr Gly Pro Ser Pro Ser Ala Ser Ala
1               5                   10                  15
Ser Val Ala Ala Ser Arg Leu Ser Ser Pro Ala Ala Ser Ser Arg Val
            20                  25                  30
Ser Ser Ala Val Ser Ser Leu Val Ser Ser Gly Pro Thr Asn Gly Ala
        35                  40                  45
Ala Val Ser Gly Ala Leu Asn Ser Leu Val Ser Gln Ile Ser Ala Ser
    50                  55                  60

```
Asn Pro Gly Leu Ser Gly Cys Asp Ala Leu Val Gln Ala Leu Leu Glu
 65                  70                  75                  80

Leu Val Ser Ala Leu Val Ala Ile Leu Ser Ala Ser Ile Gly Gln
             85                  90                  95

Val Asn Val Ser Ser Val Ser Gln Ser Thr Gln Met Ile Ser Gln Ala
            100                 105                 110

Leu Ser

<210> SEQ ID NO 11
<211> LENGTH: 6
<212> TYPE: PRT
<213> ORGANISM: Artificial
<220> FEATURE:
<223> OTHER INFORMATION: His6 tag

<400> SEQUENCE: 11

His His His His His His
1               5

<210> SEQ ID NO 12
<211> LENGTH: 10
<212> TYPE: PRT
<213> ORGANISM: Artificial
<220> FEATURE:
<223> OTHER INFORMATION: His6 tag version 2

<400> SEQUENCE: 12

Met Ser Tyr Tyr His His His His His His
1               5                   10

<210> SEQ ID NO 13
<211> LENGTH: 9
<212> TYPE: PRT
<213> ORGANISM: Artificial
<220> FEATURE:
<223> OTHER INFORMATION: HA tag

<400> SEQUENCE: 13

Tyr Pro Tyr Asp Val Pro Asp Tyr Ala
1               5

<210> SEQ ID NO 14
<211> LENGTH: 28
<212> TYPE: DNA
<213> ORGANISM: Artificial
<220> FEATURE:
<223> OTHER INFORMATION: 5'-primer

<400> SEQUENCE: 14
atatgctgca ggccctagtg gtcctgga                                          28

<210> SEQ ID NO 15
<211> LENGTH: 20
<212> TYPE: DNA
<213> ORGANISM: Artificial
<220> FEATURE:
<223> OTHER INFORMATION: 3'-primer

<400> SEQUENCE: 15
tcgacaagct tggtaccgca                                                   20

<210> SEQ ID NO 16
<211> LENGTH: 672
<212> TYPE: DNA
<213> ORGANISM: Artificial Sequence
<220> FEATURE:
```

<223> OTHER INFORMATION: DNA full sequence (N-term + 2 repeats + C-term)

<400> SEQUENCE: 16

| | | | | | |
|---|---|---|---|---|---|
| atggattacg | atatcccaac | gaccgaaaac | ctgtattttc | agggcgccat | ggatccggaa | 60 |
| ttcaaaggcc | tacgtcgacg | agctcaacta | gtgcggccgc | tttcgaatct | agataatgca | 120 |
| tctggtcctg | gaggttatgg | cccaggaagc | caaggaccat | ctggtccagg | aggatatggt | 180 |
| ccaggcggac | ctggctctag | tgcagcagct | gccgcagcag | ctgcatctgg | tcctggaggt | 240 |
| tatggcccag | gaagccaagg | accatctggt | ccaggaggat | atggtccagg | cggacctggc | 300 |
| tctagtgcag | cagctgccgc | agcagctgca | ggccctagtg | gtcctggagc | atggccca | 360 |
| tctccttctg | cttccgcatc | cgttgcagcc | tctcgtttat | cttcgcctgc | agcctcgtct | 420 |
| agagtgtctt | ccgctgtatc | gtctttagtg | tctagcggac | ctacgaatgg | tgctgctgtt | 480 |
| tctggagctt | tgaatagttt | agtatctcag | attagtgcaa | gtaatccagg | tttatcggga | 540 |
| tgtgatgctc | ttgtgcaggc | attattggaa | ttagtgtctg | ctcttgtggc | aattctttca | 600 |
| tctgcaagta | ttggccaagt | caacgtcagc | tctgttagtc | agtcaactca | aatgattagc | 660 |
| caagctcttt | ca | | | | | 672 |

<210> SEQ ID NO 17
<211> LENGTH: 882
<212> TYPE: DNA
<213> ORGANISM: Artificial Sequence
<220> FEATURE:
<223> OTHER INFORMATION: DNA full sequence (N-term + 4 repeats + C-term)

<400> SEQUENCE: 17

| | | | | | |
|---|---|---|---|---|---|
| atggattacg | atatcccaac | gaccgaaaac | ctgtattttc | agggcgccat | ggatccggaa | 60 |
| ttcaaaggcc | tacgtcgacg | agctcaacta | gtgcggccgc | tttcgaatct | agataatgca | 120 |
| tctggtcctg | gaggttatgg | cccaggaagc | caaggaccat | ctggtccagg | aggatatggt | 180 |
| ccaggcggac | ctggctctag | tgcagcagct | gccgcagcag | ctgcatctgg | tcctggaggt | 240 |
| tatggcccag | gaagccaagg | accatctggt | ccaggaggat | atggtccagg | cggacctggc | 300 |
| tctagtgcag | cagctgccgc | agcagctgca | tctggtcctg | gaggttatgg | cccaggaagc | 360 |
| caaggaccat | ctggtccagg | aggatatggt | ccaggcggac | ctggctctag | tgcagcagct | 420 |
| gccgcagcag | ctgcatctgg | tcctggaggt | tatggcccag | gaagccaagg | accatctggt | 480 |
| ccaggaggat | atggtccagg | cggacctggc | tctagtgcag | cagctgccgc | agcagctgca | 540 |
| ggccctagtg | gtcctggagc | atggccca | tctccttctg | cttccgcatc | cgttgcagcc | 600 |
| tctcgtttat | cttcgcctgc | agcctcgtct | agagtgtctt | ccgctgtatc | gtctttagtg | 660 |
| tctagcggac | ctacgaatgg | tgctgctgtt | tctggagctt | tgaatagttt | agtatctcag | 720 |
| attagtgcaa | gtaatccagg | tttatcggga | tgtgatgctc | ttgtgcaggc | attattggaa | 780 |
| ttagtgtctg | ctcttgtggc | aattctttca | tctgcaagta | ttggccaagt | caacgtcagc | 840 |
| tctgttagtc | agtcaactca | aatgattagc | caagctcttt | ca | | 882 |

<210> SEQ ID NO 18
<211> LENGTH: 1302
<212> TYPE: DNA
<213> ORGANISM: Artificial Sequence
<220> FEATURE:
<223> OTHER INFORMATION: DNA full sequence (N-term + 8 repeats + C-term)

<400> SEQUENCE: 18

| | | | | | |
|---|---|---|---|---|---|
| atggattacg | atatcccaac | gaccgaaaac | ctgtattttc | agggcgccat | ggatccggaa | 60 |

| | |
|---|---|
| ttcaaaggcc tacgtcgacg agctcaacta gtgcggccgc tttcgaatct agataatgca | 120 |
| tctggtcctg gaggttatgg cccaggaagc caaggaccat ctggtccagg aggatatggt | 180 |
| ccaggcggac ctggctctag tgcagcagct gccgcagcag ctgcatctgg tcctggaggt | 240 |
| tatgcccag gaagccaagg accatctggt ccaggaggat atggtccagg cggacctggc | 300 |
| tctagtgcag cagctgccgc agcagctgca tctggtcctg gaggttatgg cccaggaagc | 360 |
| caaggaccat ctggtccagg aggatatggt ccaggcggac ctggctctag tgcagcagct | 420 |
| gccgcagcag ctgcatctgg tcctggaggt tatgcccag gaagccaagg accatctggt | 480 |
| ccaggaggat atggtccagg cggacctggc tctagtgcag cagctgccgc agcagctgca | 540 |
| tctggtcctg gaggttatgg cccaggaagc caaggaccat ctggtccagg aggatatggt | 600 |
| ccaggcggac ctggctctag tgcagcagct gccgcagcag ctgcatctgg tcctggaggt | 660 |
| tatgcccag gaagccaagg accatctggt ccaggaggat atggtccagg cggacctggc | 720 |
| tctagtgcag cagctgccgc agcagctgca tctggtcctg gaggttatgg cccaggaagc | 780 |
| caaggaccat ctggtccagg aggatatggt ccaggcggac ctggctctag tgcagcagct | 840 |
| gccgcagcag ctgcatctgg tcctggaggt tatgcccag gaagccaagg accatctggt | 900 |
| ccaggaggat atggtccagg cggacctggc tctagtgcag cagctgccgc agcagctgca | 960 |
| ggccctagtg gtcctggagc atatggccca tctccttctg cttccgcatc cgttgcagcc | 1020 |
| tctcgtttat cttcgcctgc agcctcgtct agagtgtctt ccgctgtatc gtctttagtg | 1080 |
| tctagcggac ctacgaatgg tgctgctgtt tctggagctt tgaatagttt agtatctcag | 1140 |
| attagtgcaa gtaatccagg tttatcggga tgtgatgctc ttgtgcaggc attattggaa | 1200 |
| ttagtgtctg ctcttgtggc aattctttca tctgcaagta ttggccaagt caacgtcagc | 1260 |
| tctgttagtc agtcaactca aatgattagc caagctcttt ca | 1302 |

<210> SEQ ID NO 19
<211> LENGTH: 1722
<212> TYPE: DNA
<213> ORGANISM: Artificial Sequence
<220> FEATURE:
<223> OTHER INFORMATION: DNA full sequence (N-term + 12 repeats + C-term)

<400> SEQUENCE: 19

| | |
|---|---|
| atggattacg atatcccaac gaccgaaaac ctgtattttc agggcgccat ggatccggaa | 60 |
| ttcaaaggcc tacgtcgacg agctcaacta gtgcggccgc tttcgaatct agataatgca | 120 |
| tctggtcctg gaggttatgg cccaggaagc caaggaccat ctggtccagg aggatatggt | 180 |
| ccaggcggac ctggctctag tgcagcagct gccgcagcag ctgcatctgg tcctggaggt | 240 |
| tatgcccag gaagccaagg accatctggt ccaggaggat atggtccagg cggacctggc | 300 |
| tctagtgcag cagctgccgc agcagctgca tctggtcctg gaggttatgg cccaggaagc | 360 |
| caaggaccat ctggtccagg aggatatggt ccaggcggac ctggctctag tgcagcagct | 420 |
| gccgcagcag ctgcatctgg tcctggaggt tatgcccag gaagccaagg accatctggt | 480 |
| ccaggaggat atggtccagg cggacctggc tctagtgcag cagctgccgc agcagctgca | 540 |
| tctggtcctg gaggttatgg cccaggaagc caaggaccat ctggtccagg aggatatggt | 600 |
| ccaggcggac ctggctctag tgcagcagct gccgcagcag ctgcatctgg tcctggaggt | 660 |
| tatgcccag gaagccaagg accatctggt ccaggaggat atggtccagg cggacctggc | 720 |
| tctagtgcag cagctgccgc agcagctgca tctggtcctg gaggttatgg cccaggaagc | 780 |
| caaggaccat ctggtccagg aggatatggt ccaggcggac ctggctctag tgcagcagct | 840 |

```
gccgcagcag ctgcatctgg tcctggaggt tatgcccag gaagccaagg accatctggt    900
ccaggaggat atggtccagg cggacctggc tctagtgcag cagctgccgc agcagctgca    960
tctggtcctg gaggttatgg cccaggaagc caaggaccat ctggtccagg aggatatggt   1020
ccaggcggac ctggctctag tgcagcagct gccgcagcag ctgcatctgg tcctggaggt   1080 tatgcccag gaagccaagg accatctggt ccaggaggat atggtccagg cggacctggc    1140
tctagtgcag cagctgccgc agcagctgca tctggtcctg gaggttatgg cccaggaagc   1200
caaggaccat ctggtccagg aggatatggt ccaggcggac ctggctctag tgcagcagct   1260
gccgcagcag ctgcatctgg tcctggaggt tatgcccag gaagccaagg accatctggt    1320
ccaggaggat atggtccagg cggacctggc tctagtgcag cagctgccgc agcagctgca   1380
ggccctagtg gtcctggagc atatggccca tctccttctg cttccgcatc cgttgcagcc   1440
tctcgtttat cttcgcctgc agcctcgtct agagtgtctt ccgctgtatc gtctttagtg   1500
tctagcggac ctacgaatgg tgctgctgtt tctggagctt tgaatagttt agtatctcag   1560
attagtgcaa gtaatccagg tttatcggga tgtgatgctc ttgtgcaggc attattggaa   1620
ttagtgtctg ctcttgtggc aattctttca ctgcaagta ttggccaagt caacgtcagc    1680
tctgttagtc agtcaactca aatgattagc caagctcttt ca                      1722

<210> SEQ ID NO 20
<211> LENGTH: 2142
<212> TYPE: DNA
<213> ORGANISM: Artificial Sequence
<220> FEATURE:
<223> OTHER INFORMATION: DNA full sequence (N-term + 16 repeats +
      C-term)

<400> SEQUENCE: 20
atggattacg atatcccaac gaccgaaaac ctgtattttc agggcgccat ggatccggaa     60
ttcaaaggcc tacgtcgacg agctcaacta gtgcggccgc tttcgaatct agataatgca    120
tctggtcctg gaggttatgg cccaggaagc caaggaccat ctggtccagg aggatatggt    180
ccaggcggac ctggctctag tgcagcagct gccgcagcag ctgcatctgg tcctggaggt    240 tatgcccag gaagccaagg accatctggt ccaggaggat atggtccagg cggacctggc    300
tctagtgcag cagctgccgc agcagctgca tctggtcctg gaggttatgg cccaggaagc    360
caaggaccat ctggtccagg aggatatggt ccaggcggac ctggctctag tgcagcagct    420
gccgcagcag ctgcatctgg tcctggaggt tatgcccag gaagccaagg accatctggt    480
ccaggaggat atggtccagg cggacctggc tctagtgcag cagctgccgc agcagctgca    540
tctggtcctg gaggttatgg cccaggaagc caaggaccat ctggtccagg aggatatggt    600
ccaggcggac ctggctctag tgcagcagct gccgcagcag ctgcatctgg tcctggaggt    660 tatgcccag gaagccaagg accatctggt ccaggaggat atggtccagg cggacctggc    720
tctagtgcag cagctgccgc agcagctgca tctggtcctg gaggttatgg cccaggaagc    780
caaggaccat ctggtccagg aggatatggt ccaggcggac ctggctctag tgcagcagct    840
gccgcagcag ctgcatctgg tcctggaggt tatgcccag gaagccaagg accatctggt    900
ccaggaggat atggtccagg cggacctggc tctagtgcag cagctgccgc agcagctgca    960
tctggtcctg gaggttatgg cccaggaagc caaggaccat ctggtccagg aggatatggt   1020
ccaggcggac ctggctctag tgcagcagct gccgcagcag ctgcatctgg tcctggaggt   1080 tatgcccag gaagccaagg accatctggt ccaggaggat atggtccagg cggacctggc    1140
```

| | |
|---|---|
| tctagtgcag cagctgccgc agcagctgca tctggtcctg gaggttatgg cccaggaagc | 1200 |
| caaggaccat ctggtccagg aggatatggt ccaggcggac ctggctctag tgcagcagct | 1260 |
| gccgcagcag ctgcatctgg tcctggaggt tatgcccag gaagccaagg accatctggt | 1320 |
| ccaggaggat atggtccagg cggacctggc tctagtgcag cagctgccgc agcagctgca | 1380 |
| tctggtcctg gaggttatgg cccaggaagc caaggaccat ctggtccagg aggatatggt | 1440 |
| ccaggcggac ctggctctag tgcagcagct gccgcagcag ctgcatctgg tcctggaggt | 1500 |
| tatgcccag gaagccaagg accatctggt ccaggaggat atggtccagg cggacctggc | 1560 |
| tctagtgcag cagctgccgc agcagctgca tctggtcctg gaggttatgg cccaggaagc | 1620 |
| caaggaccat ctggtccagg aggatatggt ccaggcggac ctggctctag tgcagcagct | 1680 |
| gccgcagcag ctgcatctgg tcctggaggt tatgcccag gaagccaagg accatctggt | 1740 |
| ccaggaggat atggtccagg cggacctggc tctagtgcag cagctgccgc agcagctgca | 1800 |
| ggccctagtg gtcctggagc atatggccca tctccttctg cttccgcatc cgttgcagcc | 1860 |
| tctcgtttat cttcgcctgc agcctcgtct agagtgtctt ccgctgtatc gtctttagtg | 1920 |
| tctagcggac ctacgaatgg tgctgctgtt tctggagctt tgaatagttt agtatctcag | 1980 |
| attagtgcaa gtaatccagg tttatcggga tgtgatgctc ttgtgcaggc attattggaa | 2040 |
| ttagtgtctg ctcttgtggc aattctttca ctgcaagta ttggccaagt caacgtcagc | 2100 |
| tctgttagtc agtcaactca aatgattagc caagctcttt ca | 2142 |

<210> SEQ ID NO 21
<211> LENGTH: 2562
<212> TYPE: DNA
<213> ORGANISM: Artificial Sequence
<220> FEATURE:
<223> OTHER INFORMATION: DNA full sequence (N-term + 20 repeats + C-term)

<400> SEQUENCE: 21

| | |
|---|---|
| atggattacg atatcccaac gaccgaaaac ctgtattttc agggcgccat ggatccggaa | 60 |
| ttcaaaggcc tacgtcgacg agctcaacta gtgcggccgc tttcgaatct agataatgca | 120 |
| tctggtcctg gaggttatgg cccaggaagc caaggaccat ctggtccagg aggatatggt | 180 |
| ccaggcggac ctggctctag tgcagcagct gccgcagcag ctgcatctgg tcctggaggt | 240 |
| tatgcccag gaagccaagg accatctggt ccaggaggat atggtccagg cggacctggc | 300 |
| tctagtgcag cagctgccgc agcagctgca tctggtcctg gaggttatgg cccaggaagc | 360 |
| caaggaccat ctggtccagg aggatatggt ccaggcggac ctggctctag tgcagcagct | 420 |
| gccgcagcag ctgcatctgg tcctggaggt tatgcccag gaagccaagg accatctggt | 480 |
| ccaggaggat atggtccagg cggacctggc tctagtgcag cagctgccgc agcagctgca | 540 |
| tctggtcctg gaggttatgg cccaggaagc caaggaccat ctggtccagg aggatatggt | 600 |
| ccaggcggac ctggctctag tgcagcagct gccgcagcag ctgcatctgg tcctggaggt | 660 |
| tatgcccag gaagccaagg accatctggt ccaggaggat atggtccagg cggacctggc | 720 |
| tctagtgcag cagctgccgc agcagctgca tctggtcctg gaggttatgg cccaggaagc | 780 |
| caaggaccat ctggtccagg aggatatggt ccaggcggac ctggctctag tgcagcagct | 840 |
| gccgcagcag ctgcatctgg tcctggaggt tatgcccag gaagccaagg accatctggt | 900 |
| ccaggaggat atggtccagg cggacctggc tctagtgcag cagctgccgc agcagctgca | 960 |
| tctggtcctg gaggttatgg cccaggaagc caaggaccat ctggtccagg aggatatggt | 1020 |
| ccaggcggac ctggctctag tgcagcagct gccgcagcag ctgcatctgg tcctggaggt | 1080 |

```
tatggcccag gaagccaagg accatctggt ccaggaggat atggtccagg cggacctggc      1140
tctagtgcag cagctgccgc agcagctgca tctggtcctg gaggttatgg cccaggaagc      1200
caaggaccat ctggtccagg aggatatggt ccaggcggac ctggctctag tgcagcagct      1260
gccgcagcag ctgcatctgg tcctggaggt tatgcccag gaagccaagg accatctggt       1320
ccaggaggat atggtccagg cggacctggc tctagtgcag cagctgccgc agcagctgca      1380
tctggtcctg gaggttatgg cccaggaagc caaggaccat ctggtccagg aggatatggt      1440
ccaggcggac ctggctctag tgcagcagct gccgcagcag ctgcatctgg tcctggaggt      1500
tatggcccag gaagccaagg accatctggt ccaggaggat atggtccagg cggacctggc      1560
tctagtgcag cagctgccgc agcagctgca tctggtcctg gaggttatgg cccaggaagc      1620
caaggaccat ctggtccagg aggatatggt ccaggcggac ctggctctag tgcagcagct      1680
gccgcagcag ctgcatctgg tcctggaggt tatggcccag gaagccaagg accatctggt      1740
ccaggaggat atggtccagg cggacctggc tctagtgcag cagctgccgc agcagctgca      1800
tctggtcctg gaggttatgg cccaggaagc caaggaccat ctggtccagg aggatatggt      1860
ccaggcggac ctggctctag tgcagcagct gccgcagcag ctgcatctgg tcctggaggt      1920
tatggcccag gaagccaagg accatctggt ccaggaggat atggtccagg cggacctggc      1980
tctagtgcag cagctgccgc agcagctgca tctggtcctg gaggttatgg cccaggaagc      2040
caaggaccat ctggtccagg aggatatggt ccaggcggac ctggctctag tgcagcagct      2100
gccgcagcag ctgcatctgg tcctggaggt tatggcccag gaagccaagg accatctggt      2160
ccaggaggat atggtccagg cggacctggc tctagtgcag cagctgccgc agcagctgca      2220
ggccctagtg gtcctggagc atatggccca tctccttctg cttccgcatc cgttgcagcc      2280
tctcgtttat cttcgcctgc agcctcgtct agagtgtctt ccgctgtatc gtctttagtg      2340
tctagcggac ctacgaatgg tgctgctgtt tctggagctt tgaatagttt agtatctcag      2400
attagtgcaa gtaatccagg tttatcggga tgtgatgctc ttgtgcaggc attattggaa      2460
ttagtgtctg ctcttgtggc aattctttca ctgcaagta ttggccaagt caacgtcagc       2520
tctgttagtc agtcaactca aatgattagc caagctcttt ca                        2562

<210> SEQ ID NO 22
<211> LENGTH: 2982
<212> TYPE: DNA
<213> ORGANISM: Artificial Sequence
<220> FEATURE:
<223> OTHER INFORMATION: DNA full sequence (N-term + 24 repeats +
      C-term)

<400> SEQUENCE: 22
atggattacg atatcccaac gaccgaaaac ctgtattttc agggcgccat ggatccggaa        60
ttcaaaggcc tacgtcgacg agctcaacta gtgcggccgc tttcgaatct agataatgca      120
tctggtcctg gaggttatgg cccaggaagc caaggaccat ctggtccagg aggatatggt      180
ccaggcggac ctggctctag tgcagcagct gccgcagcag ctgcatctgg tcctggaggt      240
tatggcccag gaagccaagg accatctggt ccaggaggat atggtccagg cggacctggc      300
tctagtgcag cagctgccgc agcagctgca tctggtcctg gaggttatgg cccaggaagc      360
caaggaccat ctggtccagg aggatatggt ccaggcggac ctggctctag tgcagcagct      420
gccgcagcag ctgcatctgg tcctggaggt tatggcccag gaagccaagg accatctggt      480
ccaggaggat atggtccagg cggacctggc tctagtgcag cagctgccgc agcagctgca      540
```

```
tctggtcctg gaggttatgg cccaggaagc caaggaccat ctggtccagg aggatatggt    600
ccaggcggac ctggctctag tgcagcagct gccgcagcag ctgcatctgg tcctggaggt    660
tatggcccag gaagccaagg accatctggt ccaggaggat atggtccagg cggacctggc    720
tctagtgcag cagctgccgc agcagctgca tctggtcctg gaggttatgg cccaggaagc    780
caaggaccat ctggtccagg aggatatggt ccaggcggac ctggctctag tgcagcagct    840
gccgcagcag ctgcatctgg tcctggaggt tatggcccag gaagccaagg accatctggt    900
ccaggaggat atggtccagg cggacctggc tctagtgcag cagctgccgc agcagctgca    960
tctggtcctg gaggttatgg cccaggaagc caaggaccat ctggtccagg aggatatggt   1020
ccaggcggac ctggctctag tgcagcagct gccgcagcag ctgcatctgg tcctggaggt   1080
tatggcccag gaagccaagg accatctggt ccaggaggat atggtccagg cggacctggc   1140
tctagtgcag cagctgccgc agcagctgca tctggtcctg gaggttatgg cccaggaagc   1200
caaggaccat ctggtccagg aggatatggt ccaggcggac ctggctctag tgcagcagct   1260
gccgcagcag ctgcatctgg tcctggaggt tatggcccag gaagccaagg accatctggt   1320
ccaggaggat atggtccagg cggacctggc tctagtgcag cagctgccgc agcagctgca   1380
tctggtcctg gaggttatgg cccaggaagc caaggaccat ctggtccagg aggatatggt   1440
ccaggcggac ctggctctag tgcagcagct gccgcagcag ctgcatctgg tcctggaggt   1500
tatggcccag gaagccaagg accatctggt ccaggaggat atggtccagg cggacctggc   1560
tctagtgcag cagctgccgc agcagctgca tctggtcctg gaggttatgg cccaggaagc   1620
caaggaccat ctggtccagg aggatatggt ccaggcggac ctggctctag tgcagcagct   1680
gccgcagcag ctgcatctgg tcctggaggt tatggcccag gaagccaagg accatctggt   1740
ccaggaggat atggtccagg cggacctggc tctagtgcag cagctgccgc agcagctgca   1800
tctggtcctg gaggttatgg cccaggaagc caaggaccat ctggtccagg aggatatggt   1860
ccaggcggac ctggctctag tgcagcagct gccgcagcag ctgcatctgg tcctggaggt   1920
tatggcccag gaagccaagg accatctggt ccaggaggat atggtccagg cggacctggc   1980
tctagtgcag cagctgccgc agcagctgca tctggtcctg gaggttatgg cccaggaagc   2040
caaggaccat ctggtccagg aggatatggt ccaggcggac ctggctctag tgcagcagct   2100
gccgcagcag ctgcatctgg tcctggaggt tatggcccag gaagccaagg accatctggt   2160
ccaggaggat atggtccagg cggacctggc tctagtgcag cagctgccgc agcagctgca   2220
tctggtcctg gaggttatgg cccaggaagc caaggaccat ctggtccagg aggatatggt   2280
ccaggcggac ctggctctag tgcagcagct gccgcagcag ctgcatctgg tcctggaggt   2340
tatggcccag gaagccaagg accatctggt ccaggaggat atggtccagg cggacctggc   2400
tctagtgcag cagctgccgc agcagctgca tctggtcctg gaggttatgg cccaggaagc   2460
caaggaccat ctggtccagg aggatatggt ccaggcggac ctggctctag tgcagcagct   2520
gccgcagcag ctgcatctgg tcctggaggt tatggcccag gaagccaagg accatctggt   2580
ccaggaggat atggtccagg cggacctggc tctagtgcag cagctgccgc agcagctgca   2640
ggccctagtg gtcctggagc atatggccca tctccttctg cttccgcatc cgttgcagcc   2700
tctcgtttat cttcgcctgc agcctcgtct agagtgtctt ccgctgtatc gtctttagtg   2760
tctagcggac ctacgaatgg tgctgctgtt tctggagctt tgaatagttt agtatctcag   2820
attagtgcaa gtaatccagg tttatcggga tgtgatgctc ttgtgcaggc attattggaa   2880
ttagtgtctg ctcttgtggc aattctttca tctgcaagta ttggccaagt caacgtcagc   2940
```

```
tctgttagtc agtcaactca aatgattagc caagctcttt ca                  2982
```

<210> SEQ ID NO 23
<211> LENGTH: 3822
<212> TYPE: DNA
<213> ORGANISM: Artificial Sequence
<220> FEATURE:
<223> OTHER INFORMATION: DNA full sequence (N-term + 32 repeats + C-term)

<400> SEQUENCE: 23

```
atggattacg atatcccaac gaccgaaaac ctgtattttc agggcgccat ggatccggaa   60
ttcaaaggcc tacgtcgacg agctcaacta gtgcggccgc tttcgaatct agataatgca  120
tctggtcctg gaggttatgg cccaggaagc caaggaccat ctggtccagg aggatatggt  180
ccaggcggac ctggctctag tgcagcagct gccgcagcag ctgcatctgg tcctggaggt  240
tatggcccag gaagccaagg accatctggt ccaggaggat atggtccagg cggacctggc  300
tctagtgcag cagctgccgc agcagctgca tctggtcctg gaggttatgg cccaggaagc  360
caaggaccat ctggtccagg aggatatggt ccaggcggac ctggctctag tgcagcagct  420
gccgcagcag ctgcatctgg tcctggaggt tatggcccag gaagccaagg accatctggt  480
ccaggaggat atggtccagg cggacctggc tctagtgcag cagctgccgc agcagctgca  540
tctggtcctg gaggttatgg cccaggaagc caaggaccat ctggtccagg aggatatggt  600
ccaggcggac ctggctctag tgcagcagct gccgcagcag ctgcatctgg tcctggaggt  660
tatggcccag gaagccaagg accatctggt ccaggaggat atggtccagg cggacctggc  720
tctagtgcag cagctgccgc agcagctgca tctggtcctg gaggttatgg cccaggaagc  780
caaggaccat ctggtccagg aggatatggt ccaggcggac ctggctctag tgcagcagct  840
gccgcagcag ctgcatctgg tcctggaggt tatggcccag gaagccaagg accatctggt  900
ccaggaggat atggtccagg cggacctggc tctagtgcag cagctgccgc agcagctgca  960
tctggtcctg gaggttatgg cccaggaagc caaggaccat ctggtccagg aggatatggt 1020
ccaggcggac ctggctctag tgcagcagct gccgcagcag ctgcatctgg tcctggaggt 1080
tatggcccag gaagccaagg accatctggt ccaggaggat atggtccagg cggacctggc 1140
tctagtgcag cagctgccgc agcagctgca tctggtcctg gaggttatgg cccaggaagc 1200
caaggaccat ctggtccagg aggatatggt ccaggcggac ctggctctag tgcagcagct 1260
gccgcagcag ctgcatctgg tcctggaggt tatggcccag gaagccaagg accatctggt 1320
ccaggaggat atggtccagg cggacctggc tctagtgcag cagctgccgc agcagctgca 1380
tctggtcctg gaggttatgg cccaggaagc caaggaccat ctggtccagg aggatatggt 1440
ccaggcggac ctggctctag tgcagcagct gccgcagcag ctgcatctgg tcctggaggt 1500
tatggcccag gaagccaagg accatctggt ccaggaggat atggtccagg cggacctggc 1560
tctagtgcag cagctgccgc agcagctgca tctggtcctg gaggttatgg cccaggaagc 1620
caaggaccat ctggtccagg aggatatggt ccaggcggac ctggctctag tgcagcagct 1680
gccgcagcag ctgcatctgg tcctggaggt tatggcccag gaagccaagg accatctggt 1740
ccaggaggat atggtccagg cggacctggc tctagtgcag cagctgccgc agcagctgca 1800
tctggtcctg gaggttatgg cccaggaagc caaggaccat ctggtccagg aggatatggt 1860
ccaggcggac ctggctctag tgcagcagct gccgcagcag ctgcatctgg tcctggaggt 1920
tatggcccag gaagccaagg accatctggt ccaggaggat atggtccagg cggacctggc 1980
tctagtgcag cagctgccgc agcagctgca tctggtcctg gaggttatgg cccaggaagc 2040
```

```
caaggaccat ctggtccagg aggatatggt ccaggcggac ctggctctag tgcagcagct    2100
gccgcagcag ctgcatctgg tcctggaggt tatgcccag gaagccaagg accatctggt     2160
ccaggaggat atggtccagg cggacctggc tctagtgcag cagctgccgc agcagctgca    2220
tctggtcctg gaggttatgg cccaggaagc caaggaccat ctggtccagg aggatatggt    2280
ccaggcggac ctggctctag tgcagcagct gccgcagcag ctgcatctgg tcctggaggt    2340 tatgcccag gaagccaagg accatctggt ccaggaggat atggtccagg cggacctggc    2400
tctagtgcag cagctgccgc agcagctgca tctggtcctg gaggttatgg cccaggaagc    2460
caaggaccat ctggtccagg aggatatggt ccaggcggac ctggctctag tgcagcagct    2520
gccgcagcag ctgcatctgg tcctggaggt tatgcccag gaagccaagg accatctggt     2580
ccaggaggat atggtccagg cggacctggc tctagtgcag cagctgccgc agcagctgca    2640
tctggtcctg gaggttatgg cccaggaagc caaggaccat ctggtccagg aggatatggt    2700
ccaggcggac ctggctctag tgcagcagct gccgcagcag ctgcatctgg tcctggaggt    2760 tatgcccag gaagccaagg accatctggt ccaggaggat atggtccagg cggacctggc    2820
tctagtgcag cagctgccgc agcagctgca tctggtcctg gaggttatgg cccaggaagc    2880
caaggaccat ctggtccagg aggatatggt ccaggcggac ctggctctag tgcagcagct    2940
gccgcagcag ctgcatctgg tcctggaggt tatgcccag gaagccaagg accatctggt     3000
ccaggaggat atggtccagg cggacctggc tctagtgcag cagctgccgc agcagctgca    3060
tctggtcctg gaggttatgg cccaggaagc caaggaccat ctggtccagg aggatatggt    3120
ccaggcggac ctggctctag tgcagcagct gccgcagcag ctgcatctgg tcctggaggt    3180 tatgcccag gaagccaagg accatctggt ccaggaggat atggtccagg cggacctggc    3240
tctagtgcag cagctgccgc agcagctgca tctggtcctg gaggttatgg cccaggaagc    3300
caaggaccat ctggtccagg aggatatggt ccaggcggac ctggctctag tgcagcagct    3360
gccgcagcag ctgcatctgg tcctggaggt tatgcccag gaagccaagg accatctggt     3420
ccaggaggat atggtccagg cggacctggc tctagtgcag cagctgccgc agcagctgca    3480
ggccctagtg gtcctggagc atatggccca tctccttctg cttccgcatc cgttgcagcc    3540
tctcgtttat cttcgcctgc agcctcgtct agagtgtctt ccgctgtatc gtctttagtg    3600
tctagcggac ctacgaatgg tgctgctgtt tctggagctt tgaatagttt agtatctcag    3660
attagtgcaa gtaatccagg tttatcggga tgtgatgctc ttgtgcaggc attattggaa    3720
ttagtgtctg ctcttgtggc aattctttca tctgcaagta ttggccaagt caacgtcagc    3780
tctgttagtc agtcaactca aatgattagc caagctcttt ca                       3822
```

<210> SEQ ID NO 24
<211> LENGTH: 223
<212> TYPE: PRT
<213> ORGANISM: Artificial
<220> FEATURE:
<223> OTHER INFORMATION: Full sequence (N-domain + 2 repeats +
      C-domain) of polymerizing synthetic protein

<400> SEQUENCE: 24

```
Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
                20                  25                  30

Leu Ser Asn Leu Asp Asn Ala Ser Gly Pro Gly Gly Tyr Gly Pro Gly
            35                  40                  45
```

Ser Gln Gly Pro Ser Gly Pro Gly Gly Tyr Gly Pro Gly Gly Pro Gly
    50                  55                  60

Ser Ser Ala Ala Ala Ala Ala Ala Ala Ser Gly Pro Gly Gly Tyr
65                  70                  75                  80

Gly Pro Gly Ser Gln Gly Pro Ser Gly Pro Gly Gly Tyr Gly Pro Gly
                85                  90                  95

Gly Pro Gly Ser Ser Ala Ala Ala Ala Ala Ala Ala Gly Pro Ser
                100                 105                 110

Gly Pro Gly Ala Tyr Gly Pro Ser Pro Ser Ala Ser Ala Ser Val Ala
                115                 120                 125

Ala Ser Arg Leu Ser Ser Pro Ala Ala Ser Ser Arg Val Ser Ser Ala
                130                 135                 140

Val Ser Ser Leu Val Ser Ser Gly Pro Thr Asn Gly Ala Ala Val Ser
145                 150                 155                 160

Gly Ala Leu Asn Ser Leu Val Ser Gln Ile Ser Ala Ser Asn Pro Gly
                165                 170                 175

Leu Ser Gly Cys Asp Ala Leu Val Gln Ala Leu Leu Glu Leu Val Ser
                180                 185                 190

Ala Leu Val Ala Ile Leu Ser Ser Ala Ser Ile Gly Gln Val Asn Val
                195                 200                 205

Ser Ser Val Ser Gln Ser Thr Gln Met Ile Ser Gln Ala Leu Ser
210                 215                 220

<210> SEQ ID NO 25
<211> LENGTH: 293
<212> TYPE: PRT
<213> ORGANISM: Artificial Sequence
<220> FEATURE:
<223> OTHER INFORMATION: Full sequence (N-domain + 4 repeats + C-domain) of polymerizing synthetic protein

<400> SEQUENCE: 25

Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
                20                  25                  30

Leu Ser Asn Leu Asp Asn Ala Ser Gly Pro Gly Gly Tyr Gly Pro Gly
                35                  40                  45

Ser Gln Gly Pro Ser Gly Pro Gly Gly Tyr Gly Pro Gly Gly Pro Gly
    50                  55                  60

Ser Ser Ala Ala Ala Ala Ala Ala Ala Ser Gly Pro Gly Gly Tyr
65                  70                  75                  80

Gly Pro Gly Ser Gln Gly Pro Ser Gly Pro Gly Gly Tyr Gly Pro Gly
                85                  90                  95

Gly Pro Gly Ser Ser Ala Ala Ala Ala Ala Ala Ala Ser Gly Pro
                100                 105                 110

Gly Gly Tyr Gly Pro Gly Ser Gln Gly Pro Ser Gly Pro Gly Gly Tyr
                115                 120                 125

Gly Pro Gly Gly Pro Gly Ser Ser Ala Ala Ala Ala Ala Ala Ala
                130                 135                 140

Ser Gly Pro Gly Gly Tyr Gly Pro Gly Ser Gln Gly Pro Ser Gly Pro
145                 150                 155                 160

Gly Gly Tyr Gly Pro Gly Gly Pro Gly Ser Ser Ala Ala Ala Ala
                165                 170                 175

Ala Ala Ala Gly Pro Ser Gly Pro Gly Ala Tyr Gly Pro Ser Pro Ser
                180                 185                 190

```
Ala Ser Ala Ser Val Ala Ala Ser Arg Leu Ser Ser Pro Ala Ala Ser
            195                 200                 205

Ser Arg Val Ser Ser Ala Val Ser Ser Leu Val Ser Ser Gly Pro Thr
        210                 215                 220

Asn Gly Ala Ala Val Ser Gly Ala Leu Asn Ser Leu Val Ser Gln Ile
225                 230                 235                 240

Ser Ala Ser Asn Pro Gly Leu Ser Gly Cys Asp Ala Leu Val Gln Ala
            245                 250                 255

Leu Leu Glu Leu Val Ser Ala Leu Val Ala Ile Leu Ser Ser Ala Ser
        260                 265                 270

Ile Gly Gln Val Asn Val Ser Ser Val Ser Gln Ser Thr Gln Met Ile
    275                 280                 285

Ser Gln Ala Leu Ser
    290

<210> SEQ ID NO 26
<211> LENGTH: 433
<212> TYPE: PRT
<213> ORGANISM: Artificial Sequence
<220> FEATURE:
<223> OTHER INFORMATION: Full sequence (N-domain + 8 repeats +
      C-domain) of polymerizing  synthetic protein

<400> SEQUENCE: 26

Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
            20                  25                  30

Leu Ser Asn Leu Asp Asn Ala Ser Gly Pro Gly Gly Tyr Gly Pro Gly
        35                  40                  45

Ser Gln Gly Pro Ser Gly Pro Gly Gly Tyr Gly Pro Gly Gly Pro Gly
    50                  55                  60

Ser Ser Ala Ala Ala Ala Ala Ala Ala Ser Gly Pro Gly Gly Tyr
65                  70                  75                  80

Gly Pro Gly Ser Gln Gly Pro Ser Gly Pro Gly Gly Tyr Gly Pro Gly
            85                  90                  95

Gly Pro Gly Ser Ser Ala Ala Ala Ala Ala Ala Ala Ser Gly Pro
            100                 105                 110

Gly Gly Tyr Gly Pro Gly Ser Gln Gly Pro Ser Gly Pro Gly Gly Tyr
        115                 120                 125

Gly Pro Gly Gly Pro Gly Ser Ser Ala Ala Ala Ala Ala Ala Ala
    130                 135                 140

Ser Gly Pro Gly Gly Tyr Gly Pro Gly Ser Gln Gly Pro Ser Gly Pro
145                 150                 155                 160

Gly Gly Tyr Gly Pro Gly Gly Pro Gly Ser Ser Ala Ala Ala Ala
            165                 170                 175

Ala Ala Ala Ser Gly Pro Gly Gly Tyr Gly Pro Gly Ser Gln Gly Pro
            180                 185                 190

Ser Gly Pro Gly Gly Tyr Gly Pro Gly Gly Pro Gly Ser Ser Ala Ala
        195                 200                 205

Ala Ala Ala Ala Ala Ser Gly Pro Gly Gly Tyr Gly Pro Gly Ser
    210                 215                 220

Gln Gly Pro Ser Gly Pro Gly Gly Tyr Gly Pro Gly Gly Pro Gly Ser
225                 230                 235                 240

Ser Ala Ala Ala Ala Ala Ala Ala Ser Gly Pro Gly Gly Tyr Gly
            245                 250                 255
```

```
Pro Gly Ser Gln Gly Pro Ser Gly Gly Tyr Gly Pro Gly Gly
            260                 265                 270

Pro Gly Ser Ser Ala Ala Ala Ala Ala Ala Ala Ser Gly Pro Gly
            275                 280                 285

Gly Tyr Gly Pro Gly Ser Gln Gly Pro Ser Gly Pro Gly Tyr Gly
            290                 295                 300

Pro Gly Gly Pro Gly Ser Ser Ala Ala Ala Ala Ala Ala Ala Gly
305                 310                 315                 320

Pro Ser Gly Pro Gly Ala Tyr Gly Pro Ser Pro Ser Ala Ser Ala
                325                 330                 335

Val Ala Ala Ser Arg Leu Ser Ser Pro Ala Ala Ser Ser Arg Val Ser
                340                 345                 350

Ser Ala Val Ser Ser Leu Val Ser Ser Gly Pro Thr Asn Gly Ala Ala
                355                 360                 365

Val Ser Gly Ala Leu Asn Ser Leu Val Ser Gln Ile Ser Ala Ser Asn
                370                 375                 380

Pro Gly Leu Ser Gly Cys Asp Ala Leu Val Gln Ala Leu Leu Glu Leu
385                 390                 395                 400

Val Ser Ala Leu Val Ala Ile Leu Ser Ser Ala Ser Ile Gly Gln Val
                405                 410                 415

Asn Val Ser Ser Val Ser Gln Ser Thr Gln Met Ile Ser Gln Ala Leu
                420                 425                 430

Ser

<210> SEQ ID NO 27
<211> LENGTH: 573
<212> TYPE: PRT
<213> ORGANISM: Artificial Sequence
<220> FEATURE:
<223> OTHER INFORMATION: Full sequence (N-domain + 12 repeats +
      C-domain) of polymerizing synthetic protein

<400> SEQUENCE: 27

Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
            20                  25                  30

Leu Ser Asn Leu Asp Asn Ala Ser Gly Pro Gly Gly Tyr Gly Pro Gly
        35                  40                  45

Ser Gln Gly Pro Ser Gly Pro Gly Gly Tyr Gly Pro Gly Gly Pro Gly
    50                  55                  60

Ser Ser Ala Ala Ala Ala Ala Ala Ala Ser Gly Pro Gly Gly Tyr
65                  70                  75                  80

Gly Pro Gly Ser Gln Gly Pro Ser Gly Pro Gly Tyr Gly Pro Gly
                85                  90                  95

Gly Pro Gly Ser Ser Ala Ala Ala Ala Ala Ala Ala Ser Gly Pro
            100                 105                 110

Gly Gly Tyr Gly Pro Gly Ser Gln Gly Pro Ser Gly Pro Gly Gly Tyr
        115                 120                 125

Gly Pro Gly Gly Pro Gly Ser Ser Ala Ala Ala Ala Ala Ala Ala
    130                 135                 140

Ser Gly Pro Gly Gly Tyr Gly Pro Gly Ser Gln Gly Pro Ser Gly Pro
145                 150                 155                 160

Gly Gly Tyr Gly Pro Gly Gly Pro Gly Ser Ser Ala Ala Ala Ala Ala
                165                 170                 175
```

Ala Ala Ala Ser Gly Pro Gly Gly Tyr Gly Pro Gly Ser Gln Gly Pro
            180                 185                 190

Ser Gly Pro Gly Gly Tyr Gly Pro Gly Pro Gly Ser Ser Ala Ala
        195                 200                 205

Ala Ala Ala Ala Ala Ala Ser Gly Pro Gly Gly Tyr Gly Pro Gly Ser
            210                 215                 220

Gln Gly Pro Ser Gly Pro Gly Gly Tyr Gly Pro Gly Gly Pro Gly Ser
225                 230                 235                 240

Ser Ala Ala Ala Ala Ala Ala Ala Ser Gly Pro Gly Gly Tyr Gly
            245                 250                 255

Pro Gly Ser Gln Gly Pro Ser Gly Pro Gly Gly Tyr Gly Pro Gly Gly
        260                 265                 270

Pro Gly Ser Ser Ala Ala Ala Ala Ala Ala Ala Ser Gly Pro Gly
            275                 280                 285

Gly Tyr Gly Pro Gly Ser Gln Gly Pro Ser Gly Pro Gly Gly Tyr Gly
        290                 295                 300

Pro Gly Gly Pro Gly Ser Ser Ala Ala Ala Ala Ala Ala Ala Ser
305                 310                 315                 320

Gly Pro Gly Gly Tyr Gly Pro Gly Ser Gln Gly Pro Ser Gly Pro Gly
            325                 330                 335

Gly Tyr Gly Pro Gly Gly Pro Gly Ser Ser Ala Ala Ala Ala Ala
        340                 345                 350

Ala Ala Ser Gly Pro Gly Gly Tyr Gly Pro Gly Ser Gln Gly Pro Ser
            355                 360                 365

Gly Pro Gly Gly Tyr Gly Pro Gly Gly Pro Gly Ser Ser Ala Ala Ala
        370                 375                 380

Ala Ala Ala Ala Ser Gly Pro Gly Gly Tyr Gly Pro Gly Ser Gln
385                 390                 395                 400

Gly Pro Ser Gly Pro Gly Gly Tyr Gly Pro Gly Gly Pro Gly Ser Ser
            405                 410                 415

Ala Ala Ala Ala Ala Ala Ala Ser Gly Pro Gly Gly Tyr Gly Pro
        420                 425                 430

Gly Ser Gln Gly Pro Ser Gly Pro Gly Gly Tyr Gly Pro Gly Gly Pro
        435                 440                 445

Gly Ser Ser Ala Ala Ala Ala Ala Ala Ala Gly Pro Ser Gly Pro
        450                 455                 460

Gly Ala Tyr Gly Pro Ser Pro Ser Ala Ser Ala Ser Val Ala Ala Ser
465                 470                 475                 480

Arg Leu Ser Ser Pro Ala Ala Ser Ser Arg Val Ser Ser Ala Val Ser
            485                 490                 495

Ser Leu Val Ser Ser Gly Pro Thr Asn Gly Ala Ala Val Ser Gly Ala
        500                 505                 510

Leu Asn Ser Leu Val Ser Gln Ile Ser Ala Ser Asn Pro Gly Leu Ser
            515                 520                 525

Gly Cys Asp Ala Leu Val Gln Ala Leu Leu Glu Leu Val Ser Ala Leu
        530                 535                 540

Val Ala Ile Leu Ser Ser Ala Ser Ile Gly Gln Val Asn Val Ser Ser
545                 550                 555                 560

Val Ser Gln Ser Thr Gln Met Ile Ser Gln Ala Leu Ser
            565                 570

<210> SEQ ID NO 28
<211> LENGTH: 713
<212> TYPE: PRT
<213> ORGANISM: Artificial Sequence

```
<220> FEATURE:
<223> OTHER INFORMATION: Full sequence (N-domain + 16 repeats +
      C-domain) of polymerizing synthetic protein

<400> SEQUENCE: 28

Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
                20                  25                  30

Leu Ser Asn Leu Asp Asn Ala Ser Gly Pro Gly Gly Tyr Gly Pro Gly
            35                  40                  45

Ser Gln Gly Pro Ser Gly Pro Gly Gly Tyr Gly Pro Gly Gly Pro Gly
50                  55                  60

Ser Ser Ala Ala Ala Ala Ala Ala Ala Ser Gly Pro Gly Gly Tyr
65                  70                  75                  80

Gly Pro Gly Ser Gln Gly Pro Ser Gly Pro Gly Gly Tyr Gly Pro Gly
                85                  90                  95

Gly Pro Gly Ser Ser Ala Ala Ala Ala Ala Ala Ala Ser Gly Pro
                100                 105                 110

Gly Gly Tyr Gly Pro Gly Ser Gln Gly Pro Ser Gly Pro Gly Gly Tyr
            115                 120                 125

Gly Pro Gly Gly Pro Gly Ser Ser Ala Ala Ala Ala Ala Ala Ala
130                 135                 140

Ser Gly Pro Gly Gly Tyr Gly Pro Gly Ser Gln Gly Pro Ser Gly Pro
145                 150                 155                 160

Gly Gly Tyr Gly Pro Gly Gly Pro Gly Ser Ser Ala Ala Ala Ala
                165                 170                 175

Ala Ala Ala Ser Gly Pro Gly Gly Tyr Gly Pro Gly Ser Gln Gly Pro
                180                 185                 190

Ser Gly Pro Gly Gly Tyr Gly Pro Gly Gly Pro Gly Ser Ser Ala Ala
                195                 200                 205

Ala Ala Ala Ala Ala Ala Ser Gly Pro Gly Gly Tyr Gly Pro Gly Ser
                210                 215                 220

Gln Gly Pro Ser Gly Pro Gly Gly Tyr Gly Pro Gly Gly Pro Gly Ser
225                 230                 235                 240

Ser Ala Ala Ala Ala Ala Ala Ala Ser Gly Pro Gly Gly Tyr Gly
                245                 250                 255

Pro Gly Ser Gln Gly Pro Ser Gly Pro Gly Gly Tyr Gly Pro Gly Gly
                260                 265                 270

Pro Gly Ser Ser Ala Ala Ala Ala Ala Ala Ala Ser Gly Pro Gly
                275                 280                 285

Gly Tyr Gly Pro Gly Ser Gln Gly Pro Ser Gly Pro Gly Gly Tyr Gly
            290                 295                 300

Pro Gly Gly Pro Gly Ser Ser Ala Ala Ala Ala Ala Ala Ala Ser
305                 310                 315                 320

Gly Pro Gly Gly Tyr Gly Pro Gly Ser Gln Gly Pro Ser Gly Pro Gly
                325                 330                 335

Gly Tyr Gly Pro Gly Gly Pro Gly Ser Ser Ala Ala Ala Ala Ala
                340                 345                 350

Ala Ala Ser Gly Pro Gly Gly Tyr Gly Pro Gly Ser Gln Gly Pro Ser
            355                 360                 365

Gly Pro Gly Gly Tyr Gly Pro Gly Gly Pro Gly Ser Ser Ala Ala Ala
                370                 375                 380

Ala Ala Ala Ala Ala Ser Gly Pro Gly Gly Tyr Gly Pro Gly Ser Gln
385                 390                 395                 400
```

-continued

Gly Pro Ser Gly Pro Gly Gly Tyr Gly Pro Gly Gly Pro Ser Ser
            405                 410                 415

Ala Ala Ala Ala Ala Ala Ala Ser Gly Pro Gly Gly Tyr Gly Pro
            420                 425                 430

Gly Ser Gln Gly Pro Ser Gly Gly Tyr Gly Pro Gly Gly Pro
        435                 440                 445

Gly Ser Ser Ala Ala Ala Ala Ala Ala Ala Ser Gly Pro Gly Gly
    450                 455                 460

Tyr Gly Pro Gly Ser Gln Gly Pro Ser Gly Gly Tyr Gly Pro
465                 470                 475                 480

Gly Gly Pro Gly Ser Ser Ala Ala Ala Ala Ala Ala Ala Ser Gly
            485                 490                 495

Pro Gly Gly Tyr Gly Pro Gly Ser Gln Gly Pro Ser Gly Pro Gly Gly
            500                 505                 510

Tyr Gly Pro Gly Gly Pro Gly Ser Ser Ala Ala Ala Ala Ala Ala
            515                 520                 525

Ala Ser Gly Pro Gly Gly Tyr Gly Pro Gly Ser Gln Gly Pro Ser Gly
            530                 535                 540

Pro Gly Gly Tyr Gly Pro Gly Gly Pro Gly Ser Ser Ala Ala Ala Ala
545                 550                 555                 560

Ala Ala Ala Ala Ser Gly Pro Gly Gly Tyr Gly Pro Gly Ser Gln Gly
            565                 570                 575

Pro Ser Gly Pro Gly Gly Tyr Gly Pro Gly Gly Pro Gly Ser Ser Ala
            580                 585                 590

Ala Ala Ala Ala Ala Ala Gly Pro Ser Gly Pro Gly Ala Tyr Gly
            595                 600                 605

Pro Ser Pro Ser Ala Ser Ala Ser Val Ala Ala Ser Arg Leu Ser Ser
            610                 615                 620

Pro Ala Ala Ser Ser Arg Val Ser Ser Ala Val Ser Ser Leu Val Ser
625                 630                 635                 640

Ser Gly Pro Thr Asn Gly Ala Ala Val Ser Gly Ala Leu Asn Ser Leu
            645                 650                 655

Val Ser Gln Ile Ser Ala Ser Asn Pro Gly Leu Ser Gly Cys Asp Ala
            660                 665                 670

Leu Val Gln Ala Leu Leu Glu Leu Val Ser Ala Leu Val Ala Ile Leu
            675                 680                 685

Ser Ser Ala Ser Ile Gly Gln Val Asn Val Ser Ser Val Ser Gln Ser
            690                 695                 700

Thr Gln Met Ile Ser Gln Ala Leu Ser
705                 710

<210> SEQ ID NO 29
<211> LENGTH: 853
<212> TYPE: PRT
<213> ORGANISM: Artificial Sequence
<220> FEATURE:
<223> OTHER INFORMATION: Full sequence (N-domain + 20 repeats +
      C-domain) of polymerizing synthetic protein

<400> SEQUENCE: 29

Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
            20                  25                  30

Leu Ser Asn Leu Asp Asn Ala Ser Gly Pro Gly Gly Tyr Gly Pro Gly
        35                  40                  45

```
Ser Gln Gly Pro Ser Gly Pro Gly Tyr Gly Pro Gly Gly Pro Gly
    50                  55                  60
Ser Ser Ala Ala Ala Ala Ala Ala Ala Ser Gly Pro Gly Gly Tyr
65                  70                  75                  80
Gly Pro Gly Ser Gln Gly Pro Ser Gly Pro Gly Tyr Gly Pro Gly
                85                  90                  95
Gly Pro Gly Ser Ser Ala Ala Ala Ala Ala Ala Ala Ser Gly Pro
            100                 105                 110
Gly Gly Tyr Gly Pro Gly Ser Gln Gly Pro Ser Gly Pro Gly Tyr
        115                 120                 125
Gly Pro Gly Gly Pro Gly Ser Ser Ala Ala Ala Ala Ala Ala Ala
    130                 135                 140
Ser Gly Pro Gly Gly Tyr Gly Pro Gly Ser Gln Gly Pro Ser Gly Pro
145                 150                 155                 160
Gly Gly Tyr Gly Pro Gly Gly Pro Gly Ser Ser Ala Ala Ala Ala
                165                 170                 175
Ala Ala Ala Ser Gly Pro Gly Gly Tyr Gly Pro Gly Ser Gln Gly Pro
            180                 185                 190
Ser Gly Pro Gly Gly Tyr Gly Pro Gly Gly Pro Gly Ser Ser Ala Ala
        195                 200                 205
Ala Ala Ala Ala Ala Ser Gly Pro Gly Gly Tyr Gly Pro Gly Ser
    210                 215                 220
Gln Gly Pro Ser Gly Pro Gly Tyr Gly Pro Gly Gly Pro Gly Ser
225                 230                 235                 240
Ser Ala Ala Ala Ala Ala Ala Ala Ser Gly Pro Gly Gly Tyr Gly
                245                 250                 255
Pro Gly Ser Gln Gly Pro Ser Gly Pro Gly Gly Tyr Gly Pro Gly Gly
            260                 265                 270
Pro Gly Ser Ser Ala Ala Ala Ala Ala Ala Ala Ser Gly Pro Gly
        275                 280                 285
Gly Tyr Gly Pro Gly Ser Gln Gly Pro Ser Gly Pro Gly Gly Tyr Gly
    290                 295                 300
Pro Gly Gly Pro Gly Ser Ser Ala Ala Ala Ala Ala Ala Ala Ser
305                 310                 315                 320
Gly Pro Gly Gly Tyr Gly Pro Gly Ser Gln Gly Pro Ser Gly Pro Gly
                325                 330                 335
Gly Tyr Gly Pro Gly Gly Pro Gly Ser Ser Ala Ala Ala Ala Ala
            340                 345                 350
Ala Ala Ser Gly Pro Gly Gly Tyr Gly Pro Gly Ser Gln Gly Pro Ser
        355                 360                 365
Gly Pro Gly Gly Tyr Gly Pro Gly Gly Pro Gly Ser Ser Ala Ala Ala
    370                 375                 380
Ala Ala Ala Ala Ala Ser Gly Pro Gly Gly Tyr Gly Pro Gly Ser Gln
385                 390                 395                 400
Gly Pro Ser Gly Pro Gly Gly Tyr Gly Pro Gly Gly Pro Gly Ser Ser
                405                 410                 415
Ala Ala Ala Ala Ala Ala Ala Ser Gly Pro Gly Gly Tyr Gly Pro
            420                 425                 430
Gly Ser Gln Gly Pro Ser Gly Pro Gly Gly Tyr Gly Pro Gly Gly Pro
        435                 440                 445
Gly Ser Ser Ala Ala Ala Ala Ala Ala Ala Ser Gly Pro Gly Gly
    450                 455                 460
Tyr Gly Pro Gly Ser Gln Gly Pro Ser Gly Pro Gly Gly Tyr Gly Pro
```

```
            465                 470                 475                 480
Gly Gly Pro Gly Ser Ser Ala Ala Ala Ala Ala Ala Ala Ala Ser Gly
                485                 490                 495
Pro Gly Gly Tyr Gly Pro Gly Ser Gln Gly Pro Ser Gly Pro Gly Gly
            500                 505                 510
Tyr Gly Pro Gly Gly Pro Gly Ser Ser Ala Ala Ala Ala Ala Ala Ala
        515                 520                 525
Ala Ser Gly Pro Gly Gly Tyr Gly Pro Gly Ser Gln Gly Pro Ser Gly
    530                 535                 540
Pro Gly Gly Tyr Gly Pro Gly Gly Pro Gly Ser Ser Ala Ala Ala Ala
545                 550                 555                 560
Ala Ala Ala Ala Ser Gly Pro Gly Gly Tyr Gly Pro Gly Ser Gln Gly
                565                 570                 575
Pro Ser Gly Pro Gly Gly Tyr Gly Pro Gly Gly Pro Gly Ser Ser Ala
            580                 585                 590
Ala Ala Ala Ala Ala Ala Ala Ser Gly Pro Gly Gly Tyr Gly Pro Gly
        595                 600                 605
Ser Gln Gly Pro Ser Gly Pro Gly Gly Tyr Gly Pro Gly Gly Pro Gly
    610                 615                 620
Ser Ser Ala Ala Ala Ala Ala Ala Ala Ser Gly Pro Gly Gly Tyr
625                 630                 635                 640
Gly Pro Gly Ser Gln Gly Pro Ser Gly Pro Gly Gly Tyr Gly Pro Gly
                645                 650                 655
Gly Pro Gly Ser Ser Ala Ala Ala Ala Ala Ala Ala Ser Gly Pro
            660                 665                 670
Gly Gly Tyr Gly Pro Gly Ser Gln Gly Pro Ser Gly Pro Gly Gly Tyr
        675                 680                 685
Gly Pro Gly Gly Pro Gly Ser Ser Ala Ala Ala Ala Ala Ala Ala
    690                 695                 700
Ser Gly Pro Gly Gly Tyr Gly Pro Gly Ser Gln Gly Pro Ser Gly Pro
705                 710                 715                 720
Gly Gly Tyr Gly Pro Gly Gly Pro Gly Ser Ser Ala Ala Ala Ala Ala
                725                 730                 735
Ala Ala Ala Gly Pro Ser Gly Pro Gly Ala Tyr Gly Pro Ser Pro Ser
            740                 745                 750
Ala Ser Ala Ser Val Ala Ala Ser Arg Leu Ser Ser Pro Ala Ala Ser
        755                 760                 765
Ser Arg Val Ser Ser Ala Val Ser Ser Leu Val Ser Ser Gly Pro Thr
    770                 775                 780
Asn Gly Ala Ala Val Ser Gly Ala Leu Asn Ser Leu Val Ser Gln Ile
785                 790                 795                 800
Ser Ala Ser Asn Pro Gly Leu Ser Gly Cys Asp Ala Leu Val Gln Ala
                805                 810                 815
Leu Leu Glu Leu Val Ser Ala Leu Val Ala Ile Leu Ser Ser Ala Ser
            820                 825                 830
Ile Gly Gln Val Asn Val Ser Ser Val Ser Gln Ser Thr Gln Met Ile
        835                 840                 845
Ser Gln Ala Leu Ser
    850

<210> SEQ ID NO 30
<211> LENGTH: 993
<212> TYPE: PRT
<213> ORGANISM: Artificial Sequence
<220> FEATURE:
```

<223> OTHER INFORMATION: Full sequence (N-domain + 24 repeats + C-domain) of polymerizing synthetic protein

<400> SEQUENCE: 30

```
Asp Tyr Asp Ile Pro Thr Thr Glu Asn Leu Tyr Phe Gln Gly Ala Met
1               5                  10                  15

Asp Pro Glu Phe Lys Gly Leu Arg Arg Arg Ala Gln Leu Val Arg Pro
                20                  25                  30

Leu Ser Asn Leu Asp Asn Ala Ser Gly Pro Gly Gly Tyr Gly Pro Gly
                35                  40                  45

Ser Gln Gly Pro Ser Gly Pro Gly Gly Tyr Gly Pro Gly Gly Pro Gly
        50                  55                  60

Ser Ser Ala Ala Ala Ala Ala Ala Ala Ser Gly Pro Gly Gly Tyr
65                  70                  75                  80

Gly Pro Gly Ser Gln Gly Pro Ser Gly Pro Gly Gly Tyr Gly Pro Gly
                85                  90                  95

Gly Pro Gly Ser Ser Ala Ala Ala Ala Ala Ala Ala Ser Gly Pro
                100                 105                 110

Gly Gly Tyr Gly Pro Gly Ser Gln Gly Pro Ser Gly Pro Gly Gly Tyr
                115                 120                 125

Gly Pro Gly Gly Pro Gly Ser Ser Ala Ala Ala Ala Ala Ala Ala
                130                 135                 140

Ser Gly Pro Gly Gly Tyr Gly Pro Gly Ser Gln Gly Pro Ser Gly Pro
145                 150                 155                 160

Gly Gly Tyr Gly Pro Gly Gly Pro Gly Ser Ser Ala Ala Ala Ala
                165                 170                 175

Ala Ala Ala Ser Gly Pro Gly Gly Tyr Gly Pro Gly Ser Gln Gly Pro
                180                 185                 190

Ser Gly Pro Gly Gly Tyr Gly Pro Gly Gly Pro Gly Ser Ser Ala Ala
                195                 200                 205

Ala Ala Ala Ala Ala Ser Gly Pro Gly Gly Tyr Gly Pro Gly Ser
                210                 215                 220

Gln Gly Pro Ser Gly Pro Gly Gly Tyr Gly Pro Gly Gly Pro Gly Ser
225                 230                 235                 240

Ser Ala Ala Ala Ala Ala Ala Ala Ser Gly Pro Gly Gly Tyr Gly
                245                 250                 255

Pro Gly Ser Gln Gly Pro Ser Gly Pro Gly Gly Tyr Gly Pro Gly Gly
                260                 265                 270

Pro Gly Ser Ser Ala Ala Ala Ala Ala Ala Ala Ser Gly Pro Gly
                275                 280                 285

Gly Tyr Gly Pro Gly Ser Gln Gly Pro Ser Gly Pro Gly Gly Tyr Gly
                290                 295                 300

Pro Gly Gly Pro Gly Ser Ser Ala Ala Ala Ala Ala Ala Ala Ser
305                 310                 315                 320

Gly Pro Gly Gly Tyr Gly Pro Gly Ser Gln Gly Pro Ser Gly Pro Gly
                325                 330                 335

Gly Tyr Gly Pro Gly Gly Pro Gly Ser Ser Ala Ala Ala Ala Ala
                340                 345                 350

Ala Ala Ser Gly Pro Gly Gly Tyr Gly Pro Gly Ser Gln Gly Pro Ser
                355                 360                 365

Gly Pro Gly Gly Tyr Gly Pro Gly Gly Pro Gly Ser Ser Ala Ala Ala
                370                 375                 380

Ala Ala Ala Ala Ser Gly Pro Gly Gly Tyr Gly Pro Gly Ser Gln
385                 390                 395                 400
```

-continued

Gly Pro Ser Gly Pro Gly Gly Tyr Gly Pro Gly Pro Gly Ser Ser
                405                     410                     415

Ala Ala Ala Ala Ala Ala Ala Ser Gly Pro Gly Gly Tyr Gly Pro
                420                     425                     430

Gly Ser Gln Gly Pro Ser Gly Pro Gly Gly Tyr Gly Pro Gly Pro
                435                     440                     445

Gly Ser Ser Ala Ala Ala Ala Ala Ala Ala Ser Gly Pro Gly Gly
                450                     455                     460

Tyr Gly Pro Gly Ser Gln Gly Pro Ser Gly Pro Gly Gly Tyr Gly Pro
465                     470                     475                     480

Gly Gly Pro Gly Ser Ser Ala Ala Ala Ala Ala Ala Ala Ser Gly
                485                     490                     495

Pro Gly Gly Tyr Gly Pro Gly Ser Gln Gly Pro Ser Gly Pro Gly
                500                     505                     510

Tyr Gly Pro Gly Gly Pro Gly Ser Ser Ala Ala Ala Ala Ala Ala
                515                     520                     525

Ala Ser Gly Pro Gly Gly Tyr Gly Pro Gly Ser Gln Gly Pro Ser Gly
                530                     535                     540

Pro Gly Gly Tyr Gly Pro Gly Pro Gly Ser Ser Ala Ala Ala Ala
545                     550                     555                     560

Ala Ala Ala Ala Ser Gly Pro Gly Gly Tyr Gly Pro Gly Ser Gln Gly
                565                     570                     575

Pro Ser Gly Pro Gly Gly Tyr Gly Pro Gly Pro Gly Ser Ser Ala
                580                     585                     590

Ala Ala Ala Ala Ala Ala Ser Gly Pro Gly Gly Tyr Gly Pro Gly
                595                     600                     605

Ser Gln Gly Pro Ser Gly Pro Gly Gly Tyr Gly Pro Gly Gly Pro Gly
                610                     615                     620

Ser Ser Ala Ala Ala Ala Ala Ala Ala Ser Gly Pro Gly Gly Tyr
625                     630                     635                     640

Gly Pro Gly Ser Gln Gly Pro Ser Gly Pro Gly Gly Tyr Gly Pro Gly
                645                     650                     655

Gly Pro Gly Ser Ser Ala Ala Ala Ala Ala Ala Ala Ser Gly Pro
                660                     665                     670

Gly Gly Tyr Gly Pro Gly Ser Gln Gly Pro Ser Gly Pro Gly Gly Tyr
                675                     680                     685

Gly Pro Gly Gly Pro Gly Ser Ser Ala Ala Ala Ala Ala Ala Ala
                690                     695                     700

Ser Gly Pro Gly Gly Tyr Gly Pro Gly Ser Gln Gly Pro Ser Gly Pro
705                     710                     715                     720

Gly Gly Tyr Gly Pro Gly Gly Pro Gly Ser Ser Ala Ala Ala Ala Ala
                725                     730                     735

Ala Ala Ala Ser Gly Pro Gly Gly Tyr Gly Pro Gly Ser Gln Gly Pro
                740                     745                     750

Ser Gly Pro Gly Gly Tyr Gly Pro Gly Gly Pro Gly Ser Ser Ala Ala
                755                     760                     765

Ala Ala Ala Ala Ala Ser Gly Pro Gly Gly Tyr Gly Pro Gly Ser
                770                     775                     780

Gln Gly Pro Ser Gly Pro Gly Gly Tyr Gly Pro Gly Gly Pro Gly Ser
785                     790                     795                     800

Ser Ala Ala Ala Ala Ala Ala Ala Ser Gly Pro Gly Gly Tyr Gly
                805                     810                     815

Pro Gly Ser Gln Gly Pro Ser Gly Pro Gly Gly Tyr Gly Pro Gly Gly
                820                     825                     830

```
Pro Gly Ser Ser Ala Ala Ala Ala Ala Ala Ser Gly Pro Gly
        835                 840                 845

Gly Tyr Gly Pro Gly Ser Gln Gly Pro Ser Gly Pro Gly Tyr Gly
        850                 855                 860

Pro Gly Gly Pro Gly Ser Ala Ala Ala Ala Ala Ala Ala Ala Gly
865                 870                 875                 880

Pro Ser Gly Pro Gly Ala Tyr Gly Pro Ser Pro Ser Ala Ser Ala Ser
                885                 890                 895

Val Ala Ala Ser Arg Leu Ser Ser Pro Ala Ala Ser Ser Arg Val Ser
                900                 905                 910

Ser Ala Val Ser Ser Leu Val Ser Ser Gly Pro Thr Asn Gly Ala Ala
                915                 920                 925

Val Ser Gly Ala Leu Asn Ser Leu Val Ser Gln Ile Ser Ala Ser Asn
                930                 935                 940

Pro Gly Leu Ser Gly Cys Asp Ala Leu Val Gln Ala Leu Leu Glu Leu
945                 950                 955                 960

Val Ser Ala Leu Val Ala Ile Leu Ser Ser Ala Ser Ile Gly Gln Val
                965                 970                 975

Asn Val Ser Ser Val Ser Gln Ser Thr Gln Met Ile Ser Gln Ala Leu
                980                 985                 990

Ser
```

<210> SEQ ID NO 31
<211> LENGTH: 1273
<212> TYPE: PRT
<213> ORGANISM: Artificial Sequence
<220> FEATURE:
<223> OTHER INFORMATION: Full sequence (N-domain + 32 repeats + C-domain) of polymerizing synthetic protein

<400> SEQUENCE: 31

```
Asp Tyr Asp Ile Pro Thr Thr Glu Asn Leu Tyr Phe Gln Gly Ala Met
1               5                   10                  15

Asp Pro Glu Phe Lys Gly Leu Arg Arg Arg Ala Gln Leu Val Arg Pro
                20                  25                  30

Leu Ser Asn Leu Asp Asn Ala Ser Gly Pro Gly Gly Tyr Gly Pro Gly
            35                  40                  45

Ser Gln Gly Pro Ser Gly Pro Gly Gly Tyr Gly Pro Gly Gly Pro Gly
        50                  55                  60

Ser Ser Ala Ala Ala Ala Ala Ala Ala Ser Gly Pro Gly Gly Tyr
65                  70                  75                  80

Gly Pro Gly Ser Gln Gly Pro Ser Gly Pro Gly Gly Tyr Gly Pro Gly
                85                  90                  95

Gly Pro Gly Ser Ser Ala Ala Ala Ala Ala Ala Ala Ala Ser Gly Pro
                100                 105                 110

Gly Gly Tyr Gly Pro Gly Ser Gln Gly Pro Ser Gly Pro Gly Gly Tyr
            115                 120                 125

Gly Pro Gly Gly Pro Gly Ser Ser Ala Ala Ala Ala Ala Ala Ala Ala
        130                 135                 140

Ser Gly Pro Gly Gly Tyr Gly Pro Gly Ser Gln Gly Pro Ser Gly Pro
145                 150                 155                 160

Gly Gly Tyr Gly Pro Gly Gly Pro Gly Ser Ser Ala Ala Ala Ala Ala
                165                 170                 175

Ala Ala Ala Ser Gly Pro Gly Gly Tyr Gly Pro Gly Ser Gln Gly Pro
                180                 185                 190
```

```
Ser Gly Pro Gly Gly Tyr Gly Pro Gly Gly Pro Gly Ser Ala Ala
        195                 200                 205

Ala Ala Ala Ala Ala Ala Ser Gly Pro Gly Gly Tyr Gly Pro Gly Ser
    210                 215                 220

Gln Gly Pro Ser Gly Pro Gly Tyr Gly Pro Gly Gly Pro Gly Ser
225                 230                 235                 240

Ser Ala Ala Ala Ala Ala Ala Ala Ser Gly Pro Gly Gly Tyr Gly
                245                 250                 255

Pro Gly Ser Gln Gly Pro Ser Gly Pro Gly Tyr Gly Pro Gly Gly
        260                 265                 270

Pro Gly Ser Ser Ala Ala Ala Ala Ala Ala Ala Ser Gly Pro Gly
        275                 280                 285

Gly Tyr Gly Pro Gly Ser Gln Gly Pro Ser Gly Pro Gly Tyr Gly
        290                 295                 300

Pro Gly Gly Pro Gly Ser Ser Ala Ala Ala Ala Ala Ala Ala Ser
305                 310                 315                 320

Gly Pro Gly Gly Tyr Gly Pro Gly Ser Gln Gly Pro Ser Gly Pro
                325                 330                 335

Gly Tyr Gly Pro Gly Gly Pro Gly Ser Ser Ala Ala Ala Ala Ala
        340                 345                 350

Ala Ala Ser Gly Pro Gly Gly Tyr Gly Pro Gly Ser Gln Gly Pro Ser
        355                 360                 365

Gly Pro Gly Tyr Gly Pro Gly Gly Pro Gly Ser Ser Ala Ala Ala
        370                 375                 380

Ala Ala Ala Ala Ala Ser Gly Pro Gly Gly Tyr Gly Pro Gly Ser Gln
385                 390                 395                 400

Gly Pro Ser Gly Pro Gly Tyr Gly Pro Gly Gly Pro Gly Ser Ser
                405                 410                 415

Ala Ala Ala Ala Ala Ala Ala Ser Gly Pro Gly Gly Tyr Gly Pro
                420                 425                 430

Gly Ser Gln Gly Pro Ser Gly Pro Gly Tyr Gly Pro Gly Gly Pro
        435                 440                 445

Gly Ser Ser Ala Ala Ala Ala Ala Ala Ala Ser Gly Pro Gly Gly
        450                 455                 460

Tyr Gly Pro Gly Ser Gln Gly Pro Ser Gly Pro Gly Tyr Gly Pro
465                 470                 475                 480

Gly Gly Pro Gly Ser Ser Ala Ala Ala Ala Ala Ala Ala Ser Gly
                485                 490                 495

Pro Gly Gly Tyr Gly Pro Gly Ser Gln Gly Pro Ser Gly Pro Gly Gly
                500                 505                 510

Tyr Gly Pro Gly Gly Pro Gly Ser Ser Ala Ala Ala Ala Ala Ala
        515                 520                 525

Ala Ser Gly Pro Gly Gly Tyr Gly Pro Gly Ser Gln Gly Pro Ser Gly
        530                 535                 540

Pro Gly Gly Tyr Gly Pro Gly Gly Pro Gly Ser Ser Ala Ala Ala Ala
545                 550                 555                 560

Ala Ala Ala Ala Ser Gly Pro Gly Gly Tyr Gly Pro Gly Ser Gln Gly
                565                 570                 575

Pro Ser Gly Pro Gly Tyr Gly Pro Gly Gly Pro Gly Ser Ser Ala
        580                 585                 590

Ala Ala Ala Ala Ala Ala Ser Gly Pro Gly Gly Tyr Gly Pro Gly
        595                 600                 605

Ser Gln Gly Pro Ser Gly Pro Gly Gly Tyr Gly Pro Gly Gly Pro Gly
610                 615                 620
```

Ser Ser Ala Ala Ala Ala Ala Ala Ser Gly Pro Gly Gly Tyr
625                 630                 635                 640

Gly Pro Gly Ser Gln Gly Pro Ser Gly Pro Gly Gly Tyr Pro Gly
            645                 650                 655

Gly Pro Gly Ser Ser Ala Ala Ala Ala Ala Ala Ala Ser Gly Pro
            660                 665                 670

Gly Gly Tyr Gly Pro Gly Ser Gln Gly Pro Ser Gly Pro Gly Tyr
            675                 680                 685

Gly Pro Gly Gly Pro Gly Ser Ser Ala Ala Ala Ala Ala Ala Ala
            690                 695                 700

Ser Gly Pro Gly Gly Tyr Gly Pro Gly Ser Gln Gly Pro Ser Gly Pro
705                 710                 715                 720

Gly Gly Tyr Gly Pro Gly Gly Pro Gly Ser Ser Ala Ala Ala Ala
            725                 730                 735

Ala Ala Ala Ser Gly Pro Gly Gly Tyr Gly Pro Gly Ser Gln Gly Pro
            740                 745                 750

Ser Gly Pro Gly Gly Tyr Gly Pro Gly Gly Pro Gly Ser Ser Ala Ala
            755                 760                 765

Ala Ala Ala Ala Ala Ser Gly Pro Gly Gly Tyr Gly Pro Gly Ser
770                 775                 780

Gln Gly Pro Ser Gly Pro Gly Tyr Gly Pro Gly Gly Pro Gly Ser
785                 790                 795                 800

Ser Ala Ala Ala Ala Ala Ala Ser Gly Pro Gly Gly Tyr Gly
            805                 810                 815

Pro Gly Ser Gln Gly Pro Ser Gly Pro Gly Gly Tyr Gly Pro Gly Gly
            820                 825                 830

Pro Gly Ser Ser Ala Ala Ala Ala Ala Ala Ala Ser Gly Pro Gly
            835                 840                 845

Gly Tyr Gly Pro Gly Ser Gln Gly Pro Ser Gly Pro Gly Gly Tyr Gly
            850                 855                 860

Pro Gly Gly Pro Gly Ser Ser Ala Ala Ala Ala Ala Ala Ala Ser
865                 870                 875                 880

Gly Pro Gly Gly Tyr Gly Pro Gly Ser Gln Gly Pro Ser Gly Pro Gly
            885                 890                 895

Gly Tyr Gly Pro Gly Gly Pro Gly Ser Ser Ala Ala Ala Ala Ala
            900                 905                 910

Ala Ala Ser Gly Pro Gly Gly Tyr Gly Pro Gly Ser Gln Gly Pro Ser
            915                 920                 925

Gly Pro Gly Gly Tyr Gly Pro Gly Gly Pro Gly Ser Ser Ala Ala
            930                 935                 940

Ala Ala Ala Ala Ala Ser Gly Pro Gly Gly Tyr Gly Pro Gly Ser Gln
945                 950                 955                 960

Gly Pro Ser Gly Pro Gly Gly Tyr Gly Pro Gly Gly Pro Gly Ser Ser
            965                 970                 975

Ala Ala Ala Ala Ala Ala Ala Ser Gly Pro Gly Gly Tyr Gly Pro
            980                 985                 990

Gly Ser Gln Gly Pro Ser Gly Pro  Gly Gly Tyr Gly Pro  Gly Gly Pro
            995                 1000                1005

Gly Ser  Ser Ala Ala Ala Ala  Ala Ala Ala Ala Ser  Gly Pro Gly
            1010                1015                1020

Gly Tyr  Gly Pro Gly Ser Gln  Gly Pro Ser Gly Pro  Gly Gly Tyr
            1025                1030                1035

Gly Pro  Gly Gly Pro Gly Ser  Ser Ala Ala Ala Ala  Ala Ala Ala

```
                1040                1045                1050
Ala Ser Gly Pro Gly Gly Tyr Gly Pro Gly Ser Gln Gly Pro Ser
    1055                1060                1065

Gly Pro Gly Gly Tyr Gly Pro Gly Gly Pro Gly Ser Ser Ala Ala
    1070                1075                1080

Ala Ala Ala Ala Ala Ala Ser Gly Pro Gly Gly Tyr Gly Pro Gly
    1085                1090                1095

Ser Gln Gly Pro Ser Gly Pro Gly Gly Tyr Gly Pro Gly Gly Pro
    1100                1105                1110

Gly Ser Ser Ala Ala Ala Ala Ala Ala Ala Ser Gly Pro Gly
    1115                1120                1125

Gly Tyr Gly Pro Gly Ser Gln Gly Pro Ser Gly Pro Gly Gly Tyr
    1130                1135                1140

Gly Pro Gly Gly Pro Gly Ser Ser Ala Ala Ala Ala Ala Ala
    1145                1150                1155

Ala Gly Pro Ser Gly Pro Gly Ala Tyr Gly Pro Ser Pro Ser Ala
    1160                1165                1170

Ser Ala Ser Val Ala Ala Ser Arg Leu Ser Ser Pro Ala Ala Ser
    1175                1180                1185

Ser Arg Val Ser Ser Ala Val Ser Ser Leu Val Ser Ser Gly Pro
    1190                1195                1200

Thr Asn Gly Ala Ala Val Ser Gly Ala Leu Asn Ser Leu Val Ser
    1205                1210                1215

Gln Ile Ser Ala Ser Asn Pro Gly Leu Ser Gly Cys Asp Ala Leu
    1220                1225                1230

Val Gln Ala Leu Leu Glu Leu Val Ser Ala Leu Val Ala Ile Leu
    1235                1240                1245

Ser Ser Ala Ser Ile Gly Gln Val Asn Val Ser Ser Val Ser Gln
    1250                1255                1260

Ser Thr Gln Met Ile Ser Gln Ala Leu Ser
    1265                1270

<210> SEQ ID NO 32
<211> LENGTH: 555
<212> TYPE: DNA
<213> ORGANISM: Artificial
<220> FEATURE:
<223> OTHER INFORMATION: DNA sequence 2 repeats + C domain of
      polymerizing synthetic protein

<400> SEQUENCE: 32
atgtctggtc ctggaggtta tggcccagga agccaaggac atctggtcc aggaggatat      60 ggtccaggcg acctggctc tagtgcagca gctgccgcag cagctgcatc tggtcctgga     120
ggttatggcc caggaagcca aggaccatct ggtccaggag atatggtcc aggcggacct     180 ggctctagtg cagcagctgc cgcagcagct gcaggcccta gtggtcctgg agcatatggc     240
ccatctcctt ctgcttccgc atccgttgca gcctctcgtt tatcttcgcc tgcagcctcg     300
tctagagtgt cttccgctgt atcgtcttta gtgtctagcg gacctacgaa tggtgctgct     360
gtttctggag ctttgaatag tttagtatct cagattagtg caagtaatcc aggtttatcg     420
ggatgtgatg ctcttgtgca ggcattattg gaattagtgt ctgctcttgt ggcaattctt     480
tcatctgcaa gtattggcca agtcaacgtc agctctgtta gtcagtcaac tcaaatgatt     540
agccaagctc tttca                                                      555

<210> SEQ ID NO 33
```

```
<211> LENGTH: 765
<212> TYPE: DNA
<213> ORGANISM: Artificial
<220> FEATURE:
<223> OTHER INFORMATION: DNA sequence 4 repeats + C domain of
      polymerizing synthetic protein

<400> SEQUENCE: 33
atgtctggtc ctggaggtta tggcccagga agccaaggac catctggtcc aggaggatat      60
ggtccaggcg gacctggctc tagtgcagca gctgccgcag cagctgcatc tggtcctgga     120
ggttatggcc caggaagcca aggaccatct ggtccaggag gatatggtcc aggcggacct     180
ggctctagtg cagcagctgc cgcagcagct gcatctggtc ctggaggtta tgcccagga      240 agccaaggac catctggtcc aggaggatat ggtccaggcg gacctggctc tagtgcagca     300
gctgccgcag cagctgcatc tggtcctgga ggttatggcc caggaagcca aggaccatct     360
ggtccaggag gatatggtcc aggcggacct ggctctagtg cagcagctgc cgcagcagct     420
gcaggcccta gtggtcctgg agcatatggc ccatctcctt ctgcttccgc atccgttgca     480
gcctctcgtt tatcttcgcc tgcagcctcg tctagagtgt cttccgctgt atcgtcttta     540
gtgtctagcg gacctacgaa tggtgctgct gtttctggag ctttgaatag tttagtatct     600
cagattagtg caagtaatcc aggtttatcg ggatgtgatg ctcttgtgca ggcattattg     660
gaattagtgt ctgctcttgt ggcaattctt tcatctgcaa gtattggcca agtcaacgtc     720
agctctgtta gtcagtcaac tcaaatgatt agccaagctc tttca                    765

<210> SEQ ID NO 34
<211> LENGTH: 1185
<212> TYPE: DNA
<213> ORGANISM: Artificial
<220> FEATURE:
<223> OTHER INFORMATION: DNA sequence 8 repeats + C domain of
      polymerizing synthetic protein

<400> SEQUENCE: 34
atgtctggtc ctggaggtta tggcccagga agccaaggac catctggtcc aggaggatat      60
ggtccaggcg gacctggctc tagtgcagca gctgccgcag cagctgcatc tggtcctgga     120
ggttatggcc caggaagcca aggaccatct ggtccaggag gatatggtcc aggcggacct     180
ggctctagtg cagcagctgc cgcagcagct gcatctggtc ctggaggtta tgcccagga      240 agccaaggac catctggtcc aggaggatat ggtccaggcg gacctggctc tagtgcagca     300
gctgccgcag cagctgcatc tggtcctgga ggttatggcc caggaagcca aggaccatct     360
ggtccaggag gatatggtcc aggcggacct ggctctagtg cagcagctgc cgcagcagct     420
gcatctggtc ctggaggtta tgcccagga agccaaggac catctggtcc aggaggatat     480
ggtccaggcg gacctggctc tagtgcagca gctgccgcag cagctgcatc tggtcctgga     540
ggttatggcc caggaagcca aggaccatct ggtccaggag gatatggtcc aggcggacct     600
ggctctagtg cagcagctgc cgcagcagct gcatctggtc ctggaggtta tgcccagga     660 agccaaggac catctggtcc aggaggatat ggtccaggcg gacctggctc tagtgcagca     720
gctgccgcag cagctgcatc tggtcctgga ggttatggcc caggaagcca aggaccatct     780
ggtccaggag gatatggtcc aggcggacct ggctctagtg cagcagctgc cgcagcagct     840
gcaggcccta gtggtcctgg agcatatggc ccatctcctt ctgcttccgc atccgttgca     900
gcctctcgtt tatcttcgcc tgcagcctcg tctagagtgt cttccgctgt atcgtcttta     960
gtgtctagcg gacctacgaa tggtgctgct gtttctggag ctttgaatag tttagtatct    1020
```

-continued

```
cagattagtg caagtaatcc aggtttatcg ggatgtgatg ctcttgtgca ggcattattg     1080
gaattagtgt ctgctcttgt ggcaattctt tcatctgcaa gtattggcca agtcaacgtc     1140
agctctgtta gtcagtcaac tcaaatgatt agccaagctc tttca                     1185
```

<210> SEQ ID NO 35
<211> LENGTH: 1605
<212> TYPE: DNA
<213> ORGANISM: Artificial
<220> FEATURE:
<223> OTHER INFORMATION: DNA sequence 12 repeats + C domain of
      polymerizing synthetic protein

<400> SEQUENCE: 35

```
atgtctggtc ctggaggtta tggcccagga agccaaggac catctggtcc aggaggatat       60
ggtccaggcg gacctggctc tagtgcagca gctgccgcag cagctgcatc tggtcctgga      120
ggttatggcc caggaagcca aggaccatct ggtccaggag gatatggtcc aggcggacct      180
ggctctagtg cagcagctgc cgcagcagct gcatctggtc ctggaggtta tgccccagga     240
agccaaggac catctggtcc aggaggatat ggtccaggcg gacctggctc tagtgcagca      300
gctgccgcag cagctgcatc tggtcctgga ggttatggcc caggaagcca aggaccatct      360
ggtccaggag gatatggtcc aggcggacct ggctctagtg cagcagctgc cgcagcagct      420
gcatctggtc ctggaggtta tggcccagga agccaaggac catctggtcc aggaggatat      480
ggtccaggcg gacctggctc tagtgcagca gctgccgcag cagctgcatc tggtcctgga      540
ggttatggcc caggaagcca aggaccatct ggtccaggag gatatggtcc aggcggacct      600
ggctctagtg cagcagctgc cgcagcagct gcatctggtc ctggaggtta tgccccagga     660
agccaaggac catctggtcc aggaggatat ggtccaggcg gacctggctc tagtgcagca      720
gctgccgcag cagctgcatc tggtcctgga ggttatggcc caggaagcca aggaccatct      780
ggtccaggag gatatggtcc aggcggacct ggctctagtg cagcagctgc cgcagcagct      840
gcatctggtc ctggaggtta tgccccagga agccaaggac catctggtcc aggaggatat      900
ggtccaggcg gacctggctc tagtgcagca gctgccgcag cagctgcatc tggtcctgga      960
ggttatggcc caggaagcca aggaccatct ggtccaggag gatatggtcc aggcggacct     1020
ggctctagtg cagcagctgc cgcagcagct gcatctggtc ctggaggtta tgccccagga    1080
agccaaggac catctggtcc aggaggatat ggtccaggcg gacctggctc tagtgcagca     1140
gctgccgcag cagctgcatc tggtcctgga ggttatggcc caggaagcca aggaccatct     1200
ggtccaggag gatatggtcc aggcggacct ggctctagtg cagcagctgc cgcagcagct     1260
gcaggcccta gtggtcctgg agcatatggc ccatctcctt ctgcttccgc atccgttgca     1320
gcctctcgtt tatcttcgcc tgcagcctcg tctagagtgt cttccgctgt atcgtcttta     1380
gtgtctagcg gacctacgaa tggtgctgct gtttctggag ctttgaatag tttagtatct     1440
cagattagtg caagtaatcc aggtttatcg ggatgtgatg ctcttgtgca ggcattattg     1500
gaattagtgt ctgctcttgt ggcaattctt tcatctgcaa gtattggcca agtcaacgtc     1560
agctctgtta gtcagtcaac tcaaatgatt agccaagctc tttca                     1605
```

<210> SEQ ID NO 36
<211> LENGTH: 2025
<212> TYPE: DNA
<213> ORGANISM: Artificial
<220> FEATURE:
<223> OTHER INFORMATION: DNA sequence 16 repeats + C domain of
      polymerizing synthetic protein

<400> SEQUENCE: 36

```
atgtctggtc ctggaggtta tggcccagga agccaaggac catctggtcc aggaggatat      60
ggtccaggcg acctggctc tagtgcagca gctgccgcag cagctgcatc tggtcctgga      120
ggttatggcc caggaagcca aggaccatct ggtccaggag gatatggtcc aggcggacct    180
ggctctagtg cagcagctgc cgcagcagct gcatctggtc ctggaggtta tgcccagga     240
agccaaggac catctggtcc aggaggatat ggtccaggcg acctggctc tagtgcagca    300
gctgccgcag cagctgcatc tggtcctgga ggttatggcc caggaagcca aggaccatct   360
ggtccaggag gatatggtcc aggcggacct ggctctagtg cagcagctgc cgcagcagct   420
gcatctggtc ctggaggtta tgcccagga agccaaggac catctggtcc aggaggatat   480
ggtccaggcg acctggctc tagtgcagca gctgccgcag cagctgcatc tggtcctgga   540
ggttatggcc caggaagcca aggaccatct ggtccaggag gatatggtcc aggcggacct   600
ggctctagtg cagcagctgc cgcagcagct gcatctggtc ctggaggtta tgcccagga   660
agccaaggac catctggtcc aggaggatat ggtccaggcg acctggctc tagtgcagca   720
gctgccgcag cagctgcatc tggtcctgga ggttatggcc caggaagcca aggaccatct   780
ggtccaggag gatatggtcc aggcggacct ggctctagtg cagcagctgc cgcagcagct   840
gcatctggtc ctggaggtta tgcccagga agccaaggac catctggtcc aggaggatat   900
ggtccaggcg acctggctc tagtgcagca gctgccgcag cagctgcatc tggtcctgga   960
ggttatggcc caggaagcca aggaccatct ggtccaggag gatatggtcc aggcggacct  1020
ggctctagtg cagcagctgc cgcagcagct gcatctggtc ctggaggtta tgcccagga  1080
agccaaggac catctggtcc aggaggatat ggtccaggcg acctggctc tagtgcagca  1140
gctgccgcag cagctgcatc tggtcctgga ggttatggcc caggaagcca aggaccatct  1200
ggtccaggag gatatggtcc aggcggacct ggctctagtg cagcagctgc cgcagcagct  1260
gcatctggtc ctggaggtta tgcccagga agccaaggac catctggtcc aggaggatat  1320
ggtccaggcg acctggctc tagtgcagca gctgccgcag cagctgcatc tggtcctgga  1380
ggttatggcc caggaagcca aggaccatct ggtccaggag gatatggtcc aggcggacct  1440
ggctctagtg cagcagctgc cgcagcagct gcatctggtc ctggaggtta tgcccagga  1500
agccaaggac catctggtcc aggaggatat ggtccaggcg acctggctc tagtgcagca  1560
gctgccgcag cagctgcatc tggtcctgga ggttatggcc caggaagcca aggaccatct  1620
ggtccaggag gatatggtcc aggcggacct ggctctagtg cagcagctgc cgcagcagct  1680
gcaggcccta gtggtcctgg agcatatggc ccatctcctt ctgcttccgc atccgttgca  1740
gcctctcgtt tatcttcgcc tgcagcctcg tctagagtgt cttccgctgt atcgtcttta  1800
gtgtctagcg gacctacgaa tggtgctgct gtttctggag ctttgaatag tttagtatct  1860
cagattagtc aagtaatcc aggtttatcg ggatgtgatg ctcttgtgca ggcattattg  1920
gaattagtgt ctgctcttgt ggcaattctt tcatctgcaa gtattggcca agtcaacgtc  1980
agctctgtta gtcagtcaac tcaaatgatt agccaagctc tttca                2025
```

<210> SEQ ID NO 37
<211> LENGTH: 2445
<212> TYPE: DNA
<213> ORGANISM: Artificial
<220> FEATURE:
<223> OTHER INFORMATION: DNA sequence 20 repeats + C domain of polymerizing synthetic protein

<400> SEQUENCE: 37

```
atgtctggtc ctggaggtta tggcccagga agccaaggac catctggtcc aggaggatat    60
ggtccaggcg gacctggctc tagtgcagca gctgccgcag cagctgcatc tggtcctgga   120
ggttatggcc caggaagcca aggaccatct ggtccaggag gatatggtcc aggcggacct   180
ggctctagtg cagcagctgc cgcagcagct gcatctggtc ctggaggtta tgcccagga   240
agccaaggac catctggtcc aggaggatat ggtccaggcg gacctggctc tagtgcagca   300
gctgccgcag cagctgcatc tggtcctgga ggttatggcc caggaagcca aggaccatct   360
ggtccaggag gatatggtcc aggcggacct ggctctagtg cagcagctgc cgcagcagct   420
gcatctggtc ctggaggtta tgcccagga agccaaggac catctggtcc aggaggatat   480
ggtccaggcg gacctggctc tagtgcagca gctgccgcag cagctgcatc tggtcctgga   540
ggttatggcc caggaagcca aggaccatct ggtccaggag gatatggtcc aggcggacct   600
ggctctagtg cagcagctgc cgcagcagct gcatctggtc ctggaggtta tgcccagga   660
agccaaggac catctggtcc aggaggatat ggtccaggcg gacctggctc tagtgcagca   720
gctgccgcag cagctgcatc tggtcctgga ggttatggcc caggaagcca aggaccatct   780
ggtccaggag gatatggtcc aggcggacct ggctctagtg cagcagctgc cgcagcagct   840
gcatctggtc ctggaggtta tgcccagga agccaaggac catctggtcc aggaggatat   900
ggtccaggcg gacctggctc tagtgcagca gctgccgcag cagctgcatc tggtcctgga   960
ggttatggcc caggaagcca aggaccatct ggtccaggag gatatggtcc aggcggacct  1020
ggctctagtg cagcagctgc cgcagcagct gcatctggtc ctggaggtta tgcccagga  1080
agccaaggac catctggtcc aggaggatat ggtccaggcg gacctggctc tagtgcagca  1140
gctgccgcag cagctgcatc tggtcctgga ggttatggcc caggaagcca aggaccatct  1200
ggtccaggag gatatggtcc aggcggacct ggctctagtg cagcagctgc cgcagcagct  1260
gcatctggtc ctggaggtta tgcccagga agccaaggac catctggtcc aggaggatat  1320
ggtccaggcg gacctggctc tagtgcagca gctgccgcag cagctgcatc tggtcctgga  1380
ggttatggcc caggaagcca aggaccatct ggtccaggag gatatggtcc aggcggacct  1440
ggctctagtg cagcagctgc cgcagcagct gcatctggtc ctggaggtta tgcccagga  1500
agccaaggac catctggtcc aggaggatat ggtccaggcg gacctggctc tagtgcagca  1560
gctgccgcag cagctgcatc tggtcctgga ggttatggcc caggaagcca aggaccatct  1620
ggtccaggag gatatggtcc aggcggacct ggctctagtg cagcagctgc cgcagcagct  1680
gcatctggtc ctggaggtta tgcccagga agccaaggac catctggtcc aggaggatat  1740
ggtccaggcg gacctggctc tagtgcagca gctgccgcag cagctgcatc tggtcctgga  1800
ggttatggcc caggaagcca aggaccatct ggtccaggag gatatggtcc aggcggacct  1860
ggctctagtg cagcagctgc cgcagcagct gcatctggtc ctggaggtta tgcccagga  1920
agccaaggac catctggtcc aggaggatat ggtccaggcg gacctggctc tagtgcagca  1980
gctgccgcag cagctgcatc tggtcctgga ggttatggcc caggaagcca aggaccatct  2040
ggtccaggag gatatggtcc aggcggacct ggctctagtg cagcagctgc cgcagcagct  2100
gcaggcccta gtggtcctgg agcatatggc ccatctcctt ctgcttccgc atccgttgca  2160
gcctctcgtt tatcttcgcc tgcagcctcg tctagagtgt cttccgctgt atcgtcttta  2220
gtgtctagcg gacctacgaa tggtgctgct gtttctggag ctttgaatag tttagtatct  2280
cagattagtg caagtaatcc aggtttatcg ggatgtgatg ctcttgtgca ggcattattg  2340
gaattagtgt ctgctcttgt ggcaattctt tcatctgcaa gtattggcca agtcaacgtc  2400
```
agctctgtta gtcagtcaac tcaaatgatt agccaagctc tttca        2445

<210> SEQ ID NO 38
<211> LENGTH: 4755
<212> TYPE: DNA
<213> ORGANISM: Artificial
<220> FEATURE:
<223> OTHER INFORMATION: DNA sequence 24 repeats + C domain of
      polymerizing synthetic protein

<400> SEQUENCE: 38

| | |
|---|---:|
| atgtctggtc ctggaggtta tggcccagga agccaaggac catctggtcc aggaggatat | 60 |
| ggtccaggcg gacctggctc tagtgcagca gctgccgcag cagctgcatc tggtcctgga | 120 |
| ggttatggcc caggaagcca aggaccatct ggtccaggag gatatggtcc aggcggacct | 180 |
| ggctctagtg cagcagctgc cgcagcagct gcatctggtc ctggaggtta tgcccagga | 240 |
| agccaaggac catctggtcc aggaggatat ggtccaggcg gacctggctc tagtgcagca | 300 |
| gctgccgcag cagctgcatc tggtcctgga ggttatggcc caggaagcca aggaccatct | 360 |
| ggtccaggag gatatggtcc aggcggacct ggctctagtg cagcagctgc cgcagcagct | 420 |
| gcatctggtc ctggaggtta tgcccagga agccaaggac catctggtcc aggaggatat | 480 |
| ggtccaggcg gacctggctc tagtgcagca gctgccgcag cagctgcatc tggtcctgga | 540 |
| ggttatggcc caggaagcca aggaccatct ggtccaggag gatatggtcc aggcggacct | 600 |
| ggctctagtg cagcagctgc cgcagcagct gcatctggtc ctggaggtta tgcccagga | 660 |
| agccaaggac catctggtcc aggaggatat ggtccaggcg gacctggctc tagtgcagca | 720 |
| gctgccgcag cagctgcatc tggtcctgga ggttatggcc caggaagcca aggaccatct | 780 |
| ggtccaggag gatatggtcc aggcggacct ggctctagtg cagcagctgc cgcagcagct | 840 |
| gcatctggtc ctggaggtta tgcccagga agccaaggac catctggtcc aggaggatat | 900 |
| ggtccaggcg gacctggctc tagtgcagca gctgccgcag cagctgcatc tggtcctgga | 960 |
| ggttatggcc caggaagcca aggaccatct ggtccaggag gatatggtcc aggcggacct | 1020 |
| ggctctagtg cagcagctgc cgcagcagct gcatctggtc ctggaggtta tgcccagga | 1080 |
| agccaaggac catctggtcc aggaggatat ggtccaggcg gacctggctc tagtgcagca | 1140 |
| gctgccgcag cagctgcatc tggtcctgga ggttatggcc caggaagcca aggaccatct | 1200 |
| ggtccaggag gatatggtcc aggcggacct ggctctagtg cagcagctgc cgcagcagct | 1260 |
| gcatctggtc ctggaggtta tgcccagga agccaaggac catctggtcc aggaggatat | 1320 |
| ggtccaggcg gacctggctc tagtgcagca gctgccgcag cagctgcatc tggtcctgga | 1380 |
| ggttatggcc caggaagcca aggaccatct ggtccaggag gatatggtcc aggcggacct | 1440 |
| ggctctagtg cagcagctgc cgcagcagct gcatctggtc ctggaggtta tgcccagga | 1500 |
| agccaaggac catctggtcc aggaggatat ggtccaggcg gacctggctc tagtgcagca | 1560 |
| gctgccgcag cagctgcatc tggtcctgga ggttatggcc caggaagcca aggaccatct | 1620 |
| ggtccaggag gatatggtcc aggcggacct ggctctagtg cagcagctgc cgcagcagct | 1680 |
| gcatctggtc ctggaggtta tgcccagga agccaaggac catctggtcc aggaggatat | 1740 |
| ggtccaggcg gacctggctc tagtgcagca gctgccgcag cagctgcatc tggtcctgga | 1800 |
| ggttatggcc caggaagcca aggaccatct ggtccaggag gatatggtcc aggcggacct | 1860 |
| ggctctagtg cagcagctgc cgcagcagct gcatctggtc ctggaggtta tgcccagga | 1920 |
| agccaaggac catctggtcc aggaggatat ggtccaggcg gacctggctc tagtgcagca | 1980 |

```
gctgccgcag cagctgcatc tggtcctgga ggttatggcc caggaagcca aggaccatct    2040
ggtccaggag gatatggtcc aggcggacct ggctctagtg cagcagctgc cgcagcagct    2100
gcatctggtc ctggaggtta tgcccagga  agccaaggac catctggtcc aggaggatat    2160
ggtccaggcg gacctggctc tagtgcagca gctgccgcag cagctgcatc tggtcctgga    2220
ggttatggcc caggaagcca aggaccatct ggtccaggag gatatggtcc aggcggacct    2280
ggctctagtg cagcagctgc cgcagcagct gcatctggtc ctggaggtta tgcccagga    2340 agccaaggac catctggtcc aggaggatat ggtccaggcg gacctggctc tagtgcagca    2400
gctgccgcag cagctgcatc tggtcctgga ggttatggcc caggaagcca aggaccatct    2460
ggtccaggag gatatggtcc aggcggacct ggctctagtg cagcagctgc cgcagcagct    2520
gcatctggtc ctggaggtta tgcccagga  agccaaggac catctggtcc aggaggatat    2580
ggtccaggcg gacctggctc tagtgcagca gctgccgcag cagctgcatc tggtcctgga    2640
ggttatggcc caggaagcca aggaccatct ggtccaggag gatatggtcc aggcggacct    2700
ggctctagtg cagcagctgc cgcagcagct gcatctggtc ctggaggtta tgcccagga    2760 agccaaggac catctggtcc aggaggatat ggtccaggcg gacctggctc tagtgcagca    2820
gctgccgcag cagctgcatc tggtcctgga ggttatggcc caggaagcca aggaccatct    2880
ggtccaggag gatatggtcc aggcggacct ggctctagtg cagcagctgc cgcagcagct    2940
gcatctggtc ctggaggtta tgcccagga  agccaaggac catctggtcc aggaggatat    3000
ggtccaggcg gacctggctc tagtgcagca gctgccgcag cagctgcatc tggtcctgga    3060
ggttatggcc caggaagcca aggaccatct ggtccaggag gatatggtcc aggcggacct    3120
ggctctagtg cagcagctgc cgcagcagct gcatctggtc ctggaggtta tgcccagga    3180 agccaaggac catctggtcc aggaggatat ggtccaggcg gacctggctc tagtgcagca    3240
gctgccgcag cagctgcatc tggtcctgga ggttatggcc caggaagcca aggaccatct    3300
ggtccaggag gatatggtcc aggcggacct ggctctagtg cagcagctgc cgcagcagct    3360
gcatctggtc ctggaggtta tgcccagga  agccaaggac catctggtcc aggaggatat    3420
ggtccaggcg gacctggctc tagtgcagca gctgccgcag cagctgcatc tggtcctgga    3480
ggttatggcc caggaagcca aggaccatct ggtccaggag gatatggtcc aggcggacct    3540
ggctctagtg cagcagctgc cgcagcagct gcatctggtc ctggaggtta tgcccagga    3600 agccaaggac catctggtcc aggaggatat ggtccaggcg gacctggctc tagtgcagca    3660
gctgccgcag cagctgcatc tggtcctgga ggttatggcc caggaagcca aggaccatct    3720
ggtccaggag gatatggtcc aggcggacct ggctctagtg cagcagctgc cgcagcagct    3780
gcatctggtc ctggaggtta tgcccagga  agccaaggac catctggtcc aggaggatat    3840
ggtccaggcg gacctggctc tagtgcagca gctgccgcag cagctgcatc tggtcctgga    3900
ggttatggcc caggaagcca aggaccatct ggtccaggag gatatggtcc aggcggacct    3960
ggctctagtg cagcagctgc cgcagcagct gcatctggtc ctggaggtta tgcccagga    4020 agccaaggac catctggtcc aggaggatat ggtccaggcg gacctggctc tagtgcagca    4080
gctgccgcag cagctgcatc tggtcctgga ggttatggcc caggaagcca aggaccatct    4140
ggtccaggag gatatggtcc aggcggacct ggctctagtg cagcagctgc cgcagcagct    4200
gcatctggtc ctggaggtta tgcccagga  agccaaggac catctggtcc aggaggatat    4260
ggtccaggcg gacctggctc tagtgcagca gctgccgcag cagctgcatc tggtcctgga    4320
ggttatggcc caggaagcca aggaccatct ggtccaggag gatatggtcc aggcggacct    4380
```

```
ggctctagtg cagcagctgc cgcagcagct gcaggcccta gtggtcctgg agcatatggc    4440
ccatctcctt ctgcttccgc atccgttgca gcctctcgtt tatcttcgcc tgcagcctcg    4500
tctagagtgt cttccgctgt atcgtcttta gtgtctagcg gacctacgaa tggtgctgct    4560
gtttctggag ctttgaatag tttagtatct cagattagtg caagtaatcc aggtttatcg    4620
ggatgtgatg ctcttgtgca ggcattattg gaattagtgt ctgctcttgt ggcaattctt    4680
tcatctgcaa gtattggcca agtcaacgtc agctctgtta gtcagtcaac tcaaatgatt    4740
agccaagctc tttca                                                    4755

<210> SEQ ID NO 39
<211> LENGTH: 3705
<212> TYPE: DNA
<213> ORGANISM: Artificial
<220> FEATURE:
<223> OTHER INFORMATION: DNA sequence 32 repeats + C domain of
      polymerizing synthetic protein

<400> SEQUENCE: 39
atgtctggtc ctggaggtta tggcccagga agccaaggac catctggtcc aggaggatat      60
ggtccaggcg gacctggctc tagtgcagca gctgccgcag cagctgcatc tggtcctgga     120
ggttatggcc caggaagcca aggaccatct ggtccaggag gatatggtcc aggcggacct     180
ggctctagtg cagcagctgc cgcagcagct gcatctggtc ctggaggtta tggcccagga     240
agccaaggac catctggtcc aggaggatat ggtccaggcg gacctggctc tagtgcagca     300
gctgccgcag cagctgcatc tggtcctgga ggttatggcc caggaagcca aggaccatct     360
ggtccaggag gatatggtcc aggcggacct ggctctagtg cagcagctgc cgcagcagct     420
gcatctggtc ctggaggtta tggcccagga agccaaggac catctggtcc aggaggatat     480
ggtccaggcg gacctggctc tagtgcagca gctgccgcag cagctgcatc tggtcctgga     540
ggttatggcc caggaagcca aggaccatct ggtccaggag gatatggtcc aggcggacct     600
ggctctagtg cagcagctgc cgcagcagct gcatctggtc ctggaggtta tggcccagga     660
agccaaggac catctggtcc aggaggatat ggtccaggcg gacctggctc tagtgcagca     720
gctgccgcag cagctgcatc tggtcctgga ggttatggcc caggaagcca aggaccatct     780
ggtccaggag gatatggtcc aggcggacct ggctctagtg cagcagctgc cgcagcagct     840
gcatctggtc ctggaggtta tggcccagga agccaaggac catctggtcc aggaggatat     900
ggtccaggcg gacctggctc tagtgcagca gctgccgcag cagctgcatc tggtcctgga     960
ggttatggcc caggaagcca aggaccatct ggtccaggag gatatggtcc aggcggacct    1020
ggctctagtg cagcagctgc cgcagcagct gcatctggtc ctggaggtta tggcccagga    1080
agccaaggac catctggtcc aggaggatat ggtccaggcg gacctggctc tagtgcagca    1140
gctgccgcag cagctgcatc tggtcctgga ggttatggcc caggaagcca aggaccatct    1200
ggtccaggag gatatggtcc aggcggacct ggctctagtg cagcagctgc cgcagcagct    1260
gcatctggtc ctggaggtta tggcccagga agccaaggac catctggtcc aggaggatat    1320
ggtccaggcg gacctggctc tagtgcagca gctgccgcag cagctgcatc tggtcctgga    1380
ggttatggcc caggaagcca aggaccatct ggtccaggag gatatggtcc aggcggacct    1440
ggctctagtg cagcagctgc cgcagcagct gcatctggtc ctggaggtta tggcccagga    1500
agccaaggac catctggtcc aggaggatat ggtccaggcg gacctggctc tagtgcagca    1560
gctgccgcag cagctgcatc tggtcctgga ggttatggcc caggaagcca aggaccatct    1620
ggtccaggag gatatggtcc aggcggacct ggctctagtg cagcagctgc cgcagcagct    1680
```

```
gcatctggtc ctggaggtta tggcccagga agccaaggac catctggtcc aggaggatat    1740
ggtccaggcg gacctggctc tagtgcagca gctgccgcag cagctgcatc tggtcctgga    1800
ggttatggcc caggaagcca aggaccatct ggtccaggag gatatggtcc aggcggacct    1860
ggctctagtg cagcagctgc cgcagcagct gcatctggtc ctggaggtta tgcccagga    1920
agccaaggac catctggtcc aggaggatat ggtccaggcg gacctggctc tagtgcagca    1980
gctgccgcag cagctgcatc tggtcctgga ggttatggcc caggaagcca aggaccatct    2040
ggtccaggag gatatggtcc aggcggacct ggctctagtg cagcagctgc cgcagcagct    2100
gcatctggtc ctggaggtta tgcccagga agccaaggac catctggtcc aggaggatat    2160
ggtccaggcg gacctggctc tagtgcagca gctgccgcag cagctgcatc tggtcctgga    2220
ggttatggcc caggaagcca aggaccatct ggtccaggag gatatggtcc aggcggacct    2280
ggctctagtg cagcagctgc cgcagcagct gcatctggtc ctggaggtta tgcccagga    2340
agccaaggac catctggtcc aggaggatat ggtccaggcg gacctggctc tagtgcagca    2400
gctgccgcag cagctgcatc tggtcctgga ggttatggcc caggaagcca aggaccatct    2460
ggtccaggag gatatggtcc aggcggacct ggctctagtg cagcagctgc cgcagcagct    2520
gcatctggtc ctggaggtta tgcccagga agccaaggac catctggtcc aggaggatat    2580
ggtccaggcg gacctggctc tagtgcagca gctgccgcag cagctgcatc tggtcctgga    2640
ggttatggcc caggaagcca aggaccatct ggtccaggag gatatggtcc aggcggacct    2700
ggctctagtg cagcagctgc cgcagcagct gcatctggtc ctggaggtta tgcccagga    2760
agccaaggac catctggtcc aggaggatat ggtccaggcg gacctggctc tagtgcagca    2820
gctgccgcag cagctgcatc tggtcctgga ggttatggcc caggaagcca aggaccatct    2880
ggtccaggag gatatggtcc aggcggacct ggctctagtg cagcagctgc cgcagcagct    2940
gcatctggtc ctggaggtta tgcccagga agccaaggac catctggtcc aggaggatat    3000
ggtccaggcg gacctggctc tagtgcagca gctgccgcag cagctgcatc tggtcctgga    3060
ggttatggcc caggaagcca aggaccatct ggtccaggag gatatggtcc aggcggacct    3120
ggctctagtg cagcagctgc cgcagcagct gcatctggtc ctggaggtta tgcccagga    3180
agccaaggac catctggtcc aggaggatat ggtccaggcg gacctggctc tagtgcagca    3240
gctgccgcag cagctgcatc tggtcctgga ggttatggcc caggaagcca aggaccatct    3300
ggtccaggag gatatggtcc aggcggacct ggctctagtg cagcagctgc cgcagcagct    3360
gcaggcccta gtggtcctgg agcatatggc ccatctcctt ctgcttccgc atccgttgca    3420
gcctctcgtt tatcttcgcc tgcagcctcg tctagagtgt cttccgctgt atcgtcttta    3480
gtgtctagcg gacctacgaa tggtgctgct gtttctggag ctttgaatag tttagtatct    3540
cagattagtg caagtaatcc aggtttatcg ggatgtgatg ctcttgtgca ggcattattg    3600
gaattagtgt ctgctcttgt ggcaattctt tcatctgcaa gtattggcca agtcaacgtc    3660
agctctgtta gtcagtcaac tcaaatgatt agccaagctc tttca                   3705
```

<210> SEQ ID NO 40
<211> LENGTH: 184
<212> TYPE: PRT
<213> ORGANISM: Artificial
<220> FEATURE:
<223> OTHER INFORMATION: 2 repeats + C domain of polymerizing synthetic
      protein

<400> SEQUENCE: 40

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala
            20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
50                  55                  60

Ala Ala Ala Ala Ala Ser Gly Pro Ser Gly Pro Gly Ala Tyr Gly Pro
65                  70                  75                  80

Ser Pro Ser Ala Ser Ala Ser Val Ala Ala Ser Arg Leu Ser Ser Pro
                85                  90                  95

Ala Ala Ser Ser Arg Val Ser Ser Ala Val Ser Ser Leu Val Ser Ser
            100                 105                 110

Gly Pro Thr Asn Gly Ala Ala Val Ser Gly Ala Leu Asn Ser Leu Val
            115                 120                 125

Ser Gln Ile Ser Ala Ser Asn Pro Gly Leu Ser Gly Cys Asp Ala Leu
130                 135                 140

Val Gln Ala Leu Leu Glu Leu Val Ser Ala Leu Val Ala Ile Leu Ser
145                 150                 155                 160

Ser Ala Ser Ile Gly Gln Val Asn Val Ser Ser Val Ser Gln Ser Thr
            165                 170                 175

Gln Met Ile Ser Gln Ala Leu Ser
            180

<210> SEQ ID NO 41
<211> LENGTH: 254
<212> TYPE: PRT
<213> ORGANISM: Artificial
<220> FEATURE:
<223> OTHER INFORMATION: 4 repeats + C domain of polymerizing synthetic protein

<400> SEQUENCE: 41

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala
            20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
50                  55                  60

Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
            85                  90                  95

Ser Ala Ala Ala Ala Ala Ala Ala Ser Gly Pro Gly Gly Tyr Gly
            100                 105                 110

Pro Gly Ser Gln Gly Pro Ser Gly Pro Gly Gly Tyr Gly Pro Gly Gly
            115                 120                 125

Pro Gly Ser Ser Ala Ala Ala Ala Ala Ala Gly Pro Ser Gly
            130                 135                 140

Pro Gly Ala Tyr Gly Pro Ser Pro Ser Ala Ser Ala Ser Val Ala Ala
145                 150                 155                 160

Ser Arg Leu Ser Ser Pro Ala Ala Ser Ser Arg Val Ser Ser Ala Val
            165                 170                 175

```
Ser Ser Leu Val Ser Ser Gly Pro Thr Asn Gly Ala Ala Val Ser Gly
            180                 185                 190

Ala Leu Asn Ser Leu Val Ser Gln Ile Ser Ala Ser Asn Pro Gly Leu
        195                 200                 205

Ser Gly Cys Asp Ala Leu Val Gln Ala Leu Leu Glu Leu Val Ser Ala
    210                 215                 220

Leu Val Ala Ile Leu Ser Ser Ala Ser Ile Gly Gln Val Asn Val Ser
225                 230                 235                 240

Ser Val Ser Gln Ser Thr Gln Met Ile Ser Gln Ala Leu Ser
                245                 250

<210> SEQ ID NO 42
<211> LENGTH: 394
<212> TYPE: PRT
<213> ORGANISM: Artificial
<220> FEATURE:
<223> OTHER INFORMATION: 8 repeats + C domain of polymerizing synthetic
      protein

<400> SEQUENCE: 42

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
            20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
        50                  55                  60

Ala Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
                85                  90                  95

Ser Ala Ala Ala Ala Ala Ala Ala Ser Gly Pro Gly Gly Tyr Gly
            100                 105                 110

Pro Gly Ser Gln Gly Pro Ser Gly Pro Gly Gly Tyr Gly Pro Gly Gly
            115                 120                 125

Pro Gly Ser Ser Ala Ala Ala Ala Ala Ala Ala Ser Gly Pro Gly
        130                 135                 140

Gly Tyr Gly Pro Gly Ser Gln Gly Pro Ser Gly Pro Gly Gly Tyr Gly
145                 150                 155                 160

Pro Gly Gly Pro Gly Ser Ser Ala Ala Ala Ala Ala Ala Ala Ser
                165                 170                 175

Gly Pro Gly Gly Tyr Gly Pro Gly Ser Gln Gly Pro Ser Gly Pro Gly
            180                 185                 190

Gly Tyr Gly Pro Gly Gly Pro Gly Ser Ser Ala Ala Ala Ala Ala Ala
        195                 200                 205

Ala Ala Ser Gly Pro Gly Gly Tyr Gly Pro Gly Ser Gln Gly Pro Ser
    210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
                245                 250                 255

Gly Pro Ser Gly Pro Gly Gly Tyr Gly Pro Gly Gly Pro Gly Ser Ser
            260                 265                 270

Ala Ala Ala Ala Ala Ala Ala Ala Gly Pro Ser Gly Pro Gly Ala Tyr
        275                 280                 285
```

```
Gly Pro Ser Pro Ser Ala Ser Ala Ser Val Ala Ala Ser Arg Leu Ser
        290                 295                 300

Ser Pro Ala Ala Ser Ser Arg Val Ser Ser Ala Val Ser Ser Leu Val
305                 310                 315                 320

Ser Ser Gly Pro Thr Asn Gly Ala Ala Val Ser Gly Ala Leu Asn Ser
                325                 330                 335

Leu Val Ser Gln Ile Ser Ala Ser Asn Pro Gly Leu Ser Gly Cys Asp
            340                 345                 350

Ala Leu Val Gln Ala Leu Leu Glu Leu Val Ser Ala Leu Val Ala Ile
                355                 360                 365

Leu Ser Ser Ala Ser Ile Gly Gln Val Asn Val Ser Ser Val Ser Gln
    370                 375                 380

Ser Thr Gln Met Ile Ser Gln Ala Leu Ser
385                 390

<210> SEQ ID NO 43
<211> LENGTH: 534
<212> TYPE: PRT
<213> ORGANISM: Artificial
<220> FEATURE:
<223> OTHER INFORMATION: 12 repeats + C domain of polymerizing synthetic
      protein

<400> SEQUENCE: 43

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
                20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
    50                  55                  60

Ala Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
                85                  90                  95

Ser Ala Ala Ala Ala Ala Ala Ala Ser Gly Pro Gly Gly Tyr Gly
                100                 105                 110

Pro Gly Ser Gln Gly Pro Ser Gly Pro Gly Gly Tyr Gly Pro Gly Gly
            115                 120                 125

Pro Gly Ser Ser Ala Ala Ala Ala Ala Ala Ala Ser Gly Pro Gly
    130                 135                 140

Gly Tyr Gly Pro Gly Ser Gln Gly Pro Ser Gly Pro Gly Gly Tyr Gly
145                 150                 155                 160

Pro Gly Gly Pro Gly Ser Ser Ala Ala Ala Ala Ala Ala Ala Ser
                165                 170                 175

Gly Pro Gly Gly Tyr Gly Pro Gly Ser Gln Gly Pro Ser Gly Pro Gly
            180                 185                 190

Gly Tyr Gly Pro Gly Gly Pro Gly Ser Ser Ala Ala Ala Ala Ala
    195                 200                 205

Ala Ala Ser Gly Pro Gly Gly Tyr Gly Pro Gly Ser Gln Gly Pro Ser
210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
                245                 250                 255
```

```
Gly Pro Ser Gly Pro Gly Gly Tyr Gly Pro Gly Gly Pro Gly Ser Ser
                260                 265                 270

Ala Ala Ala Ala Ala Ala Ala Ser Gly Pro Gly Gly Tyr Gly Pro
            275                 280                 285

Gly Ser Gln Gly Pro Ser Gly Pro Gly Gly Tyr Gly Pro Gly Gly Pro
    290                 295                 300

Gly Ser Ser Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
                325                 330                 335

Gly Gly Pro Gly Ser Ser Ala Ala Ala Ala Ala Ala Ala Ser Gly
            340                 345                 350

Pro Gly Gly Tyr Gly Pro Gly Ser Gln Gly Pro Ser Gly Pro Gly Gly
        355                 360                 365

Tyr Gly Pro Gly Gly Pro Gly Ser Ser Ala Ala Ala Ala Ala Ala
    370                 375                 380

Ala Ser Gly Pro Gly Gly Tyr Gly Pro Gly Ser Gln Gly Pro Ser Gly
385                 390                 395                 400

Pro Gly Gly Tyr Gly Pro Gly Gly Pro Gly Ser Ser Ala Ala Ala Ala
                405                 410                 415

Ala Ala Ala Ala Gly Pro Ser Gly Pro Gly Ala Tyr Gly Pro Ser Pro
            420                 425                 430

Ser Ala Ser Ala Ser Val Ala Ala Ser Arg Leu Ser Ser Pro Ala Ala
    435                 440                 445

Ser Ser Arg Val Ser Ser Ala Val Ser Ser Leu Val Ser Ser Gly Pro
450                 455                 460

Thr Asn Gly Ala Ala Val Ser Gly Ala Leu Asn Ser Leu Val Ser Gln
465                 470                 475                 480

Ile Ser Ala Ser Asn Pro Gly Leu Ser Gly Cys Asp Ala Leu Val Gln
                485                 490                 495

Ala Leu Leu Glu Leu Val Ser Ala Leu Val Ala Ile Leu Ser Ser Ala
            500                 505                 510

Ser Ile Gly Gln Val Asn Val Ser Ser Val Ser Gln Ser Thr Gln Met
    515                 520                 525

Ile Ser Gln Ala Leu Ser
    530

<210> SEQ ID NO 44
<211> LENGTH: 674
<212> TYPE: PRT
<213> ORGANISM: Artificial
<220> FEATURE:
<223> OTHER INFORMATION: 16 repeats + C domain of polymerizing synthetic
      protein

<400> SEQUENCE: 44

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
            20                  25                  30

Ala Ala Ala Ser Gly Pro Gly Gly Tyr Gly Pro Gly Ser Gln Gly Pro
        35                  40                  45

Ser Gly Pro Gly Gly Tyr Gly Pro Gly Gly Pro Gly Ser Ser Ala Ala
    50                  55                  60

Ala Ala Ala Ala Ala Ala Ser Gly Pro Gly Gly Tyr Gly Pro Gly Ser
65                  70                  75                  80
```

-continued

```
Gln Gly Pro Ser Gly Pro Gly Tyr Gly Pro Gly Pro Gly Ser
                85                  90                  95

Ser Ala Ala Ala Ala Ala Ala Ser Gly Pro Gly Gly Tyr Gly
            100                 105                 110

Pro Gly Ser Gln Gly Pro Ser Gly Pro Gly Tyr Gly Pro Gly Gly
            115                 120                 125

Pro Gly Ser Ser Ala Ala Ala Ala Ala Ala Ser Gly Pro Gly
            130                 135                 140

Gly Tyr Gly Pro Gly Ser Gln Gly Pro Ser Gly Pro Gly Tyr Gly
145                 150                 155                 160

Pro Gly Gly Pro Gly Ser Ser Ala Ala Ala Ala Ala Ala Ser
                165                 170                 175

Gly Pro Gly Gly Tyr Gly Pro Gly Ser Gln Gly Pro Ser Gly Pro Gly
                180                 185                 190

Gly Tyr Gly Pro Gly Gly Pro Gly Ser Ser Ala Ala Ala Ala
            195                 200                 205

Ala Ala Ser Gly Pro Gly Gly Tyr Gly Pro Gly Ser Gln Gly Pro Ser
            210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
                245                 250                 255

Gly Pro Ser Gly Pro Gly Tyr Gly Pro Gly Gly Pro Gly Ser Ser
                260                 265                 270

Ala Ala Ala Ala Ala Ala Ala Ser Gly Pro Gly Gly Tyr Gly Pro
                275                 280                 285

Gly Ser Gln Gly Pro Ser Gly Pro Gly Gly Tyr Gly Pro Gly Gly Pro
                290                 295                 300

Gly Ser Ser Ala Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
                325                 330                 335

Gly Gly Pro Gly Ser Ser Ala Ala Ala Ala Ala Ala Ala Ser Gly
                340                 345                 350

Pro Gly Gly Tyr Gly Pro Gly Ser Gln Gly Pro Ser Gly Pro Gly Gly
                355                 360                 365

Tyr Gly Pro Gly Gly Pro Gly Ser Ser Ala Ala Ala Ala Ala
            370                 375                 380

Ala Ser Gly Pro Gly Gly Tyr Gly Pro Gly Ser Gln Gly Pro Ser Gly
385                 390                 395                 400

Pro Gly Gly Tyr Gly Pro Gly Gly Pro Gly Ser Ser Ala Ala Ala Ala
                405                 410                 415

Ala Ala Ala Ser Gly Pro Gly Gly Tyr Gly Pro Gly Ser Gln Gly
            420                 425                 430

Pro Ser Gly Pro Gly Gly Tyr Gly Pro Gly Gly Pro Gly Ser Ser Ala
            435                 440                 445

Ala Ala Ala Ala Ala Ala Ser Gly Pro Gly Gly Tyr Gly Pro Gly
            450                 455                 460

Ser Gln Gly Pro Ser Gly Pro Gly Gly Tyr Gly Pro Gly Gly Pro Gly
465                 470                 475                 480

Ser Ser Ala Ala Ala Ala Ala Ala Ala Ser Gly Pro Gly Gly Tyr
                485                 490                 495

Gly Pro Gly Ser Gln Gly Pro Ser Gly Pro Gly Gly Tyr Gly Pro Gly
                500                 505                 510
```

-continued

```
Gly Pro Gly Ser Ser Ala Ala Ala Ala Ala Ala Ser Gly Pro
            515                 520                 525
Gly Gly Tyr Gly Pro Gly Ser Gln Gly Pro Ser Gly Pro Gly Tyr
        530                 535                 540
Gly Pro Gly Gly Pro Gly Ser Ser Ala Ala Ala Ala Ala Ala Ala
545                 550                 555                 560
Gly Pro Ser Gly Pro Gly Ala Tyr Gly Pro Ser Pro Ser Ala Ser Ala
                565                 570                 575
Ser Val Ala Ala Ser Arg Leu Ser Ser Pro Ala Ala Ser Ser Arg Val
            580                 585                 590
Ser Ser Ala Val Ser Ser Leu Val Ser Ser Gly Pro Thr Asn Gly Ala
            595                 600                 605
Ala Val Ser Gly Ala Leu Asn Ser Leu Val Ser Gln Ile Ser Ala Ser
            610                 615                 620
Asn Pro Gly Leu Ser Gly Cys Asp Ala Leu Val Gln Ala Leu Leu Glu
625                 630                 635                 640
Leu Val Ser Ala Leu Val Ala Ile Leu Ser Ser Ala Ser Ile Gly Gln
                645                 650                 655
Val Asn Val Ser Ser Val Ser Gln Ser Thr Gln Met Ile Ser Gln Ala
            660                 665                 670
Leu Ser

<210> SEQ ID NO 45
<211> LENGTH: 814
<212> TYPE: PRT
<213> ORGANISM: Artificial
<220> FEATURE:
<223> OTHER INFORMATION: 20 repeats + C domain of polymerizing synthetic
      protein

<400> SEQUENCE: 45

Ser Gly Pro Gly Gly Tyr Gly Pro Gly Ser Gln Gly Pro Ser Gly Pro
1               5                   10                  15
Gly Gly Tyr Gly Pro Gly Gly Pro Gly Ser Ser Ala Ala Ala Ala Ala
            20                  25                  30
Ala Ala Ala Ser Gly Pro Gly Gly Tyr Gly Pro Gly Ser Gln Gly Pro
        35                  40                  45
Ser Gly Pro Gly Gly Tyr Gly Pro Gly Gly Pro Gly Ser Ser Ala Ala
    50                  55                  60
Ala Ala Ala Ala Ala Ala Ser Gly Pro Gly Gly Tyr Gly Pro Gly Ser
65                  70                  75                  80
Gln Gly Pro Ser Gly Pro Gly Gly Tyr Gly Pro Gly Gly Pro Gly Ser
                85                  90                  95
Ser Ala Ala Ala Ala Ala Ala Ala Ser Gly Pro Gly Gly Tyr Gly
            100                 105                 110
Pro Gly Ser Gln Gly Pro Ser Gly Pro Gly Gly Tyr Gly Pro Gly Gly
            115                 120                 125
Pro Gly Ser Ser Ala Ala Ala Ala Ala Ala Ala Ser Gly Pro Gly
        130                 135                 140
Gly Tyr Gly Pro Gly Ser Gln Gly Pro Ser Gly Pro Gly Gly Tyr Gly
145                 150                 155                 160
Pro Gly Gly Pro Gly Ser Ser Ala Ala Ala Ala Ala Ala Ala Ser
                165                 170                 175
Gly Pro Gly Gly Tyr Gly Pro Gly Ser Gln Gly Pro Ser Gly Pro Gly
            180                 185                 190
```

```
Gly Tyr Gly Pro Gly Gly Pro Gly Ser Ser Ala Ala Ala Ala Ala
        195                 200                 205
Ala Ala Ser Gly Pro Gly Gly Tyr Gly Pro Gly Ser Gln Gly Pro Ser
    210                 215                 220
Gly Pro Gly Gly Tyr Gly Pro Gly Gly Pro Gly Ser Ser Ala Ala Ala
225                 230                 235                 240
Ala Ala Ala Ala Ala Ser Gly Pro Gly Gly Tyr Gly Pro Gly Ser Gln
            245                 250                 255
Gly Pro Ser Gly Pro Gly Gly Tyr Gly Pro Gly Gly Pro Gly Ser Ser
            260                 265                 270
Ala Ala Ala Ala Ala Ala Ala Ser Gly Pro Gly Gly Tyr Gly Pro
        275                 280                 285
Gly Ser Gln Gly Pro Ser Gly Pro Gly Gly Tyr Gly Pro Gly Gly Pro
        290                 295                 300
Gly Ser Ser Ala Ala Ala Ala Ala Ala Ala Ser Gly Pro Gly Gly
305                 310                 315                 320
Tyr Gly Pro Gly Ser Gln Gly Pro Ser Gly Pro Gly Gly Tyr Gly Pro
            325                 330                 335
Gly Gly Pro Gly Ser Ser Ala Ala Ala Ala Ala Ala Ala Ser Gly
            340                 345                 350
Pro Gly Gly Tyr Gly Pro Gly Ser Gln Gly Pro Ser Gly Pro Gly Gly
            355                 360                 365
Tyr Gly Pro Gly Gly Pro Gly Ser Ser Ala Ala Ala Ala Ala Ala Ala
        370                 375                 380
Ala Ser Gly Pro Gly Gly Tyr Gly Pro Gly Ser Gln Gly Pro Ser Gly
385                 390                 395                 400
Pro Gly Gly Tyr Gly Pro Gly Gly Pro Gly Ser Ser Ala Ala Ala Ala
            405                 410                 415
Ala Ala Ala Ala Ser Gly Pro Gly Gly Tyr Gly Pro Gly Ser Gln Gly
            420                 425                 430
Pro Ser Gly Pro Gly Gly Tyr Gly Pro Gly Gly Pro Gly Ser Ser Ala
        435                 440                 445
Ala Ala Ala Ala Ala Ala Ser Gly Pro Gly Gly Tyr Gly Pro Gly
        450                 455                 460
Ser Gln Gly Pro Ser Gly Pro Gly Gly Tyr Gly Pro Gly Gly Pro Gly
465                 470                 475                 480
Ser Ser Ala Ala Ala Ala Ala Ala Ala Ser Gly Pro Gly Gly Tyr
            485                 490                 495
Gly Pro Gly Ser Gln Gly Pro Ser Gly Pro Gly Gly Tyr Gly Pro Gly
            500                 505                 510
Gly Pro Gly Ser Ser Ala Ala Ala Ala Ala Ala Ala Ser Gly Pro
        515                 520                 525
Gly Gly Tyr Gly Pro Gly Ser Gln Gly Pro Ser Gly Pro Gly Gly Tyr
        530                 535                 540
Gly Pro Gly Gly Pro Gly Ser Ser Ala Ala Ala Ala Ala Ala Ala
545                 550                 555                 560
Ser Gly Pro Gly Gly Tyr Gly Pro Gly Ser Gln Gly Pro Ser Gly Pro
            565                 570                 575
Gly Gly Tyr Gly Pro Gly Gly Pro Gly Ser Ser Ala Ala Ala Ala
            580                 585                 590
Ala Ala Ala Ser Gly Pro Gly Gly Tyr Gly Pro Gly Ser Gln Gly Pro
        595                 600                 605
Ser Gly Pro Gly Gly Tyr Gly Pro Gly Gly Pro Gly Ser Ser Ala Ala
        610                 615                 620
```

Ala Ala Ala Ala Ala Ser Gly Pro Gly Gly Tyr Gly Pro Gly Ser
625                 630                 635                 640

Gln Gly Pro Ser Gly Pro Gly Gly Tyr Gly Pro Gly Gly Pro Gly Ser
            645                 650                 655

Ser Ala Ala Ala Ala Ala Ala Ser Gly Pro Gly Gly Tyr Gly
        660                 665                 670

Pro Gly Ser Gln Gly Pro Ser Gly Pro Gly Gly Tyr Gly Pro Gly Gly
        675                 680                 685

Pro Gly Ser Ser Ala Ala Ala Ala Ala Ala Gly Pro Ser Gly
        690                 695                 700

Pro Gly Ala Tyr Gly Pro Ser Pro Ser Ala Ser Ala Ser Val Ala Ala
705                 710                 715                 720

Ser Arg Leu Ser Ser Pro Ala Ala Ser Ser Arg Val Ser Ser Ala Val
                725                 730                 735

Ser Ser Leu Val Ser Ser Gly Pro Thr Asn Gly Ala Ala Val Ser Gly
            740                 745                 750

Ala Leu Asn Ser Leu Val Ser Gln Ile Ser Ala Ser Asn Pro Gly Leu
            755                 760                 765

Ser Gly Cys Asp Ala Leu Val Gln Ala Leu Leu Glu Leu Val Ser Ala
        770                 775                 780

Leu Val Ala Ile Leu Ser Ser Ala Ser Ile Gly Gln Val Asn Val Ser
785                 790                 795                 800

Ser Val Ser Gln Ser Thr Gln Met Ile Ser Gln Ala Leu Ser
                805                 810

<210> SEQ ID NO 46
<211> LENGTH: 954
<212> TYPE: PRT
<213> ORGANISM: Artificial
<220> FEATURE:
<223> OTHER INFORMATION: 24 repeats + C domain of polymerizing synthetic
      protein

<400> SEQUENCE: 46

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
                20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
        50                  55                  60

Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
                85                  90                  95

Ser Ala Ala Ala Ala Ala Ala Ser Gly Pro Gly Gly Tyr Gly
            100                 105                 110

Pro Gly Ser Gln Gly Pro Ser Gly Pro Gly Gly Tyr Gly Pro Gly Gly
            115                 120                 125

Pro Gly Ser Ser Ala Ala Ala Ala Ala Ala Ser Gly Pro Gly
        130                 135                 140

Gly Tyr Gly Pro Gly Ser Gln Gly Pro Ser Gly Pro Gly Gly Tyr Gly
145                 150                 155                 160

Pro Gly Gly Pro Gly Ser Ser Ala Ala Ala Ala Ala Ala Ala Ser
                165                 170                 175

```
Gly Pro Gly Gly Tyr Gly Pro Gly Ser Gln Gly Pro Ser Gly Pro Gly
            180                 185                 190

Gly Tyr Gly Pro Gly Gly Pro Gly Ser Ser Ala Ala Ala Ala Ala Ala
            195                 200                 205

Ala Ala Ser Gly Pro Gly Gly Tyr Gly Pro Gly Ser Gln Gly Pro Ser
210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
            245                 250                 255

Gly Pro Ser Gly Pro Gly Gly Tyr Gly Pro Gly Gly Pro Gly Ser Ser
            260                 265                 270

Ala Ala Ala Ala Ala Ala Ala Ser Gly Pro Gly Gly Tyr Gly Pro
            275                 280                 285

Gly Ser Gln Gly Pro Ser Gly Pro Gly Gly Tyr Gly Pro Gly Gly Pro
            290                 295                 300

Gly Ser Ser Ala Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
            325                 330                 335

Gly Gly Pro Gly Ser Ser Ala Ala Ala Ala Ala Ala Ala Ser Gly
            340                 345                 350

Pro Gly Gly Tyr Gly Pro Gly Ser Gln Gly Pro Ser Gly Pro Gly Gly
            355                 360                 365

Tyr Gly Pro Gly Gly Pro Gly Ser Ser Ala Ala Ala Ala Ala Ala Ala
            370                 375                 380

Ala Ser Gly Pro Gly Gly Tyr Gly Pro Gly Ser Gln Gly Pro Ser Gly
385                 390                 395                 400

Pro Gly Gly Tyr Gly Pro Gly Gly Pro Gly Ser Ser Ala Ala Ala Ala
            405                 410                 415

Ala Ala Ala Ala Ser Gly Pro Gly Gly Tyr Gly Pro Gly Ser Gln Gly
            420                 425                 430

Pro Ser Gly Pro Gly Gly Tyr Gly Pro Gly Gly Pro Gly Ser Ser Ala
            435                 440                 445

Ala Ala Ala Ala Ala Ala Ser Gly Pro Gly Gly Tyr Gly Pro Gly
450                 455                 460

Ser Gln Gly Pro Ser Gly Pro Gly Gly Tyr Gly Pro Gly Gly Pro Gly
465                 470                 475                 480

Ser Ser Ala Ala Ala Ala Ala Ala Ala Ser Gly Pro Gly Gly Tyr
            485                 490                 495

Gly Pro Gly Ser Gln Gly Pro Ser Gly Pro Gly Gly Tyr Gly Pro Gly
            500                 505                 510

Gly Pro Gly Ser Ser Ala Ala Ala Ala Ala Ala Ala Ser Gly Pro
            515                 520                 525

Gly Gly Tyr Gly Pro Gly Ser Gln Gly Pro Ser Gly Pro Gly Gly Tyr
            530                 535                 540

Gly Pro Gly Gly Pro Gly Ser Ser Ala Ala Ala Ala Ala Ala Ala
545                 550                 555                 560

Ser Gly Pro Gly Gly Tyr Gly Pro Gly Ser Gln Gly Pro Ser Gly Pro
            565                 570                 575

Gly Gly Tyr Gly Pro Gly Gly Pro Gly Ser Ser Ala Ala Ala Ala
            580                 585                 590

Ala Ala Ala Ser Gly Pro Gly Gly Tyr Gly Pro Gly Ser Gln Gly Pro
```

595                 600                 605

Ser Gly Pro Gly Gly Tyr Gly Pro Gly Pro Gly Ser Ala Ala
    610                 615                 620

Ala Ala Ala Ala Ala Ala Ser Gly Pro Gly Gly Tyr Gly Pro Gly Ser
625                 630                 635                 640

Gln Gly Pro Ser Gly Pro Gly Gly Tyr Gly Pro Gly Pro Gly Ser
                645                 650                 655

Ser Ala Ala Ala Ala Ala Ala Ser Gly Pro Gly Gly Tyr Gly
            660                 665                 670

Pro Gly Ser Gln Gly Pro Ser Gly Pro Gly Gly Tyr Gly Pro Gly Gly
        675                 680                 685

Pro Gly Ser Ser Ala Ala Ala Ala Ala Ala Ser Gly Pro Gly
        690                 695                 700

Gly Tyr Gly Pro Gly Ser Gln Gly Pro Ser Gly Pro Gly Gly Tyr Gly
705                 710                 715                 720

Pro Gly Gly Pro Gly Ser Ser Ala Ala Ala Ala Ala Ala Ser
                725                 730                 735

Gly Pro Gly Gly Tyr Gly Pro Gly Ser Gln Gly Pro Ser Gly Pro Gly
            740                 745                 750

Gly Tyr Gly Pro Gly Gly Pro Gly Ser Ser Ala Ala Ala Ala Ala
        755                 760                 765

Ala Ala Ser Gly Pro Gly Tyr Gly Pro Gly Ser Gln Gly Pro Ser
770                 775                 780

Gly Pro Gly Gly Tyr Gly Pro Gly Gly Pro Gly Ser Ser Ala Ala Ala
785                 790                 795                 800

Ala Ala Ala Ala Ser Gly Pro Gly Gly Tyr Gly Pro Gly Ser Gln
                805                 810                 815

Gly Pro Ser Gly Pro Gly Gly Tyr Gly Pro Gly Gly Pro Gly Ser Ser
            820                 825                 830

Ala Ala Ala Ala Ala Ala Ala Gly Pro Ser Gly Pro Gly Ala Tyr
        835                 840                 845

Gly Pro Ser Pro Ser Ala Ser Ala Ser Val Ala Ala Ser Arg Leu Ser
850                 855                 860

Ser Pro Ala Ala Ser Ser Arg Val Ser Ser Ala Val Ser Ser Leu Val
865                 870                 875                 880

Ser Ser Gly Pro Thr Asn Gly Ala Ala Val Ser Gly Ala Leu Asn Ser
            885                 890                 895

Leu Val Ser Gln Ile Ser Ala Ser Asn Pro Gly Leu Ser Gly Cys Asp
        900                 905                 910

Ala Leu Val Gln Ala Leu Leu Glu Leu Val Ser Ala Leu Val Ala Ile
        915                 920                 925

Leu Ser Ser Ala Ser Ile Gly Gln Val Asn Val Ser Ser Val Ser Gln
    930                 935                 940

Ser Thr Gln Met Ile Ser Gln Ala Leu Ser
945                 950

<210> SEQ ID NO 47
<211> LENGTH: 1234
<212> TYPE: PRT
<213> ORGANISM: Artificial
<220> FEATURE:
<223> OTHER INFORMATION: 32 repeats + C domain of polymerizing synthetic
      protein

<400> SEQUENCE: 47

Ser Gly Pro Gly Gly Tyr Gly Pro Gly Ser Gln Gly Pro Ser Gly Pro

-continued

```
1               5                   10                  15
Gly Gly Tyr Gly Pro Gly Gly Pro Gly Ser Ser Ala Ala Ala Ala
            20                  25              30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
    50                  55                  60

Ala Ala Ala Ala Ala Ala Ser Gly Pro Gly Gly Tyr Gly Pro Gly Ser
65                  70                  75                  80

Gln Gly Pro Ser Gly Pro Gly Tyr Gly Pro Gly Gly Pro Gly Ser
                85                  90                  95

Ser Ala Ala Ala Ala Ala Ala Ala Ser Gly Pro Gly Gly Tyr Gly
                100                 105                 110

Pro Gly Ser Gln Gly Pro Ser Gly Pro Gly Tyr Gly Pro Gly Gly
            115                 120                 125

Pro Gly Ser Ser Ala Ala Ala Ala Ala Ala Ala Ser Gly Pro Gly
    130                 135                 140

Gly Tyr Gly Pro Gly Ser Gln Gly Pro Ser Gly Pro Gly Gly Tyr Gly
145                 150                 155                 160

Pro Gly Gly Pro Gly Ser Ser Ala Ala Ala Ala Ala Ala Ala Ser
            165                 170                 175

Gly Pro Gly Gly Tyr Gly Pro Gly Ser Gln Gly Pro Ser Gly Pro Gly
            180                 185                 190

Gly Tyr Gly Pro Gly Gly Pro Gly Ser Ser Ala Ala Ala Ala Ala
            195                 200                 205

Ala Ala Ser Gly Pro Gly Gly Tyr Gly Pro Gly Ser Gln Gly Pro Ser
    210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
            245                 250                 255

Gly Pro Ser Gly Pro Gly Gly Tyr Gly Pro Gly Gly Pro Gly Ser Ser
            260                 265                 270

Ala Ala Ala Ala Ala Ala Ala Ser Gly Pro Gly Gly Tyr Gly Pro
    275                 280                 285

Gly Ser Gln Gly Pro Ser Gly Pro Gly Gly Tyr Gly Pro Gly Gly Pro
290                 295                 300

Gly Ser Ser Ala Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
            325                 330                 335

Gly Gly Pro Gly Ser Ser Ala Ala Ala Ala Ala Ala Ala Ser Gly
            340                 345                 350

Pro Gly Gly Tyr Gly Pro Gly Ser Gln Gly Pro Ser Gly Pro Gly Gly
    355                 360                 365

Tyr Gly Pro Gly Gly Pro Gly Ser Ser Ala Ala Ala Ala Ala Ala
370                 375                 380

Ala Ser Gly Pro Gly Gly Tyr Gly Pro Gly Ser Gln Gly Pro Ser Gly
385                 390                 395                 400

Pro Gly Gly Tyr Gly Pro Gly Gly Pro Gly Ser Ser Ala Ala Ala Ala
            405                 410                 415

Ala Ala Ala Ala Ser Gly Pro Gly Gly Tyr Gly Pro Gly Ser Gln Gly
            420                 425                 430
```

-continued

```
Pro Ser Gly Pro Gly Gly Tyr Gly Pro Gly Gly Pro Gly Ser Ser Ala
        435                 440                 445
Ala Ala Ala Ala Ala Ala Ser Gly Pro Gly Gly Tyr Gly Pro Gly
    450                 455                 460
Ser Gln Gly Pro Ser Gly Pro Gly Gly Tyr Gly Pro Gly Gly Pro Gly
465                 470                 475                 480
Ser Ser Ala Ala Ala Ala Ala Ala Ser Gly Pro Gly Gly Tyr
                485                 490                 495
Gly Pro Gly Ser Gln Gly Pro Ser Gly Pro Gly Gly Tyr Gly Pro Gly
            500                 505                 510
Gly Pro Gly Ser Ser Ala Ala Ala Ala Ala Ala Ser Gly Pro
            515                 520                 525
Gly Gly Tyr Gly Pro Gly Ser Gln Gly Pro Ser Gly Pro Gly Gly Tyr
        530                 535                 540
Gly Pro Gly Gly Pro Gly Ser Ser Ala Ala Ala Ala Ala Ala
545                 550                 555                 560
Ser Gly Pro Gly Gly Tyr Gly Pro Gly Ser Gln Gly Pro Ser Gly Pro
                565                 570                 575
Gly Gly Tyr Gly Pro Gly Gly Pro Gly Ser Ser Ala Ala Ala Ala
            580                 585                 590
Ala Ala Ala Ser Gly Pro Gly Gly Tyr Gly Pro Gly Ser Gln Gly Pro
            595                 600                 605
Ser Gly Pro Gly Gly Tyr Gly Pro Gly Gly Pro Gly Ser Ser Ala Ala
        610                 615                 620
Ala Ala Ala Ala Ala Ser Gly Pro Gly Gly Tyr Gly Pro Gly Ser
625                 630                 635                 640
Gln Gly Pro Ser Gly Pro Gly Gly Tyr Gly Pro Gly Gly Pro Gly Ser
                645                 650                 655
Ser Ala Ala Ala Ala Ala Ala Ser Gly Pro Gly Gly Tyr Gly
            660                 665                 670
Pro Gly Ser Gln Gly Pro Ser Gly Pro Gly Gly Tyr Gly Pro Gly Gly
            675                 680                 685
Pro Gly Ser Ser Ala Ala Ala Ala Ala Ala Ala Ser Gly Pro Gly
            690                 695                 700
Gly Tyr Gly Pro Gly Ser Gln Gly Pro Ser Gly Pro Gly Gly Tyr Gly
705                 710                 715                 720
Pro Gly Gly Pro Gly Ser Ser Ala Ala Ala Ala Ala Ala Ser
                725                 730                 735
Gly Pro Gly Gly Tyr Gly Pro Gly Ser Gln Gly Pro Ser Pro Gly
            740                 745                 750
Gly Tyr Gly Pro Gly Gly Pro Gly Ser Ser Ala Ala Ala Ala Ala
            755                 760                 765
Ala Ala Ser Gly Pro Gly Gly Tyr Gly Pro Gly Ser Gln Gly Pro Ser
        770                 775                 780
Gly Pro Gly Gly Tyr Gly Pro Gly Gly Pro Gly Ser Ser Ala Ala
785                 790                 795                 800
Ala Ala Ala Ala Ala Ser Gly Pro Gly Gly Tyr Gly Pro Gly Ser Gln
                805                 810                 815
Gly Pro Ser Gly Pro Gly Gly Tyr Gly Pro Gly Gly Pro Gly Ser Ser
            820                 825                 830
Ala Ala Ala Ala Ala Ala Ala Ser Gly Pro Gly Gly Tyr Gly Pro
            835                 840                 845
Gly Ser Gln Gly Pro Ser Gly Pro Gly Gly Tyr Gly Pro Gly Gly Pro
            850                 855                 860
```

Gly Ser Ser Ala Ala Ala Ala Ala Ala Ser Gly Pro Gly Gly
865                 870                 875                 880

Tyr Gly Pro Gly Ser Gln Gly Pro Ser Gly Pro Gly Gly Tyr Gly Pro
            885                 890                 895

Gly Gly Pro Gly Ser Ser Ala Ala Ala Ala Ala Ala Ser Gly
            900                 905                 910

Pro Gly Gly Tyr Gly Pro Gly Ser Gln Gly Pro Ser Gly Pro Gly Gly
            915                 920                 925

Tyr Gly Pro Gly Gly Pro Gly Ser Ser Ala Ala Ala Ala Ala
930                 935                 940

Ala Ser Gly Pro Gly Gly Tyr Gly Pro Gly Ser Gln Gly Pro Ser Gly
945                 950                 955                 960

Pro Gly Gly Tyr Gly Pro Gly Gly Pro Gly Ser Ser Ala Ala Ala
            965                 970                 975

Ala Ala Ala Ala Ser Gly Pro Gly Gly Tyr Gly Pro Gly Ser Gln Gly
                980                 985                 990

Pro Ser Gly Pro Gly Gly Tyr Gly Pro Gly Gly Pro Gly Ser Ser Ala
            995                 1000                1005

Ala Ala Ala Ala Ala Ala Ser Gly Pro Gly Gly Tyr Gly Pro
    1010                1015                1020

Gly Ser Gln Gly Pro Ser Gly Pro Gly Tyr Gly Pro Gly Gly
    1025                1030                1035

Pro Gly Ser Ser Ala Ala Ala Ala Ala Ala Ala Ser Gly Pro
    1040                1045                1050

Gly Gly Tyr Gly Pro Gly Ser Gln Gly Pro Ser Gly Pro Gly Gly
    1055                1060                1065

Tyr Gly Pro Gly Gly Pro Gly Ser Ser Ala Ala Ala Ala Ala
    1070                1075                1080

Ala Ala Ser Gly Pro Gly Gly Tyr Gly Pro Gly Ser Gln Gly Pro
    1085                1090                1095

Ser Gly Pro Gly Gly Tyr Gly Pro Gly Gly Pro Gly Ser Ser Ala
    1100                1105                1110

Ala Ala Ala Ala Ala Ala Gly Pro Ser Gly Pro Gly Ala Tyr
    1115                1120                1125

Gly Pro Ser Pro Ser Ala Ser Ala Ser Val Ala Ala Ser Arg Leu
    1130                1135                1140

Ser Ser Pro Ala Ala Ser Ser Arg Val Ser Ser Ala Val Ser Ser
    1145                1150                1155

Leu Val Ser Ser Gly Pro Thr Asn Gly Ala Ala Val Ser Gly Ala
    1160                1165                1170

Leu Asn Ser Leu Val Ser Gln Ile Ser Ala Ser Asn Pro Gly Leu
    1175                1180                1185

Ser Gly Cys Asp Ala Leu Val Gln Ala Leu Leu Glu Leu Val Ser
    1190                1195                1200

Ala Leu Val Ala Ile Leu Ser Ser Ala Ser Ile Gly Gln Val Asn
    1205                1210                1215

Val Ser Ser Val Ser Gln Ser Thr Gln Met Ile Ser Gln Ala Leu
    1220                1225                1230

Ser

<210> SEQ ID NO 48
<211> LENGTH: 70
<212> TYPE: PRT
<213> ORGANISM: Artificial

<220> FEATURE:
<223> OTHER INFORMATION: 2X amino acid repeat sequence

<400> SEQUENCE: 48

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
                20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
        50                  55                  60

Ala Ala Ala Ala Ala Ala
65              70

<210> SEQ ID NO 49
<211> LENGTH: 140
<212> TYPE: PRT
<213> ORGANISM: Artificial
<220> FEATURE:
<223> OTHER INFORMATION: 4X amino acid repeat sequence

<400> SEQUENCE: 49

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
                20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
        50                  55                  60

Ala Ala Ala Ala Ala Ala Ser Gly Pro Gly Gly Tyr Gly Pro Gly Ser
65              70                  75                  80

Gln Gly Pro Ser Gly Pro Gly Gly Tyr Gly Pro Gly Gly Pro Gly Ser
                85                  90                  95

Ser Ala Ala Ala Ala Ala Ala Ala Ser Gly Pro Gly Gly Tyr Gly
            100                 105                 110

Pro Gly Ser Gln Gly Pro Ser Gly Pro Gly Gly Tyr Gly Pro Gly Gly
        115                 120                 125

Pro Gly Ser Ser Ala Ala Ala Ala Ala Ala Ala
    130                 135                 140

<210> SEQ ID NO 50
<211> LENGTH: 280
<212> TYPE: PRT
<213> ORGANISM: Artificial
<220> FEATURE:
<223> OTHER INFORMATION: 8X amino acid repeat sequence

<400> SEQUENCE: 50

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
                20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
        50                  55                  60

Ala Ala Ala Ala Ala Ala Ser Gly Pro Gly Gly Tyr Gly Pro Gly Ser

-continued

```
                65                  70                  75                  80
Gln Gly Pro Ser Gly Pro Gly Gly Tyr Gly Pro Gly Gly Pro Gly Ser
                    85                  90                  95

Ser Ala Ala Ala Ala Ala Ala Ala Ser Gly Pro Gly Gly Tyr Gly
                100                 105                 110

Pro Gly Ser Gln Gly Pro Ser Gly Pro Gly Gly Tyr Gly Pro Gly Gly
                115                 120                 125

Pro Gly Ser Ser Ala Ala Ala Ala Ala Ala Ala Ser Gly Pro Gly
            130                 135                 140

Gly Tyr Gly Pro Gly Ser Gln Gly Pro Ser Gly Pro Gly Gly Tyr Gly
145                 150                 155                 160

Pro Gly Gly Pro Gly Ser Ser Ala Ala Ala Ala Ala Ala Ala Ser
                165                 170                 175

Gly Pro Gly Gly Tyr Gly Pro Gly Ser Gln Gly Pro Ser Gly Pro Gly
                180                 185                 190

Gly Tyr Gly Pro Gly Gly Pro Gly Ser Ser Ala Ala Ala Ala Ala
            195                 200                 205

Ala Ala Ser Gly Pro Gly Gly Tyr Gly Pro Gly Ser Gln Gly Pro Ser
            210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
                245                 250                 255

Gly Pro Ser Gly Pro Gly Gly Tyr Gly Pro Gly Gly Pro Gly Ser Ser
                260                 265                 270

Ala Ala Ala Ala Ala Ala Ala Ala
            275                 280

<210> SEQ ID NO 51
<211> LENGTH: 420
<212> TYPE: PRT
<213> ORGANISM: Artificial
<220> FEATURE:
<223> OTHER INFORMATION: 12X amino acid repeat sequence

<400> SEQUENCE: 51

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
                20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
        50                  55                  60

Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
                85                  90                  95

Ser Ala Ala Ala Ala Ala Ala Ala Ser Gly Pro Gly Gly Tyr Gly
                100                 105                 110

Pro Gly Ser Gln Gly Pro Ser Gly Pro Gly Gly Tyr Gly Pro Gly Gly
            115                 120                 125

Pro Gly Ser Ser Ala Ala Ala Ala Ala Ala Ala Ser Gly Pro Gly
        130                 135                 140

Gly Tyr Gly Pro Gly Ser Gln Gly Pro Ser Gly Pro Gly Gly Tyr Gly
145                 150                 155                 160
```

```
Pro Gly Gly Pro Gly Ser Ser Ala Ala Ala Ala Ala Ala Ser
            165                 170                 175

Gly Pro Gly Gly Tyr Gly Pro Gly Ser Gln Gly Pro Ser Pro Gly
            180                 185                 190

Gly Tyr Gly Pro Gly Gly Pro Gly Ser Ser Ala Ala Ala Ala Ala
            195                 200                 205

Ala Ala Ser Gly Pro Gly Gly Tyr Gly Pro Gly Ser Gln Gly Pro Ser
    210                 215                 220

Gly Pro Gly Gly Tyr Gly Pro Gly Gly Pro Gly Ser Ser Ala Ala
225                 230                 235                 240

Ala Ala Ala Ala Ala Ser Gly Pro Gly Gly Tyr Gly Pro Gly Ser Gln
                245                 250                 255

Gly Pro Ser Gly Pro Gly Gly Tyr Gly Pro Gly Gly Pro Gly Ser Ser
            260                 265                 270

Ala Ala Ala Ala Ala Ala Ala Ser Gly Pro Gly Gly Tyr Gly Pro
            275                 280                 285

Gly Ser Gln Gly Pro Ser Gly Pro Gly Gly Tyr Gly Pro Gly Gly Pro
    290                 295                 300

Gly Ser Ser Ala Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
                325                 330                 335

Gly Gly Pro Gly Ser Ser Ala Ala Ala Ala Ala Ala Ala Ser Gly
            340                 345                 350

Pro Gly Gly Tyr Gly Pro Gly Ser Gln Gly Pro Ser Gly Pro Gly Gly
            355                 360                 365

Tyr Gly Pro Gly Gly Pro Gly Ser Ser Ala Ala Ala Ala Ala Ala
            370                 375                 380

Ala Ser Gly Pro Gly Gly Tyr Gly Pro Gly Ser Gln Gly Pro Ser Gly
385                 390                 395                 400

Pro Gly Gly Tyr Gly Pro Gly Gly Pro Gly Ser Ser Ala Ala Ala Ala
            405                 410                 415

Ala Ala Ala Ala
        420

<210> SEQ ID NO 52
<211> LENGTH: 560
<212> TYPE: PRT
<213> ORGANISM: Artificial
<220> FEATURE:
<223> OTHER INFORMATION: 16X amino acid repeat sequence

<400> SEQUENCE: 52

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
            20                  25                  30

Ala Ala Ala Ser Gly Pro Gly Gly Tyr Gly Pro Gly Ser Gln Gly Pro
        35                  40                  45

Ser Gly Pro Gly Gly Tyr Gly Pro Gly Gly Pro Gly Ser Ser Ala Ala
    50                  55                  60

Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
                85                  90                  95
```

```
Ser Ala Ala Ala Ala Ala Ala Ser Gly Pro Gly Gly Tyr Gly
        100                 105                 110

Pro Gly Ser Gln Gly Pro Ser Pro Gly Gly Tyr Gly Pro Gly
            115                 120                 125

Pro Gly Ser Ser Ala Ala Ala Ala Ala Ala Ser Gly Pro Gly
    130                 135                 140

Gly Tyr Gly Pro Gly Ser Gln Gly Pro Ser Pro Gly Gly Tyr Gly
145                 150                 155                 160

Pro Gly Gly Pro Gly Ser Ser Ala Ala Ala Ala Ala Ala Ser
                165                 170                 175

Gly Pro Gly Gly Tyr Gly Pro Gly Ser Gln Gly Pro Ser Pro Gly
                180                 185                 190

Gly Tyr Gly Pro Gly Gly Pro Gly Ser Ser Ala Ala Ala Ala
                195                 200                 205

Ala Ala Ser Gly Pro Gly Gly Tyr Gly Pro Gly Ser Gln Gly Pro Ser
    210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
                245                 250                 255

Gly Pro Ser Gly Pro Gly Gly Tyr Gly Pro Gly Gly Pro Gly Ser Ser
                260                 265                 270

Ala Ala Ala Ala Ala Ala Ala Ser Gly Pro Gly Gly Tyr Gly Pro
    275                 280                 285

Gly Ser Gln Gly Pro Ser Gly Pro Gly Gly Tyr Gly Pro Gly Gly Pro
    290                 295                 300

Gly Ser Ser Ala Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
                325                 330                 335

Gly Gly Pro Gly Ser Ser Ala Ala Ala Ala Ala Ala Ala Ser Gly
                340                 345                 350

Pro Gly Gly Tyr Gly Pro Gly Ser Gln Gly Pro Ser Gly Pro Gly Gly
        355                 360                 365

Tyr Gly Pro Gly Gly Pro Gly Ser Ser Ala Ala Ala Ala Ala Ala
    370                 375                 380

Ala Ser Gly Pro Gly Gly Tyr Gly Pro Gly Ser Gln Gly Pro Ser Gly
385                 390                 395                 400

Pro Gly Gly Tyr Gly Pro Gly Gly Pro Gly Ser Ser Ala Ala Ala Ala
                405                 410                 415

Ala Ala Ala Ala Ser Gly Pro Gly Gly Tyr Gly Pro Gly Ser Gln Gly
        420                 425                 430

Pro Ser Gly Pro Gly Gly Tyr Gly Pro Gly Gly Pro Gly Ser Ser Ala
        435                 440                 445

Ala Ala Ala Ala Ala Ser Gly Pro Gly Gly Tyr Gly Pro Gly
    450                 455                 460

Ser Gln Gly Pro Ser Gly Pro Gly Gly Tyr Gly Pro Gly Gly Pro Gly
465                 470                 475                 480

Ser Ser Ala Ala Ala Ala Ala Ala Ala Ser Gly Pro Gly Gly Tyr
                485                 490                 495

Gly Pro Gly Ser Gln Gly Pro Ser Gly Pro Gly Gly Tyr Gly Pro Gly
            500                 505                 510

Gly Pro Gly Ser Ser Ala Ala Ala Ala Ala Ala Ala Ser Gly Pro
                515                 520                 525
```

-continued

Gly Gly Tyr Gly Pro Gly Ser Gln Gly Pro Ser Gly Pro Gly Tyr
            530                 535                 540

Gly Pro Gly Gly Pro Gly Ser Ser Ala Ala Ala Ala Ala Ala Ala
545                 550                 555                 560

<210> SEQ ID NO 53
<211> LENGTH: 700
<212> TYPE: PRT
<213> ORGANISM: Artificial
<220> FEATURE:
<223> OTHER INFORMATION: 20X amino acid repeat sequence

<400> SEQUENCE: 53

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
            20                  25                  30

Ala Ala Ala Ser Gly Pro Gly Gly Tyr Gly Pro Gly Ser Gln Gly Pro
        35                  40                  45

Ser Gly Pro Gly Gly Tyr Gly Pro Gly Gly Pro Gly Ser Ser Ala Ala
    50                  55                  60

Ala Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
                85                  90                  95

Ser Ala Ala Ala Ala Ala Ala Ala Ser Gly Pro Gly Gly Tyr Gly
            100                 105                 110

Pro Gly Ser Gln Gly Pro Ser Gly Pro Gly Gly Tyr Gly Pro Gly Gly
            115                 120                 125

Pro Gly Ser Ser Ala Ala Ala Ala Ala Ala Ala Ser Gly Pro Gly
            130                 135                 140

Gly Tyr Gly Pro Gly Ser Gln Gly Pro Ser Gly Pro Gly Gly Tyr Gly
145                 150                 155                 160

Pro Gly Gly Pro Gly Ser Ser Ala Ala Ala Ala Ala Ala Ala Ser
            165                 170                 175

Gly Pro Gly Gly Tyr Gly Pro Gly Ser Gln Gly Pro Ser Gly Pro Gly
            180                 185                 190

Gly Tyr Gly Pro Gly Gly Pro Gly Ser Ser Ala Ala Ala Ala Ala Ala
            195                 200                 205

Ala Ala Ser Gly Pro Gly Gly Tyr Gly Pro Gly Ser Gln Gly Pro Ser
210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
            245                 250                 255

Gly Pro Ser Gly Pro Gly Gly Tyr Gly Pro Gly Gly Pro Gly Ser Ser
            260                 265                 270

Ala Ala Ala Ala Ala Ala Ala Ser Gly Pro Gly Gly Tyr Gly Pro
            275                 280                 285

Gly Ser Gln Gly Pro Ser Gly Pro Gly Gly Tyr Gly Pro Gly Gly Pro
            290                 295                 300

Gly Ser Ser Ala Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
                325                 330                 335

-continued

```
Gly Gly Pro Gly Ser Ser Ala Ala Ala Ala Ala Ala Ser Gly
            340                 345                 350

Pro Gly Gly Tyr Gly Pro Gly Ser Gln Gly Pro Ser Gly Gly
            355                 360                 365

Tyr Gly Pro Gly Gly Pro Gly Ser Ser Ala Ala Ala Ala Ala
    370                 375                 380

Ala Ser Gly Pro Gly Gly Tyr Gly Pro Gly Ser Gln Gly Ser
385                 390                 395                 400

Pro Gly Gly Tyr Gly Pro Gly Pro Gly Ser Ser Ala Ala Ala
            405                 410                 415

Ala Ala Ala Ala Ser Gly Pro Gly Gly Tyr Gly Pro Ser Gln Gly
            420                 425                 430

Pro Ser Gly Pro Gly Gly Tyr Gly Pro Gly Pro Gly Ser Ser Ala
            435                 440                 445

Ala Ala Ala Ala Ala Ala Ser Gly Pro Gly Gly Tyr Gly Pro Gly
            450                 455                 460

Ser Gln Gly Pro Ser Gly Pro Gly Gly Tyr Gly Pro Gly Pro Gly
465                 470                 475                 480

Ser Ser Ala Ala Ala Ala Ala Ala Ala Ser Gly Pro Gly Gly Tyr
            485                 490                 495

Gly Pro Gly Ser Gln Gly Pro Ser Gly Pro Gly Gly Tyr Gly Pro Gly
            500                 505                 510

Gly Pro Gly Ser Ser Ala Ala Ala Ala Ala Ala Ala Ser Gly Pro
            515                 520                 525

Gly Gly Tyr Gly Pro Gly Ser Gln Gly Pro Ser Gly Pro Gly Gly Tyr
            530                 535                 540

Gly Pro Gly Gly Pro Gly Ser Ser Ala Ala Ala Ala Ala Ala Ala
545                 550                 555                 560

Ser Gly Pro Gly Gly Tyr Gly Pro Gly Ser Gln Gly Pro Ser Gly Pro
            565                 570                 575

Gly Gly Tyr Gly Pro Gly Gly Pro Gly Ser Ser Ala Ala Ala Ala
            580                 585                 590

Ala Ala Ala Ser Gly Pro Gly Gly Tyr Gly Pro Gly Ser Gln Gly Pro
            595                 600                 605

Ser Gly Pro Gly Gly Tyr Gly Pro Gly Gly Pro Gly Ser Ser Ala Ala
            610                 615                 620

Ala Ala Ala Ala Ser Gly Pro Gly Gly Tyr Gly Pro Gly Ser
625                 630                 635                 640

Gln Gly Pro Ser Gly Pro Gly Gly Tyr Gly Pro Gly Gly Pro Gly Ser
            645                 650                 655

Ser Ala Ala Ala Ala Ala Ala Ala Ser Gly Pro Gly Gly Tyr Gly
            660                 665                 670

Pro Gly Ser Gln Gly Pro Ser Gly Pro Gly Gly Tyr Gly Pro Gly Gly
            675                 680                 685

Pro Gly Ser Ser Ala Ala Ala Ala Ala Ala Ala
            690                 695                 700

<210> SEQ ID NO 54
<211> LENGTH: 840
<212> TYPE: PRT
<213> ORGANISM: Artificial
<220> FEATURE:
<223> OTHER INFORMATION: 24X amino acid repeat sequence

<400> SEQUENCE: 54

Ser Gly Pro Gly Gly Tyr Gly Pro Gly Ser Gln Gly Pro Ser Gly Pro
```

-continued

```
1               5                   10                  15
Gly Gly Tyr Gly Pro Gly Gly Pro Gly Ser Ser Ala Ala Ala Ala
                20                  25                  30
Ala Ala Ala Ser Gly Pro Gly Gly Tyr Gly Pro Gly Ser Gln Gly Pro
                35                  40                  45
Ser Gly Pro Gly Gly Tyr Gly Pro Gly Gly Pro Gly Ser Ser Ala Ala
            50                  55                  60
Ala Ala Ala Ala Ala Ala Ser Gly Pro Gly Gly Tyr Gly Pro Gly Ser
65                  70                  75                  80
Gln Gly Pro Ser Gly Pro Gly Tyr Gly Pro Gly Gly Pro Gly Ser
                85                  90                  95
Ser Ala Ala Ala Ala Ala Ala Ala Ser Gly Pro Gly Gly Tyr Gly
                100                 105                 110
Pro Gly Ser Gln Gly Pro Ser Gly Pro Gly Gly Tyr Gly Pro Gly Gly
                115                 120                 125
Pro Gly Ser Ser Ala Ala Ala Ala Ala Ala Ala Ser Gly Pro Gly
                130                 135                 140
Gly Tyr Gly Pro Gly Ser Gln Gly Pro Ser Gly Pro Gly Gly Tyr Gly
145                 150                 155                 160
Pro Gly Gly Pro Gly Ser Ser Ala Ala Ala Ala Ala Ala Ala Ser
                165                 170                 175
Gly Pro Gly Gly Tyr Gly Pro Gly Ser Gln Gly Pro Ser Gly Pro Gly
                180                 185                 190
Gly Tyr Gly Pro Gly Gly Pro Gly Ser Ser Ala Ala Ala Ala Ala
                195                 200                 205
Ala Ala Ser Gly Pro Gly Gly Tyr Gly Pro Gly Ser Gln Gly Pro Ser
                210                 215                 220
Gly Pro Gly Gly Tyr Gly Pro Gly Gly Pro Gly Ser Ser Ala Ala Ala
225                 230                 235                 240
Ala Ala Ala Ala Ala Ser Gly Pro Gly Gly Tyr Gly Pro Gly Ser Gln
                245                 250                 255
Gly Pro Ser Gly Pro Gly Gly Tyr Gly Pro Gly Gly Pro Gly Ser Ser
                260                 265                 270
Ala Ala Ala Ala Ala Ala Ala Ser Gly Pro Gly Gly Tyr Gly Pro
                275                 280                 285
Gly Ser Gln Gly Pro Ser Gly Pro Gly Gly Tyr Gly Pro Gly Gly Pro
                290                 295                 300
Gly Ser Ser Ala Ala Ala Ala Ala Ala Ala Ser Gly Pro Gly Gly
305                 310                 315                 320
Tyr Gly Pro Gly Ser Gln Gly Pro Ser Gly Pro Gly Gly Tyr Gly Pro
                325                 330                 335
Gly Gly Pro Gly Ser Ser Ala Ala Ala Ala Ala Ala Ala Ser Gly
                340                 345                 350
Pro Gly Gly Tyr Gly Pro Gly Ser Gln Gly Pro Ser Gly Pro Gly Gly
                355                 360                 365
Tyr Gly Pro Gly Gly Pro Gly Ser Ser Ala Ala Ala Ala Ala Ala
                370                 375                 380
Ala Ser Gly Pro Gly Gly Tyr Gly Pro Gly Ser Gln Gly Pro Ser Gly
385                 390                 395                 400
Pro Gly Gly Tyr Gly Pro Gly Gly Pro Gly Ser Ser Ala Ala Ala Ala
                405                 410                 415
Ala Ala Ala Ala Ser Gly Pro Gly Gly Tyr Gly Pro Gly Ser Gln Gly
                420                 425                 430
```

```
Pro Ser Gly Pro Gly Tyr Gly Pro Gly Pro Gly Ser Ser Ala
        435                 440                 445

Ala Ala Ala Ala Ala Ala Ser Gly Pro Gly Gly Tyr Gly Pro Gly
        450                 455                 460

Ser Gln Gly Pro Ser Gly Pro Gly Gly Tyr Gly Pro Gly Gly Pro Gly
465                 470                 475                 480

Ser Ser Ala Ala Ala Ala Ala Ala Ser Gly Pro Gly Gly Tyr
                485                 490                 495

Gly Pro Gly Ser Gln Gly Pro Ser Gly Pro Gly Gly Tyr Gly Pro Gly
                500                 505                 510

Gly Pro Gly Ser Ser Ala Ala Ala Ala Ala Ala Ser Gly Pro
        515                 520                 525

Gly Gly Tyr Gly Pro Gly Ser Gln Gly Pro Ser Gly Pro Gly Gly Tyr
        530                 535                 540

Gly Pro Gly Gly Pro Gly Ser Ser Ala Ala Ala Ala Ala Ala
545                 550                 555                 560

Ser Gly Pro Gly Gly Tyr Gly Pro Gly Ser Gln Gly Pro Ser Gly Pro
                565                 570                 575

Gly Gly Tyr Gly Pro Gly Gly Pro Gly Ser Ser Ala Ala Ala Ala
                580                 585                 590

Ala Ala Ala Ser Gly Pro Gly Gly Tyr Gly Pro Gly Ser Gln Gly Pro
        595                 600                 605

Ser Gly Pro Gly Gly Tyr Gly Pro Gly Gly Pro Gly Ser Ser Ala Ala
610                 615                 620

Ala Ala Ala Ala Ala Ser Gly Pro Gly Gly Tyr Gly Pro Gly Ser
625                 630                 635                 640

Gln Gly Pro Ser Gly Pro Gly Gly Tyr Gly Pro Gly Gly Pro Gly Ser
                645                 650                 655

Ser Ala Ala Ala Ala Ala Ala Ala Ser Gly Pro Gly Gly Tyr Gly
                660                 665                 670

Pro Gly Ser Gln Gly Pro Ser Gly Pro Gly Gly Tyr Gly Pro Gly Gly
        675                 680                 685

Pro Gly Ser Ser Ala Ala Ala Ala Ala Ala Ala Ser Gly Pro Gly
        690                 695                 700

Gly Tyr Gly Pro Gly Ser Gln Gly Pro Ser Gly Pro Gly Gly Tyr Gly
705                 710                 715                 720

Pro Gly Gly Pro Gly Ser Ser Ala Ala Ala Ala Ala Ala Ala Ser
                725                 730                 735

Gly Pro Gly Gly Tyr Gly Pro Gly Ser Gln Gly Pro Ser Pro Gly
                740                 745                 750

Gly Tyr Gly Pro Gly Gly Pro Gly Ser Ser Ala Ala Ala Ala Ala
        755                 760                 765

Ala Ala Ser Gly Pro Gly Gly Tyr Gly Pro Gly Ser Gln Gly Pro Ser
        770                 775                 780

Gly Pro Gly Gly Tyr Gly Pro Gly Gly Pro Gly Ser Ser Ala Ala
785                 790                 795                 800

Ala Ala Ala Ala Ala Ser Gly Pro Gly Gly Tyr Gly Pro Gly Ser Gln
                805                 810                 815

Gly Pro Ser Gly Pro Gly Gly Tyr Gly Pro Gly Gly Pro Gly Ser Ser
                820                 825                 830

Ala Ala Ala Ala Ala Ala Ala
        835                 840

<210> SEQ ID NO 55
```

-continued

```
<211> LENGTH: 1120
<212> TYPE: PRT
<213> ORGANISM: Artificial
<220> FEATURE:
<223> OTHER INFORMATION: 32X amino acid repeat sequence

<400> SEQUENCE: 55

Ser Gly Pro Gly Gly Tyr Gly Pro Gly Ser Gln Gly Pro Ser Gly Pro
1               5                  10                  15

Gly Gly Tyr Gly Pro Gly Gly Pro Gly Ser Ser Ala Ala Ala Ala Ala
                20                  25                  30

Ala Ala Ala Ser Gly Pro Gly Gly Tyr Gly Pro Gly Ser Gln Gly Pro
            35                  40                  45

Ser Gly Pro Gly Gly Tyr Gly Pro Gly Gly Pro Gly Ser Ser Ala Ala
    50                  55                  60

Ala Ala Ala Ala Ala Ala Ser Gly Pro Gly Gly Tyr Gly Pro Gly Ser
65                  70                  75                  80

Gln Gly Pro Ser Gly Pro Gly Gly Tyr Gly Pro Gly Gly Pro Gly Ser
                85                  90                  95

Ser Ala Ala Ala Ala Ala Ala Ala Ser Gly Pro Gly Gly Tyr Gly Pro
            100                 105                 110

Pro Gly Ser Gln Gly Pro Ser Gly Pro Gly Gly Tyr Gly Pro Gly Gly
            115                 120                 125

Pro Gly Ser Ser Ala Ala Ala Ala Ala Ala Ala Ser Gly Pro Gly Gly
    130                 135                 140

Gly Tyr Gly Pro Gly Ser Gln Gly Pro Ser Gly Pro Gly Gly Tyr Gly
145                 150                 155                 160

Pro Gly Gly Pro Gly Ser Ser Ala Ala Ala Ala Ala Ala Ala Ala Ser
                165                 170                 175

Gly Pro Gly Gly Tyr Gly Pro Gly Ser Gln Gly Pro Ser Gly Pro Gly
            180                 185                 190

Gly Tyr Gly Pro Gly Gly Pro Gly Ser Ser Ala Ala Ala Ala Ala Ala
        195                 200                 205

Ala Ala Ser Gly Pro Gly Gly Tyr Gly Pro Gly Ser Gln Gly Pro Ser
210                 215                 220

Gly Pro Gly Gly Tyr Gly Pro Gly Gly Pro Gly Ser Ser Ala Ala Ala
225                 230                 235                 240

Ala Ala Ala Ala Ala Ser Gly Pro Gly Gly Tyr Gly Pro Gly Ser Gln
                245                 250                 255

Gly Pro Ser Gly Pro Gly Gly Tyr Gly Pro Gly Gly Pro Gly Ser Ser
            260                 265                 270

Ala Ala Ala Ala Ala Ala Ala Ser Gly Pro Gly Gly Tyr Gly Pro
        275                 280                 285

Gly Ser Gln Gly Pro Ser Gly Pro Gly Gly Tyr Gly Pro Gly Gly Pro
290                 295                 300

Gly Ser Ser Ala Ala Ala Ala Ala Ala Ser Gly Pro Gly Gly
305                 310                 315                 320

Tyr Gly Pro Gly Ser Gln Gly Pro Ser Gly Pro Gly Gly Tyr Gly Pro
                325                 330                 335

Gly Gly Pro Gly Ser Ser Ala Ala Ala Ala Ala Ala Ala Ser Gly
            340                 345                 350

Pro Gly Gly Tyr Gly Pro Gly Ser Gln Gly Pro Ser Gly Pro Gly Gly
        355                 360                 365

Tyr Gly Pro Gly Gly Pro Gly Ser Ser Ala Ala Ala Ala Ala Ala
    370                 375                 380
```

-continued

```
Ala Ser Gly Pro Gly Gly Tyr Gly Pro Gly Ser Gln Gly Pro Ser Gly
385                 390                 395                 400
Pro Gly Gly Tyr Gly Pro Gly Pro Gly Ser Ser Ala Ala Ala Ala Ala
                405                 410                 415
Ala Ala Ala Ala Ser Gly Pro Gly Gly Tyr Gly Pro Gly Ser Gln Gly
        420                 425                 430
Pro Ser Gly Pro Gly Gly Tyr Gly Pro Gly Pro Gly Ser Ser Ala Ala
        435                 440                 445
Ala Ala Ala Ala Ala Ala Ser Gly Pro Gly Gly Tyr Gly Pro Gly Ser
450                 455                 460
Ser Gln Gly Pro Ser Gly Pro Gly Gly Tyr Gly Pro Gly Pro Gly Ser
465                 470                 475                 480
Ser Ala Ala Ala Ala Ala Ala Ala Ala Ser Gly Pro Gly Gly Tyr Gly
                485                 490                 495
Gly Pro Gly Ser Gln Gly Pro Ser Gly Pro Gly Gly Tyr Gly Pro Gly
                500                 505                 510
Gly Pro Gly Ser Ser Ala Ala Ala Ala Ala Ala Ala Ala Ser Gly Pro
            515                 520                 525
Gly Gly Tyr Gly Pro Gly Ser Gln Gly Pro Ser Gly Pro Gly Gly Tyr
            530                 535                 540
Gly Pro Gly Gly Pro Gly Ser Ser Ala Ala Ala Ala Ala Ala Ala Ala
545                 550                 555                 560
Ser Gly Pro Gly Gly Tyr Gly Pro Gly Ser Gln Gly Pro Ser Gly Pro
                565                 570                 575
Gly Gly Tyr Gly Pro Gly Gly Pro Gly Ser Ser Ala Ala Ala Ala Ala
            580                 585                 590
Ala Ala Ala Ser Gly Pro Gly Gly Tyr Gly Pro Gly Ser Gln Gly Pro
        595                 600                 605
Ser Gly Pro Gly Gly Tyr Gly Pro Gly Gly Pro Gly Ser Ser Ala Ala
        610                 615                 620
Ala Ala Ala Ala Ala Ala Ser Gly Pro Gly Gly Tyr Gly Pro Gly Ser
625                 630                 635                 640
Gln Gly Pro Ser Gly Pro Gly Gly Tyr Gly Pro Gly Gly Pro Gly Ser
                645                 650                 655
Ser Ala Ala Ala Ala Ala Ala Ala Ser Gly Pro Gly Gly Tyr Gly
            660                 665                 670
Pro Gly Ser Gln Gly Pro Ser Gly Pro Gly Gly Tyr Gly Pro Gly Gly
            675                 680                 685
Pro Gly Ser Ser Ala Ala Ala Ala Ala Ala Ala Ser Gly Pro Gly
        690                 695                 700
Gly Tyr Gly Pro Gly Ser Gln Gly Pro Ser Gly Pro Gly Gly Tyr Gly
705                 710                 715                 720
Pro Gly Gly Pro Gly Ser Ser Ala Ala Ala Ala Ala Ala Ala Ala Ser
                725                 730                 735
Gly Pro Gly Gly Tyr Gly Pro Gly Ser Gln Gly Pro Ser Gly Pro Gly
            740                 745                 750
Gly Tyr Gly Pro Gly Gly Pro Gly Ser Ser Ala Ala Ala Ala Ala Ala
            755                 760                 765
Ala Ala Ser Gly Pro Gly Gly Tyr Gly Pro Gly Ser Gln Gly Pro Ser
    770                 775                 780
Gly Pro Gly Gly Tyr Gly Pro Gly Gly Pro Gly Ser Ser Ala Ala Ala
785                 790                 795                 800
Ala Ala Ala Ala Ala Ser Gly Pro Gly Gly Tyr Gly Pro Gly Ser Gln
                805                 810                 815
```

Gly Pro Ser Gly Pro Gly Gly Tyr Gly Pro Gly Gly Pro Ser Ser
                820                 825                 830

Ala Ala Ala Ala Ala Ala Ala Ser Gly Pro Gly Gly Tyr Gly Pro
            835                 840                 845

Gly Ser Gln Gly Pro Ser Pro Gly Gly Tyr Gly Pro Gly Gly Pro
        850                 855                 860

Gly Ser Ser Ala Ala Ala Ala Ala Ala Ala Ser Gly Pro Gly Gly
865                 870                 875                 880

Tyr Gly Pro Gly Ser Gln Gly Pro Ser Pro Gly Gly Tyr Gly Pro
                885                 890                 895

Gly Gly Pro Gly Ser Ser Ala Ala Ala Ala Ala Ala Ala Ser Gly
            900                 905                 910

Pro Gly Gly Tyr Gly Pro Gly Ser Gln Gly Pro Ser Pro Gly Gly
        915                 920                 925

Tyr Gly Pro Gly Gly Pro Gly Ser Ser Ala Ala Ala Ala Ala Ala
    930                 935                 940

Ala Ser Gly Pro Gly Gly Tyr Gly Pro Gly Ser Gln Gly Pro Ser Gly
945                 950                 955                 960

Pro Gly Gly Tyr Gly Pro Gly Gly Pro Gly Ser Ser Ala Ala Ala
            965                 970                 975

Ala Ala Ala Ala Ser Gly Pro Gly Gly Tyr Gly Pro Gly Ser Gln Gly
        980                 985                 990

Pro Ser Gly Pro Gly Gly Tyr Gly Pro Gly Gly Pro Gly Ser Ser Ala
            995                1000                1005

Ala Ala Ala Ala Ala Ala Ser Gly Pro Gly Gly Tyr Gly Pro
    1010                1015                1020

Gly Ser Gln Gly Pro Ser Gly Pro Gly Gly Tyr Gly Pro Gly Gly
    1025                1030                1035

Pro Gly Ser Ser Ala Ala Ala Ala Ala Ala Ala Ser Gly Pro
    1040                1045                1050

Gly Gly Tyr Gly Pro Gly Ser Gln Gly Pro Ser Gly Pro Gly Gly
    1055                1060                1065

Tyr Gly Pro Gly Gly Pro Gly Ser Ser Ala Ala Ala Ala Ala Ala
    1070                1075                1080

Ala Ala Ser Gly Pro Gly Gly Tyr Gly Pro Gly Ser Gln Gly Pro
    1085                1090                1095

Ser Gly Pro Gly Gly Tyr Gly Pro Gly Gly Pro Gly Ser Ser Ala
    1100                1105                1110

Ala Ala Ala Ala Ala Ala
    1115                1120

<210> SEQ ID NO 56
<211> LENGTH: 108
<212> TYPE: DNA
<213> ORGANISM: Artificial
<220> FEATURE:
<223> OTHER INFORMATION: DNA encoding 2x repeating sequence

<400> SEQUENCE: 56
atgtctggtc ctggaggtta tggcccagga agccaaggac catctggtcc aggaggatat    60
ggtccaggcg gacctggctc tagtgcagca gctgccgcag cagctgca                108

<210> SEQ ID NO 57
<211> LENGTH: 213
<212> TYPE: DNA
<213> ORGANISM: Artificial

<220> FEATURE:
<223> OTHER INFORMATION: DNA encoding 4X repeating sequence

<400> SEQUENCE: 57

| | |
|---|---|
| atgtctggtc ctggaggtta tggcccagga agccaaggac catctggtcc aggaggatat | 60 |
| ggtccaggcg gacctggctc tagtgcagca gctgccgcag cagctgcatc tggtcctgga | 120 |
| ggttatggcc caggaagcca aggaccatct ggtccaggag gatatggtcc aggcggacct | 180 |
| ggctctagtg cagcagctgc cgcagcagct gca | 213 |

<210> SEQ ID NO 58
<211> LENGTH: 423
<212> TYPE: DNA
<213> ORGANISM: Artificial
<220> FEATURE:
<223> OTHER INFORMATION: DNA encoding 8X repeating sequence

<400> SEQUENCE: 58

| | |
|---|---|
| atgtctggtc ctggaggtta tggcccagga agccaaggac catctggtcc aggaggatat | 60 |
| ggtccaggcg gacctggctc tagtgcagca gctgccgcag cagctgcatc tggtcctgga | 120 |
| ggttatggcc caggaagcca aggaccatct ggtccaggag gatatggtcc aggcggacct | 180 |
| ggctctagtg cagcagctgc cgcagcagct gcatctggtc ctggaggtta tgggcccagga | 240 |
| agccaaggac catctggtcc aggaggatat ggtccaggcg gacctggctc tagtgcagca | 300 |
| gctgccgcag cagctgcatc tggtcctgga ggttatggcc caggaagcca aggaccatct | 360 |
| ggtccaggag gatatggtcc aggcggacct ggctctagtg cagcagctgc cgcagcagct | 420 |
| gca | 423 |

<210> SEQ ID NO 59
<211> LENGTH: 633
<212> TYPE: DNA
<213> ORGANISM: Artificial
<220> FEATURE:
<223> OTHER INFORMATION: DNA encoding 12X repeating sequence

<400> SEQUENCE: 59

| | |
|---|---|
| atgtctggtc ctggaggtta tggcccagga agccaaggac catctggtcc aggaggatat | 60 |
| ggtccaggcg gacctggctc tagtgcagca gctgccgcag cagctgcatc tggtcctgga | 120 |
| ggttatggcc caggaagcca aggaccatct ggtccaggag gatatggtcc aggcggacct | 180 |
| ggctctagtg cagcagctgc cgcagcagct gcatctggtc ctggaggtta tgggcccagga | 240 |
| agccaaggac catctggtcc aggaggatat ggtccaggcg gacctggctc tagtgcagca | 300 |
| gctgccgcag cagctgcatc tggtcctgga ggttatggcc caggaagcca aggaccatct | 360 |
| ggtccaggag gatatggtcc aggcggacct ggctctagtg cagcagctgc cgcagcagct | 420 |
| gcatctggtc ctggaggtta tgggcccagga agccaaggac catctggtcc aggaggatat | 480 |
| ggtccaggcg gacctggctc tagtgcagca gctgccgcag cagctgcatc tggtcctgga | 540 |
| ggttatggcc caggaagcca aggaccatct ggtccaggag gatatggtcc aggcggacct | 600 |
| ggctctagtg cagcagctgc cgcagcagct gca | 633 |

<210> SEQ ID NO 60
<211> LENGTH: 843
<212> TYPE: DNA
<213> ORGANISM: Artificial
<220> FEATURE:
<223> OTHER INFORMATION: DNA encoding 16X repeating sequence

<400> SEQUENCE: 60

```
atgtctggtc ctggaggtta tggcccagga agccaaggac catctggtcc aggaggatat      60
ggtccaggcg gacctggctc tagtgcagca gctgccgcag cagctgcatc tggtcctgga     120
ggttatggcc caggaagcca aggaccatct ggtccaggag gatatggtcc aggcggacct     180
ggctctagtg cagcagctgc cgcagcagct gcatctggtc ctggaggtta tgcccagga      240 agccaaggac catctggtcc aggaggatat ggtccaggcg gacctggctc tagtgcagca     300
gctgccgcag cagctgcatc tggtcctgga ggttatggcc caggaagcca aggaccatct     360
ggtccaggag gatatggtcc aggcggacct ggctctagtg cagcagctgc cgcagcagct     420
gcatctggtc ctggaggtta tgcccagga agccaaggac catctggtcc aggaggatat      480
ggtccaggcg gacctggctc tagtgcagca gctgccgcag cagctgcatc tggtcctgga     540
ggttatggcc caggaagcca aggaccatct ggtccaggag gatatggtcc aggcggacct     600
ggctctagtg cagcagctgc cgcagcagct gcatctggtc ctggaggtta tgcccagga      660 agccaaggac catctggtcc aggaggatat ggtccaggcg gacctggctc tagtgcagca     720
gctgccgcag cagctgcatc tggtcctgga ggttatggcc caggaagcca aggaccatct     780
ggtccaggag gatatggtcc aggcggacct ggctctagtg cagcagctgc cgcagcagct     840
gca                                                                   843
```

<210> SEQ ID NO 61
<211> LENGTH: 1053
<212> TYPE: DNA
<213> ORGANISM: Artificial
<220> FEATURE:
<223> OTHER INFORMATION: DNA encoding 20X repeating sequence

<400> SEQUENCE: 61

```
atgtctggtc ctggaggtta tggcccagga agccaaggac catctggtcc aggaggatat      60
ggtccaggcg gacctggctc tagtgcagca gctgccgcag cagctgcatc tggtcctgga     120
ggttatggcc caggaagcca aggaccatct ggtccaggag gatatggtcc aggcggacct     180
ggctctagtg cagcagctgc cgcagcagct gcatctggtc ctggaggtta tgcccagga      240 agccaaggac catctggtcc aggaggatat ggtccaggcg gacctggctc tagtgcagca     300
gctgccgcag cagctgcatc tggtcctgga ggttatggcc caggaagcca aggaccatct     360
ggtccaggag gatatggtcc aggcggacct ggctctagtg cagcagctgc cgcagcagct     420
gcatctggtc ctggaggtta tgcccagga agccaaggac catctggtcc aggaggatat      480
ggtccaggcg gacctggctc tagtgcagca gctgccgcag cagctgcatc tggtcctgga     540
ggttatggcc caggaagcca aggaccatct ggtccaggag gatatggtcc aggcggacct     600
ggctctagtg cagcagctgc cgcagcagct gcatctggtc ctggaggtta tgcccagga      660 agccaaggac catctggtcc aggaggatat ggtccaggcg gacctggctc tagtgcagca     720
gctgccgcag cagctgcatc tggtcctgga ggttatggcc caggaagcca aggaccatct     780
ggtccaggag gatatggtcc aggcggacct ggctctagtg cagcagctgc cgcagcagct     840
gcatctggtc ctggaggtta tgcccagga agccaaggac catctggtcc aggaggatat      900
ggtccaggcg gacctggctc tagtgcagca gctgccgcag cagctgcatc tggtcctgga     960
ggttatggcc caggaagcca aggaccatct ggtccaggag gatatggtcc aggcggacct    1020
ggctctagtg cagcagctgc cgcagcagct gca                                 1053
```

<210> SEQ ID NO 62
<211> LENGTH: 1263

```
<212> TYPE: DNA
<213> ORGANISM: Artificial
<220> FEATURE:
<223> OTHER INFORMATION: DNA encoding 24X repeating sequence

<400> SEQUENCE: 62
atgtctggtc ctggaggtta tgcccagga agccaaggac catctggtcc aggaggatat        60
ggtccaggcg acctggctc tagtgcagca gctgccgcag cagctgcatc tggtcctgga       120
ggttatggcc caggaagcca aggaccatct ggtccaggag gatatggtcc aggcggacct       180
ggctctagtg cagcagctgc cgcagcagct gcatctggtc ctggaggtta tgcccagga        240 agccaaggac catctggtcc aggaggatat ggtccaggcg acctggctc tagtgcagca       300 gctgccgcag cagctgcatc tggtcctgga ggttatggcc caggaagcca aggaccatct       360
ggtccaggag gatatggtcc aggcggacct ggctctagtg cagcagctgc cgcagcagct       420
gcatctggtc ctggaggtta tgcccagga agccaaggac catctggtcc aggaggatat        480
ggtccaggcg acctggctc tagtgcagca gctgccgcag cagctgcatc tggtcctgga       540
ggttatggcc caggaagcca aggaccatct ggtccaggag gatatggtcc aggcggacct       600
ggctctagtg cagcagctgc cgcagcagct gcatctggtc ctggaggtta tgcccagga        660 agccaaggac catctggtcc aggaggatat ggtccaggcg acctggctc tagtgcagca       720 gctgccgcag cagctgcatc tggtcctgga ggttatggcc caggaagcca aggaccatct       780
ggtccaggag gatatggtcc aggcggacct ggctctagtg cagcagctgc cgcagcagct       840
gcatctggtc ctggaggtta tgcccagga agccaaggac catctggtcc aggaggatat        900
ggtccaggcg acctggctc tagtgcagca gctgccgcag cagctgcatc tggtcctgga       960
ggttatggcc caggaagcca aggaccatct ggtccaggag gatatggtcc aggcggacct      1020
ggctctagtg cagcagctgc cgcagcagct gcatctggtc ctggaggtta tgcccagga       1080 agccaaggac catctggtcc aggaggatat ggtccaggcg acctggctc tagtgcagca      1140 gctgccgcag cagctgcatc tggtcctgga ggttatggcc caggaagcca aggaccatct      1200
ggtccaggag gatatggtcc aggcggacct ggctctagtg cagcagctgc cgcagcagct      1260
gca                                                                    1263

<210> SEQ ID NO 63
<211> LENGTH: 1680
<212> TYPE: DNA
<213> ORGANISM: Artificial
<220> FEATURE:
<223> OTHER INFORMATION: DNA encoding 32X repeating sequence

<400> SEQUENCE: 63
tctggtcctg gaggttatgg cccaggaagc caaggaccat ctggtccagg aggatatggt        60
ccaggcggac ctggctctag tgcagcagct gccgcagcag ctgcatctgg tcctggaggt       120 tatgcccag gaagccaagg accatctggt ccaggaggat atggtccagg cggacctggc       180
tctagtgcag cagctgccgc agcagctgca tctggtcctg gaggttatgg cccaggaagc      240
caaggaccat ctggtccagg aggatatggt ccaggcggac ctggctctag tgcagcagct       300
gccgcagcag ctgcatctgg tcctggaggt tatgcccag gaagccaagg accatctggt        360
ccaggaggat atggtccagg cggacctggc tctagtgcag cagctgccgc agcagctgca       420
tctggtcctg gaggttatgg cccaggaagc caaggaccat ctggtccagg aggatatggt       480
ccaggcggac ctggctctag tgcagcagct gccgcagcag ctgcatctgg tcctggaggt       540 tatgcccag gaagccaagg accatctggt ccaggaggat atggtccagg cggacctggc        600
```

```
tctagtgcag cagctgccgc agcagctgca tctggtcctg gaggttatgg cccaggaagc    660
caaggaccat ctggtccagg aggatatggt ccaggcggac ctggctctag tgcagcagct    720
gccgcagcag ctgcatctgg tcctggaggt tatgggccag gaagccaagg accatctggt    780
ccaggaggat atggtccagg cggacctggc tctagtgcag cagctgccgc agcagctgca    840
tctggtcctg gaggttatgg cccaggaagc caaggaccat ctggtccagg aggatatggt    900
ccaggcggac ctggctctag tgcagcagct gccgcagcag ctgcatctgg tcctggaggt    960
tatggcccag gaagccaagg accatctggt ccaggaggat atggtccagg cggacctggc   1020
tctagtgcag cagctgccgc agcagctgca tctggtcctg gaggttatgg cccaggaagc   1080
caaggaccat ctggtccagg aggatatggt ccaggcggac ctggctctag tgcagcagct   1140
gccgcagcag ctgcatctgg tcctggaggt tatggcccag gaagccaagg accatctggt   1200
ccaggaggat atggtccagg cggacctggc tctagtgcag cagctgccgc agcagctgca   1260
tctggtcctg gaggttatgg cccaggaagc caaggaccat ctggtccagg aggatatggt   1320
ccaggcggac ctggctctag tgcagcagct gccgcagcag ctgcatctgg tcctggaggt   1380
tatggcccag gaagccaagg accatctggt ccaggaggat atggtccagg cggacctggc   1440
tctagtgcag cagctgccgc agcagctgca tctggtcctg gaggttatgg cccaggaagc   1500
caaggaccat ctggtccagg aggatatggt ccaggcggac ctggctctag tgcagcagct   1560
gccgcagcag ctgcatctgg tcctggaggt tatggcccag gaagccaagg accatctggt   1620
ccaggaggat atggtccagg cggacctggc tctagtgcag cagctgccgc agcagctgca   1680
```

<210> SEQ ID NO 64
<211> LENGTH: 702
<212> TYPE: DNA
<213> ORGANISM: Artificial
<220> FEATURE:
<223> OTHER INFORMATION: Full DNA sequence (N-domain + 2 repeats + C-domain) + N-terminal tag

<400> SEQUENCE: 64

```
atgatgtcgt actaccatca ccatcaccat cacgattacg atatcccaac gaccgaaaac     60
ctgtattttc agggcgccat ggatccggaa ttcaaaggcc tacgtcgacg agctcaacta    120
gtgcggccgc tttcgaatct agataatgca tctggtcctg gaggttatgg cccaggaagc    180
caaggaccat ctggtccagg aggatatggt ccaggcggac ctggctctag tgcagcagct    240
gccgcagcag ctgcatctgg tcctggaggt tatggcccag gaagccaagg accatctggt    300
ccaggaggat atggtccagg cggacctggc tctagtgcag cagctgccgc agcagctgca    360
ggccctagtg gtcctggagc atatggccca tctccttctg cttccgcatc cgttgcagcc    420
tctcgtttat cttcgcctgc agcctcgtct agagtgtctt ccgctgtatc gtctttagtg    480
tctagcggac ctacgaatgg tgctgctgtt tctggagctt gaatagtttt agtatctcag    540
attagtgcaa gtaatccagg tttatcggga tgtgatgctc ttgtgcaggc attattggaa    600
ttagtgtctg ctcttgtggc aattctttca tctgcaagta ttggccaagt caacgtcagc    660
tctgttagtc agtcaactca aatgattagc caagctcttt ca                       702
```

<210> SEQ ID NO 65
<211> LENGTH: 909
<212> TYPE: DNA
<213> ORGANISM: Artificial
<220> FEATURE:
<223> OTHER INFORMATION: Full DNA sequence (N-domain + 4 repeats + C-domain) + N-terminal tag

<400> SEQUENCE: 65

```
atgtcgtact accatcacca tcaccatcac gattacgata tcccaacgac cgaaaacctg    60
tattttcagg gcgccatgga tccggaattc aaaggcctac gtcgacgagc tcaactagtg   120
cggccgcttt cgaatctaga taatgcatct ggtcctggag ttatggccc aggaagccaa   180
ggaccatctg gtccaggagg atatggtcca ggcggacctg gctctagtgc agcagctgcc   240
gcagcagctg catctggtcc tggaggttat ggcccaggaa gccaaggacc atctggtcca   300
ggaggatatg gtccaggcgg acctggctct agtgcagcag ctgccgcagc agctgcatct   360
ggtcctggag ttatggcccc aggaagccaa ggaccatctg gtccaggagg atatggtcca   420
ggcggacctg gctctagtgc agcagctgcc gcagcagctg catctggtcc tggaggttat   480
ggcccaggaa gccaaggacc atctggtcca ggaggatatg gtccaggcgg acctggctct   540
agtgcagcag ctgccgcagc agctgcaggc cctagtggtc ctggagcata tggcccatct   600
ccttctgctt ccgcatccgt tgcagcctct cgtttatctt cgcctgcagc ctcgtctaga   660
gtgtcttccg ctgtatcgtc tttagtgtct agcggaccta cgaatggtgc tgctgtttct   720
ggagctttga atagtttagt atctcagatt agtgcaagta atccaggttt atcgggatgt   780
gatgctcttg tgcaggcatt attggaatta gtgtctgctc ttgtggcaat tctttcatct   840
gcaagtattg gccaagtcaa cgtcagctct gttagtcagt caactcaaat gattagccaa   900
gctctttca                                                            909
```

<210> SEQ ID NO 66
<211> LENGTH: 1329
<212> TYPE: DNA
<213> ORGANISM: Artificial
<220> FEATURE:
<223> OTHER INFORMATION: Full DNA sequence (N-domain + 8 repeats + C-domain) + N-terminal tag

<400> SEQUENCE: 66

```
atgtcgtact accatcacca tcaccatcac gattacgata tcccaacgac cgaaaacctg    60
tattttcagg gcgccatgga tccggaattc aaaggcctac gtcgacgagc tcaactagtg   120
cggccgcttt cgaatctaga taatgcatct ggtcctggag ttatggccc aggaagccaa   180
ggaccatctg gtccaggagg atatggtcca ggcggacctg gctctagtgc agcagctgcc   240
gcagcagctg catctggtcc tggaggttat ggcccaggaa gccaaggacc atctggtcca   300
ggaggatatg gtccaggcgg acctggctct agtgcagcag ctgccgcagc agctgcatct   360
ggtcctggag ttatggcccc aggaagccaa ggaccatctg gtccaggagg atatggtcca   420
ggcggacctg gctctagtgc agcagctgcc gcagcagctg catctggtcc tggaggttat   480
ggcccaggaa gccaaggacc atctggtcca ggaggatatg gtccaggcgg acctggctct   540
agtgcagcag ctgccgcagc agctgcatct ggtcctggag ttatggcccc aggaagccaa   600
ggaccatctg gtccaggagg atatggtcca ggcggacctg gctctagtgc agcagctgcc   660
gcagcagctg catctggtcc tggaggttat ggcccaggaa gccaaggacc atctggtcca   720
ggaggatatg gtccaggcgg acctggctct agtgcagcag ctgccgcagc agctgcatct   780
ggtcctggag ttatggcccc aggaagccaa ggaccatctg gtccaggagg atatggtcca   840
ggcggacctg gctctagtgc agcagctgcc gcagcagctg catctggtcc tggaggttat   900
ggcccaggaa gccaaggacc atctggtcca ggaggatatg gtccaggcgg acctggctct   960
agtgcagcag ctgccgcagc agctgcaggc cctagtggtc ctggagcata tggcccatct  1020
```

| | |
|---|---|
| ccttctgctt ccgcatccgt tgcagcctct cgtttatctt cgcctgcagc ctcgtctaga | 1080 |
| gtgtcttccg ctgtatcgtc tttagtgtct agcggaccta cgaatggtgc tgctgtttct | 1140 |
| ggagctttga atagtttagt atctcagatt agtgcaagta atccaggttt atcgggatgt | 1200 |
| gatgctcttg tgcaggcatt attggaatta gtgtctgctc ttgtggcaat tctttcatct | 1260 |
| gcaagtattg gccaagtcaa cgtcagctct gttagtcagt caactcaaat gattagccaa | 1320 |
| gctcttttca | 1329 |

<210> SEQ ID NO 67
<211> LENGTH: 1749
<212> TYPE: DNA
<213> ORGANISM: Artificial
<220> FEATURE:
<223> OTHER INFORMATION: Full DNA sequence (N-domain + 12 repeats + C-domain) + N-terminal tag

<400> SEQUENCE: 67

| | |
|---|---|
| atgtcgtact accatcacca tcaccatcac gattacgata tcccaacgac cgaaaacctg | 60 |
| tattttcagg gcgccatgga tccggaattc aaaggcctac gtcgacgagc tcaactagtg | 120 |
| cggccgcttt cgaatctaga taatgcatct ggtcctggag ttatggccc aggaagccaa | 180 |
| ggaccatctg gtccaggagg atatggtcca ggcggacctg gctctagtgc agcagctgcc | 240 |
| gcagcagctg catctggtcc tggaggttat ggcccaggaa gccaaggacc atctggtcca | 300 |
| ggaggatatg gtccaggcgg acctggctct agtgcagcag ctgccgcagc agctgcatct | 360 |
| ggtcctggag ttatggccc aggaagccaa ggaccatctg gtccaggagg atatggtcca | 420 |
| ggcggacctg gctctagtgc agcagctgcc gcagcagctg catctggtcc tggaggttat | 480 |
| ggcccaggaa gccaaggacc atctggtcca ggaggatatg gtccaggcgg acctggctct | 540 |
| agtgcagcag ctgccgcagc agctgcatct ggtcctggag ttatggccc aggaagccaa | 600 |
| ggaccatctg gtccaggagg atatggtcca ggcggacctg gctctagtgc agcagctgcc | 660 |
| gcagcagctg catctggtcc tggaggttat ggcccaggaa gccaaggacc atctggtcca | 720 |
| ggaggatatg gtccaggcgg acctggctct agtgcagcag ctgccgcagc agctgcatct | 780 |
| ggtcctggag ttatggccc aggaagccaa ggaccatctg gtccaggagg atatggtcca | 840 |
| ggcggacctg gctctagtgc agcagctgcc gcagcagctg catctggtcc tggaggttat | 900 |
| ggcccaggaa gccaaggacc atctggtcca ggaggatatg gtccaggcgg acctggctct | 960 |
| agtgcagcag ctgccgcagc agctgcatct ggtcctggag ttatggccc aggaagccaa | 1020 |
| ggaccatctg gtccaggagg atatggtcca ggcggacctg gctctagtgc agcagctgcc | 1080 |
| gcagcagctg catctggtcc tggaggttat ggcccaggaa gccaaggacc atctggtcca | 1140 |
| ggaggatatg gtccaggcgg acctggctct agtgcagcag ctgccgcagc agctgcatct | 1200 |
| ggtcctggag ttatggccc aggaagccaa ggaccatctg gtccaggagg atatggtcca | 1260 |
| ggcggacctg gctctagtgc agcagctgcc gcagcagctg catctggtcc tggaggttat | 1320 |
| ggcccaggaa gccaaggacc atctggtcca ggaggatatg gtccaggcgg acctggctct | 1380 |
| agtgcagcag ctgccgcagc agctgcaggc cctagtggtc ctggagcata tggcccatct | 1440 |
| ccttctgctt ccgcatccgt tgcagcctct cgtttatctt cgcctgcagc ctcgtctaga | 1500 |
| gtgtcttccg ctgtatcgtc tttagtgtct agcggaccta cgaatggtgc tgctgtttct | 1560 |
| ggagctttga atagtttagt atctcagatt agtgcaagta atccaggttt atcgggatgt | 1620 |
| gatgctcttg tgcaggcatt attggaatta gtgtctgctc ttgtggcaat tctttcatct | 1680 |
| gcaagtattg gccaagtcaa cgtcagctct gttagtcagt caactcaaat gattagccaa | 1740 |

```
gctctttca                                                           1749

<210> SEQ ID NO 68
<211> LENGTH: 2169
<212> TYPE: DNA
<213> ORGANISM: Artificial
<220> FEATURE:
<223> OTHER INFORMATION: Full DNA sequence (N-domain + 16 repeats +
      C-domain) + N-terminal tag

<400> SEQUENCE: 68
atgtcgtact accatcacca tcaccatcac gattacgata tcccaacgac cgaaaacctg    60
tattttcagg gcgccatgga tccggaattc aaaggcctac gtcgacgagc tcaactagtg   120
cggccgcttt cgaatctaga taatgcatct ggtcctggag ttatggccc aggaagccaa    180 ggaccatctg gtccaggagg atatggtcca ggcggacctg gctctagtgc agcagctgcc   240
gcagcagctg catctggtcc tgaggttat ggcccaggaa gccaaggacc atctggtcca    300
ggaggatatg gtccaggcgg acctggctct agtgcagcag ctgccgcagc agctgcatct   360
ggtcctggag ttatggccc aggaagccaa ggaccatctg gtccaggagg atatggtcca    420
ggcggacctg gctctagtgc agcagctgcc gcagcagctg catctggtcc tgaggttat    480 ggcccaggaa gccaaggacc atctggtcca ggaggatatg gtccaggcgg acctggctct   540
agtgcagcag ctgccgcagc agctgcatct ggtcctggag ttatggccc aggaagccaa    600 ggaccatctg gtccaggagg atatggtcca ggcggacctg gctctagtgc agcagctgcc   660
gcagcagctg catctggtcc tgaggttat ggcccaggaa gccaaggacc atctggtcca    720
ggaggatatg gtccaggcgg acctggctct agtgcagcag ctgccgcagc agctgcatct   780
ggtcctggag ttatggccc aggaagccaa ggaccatctg gtccaggagg atatggtcca    840
ggcggacctg gctctagtgc agcagctgcc gcagcagctg catctggtcc tgaggttat    900 ggcccaggaa gccaaggacc atctggtcca ggaggatatg gtccaggcgg acctggctct   960
agtgcagcag ctgccgcagc agctgcatct ggtcctggag ttatggccc aggaagccaa   1020 ggaccatctg gtccaggagg atatggtcca ggcggacctg gctctagtgc agcagctgcc  1080
gcagcagctg catctggtcc tgaggttat ggcccaggaa gccaaggacc atctggtcca   1140
ggaggatatg gtccaggcgg acctggctct agtgcagcag ctgccgcagc agctgcatct  1200
ggtcctggag ttatggccc aggaagccaa ggaccatctg gtccaggagg atatggtcca   1260
ggcggacctg gctctagtgc agcagctgcc gcagcagctg catctggtcc tgaggttat   1320 ggcccaggaa gccaaggacc atctggtcca ggaggatatg gtccaggcgg acctggctct  1380
agtgcagcag ctgccgcagc agctgcatct ggtcctggag ttatggccc aggaagccaa   1440 ggaccatctg gtccaggagg atatggtcca ggcggacctg gctctagtgc agcagctgcc  1500
gcagcagctg catctggtcc tgaggttat ggcccaggaa gccaaggacc atctggtcca   1560
ggaggatatg gtccaggcgg acctggctct agtgcagcag ctgccgcagc agctgcatct  1620
ggtcctggag ttatggccc aggaagccaa ggaccatctg gtccaggagg atatggtcca   1680
ggcggacctg gctctagtgc agcagctgcc gcagcagctg catctggtcc tgaggttat   1740 ggcccaggaa gccaaggacc atctggtcca ggaggatatg gtccaggcgg acctggctct  1800
agtgcagcag ctgccgcagc agctgcaggc cctagtggtc ctggagcata tggcccatct  1860
ccttctgctt ccgcatccgt tgcagcctct cgtttatctt cgcctgcagc ctcgtctaga  1920
gtgtcttccg ctgtatcgtc tttagtgtct agcggaccta cgaatggtgc tgctgtttct  1980
```

```
ggagctttga atagtttagt atctcagatt agtgcaagta atccaggttt atcgggatgt    2040
gatgctcttg tgcaggcatt attggaatta gtgtctgctc ttgtggcaat tctttcatct    2100
gcaagtattg ccaagtcaa  cgtcagctct gttagtcagt caactcaaat gattagccaa    2160
gctctttca                                                             2169
```

<210> SEQ ID NO 69
<211> LENGTH: 2589
<212> TYPE: DNA
<213> ORGANISM: Artificial
<220> FEATURE:
<223> OTHER INFORMATION: Full DNA sequence (N-domain + 20 repeats +
      C-domain) + N-terminal tag

<400> SEQUENCE: 69

```
atgtcgtact accatcacca tcaccatcac gattacgata tcccaacgac cgaaaacctg      60
tattttcagg gcgccatgga tccggaattc aaaggcctac gtcgacgagc tcaactagtg     120
cggccgcttt cgaatctaga taatgcatct ggtcctggag ttatggccc  aggaagccaa     180 ggaccatctg gtccaggagg atatggtcca ggcggacctg gctctagtgc agcagctgcc     240
gcagcagctg catctggtcc tggaggttat ggcccaggaa gccaaggacc atctggtcca     300
ggaggatatg gtccaggcgg acctggctct agtgcagcag ctgccgcagc agctgcatct     360
ggtcctggag ttatggccc  aggaagccaa ggaccatctg gtccaggagg atatggtcca     420
ggcggacctg gctctagtgc agcagctgcc gcagcagctg catctggtcc tggaggttat     480
ggcccaggaa gccaaggacc atctggtcca ggaggatatg gtccaggcgg acctggctct     540
agtgcagcag ctgccgcagc agctgcatct ggtcctggag ttatggccc  aggaagccaa     600 ggaccatctg gtccaggagg atatggtcca ggcggacctg gctctagtgc agcagctgcc     660
gcagcagctg catctggtcc tggaggttat ggcccaggaa gccaaggacc atctggtcca     720
ggaggatatg gtccaggcgg acctggctct agtgcagcag ctgccgcagc agctgcatct     780
ggtcctggag ttatggccc  aggaagccaa ggaccatctg gtccaggagg atatggtcca     840
ggcggacctg gctctagtgc agcagctgcc gcagcagctg catctggtcc tggaggttat     900
ggcccaggaa gccaaggacc atctggtcca ggaggatatg gtccaggcgg acctggctct     960
agtgcagcag ctgccgcagc agctgcatct ggtcctggag ttatggccc  aggaagccaa    1020 ggaccatctg gtccaggagg atatggtcca ggcggacctg gctctagtgc agcagctgcc    1080
gcagcagctg catctggtcc tggaggttat ggcccaggaa gccaaggacc atctggtcca    1140
ggaggatatg gtccaggcgg acctggctct agtgcagcag ctgccgcagc agctgcatct    1200
ggtcctggag ttatggccc  aggaagccaa ggaccatctg gtccaggagg atatggtcca    1260
ggcggacctg gctctagtgc agcagctgcc gcagcagctg catctggtcc tggaggttat    1320
ggcccaggaa gccaaggacc atctggtcca ggaggatatg gtccaggcgg acctggctct    1380
agtgcagcag ctgccgcagc agctgcatct ggtcctggag ttatggccc  aggaagccaa    1440 ggaccatctg gtccaggagg atatggtcca ggcggacctg gctctagtgc agcagctgcc    1500
gcagcagctg catctggtcc tggaggttat ggcccaggaa gccaaggacc atctggtcca    1560
ggaggatatg gtccaggcgg acctggctct agtgcagcag ctgccgcagc agctgcatct    1620
ggtcctggag ttatggccc  aggaagccaa ggaccatctg gtccaggagg atatggtcca    1680
ggcggacctg gctctagtgc agcagctgcc gcagcagctg catctggtcc tggaggttat    1740
ggcccaggaa gccaaggacc atctggtcca ggaggatatg gtccaggcgg acctggctct    1800
agtgcagcag ctgccgcagc agctgcatct ggtcctggag ttatggccc  aggaagccaa    1860
```

-continued

```
ggaccatctg gtccaggagg atatggtcca ggcggacctg gctctagtgc agcagctgcc    1920
gcagcagctg catctggtcc tggaggttat ggcccaggaa gccaaggacc atctggtcca    1980
ggaggatatg gtccaggcgg acctggctct agtgcagcag ctgccgcagc agctgcatct    2040
ggtcctggag gttatggccc aggaagccaa ggaccatctg gtccaggagg atatggtcca    2100
ggcggacctg gctctagtgc agcagctgcc gcagcagctg catctggtcc tggaggttat    2160
ggcccaggaa gccaaggacc atctggtcca ggaggatatg gtccaggcgg acctggctct    2220
agtgcagcag ctgccgcagc agctgcaggc cctagtggtc ctggagcata tggcccatct    2280
ccttctgctt ccgcatccgt tgcagcctct cgtttatctt cgcctgcagc ctcgtctaga    2340
gtgtcttccg ctgtatcgtc tttagtgtct agcggaccta cgaatggtgc tgctgttttct    2400 ggagctttga atagtttagt atctcagatt agtgcaagta atccaggttt atcgggatgt    2460
gatgctcttg tgcaggcatt attggaatta gtgtctgctc ttgtggcaat tctttcatct    2520
gcaagtattg gccaagtcaa cgtcagctct gttagtcagt caactcaaat gattagccaa    2580
gctctttca                                                            2589
```

```
<210> SEQ ID NO 70
<211> LENGTH: 3009
<212> TYPE: DNA
<213> ORGANISM: Artificial
<220> FEATURE:
<223> OTHER INFORMATION: Full DNA sequence (N-domain + 24 repeats +
      C-domain) + N-terminal tag

<400> SEQUENCE: 70
```

```
atgtcgtact accatcacca tcaccatcac gattacgata tcccaacgac cgaaaacctg      60
tattttcagg gcgccatgga tccggaattc aaaggcctac gtcgacgagc tcaactagtg     120
cggccgcttt cgaatctaga taatgcatct ggtcctggag ttatggcccc aggaagccaa     180
ggaccatctg gtccaggagg atatggtcca ggcggacctg gctctagtgc agcagctgcc     240
gcagcagctg catctggtcc tggaggttat ggcccaggaa gccaaggacc atctggtcca     300
ggaggatatg gtccaggcgg acctggctct agtgcagcag ctgccgcagc agctgcatct     360
ggtcctggag gttatggccc aggaagccaa ggaccatctg gtccaggagg atatggtcca     420
ggcggacctg gctctagtgc agcagctgcc gcagcagctg catctggtcc tggaggttat     480
ggcccaggaa gccaaggacc atctggtcca ggaggatatg gtccaggcgg acctggctct     540
agtgcagcag ctgccgcagc agctgcatct ggtcctggag gttatggccc aggaagccaa     600
ggaccatctg gtccaggagg atatggtcca ggcggacctg gctctagtgc agcagctgcc     660
gcagcagctg catctggtcc tggaggttat ggcccaggaa gccaaggacc atctggtcca     720
ggaggatatg gtccaggcgg acctggctct agtgcagcag ctgccgcagc agctgcatct     780
ggtcctggag gttatggccc aggaagccaa ggaccatctg gtccaggagg atatggtcca     840
ggcggacctg gctctagtgc agcagctgcc gcagcagctg catctggtcc tggaggttat     900
ggcccaggaa gccaaggacc atctggtcca ggaggatatg gtccaggcgg acctggctct     960
agtgcagcag ctgccgcagc agctgcatct ggtcctggag gttatggccc aggaagccaa    1020
ggaccatctg gtccaggagg atatggtcca ggcggacctg gctctagtgc agcagctgcc    1080
gcagcagctg catctggtcc tggaggttat ggcccaggaa gccaaggacc atctggtcca    1140
ggaggatatg gtccaggcgg acctggctct agtgcagcag ctgccgcagc agctgcatct    1200
ggtcctggag gttatggccc aggaagccaa ggaccatctg gtccaggagg atatggtcca    1260
```

```
ggcggacctg gctctagtgc agcagctgcc gcagcagctg catctggtcc tggaggttat    1320 gcccaggaa gccaaggacc atctggtcca ggaggatatg gtccaggcgg acctggctct    1380
agtgcagcag ctgccgcagc agctgcatct ggtcctggag gttatggccc aggaagccaa    1440
ggaccatctg gtccaggagg atatggtcca ggcggacctg gctctagtgc agcagctgcc    1500
gcagcagctg catctggtcc tggaggttat ggcccaggaa gccaaggacc atctggtcca    1560
ggaggatatg gtccaggcgg acctggctct agtgcagcag ctgccgcagc agctgcatct    1620
ggtcctggag gttatggccc aggaagccaa ggaccatctg gtccaggagg atatggtcca    1680
ggcggacctg gctctagtgc agcagctgcc gcagcagctg catctggtcc tggaggttat    1740 gcccaggaa gccaaggacc atctggtcca ggaggatatg gtccaggcgg acctggctct    1800
agtgcagcag ctgccgcagc agctgcatct ggtcctggag gttatggccc aggaagccaa    1860
ggaccatctg gtccaggagg atatggtcca ggcggacctg gctctagtgc agcagctgcc    1920
gcagcagctg catctggtcc tggaggttat ggcccaggaa gccaaggacc atctggtcca    1980
ggaggatatg gtccaggcgg acctggctct agtgcagcag ctgccgcagc agctgcatct    2040
ggtcctggag gttatggccc aggaagccaa ggaccatctg gtccaggagg atatggtcca    2100
ggcggacctg gctctagtgc agcagctgcc gcagcagctg catctggtcc tggaggttat    2160 gcccaggaa gccaaggacc atctggtcca ggaggatatg gtccaggcgg acctggctct    2220
agtgcagcag ctgccgcagc agctgcatct ggtcctggag gttatggccc aggaagccaa    2280
ggaccatctg gtccaggagg atatggtcca ggcggacctg gctctagtgc agcagctgcc    2340
gcagcagctg catctggtcc tggaggttat ggcccaggaa gccaaggacc atctggtcca    2400
ggaggatatg gtccaggcgg acctggctct agtgcagcag ctgccgcagc agctgcatct    2460
ggtcctggag gttatggccc aggaagccaa ggaccatctg gtccaggagg atatggtcca    2520
ggcggacctg gctctagtgc agcagctgcc gcagcagctg catctggtcc tggaggttat    2580 gcccaggaa gccaaggacc atctggtcca ggaggatatg gtccaggcgg acctggctct    2640
agtgcagcag ctgccgcagc agctgcaggc cctagtggtc ctggagcata tggcccatct    2700
ccttctgctt ccgcatccgt tgcagcctct cgtttatctt cgcctgcagc ctcgtctaga    2760
gtgtcttccg ctgtatcgtc tttagtgtct agcggaccta cgaatggtgc tgctgtttct    2820
ggagctttga atagtttagt atctcagatt agtgcaagta atccaggttt atcgggatgt    2880
gatgctcttg tgcaggcatt attggaatta gtgtctgctc ttgtggcaat tctttcatct    2940
gcaagtattg ccaagtcaa cgtcagctct gttagtcagt caactcaaat gattagccaa    3000
gctctttca                                                            3009
```

<210> SEQ ID NO 71
<211> LENGTH: 3849
<212> TYPE: DNA
<213> ORGANISM: Artificial
<220> FEATURE:
<223> OTHER INFORMATION: Full DNA sequence (N-domain + 32 repeats + C-domain) + N-terminal tag

<400> SEQUENCE: 71

```
atgtcgtact accatcacca tcaccatcac gattacgata tcccaacgac cgaaaacctg     60
tattttcagg gcgccatgga tccggaattc aaaggcctac gtcgacgagc tcaactagtg    120
cggccgcttt cgaatctaga taatgcatct ggtcctggag gttatggccc aggaagccaa    180
ggaccatctg gtccaggagg atatggtcca ggcggacctg gctctagtgc agcagctgcc    240
gcagcagctg catctggtcc tggaggttat ggcccaggaa gccaaggacc atctggtcca    300
```

```
ggaggatatg gtccaggcgg acctggctct agtgcagcag ctgccgcagc agctgcatct    360
ggtcctggag gttatggccc aggaagccaa ggaccatctg gtccaggagg atatggtcca    420
ggcggacctg gctctagtgc agcagctgcc gcagcagctg catctggtcc tggaggttat    480
ggcccaggaa gccaaggacc atctggtcca ggaggatatg gtccaggcgg acctggctct    540
agtgcagcag ctgccgcagc agctgcatct ggtcctggag gttatggccc aggaagccaa    600
ggaccatctg gtccaggagg atatggtcca ggcggacctg gctctagtgc agcagctgcc    660
gcagcagctg catctggtcc tggaggttat ggcccaggaa gccaaggacc atctggtcca    720
ggaggatatg gtccaggcgg acctggctct agtgcagcag ctgccgcagc agctgcatct    780
ggtcctggag gttatggccc aggaagccaa ggaccatctg gtccaggagg atatggtcca    840
ggcggacctg gctctagtgc agcagctgcc gcagcagctg catctggtcc tggaggttat    900
ggcccaggaa gccaaggacc atctggtcca ggaggatatg gtccaggcgg acctggctct    960
agtgcagcag ctgccgcagc agctgcatct ggtcctggag gttatggccc aggaagccaa   1020
ggaccatctg gtccaggagg atatggtcca ggcggacctg gctctagtgc agcagctgcc   1080
gcagcagctg catctggtcc tggaggttat ggcccaggaa gccaaggacc atctggtcca   1140
ggaggatatg gtccaggcgg acctggctct agtgcagcag ctgccgcagc agctgcatct   1200
ggtcctggag gttatggccc aggaagccaa ggaccatctg gtccaggagg atatggtcca   1260
ggcggacctg gctctagtgc agcagctgcc gcagcagctg catctggtcc tggaggttat   1320
ggcccaggaa gccaaggacc atctggtcca ggaggatatg gtccaggcgg acctggctct   1380
agtgcagcag ctgccgcagc agctgcatct ggtcctggag gttatggccc aggaagccaa   1440
ggaccatctg gtccaggagg atatggtcca ggcggacctg gctctagtgc agcagctgcc   1500
gcagcagctg catctggtcc tggaggttat ggcccaggaa gccaaggacc atctggtcca   1560
ggaggatatg gtccaggcgg acctggctct agtgcagcag ctgccgcagc agctgcatct   1620
ggtcctggag gttatggccc aggaagccaa ggaccatctg gtccaggagg atatggtcca   1680
ggcggacctg gctctagtgc agcagctgcc gcagcagctg catctggtcc tggaggttat   1740
ggcccaggaa gccaaggacc atctggtcca ggaggatatg gtccaggcgg acctggctct   1800
agtgcagcag ctgccgcagc agctgcatct ggtcctggag gttatggccc aggaagccaa   1860
ggaccatctg gtccaggagg atatggtcca ggcggacctg gctctagtgc agcagctgcc   1920
gcagcagctg catctggtcc tggaggttat ggcccaggaa gccaaggacc atctggtcca   1980
ggaggatatg gtccaggcgg acctggctct agtgcagcag ctgccgcagc agctgcatct   2040
ggtcctggag gttatggccc aggaagccaa ggaccatctg gtccaggagg atatggtcca   2100
ggcggacctg gctctagtgc agcagctgcc gcagcagctg catctggtcc tggaggttat   2160
ggcccaggaa gccaaggacc atctggtcca ggaggatatg gtccaggcgg acctggctct   2220
agtgcagcag ctgccgcagc agctgcatct ggtcctggag gttatggccc aggaagccaa   2280
ggaccatctg gtccaggagg atatggtcca ggcggacctg gctctagtgc agcagctgcc   2340
gcagcagctg catctggtcc tggaggttat ggcccaggaa gccaaggacc atctggtcca   2400
ggaggatatg gtccaggcgg acctggctct agtgcagcag ctgccgcagc agctgcatct   2460
ggtcctggag gttatggccc aggaagccaa ggaccatctg gtccaggagg atatggtcca   2520
ggcggacctg gctctagtgc agcagctgcc gcagcagctg catctggtcc tggaggttat   2580
ggcccaggaa gccaaggacc atctggtcca ggaggatatg gtccaggcgg acctggctct   2640
agtgcagcag ctgccgcagc agctgcatct ggtcctggag gttatggccc aggaagccaa   2700
```

```
ggaccatctg gtccaggagg atatggtcca ggcggacctg gctctagtgc agcagctgcc   2760
gcagcagctg catctggtcc tggaggttat ggcccaggaa gccaaggacc atctggtcca   2820
ggaggatatg gtccaggcgg acctggctct agtgcagcag ctgccgcagc agctgcatct   2880
ggtcctggag gttatggccc aggaagccaa ggaccatctg gtccaggagg atatggtcca   2940
ggcggacctg gctctagtgc agcagctgcc gcagcagctg catctggtcc tggaggttat   3000
ggcccaggaa gccaaggacc atctggtcca ggaggatatg gtccaggcgg acctggctct   3060
agtgcagcag ctgccgcagc agctgcatct ggtcctggag gttatggccc aggaagccaa   3120
ggaccatctg gtccaggagg atatggtcca ggcggacctg gctctagtgc agcagctgcc   3180
gcagcagctg catctggtcc tggaggttat ggcccaggaa gccaaggacc atctggtcca   3240
ggaggatatg gtccaggcgg acctggctct agtgcagcag ctgccgcagc agctgcatct   3300
ggtcctggag gttatggccc aggaagccaa ggaccatctg gtccaggagg atatggtcca   3360
ggcggacctg gctctagtgc agcagctgcc gcagcagctg catctggtcc tggaggttat   3420
ggcccaggaa gccaaggacc atctggtcca ggaggatatg gtccaggcgg acctggctct   3480
agtgcagcag ctgccgcagc agctgcaggc cctagtggtc ctggagcata tggcccatct   3540
ccttctgctt ccgcatccgt tgcagcctct cgtttatctt cgcctgcagc ctcgtctaga   3600
gtgtcttccg ctgtatcgtc tttagtgtct agcggaccta cgaatggtgc tgctgttcct   3660
ggagctttga atagtttagt atctcagatt agtgcaagta atccaggttt atcgggatgt   3720
gatgctcttg tgcaggcatt attggaatta gtgtctgctc ttgtggcaat tctttcatct   3780
gcaagtattg ccaagtcaa cgtcagctct gttagtcagt caactcaaat gattagccaa   3840
gctctttca                                                           3849

<210> SEQ ID NO 72
<211> LENGTH: 233
<212> TYPE: PRT
<213> ORGANISM: Artificial
<220> FEATURE:
<223> OTHER INFORMATION: Full peptide sequence (N-domain + 2 repeats +
      C-domain) + N-terminal tag

<400> SEQUENCE: 72

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
                20                  25                  30

Leu Arg Arg Arg Ala Gln Leu Val Arg Pro Leu Ser Asn Leu Asp Asn
            35                  40                  45

Ala Ser Gly Pro Gly Gly Tyr Gly Pro Gly Ser Gln Gly Pro Ser Gly
        50                  55                  60

Pro Gly Gly Tyr Gly Pro Gly Gly Pro Gly Ser Ala Ala Ala Ala
65                  70                  75                  80

Ala Ala Ala Ala Ser Gly Pro Gly Gly Tyr Gly Pro Gly Ser Gln Gly
                85                  90                  95

Pro Ser Gly Pro Gly Gly Tyr Gly Pro Gly Gly Pro Gly Ser Ser Ala
                100                 105                 110

Ala Ala Ala Ala Ala Ala Gly Pro Ser Gly Pro Gly Ala Tyr Gly
        115                 120                 125

Pro Ser Pro Ser Ala Ser Ala Ser Val Ala Ala Ser Arg Leu Ser Ser
    130                 135                 140

Pro Ala Ala Ser Ser Arg Val Ser Ser Ala Val Ser Ser Leu Val Ser
```

-continued

```
                145                 150                 155                 160
Ser Gly Pro Thr Asn Gly Ala Ala Val Ser Gly Ala Leu Asn Ser Leu
                    165                 170                 175

Val Ser Gln Ile Ser Ala Ser Asn Pro Gly Leu Ser Gly Cys Asp Ala
                180                 185                 190

Leu Val Gln Ala Leu Leu Glu Leu Val Ser Ala Leu Val Ala Ile Leu
            195                 200                 205

Ser Ser Ala Ser Ile Gly Gln Val Asn Val Ser Ser Val Ser Gln Ser
        210                 215                 220

Thr Gln Met Ile Ser Gln Ala Leu Ser
225                 230

<210> SEQ ID NO 73
<211> LENGTH: 303
<212> TYPE: PRT
<213> ORGANISM: Artificial
<220> FEATURE:
<223> OTHER INFORMATION: Full peptide sequence (N-domain + 4 repeats +
      C-domain) + N-terminal tag

<400> SEQUENCE: 73

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
                20                  25                  30

Leu Arg Arg Arg Ala Gln Leu Val Arg Pro Leu Ser Asn Leu Asp Asn
            35                  40                  45

Ala Ser Gly Pro Gly Gly Tyr Gly Pro Gly Ser Gln Gly Pro Ser Gly
        50                  55                  60

Pro Gly Gly Tyr Gly Pro Gly Gly Pro Gly Ser Ser Ala Ala Ala Ala
65                  70                  75                  80

Ala Ala Ala Ala Ser Gly Pro Gly Gly Tyr Gly Pro Gly Ser Gln Gly
                85                  90                  95

Pro Ser Gly Pro Gly Gly Tyr Gly Pro Gly Gly Pro Gly Ser Ser Ala
                100                 105                 110

Ala Ala Ala Ala Ala Ala Ala Ser Gly Pro Gly Gly Tyr Gly Pro Gly
            115                 120                 125

Ser Gln Gly Pro Ser Gly Pro Gly Gly Tyr Gly Pro Gly Gly Pro Gly
        130                 135                 140

Ser Ser Ala Ala Ala Ala Ala Ala Ala Ala Ser Gly Pro Gly Gly Tyr
145                 150                 155                 160

Gly Pro Gly Ser Gln Gly Pro Ser Gly Pro Gly Gly Tyr Gly Pro Gly
                165                 170                 175

Gly Pro Gly Ser Ser Ala Ala Ala Ala Ala Ala Ala Ala Gly Pro Ser
                180                 185                 190

Gly Pro Gly Ala Tyr Gly Pro Ser Pro Ser Ala Ser Ala Ser Val Ala
            195                 200                 205

Ala Ser Arg Leu Ser Ser Pro Ala Ala Ser Ser Arg Val Ser Ser Ala
        210                 215                 220

Val Ser Ser Leu Val Ser Ser Gly Pro Thr Asn Gly Ala Ala Val Ser
225                 230                 235                 240

Gly Ala Leu Asn Ser Leu Val Ser Gln Ile Ser Ala Ser Asn Pro Gly
                245                 250                 255

Leu Ser Gly Cys Asp Ala Leu Val Gln Ala Leu Leu Glu Leu Val Ser
                260                 265                 270

Ala Leu Val Ala Ile Leu Ser Ser Ala Ser Ile Gly Gln Val Asn Val
```

275                 280                 285
Ser Ser Val Ser Gln Ser Thr Gln Met Ile Ser Gln Ala Leu Ser
        290                 295                 300

<210> SEQ ID NO 74
<211> LENGTH: 443
<212> TYPE: PRT
<213> ORGANISM: Artificial
<220> FEATURE:
<223> OTHER INFORMATION: Full peptide sequence (N-domain + 8 repeats +
      C-domain) + N-terminal tag

<400> SEQUENCE: 74

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Arg Pro Leu Ser Asn Leu Asp Asn
        35                  40                  45

Ala Ser Gly Pro Gly Gly Tyr Gly Pro Gly Ser Gln Gly Pro Ser Gly
    50                  55                  60

Pro Gly Gly Tyr Gly Pro Gly Gly Pro Gly Ser Ser Ala Ala Ala Ala
65                  70                  75                  80

Ala Ala Ala Ala Ser Gly Pro Gly Gly Tyr Gly Pro Gly Ser Gln Gly
                85                  90                  95

Pro Ser Gly Pro Gly Gly Tyr Gly Pro Gly Gly Pro Gly Ser Ser Ala
            100                 105                 110

Ala Ala Ala Ala Ala Ala Ser Gly Pro Gly Gly Tyr Gly Pro Gly
        115                 120                 125

Ser Gln Gly Pro Ser Gly Pro Gly Gly Tyr Gly Pro Gly Gly Pro Gly
    130                 135                 140

Ser Ser Ala Ala Ala Ala Ala Ala Ala Ser Gly Pro Gly Gly Tyr
145                 150                 155                 160

Gly Pro Gly Ser Gln Gly Pro Ser Gly Pro Gly Gly Tyr Gly Pro Gly
                165                 170                 175

Gly Pro Gly Ser Ser Ala Ala Ala Ala Ala Ala Ala Ser Gly Pro
            180                 185                 190

Gly Gly Tyr Gly Pro Gly Ser Gln Gly Pro Ser Gly Pro Gly Gly Tyr
        195                 200                 205

Gly Pro Gly Gly Pro Gly Ser Ser Ala Ala Ala Ala Ala Ala Ala
    210                 215                 220

Ser Gly Pro Gly Gly Tyr Gly Pro Gly Ser Gln Gly Pro Ser Gly Pro
225                 230                 235                 240

Gly Gly Tyr Gly Pro Gly Gly Pro Gly Ser Ser Ala Ala Ala Ala
                245                 250                 255

Ala Ala Ala Ser Gly Pro Gly Gly Tyr Gly Pro Gly Ser Gln Gly Pro
            260                 265                 270

Ser Gly Pro Gly Gly Tyr Gly Pro Gly Gly Pro Gly Ser Ser Ala Ala
        275                 280                 285

Ala Ala Ala Ala Ala Ser Gly Pro Gly Gly Tyr Gly Pro Gly Ser
    290                 295                 300

Gln Gly Pro Ser Gly Pro Gly Gly Tyr Gly Pro Gly Gly Pro Gly Ser
305                 310                 315                 320

Ser Ala Ala Ala Ala Ala Ala Ala Gly Pro Ser Gly Pro Gly Ala
                325                 330                 335

Tyr Gly Pro Ser Pro Ser Ala Ser Ala Ser Val Ala Ala Ser Arg Leu

```
                    340              345              350
Ser Ser Pro Ala Ala Ser Ser Arg Val Ser Ala Val Ser Ser Leu
            355              360              365
Val Ser Ser Gly Pro Thr Asn Gly Ala Val Ser Gly Ala Leu Asn
        370              375              380
Ser Leu Val Ser Gln Ile Ser Ala Ser Asn Pro Gly Leu Ser Gly Cys
385              390              395              400
Asp Ala Leu Val Gln Ala Leu Leu Glu Leu Val Ser Ala Leu Val Ala
                405              410              415
Ile Leu Ser Ser Ala Ser Ile Gly Gln Val Asn Val Ser Ser Val Ser
            420              425              430
Gln Ser Thr Gln Met Ile Ser Gln Ala Leu Ser
            435              440
```

<210> SEQ ID NO 75
<211> LENGTH: 583
<212> TYPE: PRT
<213> ORGANISM: Artificial
<220> FEATURE:
<223> OTHER INFORMATION: Full peptide sequence (N-domain + 12 repeats + C-domain) + N-terminal tag

<400> SEQUENCE: 75

```
Met Ser Tyr Tyr His His His His His His Asp Tyr Asp Ile Pro Thr
1               5                   10                  15
Thr Glu Asn Leu Tyr Phe Gln Gly Ala Met Asp Pro Glu Phe Lys Gly
            20                  25                  30
Leu Arg Arg Arg Ala Gln Leu Val Arg Pro Leu Ser Asn Leu Asp Asn
        35                  40                  45
Ala Ser Gly Pro Gly Gly Tyr Gly Pro Gly Ser Gln Gly Pro Ser Gly
    50                  55                  60
Pro Gly Gly Tyr Gly Pro Gly Gly Pro Gly Ser Ser Ala Ala Ala Ala
65                  70                  75                  80
Ala Ala Ala Ala Ser Gly Pro Gly Gly Tyr Gly Pro Gly Ser Gln Gly
                85                  90                  95
Pro Ser Gly Pro Gly Gly Tyr Gly Pro Gly Gly Pro Gly Ser Ser Ala
            100                 105                 110
Ala Ala Ala Ala Ala Ala Ser Gly Pro Gly Gly Tyr Gly Pro Gly
        115                 120                 125
Ser Gln Gly Pro Ser Gly Pro Gly Gly Tyr Gly Pro Gly Gly Pro Gly
    130                 135                 140
Ser Ser Ala Ala Ala Ala Ala Ala Ala Ser Gly Pro Gly Gly Tyr
145                 150                 155                 160
Gly Pro Gly Ser Gln Gly Pro Ser Gly Pro Gly Gly Tyr Gly Pro Gly
                165                 170                 175
Gly Pro Gly Ser Ser Ala Ala Ala Ala Ala Ala Ala Ser Gly Pro
            180                 185                 190
Gly Gly Tyr Gly Pro Gly Ser Gln Gly Pro Ser Gly Pro Gly Gly Tyr
        195                 200                 205
Gly Pro Gly Gly Pro Gly Ser Ser Ala Ala Ala Ala Ala Ala Ala
    210                 215                 220
Ser Gly Pro Gly Gly Tyr Gly Pro Gly Ser Gln Gly Pro Ser Gly Pro
225                 230                 235                 240
Gly Gly Tyr Gly Pro Gly Gly Pro Gly Ser Ser Ala Ala Ala Ala Ala
                245                 250                 255
Ala Ala Ala Ser Gly Pro Gly Gly Tyr Gly Pro Gly Ser Gln Gly Pro
```

```
                260                 265                 270
Ser Gly Pro Gly Gly Tyr Gly Pro Gly Pro Gly Ser Ala Ala
            275                 280                 285

Ala Ala Ala Ala Ala Ser Gly Pro Gly Gly Tyr Gly Pro Gly Ser
        290                 295                 300

Gln Gly Pro Ser Gly Pro Gly Gly Tyr Gly Pro Gly Pro Gly Ser
305                 310                 315                 320

Ser Ala Ala Ala Ala Ala Ala Ser Gly Pro Gly Gly Tyr Gly
                325                 330                 335

Pro Gly Ser Gln Gly Pro Ser Gly Pro Gly Gly Tyr Gly Pro Gly Gly
            340                 345                 350

Pro Gly Ser Ser Ala Ala Ala Ala Ala Ala Ser Gly Pro Gly
            355                 360                 365

Gly Tyr Gly Pro Gly Ser Gln Gly Pro Ser Gly Pro Gly Gly Tyr Gly
        370                 375                 380

Pro Gly Gly Pro Gly Ser Ser Ala Ala Ala Ala Ala Ala Ser
385                 390                 395                 400

Gly Pro Gly Gly Tyr Gly Pro Gly Ser Gln Gly Pro Ser Gly Pro Gly
                405                 410                 415

Gly Tyr Gly Pro Gly Gly Pro Gly Ser Ser Ala Ala Ala Ala Ala
                420                 425                 430

Ala Ala Ser Gly Pro Gly Gly Tyr Gly Pro Gly Ser Gln Gly Pro Ser
            435                 440                 445

Gly Pro Gly Gly Tyr Gly Pro Gly Gly Pro Gly Ser Ser Ala Ala Ala
            450                 455                 460

Ala Ala Ala Ala Gly Pro Ser Gly Pro Gly Ala Tyr Gly Pro Ser
465                 470                 475                 480

Pro Ser Ala Ser Ala Ser Val Ala Ala Ser Arg Leu Ser Pro Ala
                485                 490                 495

Ala Ser Ser Arg Val Ser Ser Ala Val Ser Ser Leu Val Ser Ser Gly
            500                 505                 510

Pro Thr Asn Gly Ala Ala Val Ser Gly Ala Leu Asn Ser Leu Val Ser
            515                 520                 525

Gln Ile Ser Ala Ser Asn Pro Gly Leu Ser Gly Cys Asp Ala Leu Val
        530                 535                 540

Gln Ala Leu Leu Glu Leu Val Ser Ala Leu Val Ala Ile Leu Ser Ser
545                 550                 555                 560

Ala Ser Ile Gly Gln Val Asn Val Ser Ser Val Ser Gln Ser Thr Gln
                565                 570                 575

Met Ile Ser Gln Ala Leu Ser
            580

<210> SEQ ID NO 76
<211> LENGTH: 723
<212> TYPE: PRT
<213> ORGANISM: Artificial
<220> FEATURE:
<223> OTHER INFORMATION: Full peptide sequence (N-domain + 16 repeats +
      C-domain) + N-terminal tag

<400> SEQUENCE: 76

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Arg Pro Leu Ser Asn Leu Asp Asn
```

```
                35                  40                  45
Ala Ser Gly Pro Gly Gly Tyr Gly Pro Gly Ser Gln Gly Pro Ser Gly
        50                  55                  60
Pro Gly Gly Tyr Gly Pro Gly Gly Pro Gly Ser Ser Ala Ala Ala Ala
65                  70                  75                  80
Ala Ala Ala Ala Ser Gly Pro Gly Gly Tyr Gly Pro Gly Ser Gln Gly
                85                  90                  95
Pro Ser Gly Pro Gly Gly Tyr Gly Pro Gly Gly Pro Gly Ser Ser Ala
            100                 105                 110
Ala Ala Ala Ala Ala Ala Ser Gly Pro Gly Gly Tyr Gly Pro Gly
            115                 120                 125
Ser Gln Gly Pro Ser Gly Pro Gly Gly Tyr Gly Pro Gly Gly Pro Gly
        130                 135                 140
Ser Ser Ala Ala Ala Ala Ala Ala Ala Ser Gly Pro Gly Gly Tyr
145                 150                 155                 160
Gly Pro Gly Ser Gln Gly Pro Ser Gly Pro Gly Gly Tyr Gly Pro Gly
                165                 170                 175
Gly Pro Gly Ser Ser Ala Ala Ala Ala Ala Ala Ala Ser Gly Pro
            180                 185                 190
Gly Gly Tyr Gly Pro Gly Ser Gln Gly Pro Ser Gly Pro Gly Gly Tyr
        195                 200                 205
Gly Pro Gly Gly Pro Gly Ser Ser Ala Ala Ala Ala Ala Ala Ala
    210                 215                 220
Ser Gly Pro Gly Gly Tyr Gly Pro Gly Ser Gln Gly Pro Ser Gly Pro
225                 230                 235                 240
Gly Gly Tyr Gly Pro Gly Gly Pro Gly Ser Ser Ala Ala Ala Ala
            245                 250                 255
Ala Ala Ala Ser Gly Pro Gly Gly Tyr Gly Pro Gly Ser Gln Gly Pro
            260                 265                 270
Ser Gly Pro Gly Gly Tyr Gly Pro Gly Gly Pro Gly Ser Ser Ala Ala
        275                 280                 285
Ala Ala Ala Ala Ala Ser Gly Pro Gly Gly Tyr Gly Pro Gly Ser
    290                 295                 300
Gln Gly Pro Ser Gly Pro Gly Gly Tyr Gly Pro Gly Gly Pro Gly Ser
305                 310                 315                 320
Ser Ala Ala Ala Ala Ala Ala Ala Ser Gly Pro Gly Gly Tyr Gly
            325                 330                 335
Pro Gly Ser Gln Gly Pro Ser Gly Pro Gly Gly Tyr Gly Pro Gly Gly
            340                 345                 350
Pro Gly Ser Ser Ala Ala Ala Ala Ala Ala Ala Ser Gly Pro Gly
        355                 360                 365
Gly Tyr Gly Pro Gly Ser Gln Gly Pro Ser Gly Pro Gly Gly Tyr Gly
    370                 375                 380
Pro Gly Gly Pro Gly Ser Ser Ala Ala Ala Ala Ala Ala Ala Ser
385                 390                 395                 400
Gly Pro Gly Gly Tyr Gly Pro Gly Ser Gln Gly Pro Ser Gly Pro Gly
            405                 410                 415
Gly Tyr Gly Pro Gly Gly Pro Gly Ser Ser Ala Ala Ala Ala Ala
            420                 425                 430
Ala Ala Ser Gly Pro Gly Gly Tyr Gly Pro Gly Ser Gln Gly Pro Ser
        435                 440                 445
Gly Pro Gly Gly Tyr Gly Pro Gly Gly Pro Gly Ser Ser Ala Ala Ala
    450                 455                 460
```

```
Ala Ala Ala Ala Ala Ser Gly Pro Gly Gly Tyr Gly Pro Gly Ser Gln
465                 470                 475                 480

Gly Pro Ser Gly Pro Gly Gly Tyr Gly Pro Gly Gly Pro Gly Ser Ser
                485                 490                 495

Ala Ala Ala Ala Ala Ala Ala Ser Gly Pro Gly Gly Tyr Gly Pro
            500                 505                 510

Gly Ser Gln Gly Pro Ser Gly Pro Gly Gly Tyr Gly Pro Gly Gly Pro
        515                 520                 525

Gly Ser Ser Ala Ala Ala Ala Ala Ala Ala Ser Gly Pro Gly Gly
    530                 535                 540

Tyr Gly Pro Gly Ser Gln Gly Pro Ser Gly Pro Gly Gly Tyr Gly Pro
545                 550                 555                 560

Gly Gly Pro Gly Ser Ser Ala Ala Ala Ala Ala Ala Ala Ser Gly
                565                 570                 575

Pro Gly Gly Tyr Gly Pro Gly Ser Gln Gly Pro Ser Gly Pro Gly Gly
            580                 585                 590

Tyr Gly Pro Gly Gly Pro Gly Ser Ser Ala Ala Ala Ala Ala Ala Ala
                595                 600                 605

Ala Gly Pro Ser Gly Pro Gly Ala Tyr Gly Pro Ser Pro Ser Ala Ser
            610                 615                 620

Ala Ser Val Ala Ala Ser Arg Leu Ser Ser Pro Ala Ala Ser Ser Arg
625                 630                 635                 640

Val Ser Ser Ala Val Ser Ser Leu Val Ser Ser Gly Pro Thr Asn Gly
                645                 650                 655

Ala Ala Val Ser Gly Ala Leu Asn Ser Leu Val Ser Gln Ile Ser Ala
            660                 665                 670

Ser Asn Pro Gly Leu Ser Gly Cys Asp Ala Leu Val Gln Ala Leu Leu
            675                 680                 685

Glu Leu Val Ser Ala Leu Val Ala Ile Leu Ser Ser Ala Ser Ile Gly
        690                 695                 700

Gln Val Asn Val Ser Ser Val Ser Gln Ser Thr Gln Met Ile Ser Gln
705                 710                 715                 720

Ala Leu Ser

<210> SEQ ID NO 77
<211> LENGTH: 863
<212> TYPE: PRT
<213> ORGANISM: Artificial
<220> FEATURE:
<223> OTHER INFORMATION: Full peptide sequence (N-domain + 20 repeats +
      C-domain) + N-terminal tag

<400> SEQUENCE: 77

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Arg Pro Leu Ser Asn Leu Asp Asn
        35                  40                  45

Ala Ser Gly Pro Gly Gly Tyr Gly Pro Gly Ser Gln Gly Pro Ser Gly
    50                  55                  60

Pro Gly Tyr Gly Pro Gly Pro Gly Ser Ser Ala Ala Ala Ala Ala Ala
65                  70                  75                  80

Ala Ala Ala Ala Ser Gly Pro Gly Gly Tyr Gly Pro Gly Ser Gln Gly
                85                  90                  95

Pro Ser Gly Pro Gly Gly Tyr Gly Pro Gly Gly Pro Gly Ser Ser Ala
```

-continued

```
                    100                 105                 110
Ala Ala Ala Ala Ala Ala Ser Gly Pro Gly Gly Tyr Gly Pro Gly
            115                 120                 125

Ser Gln Gly Pro Ser Gly Pro Gly Gly Tyr Gly Pro Gly Gly Pro Gly
130                 135                 140

Ser Ser Ala Ala Ala Ala Ala Ala Ala Ser Gly Pro Gly Tyr
145                 150                 155                 160

Gly Pro Gly Ser Gln Gly Pro Ser Gly Pro Gly Gly Tyr Gly Pro Gly
                165                 170                 175

Gly Pro Gly Ser Ser Ala Ala Ala Ala Ala Ala Ala Ser Gly Pro
            180                 185                 190

Gly Gly Tyr Gly Pro Gly Ser Gln Gly Pro Ser Gly Pro Gly Gly Tyr
        195                 200                 205

Gly Pro Gly Gly Pro Gly Ser Ser Ala Ala Ala Ala Ala Ala Ala
        210                 215                 220

Ser Gly Pro Gly Gly Tyr Gly Pro Gly Ser Gln Gly Pro Ser Gly Pro
225                 230                 235                 240

Gly Gly Tyr Gly Pro Gly Gly Pro Gly Ser Ser Ala Ala Ala Ala
        245                 250                 255

Ala Ala Ala Ser Gly Pro Gly Gly Tyr Gly Pro Gly Ser Gln Gly Pro
            260                 265                 270

Ser Gly Pro Gly Gly Tyr Gly Pro Gly Gly Pro Gly Ser Ser Ala Ala
        275                 280                 285

Ala Ala Ala Ala Ala Ser Gly Pro Gly Gly Tyr Gly Pro Gly Ser
        290                 295                 300

Gln Gly Pro Ser Gly Pro Gly Gly Tyr Gly Pro Gly Gly Pro Gly Ser
305                 310                 315                 320

Ser Ala Ala Ala Ala Ala Ala Ala Ser Gly Pro Gly Gly Tyr Gly
            325                 330                 335

Pro Gly Ser Gln Gly Pro Ser Gly Pro Gly Gly Tyr Gly Pro Gly Gly
                340                 345                 350

Pro Gly Ser Ser Ala Ala Ala Ala Ala Ala Ala Ser Gly Pro Gly
            355                 360                 365

Gly Tyr Gly Pro Gly Ser Gln Gly Pro Ser Gly Pro Gly Gly Tyr Gly
        370                 375                 380

Pro Gly Gly Pro Gly Ser Ser Ala Ala Ala Ala Ala Ala Ala Ser
385                 390                 395                 400

Gly Pro Gly Gly Tyr Gly Pro Gly Ser Gln Gly Pro Ser Gly Pro Gly
                405                 410                 415

Gly Tyr Gly Pro Gly Gly Pro Gly Ser Ser Ala Ala Ala Ala Ala
        420                 425                 430

Ala Ala Ser Gly Pro Gly Gly Tyr Gly Pro Gly Ser Gln Gly Pro Ser
            435                 440                 445

Gly Pro Gly Gly Tyr Gly Pro Gly Gly Pro Gly Ser Ser Ala Ala Ala
        450                 455                 460

Ala Ala Ala Ala Ala Ser Gly Pro Gly Gly Tyr Gly Pro Gly Ser Gln
465                 470                 475                 480

Gly Pro Ser Gly Pro Gly Gly Tyr Gly Pro Gly Gly Pro Gly Ser Ser
                485                 490                 495

Ala Ala Ala Ala Ala Ala Ala Ser Gly Pro Gly Gly Tyr Gly Pro
            500                 505                 510

Gly Ser Gln Gly Pro Ser Gly Pro Gly Gly Tyr Gly Pro Gly Gly Pro
        515                 520                 525
```

```
Gly Ser Ser Ala Ala Ala Ala Ala Ala Ser Gly Pro Gly Gly
        530                 535                 540

Tyr Gly Pro Gly Ser Gln Gly Pro Ser Gly Pro Gly Tyr Gly Pro
545                 550                 555                 560

Gly Gly Pro Gly Ser Ser Ala Ala Ala Ala Ala Ala Ala Ser Gly
                565                 570                 575

Pro Gly Gly Tyr Gly Pro Gly Ser Gln Gly Pro Ser Gly Pro Gly Gly
                580                 585                 590

Tyr Gly Pro Gly Gly Pro Gly Ser Ser Ala Ala Ala Ala Ala Ala
            595                 600                 605

Ala Ser Gly Pro Gly Gly Tyr Gly Pro Gly Ser Gln Gly Pro Ser Gly
    610                 615                 620

Pro Gly Gly Tyr Gly Pro Gly Gly Pro Gly Ser Ser Ala Ala Ala Ala
625                 630                 635                 640

Ala Ala Ala Ala Ser Gly Pro Gly Gly Tyr Gly Pro Gly Ser Gln Gly
                645                 650                 655

Pro Ser Gly Pro Gly Gly Tyr Gly Pro Gly Gly Pro Gly Ser Ser Ala
            660                 665                 670

Ala Ala Ala Ala Ala Ala Ser Gly Pro Gly Gly Tyr Gly Pro Gly
    675                 680                 685

Ser Gln Gly Pro Ser Gly Pro Gly Gly Tyr Gly Pro Gly Gly Pro Gly
    690                 695                 700

Ser Ser Ala Ala Ala Ala Ala Ala Ala Ser Gly Pro Gly Gly Tyr
705                 710                 715                 720

Gly Pro Gly Ser Gln Gly Pro Ser Gly Pro Gly Gly Tyr Gly Pro Gly
                725                 730                 735

Gly Pro Gly Ser Ser Ala Ala Ala Ala Ala Ala Ala Gly Pro Ser
            740                 745                 750

Gly Pro Gly Ala Tyr Gly Pro Ser Pro Ser Ala Ser Ala Ser Val Ala
            755                 760                 765

Ala Ser Arg Leu Ser Ser Pro Ala Ser Ser Arg Val Ser Ser Ala
    770                 775                 780

Val Ser Ser Leu Val Ser Ser Gly Pro Thr Asn Gly Ala Ala Val Ser
785                 790                 795                 800

Gly Ala Leu Asn Ser Leu Val Ser Gln Ile Ser Ala Ser Asn Pro Gly
                805                 810                 815

Leu Ser Gly Cys Asp Ala Leu Val Gln Ala Leu Leu Glu Leu Val Ser
            820                 825                 830

Ala Leu Val Ala Ile Leu Ser Ser Ala Ser Ile Gly Gln Val Asn Val
    835                 840                 845

Ser Ser Val Ser Gln Ser Thr Gln Met Ile Ser Gln Ala Leu Ser
    850                 855                 860

<210> SEQ ID NO 78
<211> LENGTH: 1003
<212> TYPE: PRT
<213> ORGANISM: Artificial
<220> FEATURE:
<223> OTHER INFORMATION: Full peptide sequence (N-domain + 24 repeats +
      C-domain) + N-terminal tag

<400> SEQUENCE: 78

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30
```

```
Leu Arg Arg Arg Ala Gln Leu Val Arg Pro Leu Ser Asn Leu Asp Asn
         35                  40                  45

Ala Ser Gly Pro Gly Gly Tyr Gly Pro Gly Ser Gln Gly Pro Ser Gly
 50                  55                  60

Pro Gly Gly Tyr Gly Pro Gly Gly Pro Gly Ser Ser Ala Ala Ala Ala
 65                  70                  75                  80

Ala Ala Ala Ala Ser Gly Pro Gly Gly Tyr Gly Pro Gly Ser Gln Gly
                 85                  90                  95

Pro Ser Gly Pro Gly Gly Tyr Gly Pro Gly Gly Pro Gly Ser Ser Ala
             100                 105                 110

Ala Ala Ala Ala Ala Ala Ser Gly Pro Gly Gly Tyr Gly Pro Gly
         115                 120                 125

Ser Gln Gly Pro Ser Gly Pro Gly Gly Tyr Gly Pro Gly Gly Pro Gly
         130                 135                 140

Ser Ser Ala Ala Ala Ala Ala Ala Ala Ser Gly Pro Gly Gly Tyr
145                 150                 155                 160

Gly Pro Gly Ser Gln Gly Pro Ser Gly Pro Gly Gly Tyr Gly Pro Gly
                 165                 170                 175

Gly Pro Gly Ser Ser Ala Ala Ala Ala Ala Ala Ala Ser Gly Pro
             180                 185                 190

Gly Gly Tyr Gly Pro Gly Ser Gln Gly Pro Ser Gly Pro Gly Gly Tyr
         195                 200                 205

Gly Pro Gly Gly Pro Gly Ser Ser Ala Ala Ala Ala Ala Ala Ala
         210                 215                 220

Ser Gly Pro Gly Gly Tyr Gly Pro Gly Ser Gln Gly Pro Ser Gly Pro
225                 230                 235                 240

Gly Gly Tyr Gly Pro Gly Gly Pro Gly Ser Ser Ala Ala Ala Ala
             245                 250                 255

Ala Ala Ala Ser Gly Pro Gly Gly Tyr Gly Pro Gly Ser Gln Gly Pro
             260                 265                 270

Ser Gly Pro Gly Gly Tyr Gly Pro Gly Gly Pro Gly Ser Ser Ala Ala
         275                 280                 285

Ala Ala Ala Ala Ala Ser Gly Pro Gly Gly Tyr Gly Pro Gly Ser
         290                 295                 300

Gln Gly Pro Ser Gly Pro Gly Gly Tyr Gly Pro Gly Gly Pro Gly Ser
305                 310                 315                 320

Ser Ala Ala Ala Ala Ala Ala Ala Ser Gly Pro Gly Gly Tyr Gly
             325                 330                 335

Pro Gly Ser Gln Gly Pro Ser Gly Pro Gly Gly Tyr Gly Pro Gly Gly
             340                 345                 350

Pro Gly Ser Ser Ala Ala Ala Ala Ala Ala Ala Ser Gly Pro Gly
         355                 360                 365

Gly Tyr Gly Pro Gly Ser Gln Gly Pro Ser Gly Pro Gly Gly Tyr Gly
         370                 375                 380

Pro Gly Gly Pro Gly Ser Ser Ala Ala Ala Ala Ala Ala Ala Ser
385                 390                 395                 400

Gly Pro Gly Gly Tyr Gly Pro Gly Ser Gln Gly Pro Ser Gly Pro Gly
                 405                 410                 415

Gly Tyr Gly Pro Gly Gly Pro Gly Ser Ser Ala Ala Ala Ala Ala
             420                 425                 430

Ala Ala Ser Gly Pro Gly Gly Tyr Gly Pro Gly Ser Gln Gly Pro Ser
         435                 440                 445

Gly Pro Gly Gly Tyr Gly Pro Gly Gly Pro Gly Ser Ser Ala Ala Ala
         450                 455                 460
```

Ala Ala Ala Ala Ala Ser Gly Pro Gly Gly Tyr Gly Pro Gly Ser Gln
465                 470                 475                 480

Gly Pro Ser Gly Pro Gly Gly Tyr Gly Pro Gly Gly Pro Ser Ser
        485                 490                 495

Ala Ala Ala Ala Ala Ala Ala Ser Gly Pro Gly Gly Tyr Gly Pro
            500                 505                 510

Gly Ser Gln Gly Pro Ser Gly Pro Gly Gly Tyr Gly Pro Gly Gly Pro
                515                 520                 525

Gly Ser Ser Ala Ala Ala Ala Ala Ala Ala Ser Gly Pro Gly Gly
    530                 535                 540

Tyr Gly Pro Gly Ser Gln Gly Pro Ser Gly Pro Gly Gly Tyr Gly Pro
545                 550                 555                 560

Gly Gly Pro Gly Ser Ser Ala Ala Ala Ala Ala Ala Ala Ser Gly
        565                 570                 575

Pro Gly Gly Tyr Gly Pro Gly Ser Gln Gly Pro Ser Gly Pro Gly Gly
            580                 585                 590

Tyr Gly Pro Gly Gly Pro Gly Ser Ser Ala Ala Ala Ala Ala Ala
                595                 600                 605

Ala Ser Gly Pro Gly Gly Tyr Gly Pro Gly Ser Gln Gly Pro Ser Gly
    610                 615                 620

Pro Gly Gly Tyr Gly Pro Gly Gly Pro Gly Ser Ser Ala Ala Ala Ala
625                 630                 635                 640

Ala Ala Ala Ala Ser Gly Pro Gly Gly Tyr Gly Pro Gly Ser Gln Gly
            645                 650                 655

Pro Ser Gly Pro Gly Gly Tyr Gly Pro Gly Gly Pro Gly Ser Ser Ala
                660                 665                 670

Ala Ala Ala Ala Ala Ala Ser Gly Pro Gly Gly Tyr Gly Pro Gly
    675                 680                 685

Ser Gln Gly Pro Ser Gly Pro Gly Gly Tyr Gly Pro Gly Gly Pro Gly
    690                 695                 700

Ser Ser Ala Ala Ala Ala Ala Ala Ala Ser Gly Pro Gly Gly Tyr
705                 710                 715                 720

Gly Pro Gly Ser Gln Gly Pro Ser Gly Pro Gly Gly Tyr Gly Pro Gly
            725                 730                 735

Gly Pro Gly Ser Ser Ala Ala Ala Ala Ala Ala Ala Ser Gly Pro
                740                 745                 750

Gly Gly Tyr Gly Pro Gly Ser Gln Gly Pro Ser Gly Pro Gly Gly Tyr
    755                 760                 765

Gly Pro Gly Gly Pro Gly Ser Ser Ala Ala Ala Ala Ala Ala Ala
    770                 775                 780

Ser Gly Pro Gly Gly Tyr Gly Pro Gly Ser Gln Gly Pro Ser Gly Pro
785                 790                 795                 800

Gly Gly Tyr Gly Pro Gly Gly Pro Gly Ser Ser Ala Ala Ala Ala
            805                 810                 815

Ala Ala Ala Ser Gly Pro Gly Gly Tyr Gly Pro Gly Ser Gln Gly Pro
                820                 825                 830

Ser Gly Pro Gly Gly Tyr Gly Pro Gly Gly Pro Gly Ser Ser Ala Ala
            835                 840                 845

Ala Ala Ala Ala Ala Ser Gly Pro Gly Gly Tyr Gly Pro Gly Ser
    850                 855                 860

Gln Gly Pro Ser Gly Pro Gly Gly Tyr Gly Pro Gly Gly Pro Gly Ser
865                 870                 875                 880

Ser Ala Ala Ala Ala Ala Ala Ala Gly Pro Ser Gly Pro Gly Ala

```
                      885                 890                 895
Tyr Gly Pro Ser Pro Ser Ala Ser Ala Ser Val Ala Ser Arg Leu
            900                 905                 910

Ser Ser Pro Ala Ala Ser Ser Arg Val Ser Ser Ala Val Ser Ser Leu
            915                 920                 925

Val Ser Gly Pro Thr Asn Gly Ala Ala Val Ser Gly Ala Leu Asn
            930                 935                 940

Ser Leu Val Ser Gln Ile Ser Ala Ser Asn Pro Gly Leu Ser Gly Cys
945                 950                 955                 960

Asp Ala Leu Val Gln Ala Leu Leu Glu Leu Val Ser Ala Leu Val Ala
            965                 970                 975

Ile Leu Ser Ser Ala Ser Ile Gly Gln Val Asn Val Ser Ser Val Ser
            980                 985                 990

Gln Ser Thr Gln Met Ile Ser Gln  Ala Leu Ser
            995                 1000

<210> SEQ ID NO 79
<211> LENGTH: 1283
<212> TYPE: PRT
<213> ORGANISM: Artificial
<220> FEATURE:
<223> OTHER INFORMATION: Full peptide sequence (N-domain + 32 repeats +
      C-domain) + N-terminal tag

<400> SEQUENCE: 79

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Arg Pro Leu Ser Asn Leu Asp Asn
        35                  40                  45

Ala Ser Gly Pro Gly Gly Tyr Gly Pro Gly Ser Gln Gly Pro Ser Gly
50                  55                  60

Pro Gly Gly Tyr Gly Pro Gly Gly Pro Gly Ser Ser Ala Ala Ala Ala
65                  70                  75                  80

Ala Ala Ala Ala Ser Gly Pro Gly Gly Tyr Gly Pro Gly Ser Gln Gly
                85                  90                  95

Pro Ser Gly Pro Gly Gly Tyr Gly Pro Gly Gly Pro Gly Ser Ser Ala
                100                 105                 110

Ala Ala Ala Ala Ala Ala Ser Gly Pro Gly Gly Tyr Gly Pro Gly
            115                 120                 125

Ser Gln Gly Pro Ser Gly Pro Gly Gly Tyr Gly Pro Gly Gly Pro Gly
        130                 135                 140

Ser Ser Ala Ala Ala Ala Ala Ala Ala Ser Gly Pro Gly Gly Tyr
145                 150                 155                 160

Gly Pro Gly Ser Gln Gly Pro Ser Gly Pro Gly Gly Tyr Gly Pro Gly
                165                 170                 175

Gly Pro Gly Ser Ser Ala Ala Ala Ala Ala Ala Ala Ser Gly Pro
                180                 185                 190

Gly Gly Tyr Gly Pro Gly Ser Gln Gly Pro Ser Gly Pro Gly Gly Tyr
            195                 200                 205

Gly Pro Gly Gly Pro Gly Ser Ser Ala Ala Ala Ala Ala Ala Ala
        210                 215                 220

Ser Gly Pro Gly Gly Tyr Gly Pro Gly Ser Gln Gly Pro Ser Gly Pro
225                 230                 235                 240

Gly Gly Tyr Gly Pro Gly Gly Pro Gly Ser Ser Ala Ala Ala Ala Ala
```

-continued

```
                245                 250                 255
Ala Ala Ala Ser Gly Pro Gly Gly Tyr Gly Pro Gly Ser Gln Gly Pro
                260                 265                 270

Ser Gly Pro Gly Gly Tyr Gly Pro Gly Pro Gly Ser Ser Ala Ala
            275                 280                 285

Ala Ala Ala Ala Ala Ala Ser Gly Pro Gly Gly Tyr Gly Pro Gly Ser
            290                 295                 300

Gln Gly Pro Ser Gly Pro Gly Gly Tyr Gly Pro Gly Pro Gly Ser
305                 310                 315                 320

Ser Ala Ala Ala Ala Ala Ala Ala Ser Gly Pro Gly Gly Tyr Gly
                325                 330                 335

Pro Gly Ser Gln Gly Pro Ser Gly Pro Gly Gly Tyr Gly Pro Gly Gly
                340                 345                 350

Pro Gly Ser Ser Ala Ala Ala Ala Ala Ala Ala Ser Gly Pro Gly
            355                 360                 365

Gly Tyr Gly Pro Gly Ser Gln Gly Pro Ser Gly Pro Gly Gly Tyr Gly
            370                 375                 380

Pro Gly Gly Pro Gly Ser Ser Ala Ala Ala Ala Ala Ala Ala Ser
385                 390                 395                 400

Gly Pro Gly Gly Tyr Gly Pro Gly Ser Gln Gly Pro Ser Gly Pro Gly
                405                 410                 415

Gly Tyr Gly Pro Gly Gly Pro Gly Ser Ser Ala Ala Ala Ala Ala
            420                 425                 430

Ala Ala Ser Gly Pro Gly Gly Tyr Gly Pro Gly Ser Gln Gly Pro Ser
            435                 440                 445

Gly Pro Gly Gly Tyr Gly Pro Gly Gly Pro Gly Ser Ser Ala Ala Ala
            450                 455                 460

Ala Ala Ala Ala Ala Ser Gly Pro Gly Gly Tyr Gly Pro Gly Ser Gln
465                 470                 475                 480

Gly Pro Ser Gly Pro Gly Gly Tyr Gly Pro Gly Gly Pro Gly Ser Ser
                485                 490                 495

Ala Ala Ala Ala Ala Ala Ala Ser Gly Pro Gly Gly Tyr Gly Pro
            500                 505                 510

Gly Ser Gln Gly Pro Ser Gly Pro Gly Gly Tyr Gly Pro Gly Gly Pro
            515                 520                 525

Gly Ser Ser Ala Ala Ala Ala Ala Ala Ala Ser Gly Pro Gly Gly
            530                 535                 540

Tyr Gly Pro Gly Ser Gln Gly Pro Ser Gly Pro Gly Gly Tyr Gly Pro
545                 550                 555                 560

Gly Gly Pro Gly Ser Ser Ala Ala Ala Ala Ala Ala Ala Ser Gly
                565                 570                 575

Pro Gly Gly Tyr Gly Pro Gly Ser Gln Gly Pro Ser Gly Pro Gly Gly
                580                 585                 590

Tyr Gly Pro Gly Gly Pro Gly Ser Ser Ala Ala Ala Ala Ala Ala
            595                 600                 605

Ala Ser Gly Pro Gly Gly Tyr Gly Pro Gly Ser Gln Gly Pro Ser Gly
            610                 615                 620

Pro Gly Gly Tyr Gly Pro Gly Gly Pro Gly Ser Ser Ala Ala Ala Ala
625                 630                 635                 640

Ala Ala Ala Ser Gly Pro Gly Gly Tyr Gly Pro Gly Ser Gln Gly
                645                 650                 655

Pro Ser Gly Pro Gly Gly Tyr Gly Pro Gly Gly Pro Gly Ser Ser Ala
                660                 665                 670
```

-continued

```
Ala Ala Ala Ala Ala Ala Ser Gly Pro Gly Gly Tyr Gly Pro Gly
        675                 680                 685

Ser Gln Gly Pro Ser Gly Pro Gly Gly Tyr Gly Pro Gly Gly Pro Gly
    690                 695                 700

Ser Ser Ala Ala Ala Ala Ala Ala Ala Ser Gly Pro Gly Gly Tyr
705                 710                 715                 720

Gly Pro Gly Ser Gln Gly Pro Ser Gly Pro Gly Gly Tyr Gly Pro Gly
            725                 730                 735

Gly Pro Gly Ser Ser Ala Ala Ala Ala Ala Ala Ala Ser Gly Pro
            740                 745                 750

Gly Gly Tyr Gly Pro Gly Ser Gln Gly Pro Ser Gly Pro Gly Gly Tyr
            755                 760                 765

Gly Pro Gly Gly Pro Gly Ser Ser Ala Ala Ala Ala Ala Ala Ala
            770                 775                 780

Ser Gly Pro Gly Gly Tyr Gly Pro Gly Ser Gln Gly Pro Ser Gly Pro
785                 790                 795                 800

Gly Gly Tyr Gly Pro Gly Gly Pro Gly Ser Ser Ala Ala Ala Ala
            805                 810                 815

Ala Ala Ala Ser Gly Pro Gly Gly Tyr Gly Pro Gly Ser Gln Gly Pro
        820                 825                 830

Ser Gly Pro Gly Gly Tyr Gly Pro Gly Gly Pro Gly Ser Ser Ala Ala
        835                 840                 845

Ala Ala Ala Ala Ala Ala Ser Gly Pro Gly Gly Tyr Gly Pro Gly Ser
        850                 855                 860

Gln Gly Pro Ser Gly Pro Gly Gly Tyr Gly Pro Gly Gly Pro Gly Ser
865                 870                 875                 880

Ser Ala Ala Ala Ala Ala Ala Ala Ser Gly Pro Gly Gly Tyr Gly
            885                 890                 895

Pro Gly Ser Gln Gly Pro Ser Gly Pro Gly Gly Tyr Gly Pro Gly Gly
            900                 905                 910

Pro Gly Ser Ser Ala Ala Ala Ala Ala Ala Ala Ser Gly Pro Gly
            915                 920                 925

Gly Tyr Gly Pro Gly Ser Gln Gly Pro Ser Gly Pro Gly Gly Tyr Gly
        930                 935                 940

Pro Gly Gly Pro Gly Ser Ser Ala Ala Ala Ala Ala Ala Ala Ser
945                 950                 955                 960

Gly Pro Gly Gly Tyr Gly Pro Gly Ser Gln Gly Pro Ser Gly Pro Gly
            965                 970                 975

Gly Tyr Gly Pro Gly Gly Pro Gly Ser Ser Ala Ala Ala Ala Ala
            980                 985                 990

Ala Ala Ser Gly Pro Gly Gly Tyr Gly Pro Gly Ser Gln Gly Pro Ser
        995                 1000                1005

Gly Pro Gly Gly Tyr Gly Pro Gly Gly Pro Gly Ser Ser Ala Ala
        1010                1015                1020

Ala Ala Ala Ala Ala Ala Ser Gly Pro Gly Gly Tyr Gly Pro Gly
        1025                1030                1035

Ser Gln Gly Pro Ser Gly Pro Gly Gly Tyr Gly Pro Gly Gly Pro
        1040                1045                1050

Gly Ser Ser Ala Ala Ala Ala Ala Ala Ala Ala Ser Gly Pro Gly
        1055                1060                1065

Gly Tyr Gly Pro Gly Ser Gln Gly Pro Ser Gly Pro Gly Gly Tyr
        1070                1075                1080

Gly Pro Gly Gly Pro Gly Ser Ser Ala Ala Ala Ala Ala Ala Ala
        1085                1090                1095
```

```
Ala Ser Gly Pro Gly Gly Tyr Gly Pro Gly Ser Gln Gly Pro Ser
    1100                1105                1110

Gly Pro Gly Gly Tyr Gly Pro Gly Gly Pro Gly Ser Ser Ala Ala
    1115                1120                1125

Ala Ala Ala Ala Ala Ala Ser Gly Pro Gly Gly Tyr Gly Pro Gly
    1130                1135                1140

Ser Gln Gly Pro Ser Gly Pro Gly Gly Tyr Gly Pro Gly Gly Pro
    1145                1150                1155

Gly Ser Ser Ala Ala Ala Ala Ala Ala Ala Gly Pro Ser Gly
    1160                1165                1170

Pro Gly Ala Tyr Gly Pro Ser Pro Ser Ala Ser Ala Ser Val Ala
    1175                1180                1185

Ala Ser Arg Leu Ser Ser Pro Ala Ala Ser Ser Arg Val Ser Ser
    1190                1195                1200

Ala Val Ser Ser Leu Val Ser Ser Gly Pro Thr Asn Gly Ala Ala
    1205                1210                1215

Val Ser Gly Ala Leu Asn Ser Leu Val Ser Gln Ile Ser Ala Ser
    1220                1225                1230

Asn Pro Gly Leu Ser Gly Cys Asp Ala Leu Val Gln Ala Leu Leu
    1235                1240                1245

Glu Leu Val Ser Ala Leu Val Ala Ile Leu Ser Ser Ala Ser Ile
    1250                1255                1260

Gly Gln Val Asn Val Ser Ser Val Ser Gln Ser Thr Gln Met Ile
    1265                1270                1275

Ser Gln Ala Leu Ser
    1280

<210> SEQ ID NO 80
<211> LENGTH: 18
<212> TYPE: DNA
<213> ORGANISM: Artificial
<220> FEATURE:
<223> OTHER INFORMATION: His6 tag DNA

<400> SEQUENCE: 80
catcaccatc accatcac                                                18

<210> SEQ ID NO 81
<211> LENGTH: 30
<212> TYPE: DNA
<213> ORGANISM: Artificial
<220> FEATURE:
<223> OTHER INFORMATION: His6 tag version 2 DNA

<400> SEQUENCE: 81
atgtcgtact accatcacca tcaccatcac                                   30

<210> SEQ ID NO 82
<211> LENGTH: 27
<212> TYPE: DNA
<213> ORGANISM: Artificial
<220> FEATURE:
<223> OTHER INFORMATION: HA tag DNA

<400> SEQUENCE: 82
tacccatacg atgttccaga ttacgct                                      27

<210> SEQ ID NO 83
<211> LENGTH: 204
<212> TYPE: PRT
```

-continued

<213> ORGANISM: Latrodectus Hesperus

<400> SEQUENCE: 83

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Ala
            195                 200

<210> SEQ ID NO 84
<211> LENGTH: 615
<212> TYPE: DNA
<213> ORGANISM: Latrodectus Hesperus

<400> SEQUENCE: 84

```
atgacatggt ccacccgttt ggctctctcc ttcctcttcg ttctctgcac ccagtcgctc      60
tacgctctcg ctcaagctaa cactccctgg tcctctaagg ccaacgctga cgccttcatc     120
aacagcttca tctcagctgc ctcgaacacc ggctcattct cgcaggacca aatggaggat     180
atgtccttga tcggaaacac tctgatggct gccatggaca catgggtgg caggatcaca      240
ccctccaagc tccaggctct ggacatggct ttcgccagct cagttgctga gatcgctgcc     300
agcgaaggag gtgacctcgg agtgaccact aacgctatcg ccgatgcttt gacttcagct     360
ttctaccaga caaccggcgt ggtcaactcc cgtttcatct ctgaaatccg cagcctgatc     420
ggcatgttcg cccaggcttc cgccaacgac gtctacgctt cggccggatc gtccggcgga     480
ggtggctacg gtgcctctag cgcttccgct gcctccgctt ctgctgccgc tccatctgga     540
gttgcttacc aagctcctgc ccaggctcaa atctccttca ccctccgtgg tcaacagccc     600
gtctcctatg catcc                                                       615
```